US010125125B2

(12) United States Patent
Fritzson et al.

(10) Patent No.: US 10,125,125 B2
(45) Date of Patent: *Nov. 13, 2018

(54) N-(HETEROARYL)-SULFONAMIDE DERIVATIVES USEFUL AS S100-INHIBITORS

(71) Applicant: Active Biotech AB, Lund (SE)

(72) Inventors: Ingela Fritzson, Lund (SE); David Liberg, Vintrie (SE); Stephen East, Wallingford (GB); Colin Mackinnon, Newport Pagnell (GB); Natacha Prevost, Juvignac (FR)

(73) Assignee: Active Biotech AB, Lund (SE)

( * ) Notice: Subject to any disclaimer, the term of this patent is extended or adjusted under 35 U.S.C. 154(b) by 0 days.

This patent is subject to a terminal disclaimer.

(21) Appl. No.: 15/836,036

(22) Filed: Dec. 8, 2017

(65) Prior Publication Data
US 2018/0155330 A1 Jun. 7, 2018

Related U.S. Application Data

(63) Continuation of application No. 14/890,938, filed as application No. PCT/EP2014/059829 on May 14, 2014, now Pat. No. 9,873,687.

(30) Foreign Application Priority Data

May 14, 2013 (EP) ..................................... 13167680

(51) Int. Cl.
| C07D 409/12 | (2006.01) |
| C07D 213/75 | (2006.01) |
| C07D 213/76 | (2006.01) |
| C07D 237/22 | (2006.01) |
| C07D 241/20 | (2006.01) |
| C07D 401/12 | (2006.01) |
| C07D 401/14 | (2006.01) |
| C07D 239/47 | (2006.01) |

(52) U.S. Cl.
CPC ......... *C07D 409/12* (2013.01); *C07D 213/75* (2013.01); *C07D 213/76* (2013.01); *C07D 237/22* (2013.01); *C07D 239/47* (2013.01); *C07D 241/20* (2013.01); *C07D 401/12* (2013.01); *C07D 401/14* (2013.01); *Y02P 20/582* (2015.11)

(58) Field of Classification Search
CPC .... A61K 31/435; A61K 31/44; A61K 31/495; A61K 31/496; A61K 31/4965; C07D 409/12; C07D 213/75; C07D 213/76; C07D 237/22; C07D 241/20; C07D 401/12
See application file for complete search history.

(56) References Cited

U.S. PATENT DOCUMENTS

| 3,313,806 A | 4/1967 | Nakagome et al. |
| 2006/0004085 A1 | 1/2006 | Weber et al. |
| 2006/0211702 A1 | 9/2006 | Oslob et al. |

FOREIGN PATENT DOCUMENTS

| BE | 649968 A | 11/1964 |
| EP | 1 661 889 | 5/2006 |
| WO | WO 1997/010214 | 3/1997 |
| WO | WO 2011/063339 | 5/2001 |
| WO | WO 2003/080610 | 10/2003 |
| WO | WO 2004/108690 | 12/2004 |
| WO | WO 2006/067445 | 6/2006 |
| WO | WO 2006/122723 | 11/2006 |
| WO | WO 2006/124874 | 11/2006 |
| WO | WO 2007/023186 | 3/2007 |
| WO | WO 2007/067875 | 6/2007 |
| WO | WO 2008/050732 | 5/2008 |
| WO | WO 2010/100127 | 9/2010 |
| WO | WO 2010/132999 | 11/2010 |
| WO | WO 2011/023677 | 3/2011 |
| WO | WO 2011/085126 | 7/2011 |
| WO | WO 2011/133444 | 10/2011 |
| WO | WO 2012/035171 | 3/2012 |

OTHER PUBLICATIONS

International Search Report for corresponding International Application No. PCT/EP2014/059829 dated Jul. 4, 2014.
Written Opinion of the International Search Authority for corresponding International Application No. PCT/EP2014/059829 dated Jul. 4, 2014.
Pecorari et al., "Compounds With Potential Anticancer Activity Benzenesulfonamido-Pyrimidine Derivatives", Farmaco, vol. 42, No. 7, Jan. 1, 1987, pp. 499-503.
Acharyya et al., "A CXCL1 Paracrine Network Links Cancer Chemoresistance and Metastasis", Cell, 150, Jul. 6, 2012, pp. 165-178.
Andersen et al., "Endocyclic Nucleophilic substitution at Tetracoordinate Sulfur (VI)", J. Org. Chem., vol. 53, No. 20, Nov. 20, 1988, pp. 4667-4675.
Andersen et al., "Substitution at Tetracoordinate Sulfur (VI). Rearrangment of 2-Aminoaryl Arenesulfonates to N-(2-Hydroxyaryl)arenesulfonamides", J. Org. Chem., vol. 47, No. 10, 1982, pp. 1884-1889.
Arai et al., "S100A8 and S100A9 Overexpression is Associated with Poor Pathological Parameters in Invasive Ductal Carcinoma of the Breast", Current Cancer Drug Targets, vol. 8, No. 4, 2008, pp. 243-252.
Attia et al., "Immunology of Spontaneous Mammary Carcinomas in Mice V. Acquired Tumor Resistance and Enhancement in Strain A Mice Infected with Mammary Tumor Virus", Cancer Research, vol. 26, Part 1, Aug. 1966, pp. 1787-1800.

(Continued)

*Primary Examiner* — Sahar Javanmard
(74) *Attorney, Agent, or Firm* — Renner, Otto, Boisselle & Sklar, LLP

(57) ABSTRACT

A compound of formula (I), or a pharmaceutically acceptable salt thereof and a pharmaceutical composition comprising the compound. The compound is an inhibitor of interactions between SI 00A9 and interaction partners such as RAGE, TLR4 and EMMPRIN and as such is useful in the treatment of disorders such as cancer, autoimmune disorders, inflammatory disorders and neurodegenerative disorders.

39 Claims, 3 Drawing Sheets

(56) References Cited

OTHER PUBLICATIONS

Bhardwaj et al., "The calcium-binding proteins MRP8 and MRP14 form a membrane-associated heterodimer in a subset of monocytes/macrophages present in acute but absent in chronic inflammatory lesions", Eur J. Immunol. vol. 22, 1992, pp. 1891-1897.

Björk et al., "Identification of Human S100A9 as a Novel Target for Treatment of Autoimmune Disease via Binding to Quinoline-3-Carboxamides", PLoS Biology, vol. 7, Issue 4, Apr. 2009, pp. 0800-0812.

Cesaro et al., "An Inflammation Loop Orchestrated by S100A9 and Calprotectin is Critical for Development of Arthritis". PLoS One, vol. 7, Issue 9, Sep. 2012, pp. 1-12.

Chang et al., "The Role of S100a9 in the Pathogenesis in Alzheimer's Disease: The Therapeutic Effects of S100a9 Knockdown or Knockout", Neurodegenerative Diseases, Jun. 6, 2011, pp. 1-3.

Cheng et al., "Inhibition of dendritic cell differentiation and accumulation of myeloid-derived suppressor cells in cancer is regulated by S100A9 protein", J. Exp. Med., Sep. 22, 2008, pp. 1-15.β.

Deane et al., "A multimodal RAGE-specific inhibitor reduces amyloid β-mediated brain disorder in a mouse model of Alzheimer disease", The Journal of Clinical Investigation, vol. 122, No. 4, Apr. 2002. pp. 1377-1392.

Foell et al., "S100 proteins in phagocytes: a novel group of damage-associated moleculat pattern molecules", Journal of Leukocyte Biology, vol. 81, Jan. 2007, pp. 28-37.

Ghavami et al., "S100A8/S100A9 at low concentration promotes tumor cell growth via RAGE ligation and MAP kinase-dependent pathway", Journal of Leukocyte Biology, vol. 83. Jun. 2008, pp. 1-9.

Ha et al., "S100a9 Knockdown Decreases the Memory Impairment and the Neuropathology in Tg2576 Mice", AD Animal Model, PLoS One, vol. 5, Issue, 1, Jan. 2010, pp. 1-11.

Hibino et al., "S100A9 is a Novel Ligand of EMMPRIN That Promotes Melanoma Metastasis", Cancer Research, vol. 73, No. 1, first published on-line Nov. 7, 2012, pp. 172-183.

Hiratsuka et al., "Tumour-mediated upregulation of chemoattractants and recruitment of myeloid cells predetermines lung metastasis", Nature Cell Biology, vol. 8, No. 12, Dec. 2006, 14 pages.

Hsieh et al, "Differentiation of AmpC beta-lactamase binders vs. decoys using classification κNN QSAR modeling and application of the QSAR classifier to virtual screening", J. Comput Aided Mol Des. vol. 22, 2008, pp. 593-609.

Koshiro, "Syntheses of Heterocyclic Compounds of Nitrogen. CXX. Syntheses of Oxazolopyridines and Related Compounds", Chemical and Pharmaceutical Bulletin, vol. 7, No. 6, 1959, pp. 725-730.

Marenholz et al., "S100 proteins in mouse and man: from evolution to function and pathology (including an update of the nomenclature)", Biochemical and Biophysical Research Communications, vol. 322, 2004, pp. 1111-1122.

Nakagome et al, "Synthesis of Pyridazine Derivatives. XII. Reaction of Amico-3 (2H) pyridazinone Derivatives with Tosyl Chloride", Chemical and Pharmaceutical Bulletin, vol. 14, No. 10, Jan. 17, 1966, pp. 1074-1081.

Riva et al., "Induction of nuclear factor-κB responses by the S100A9 protein is Toll-like receptor-4-dependent", Immunology, The Journal of Cells, Molecules, Systems and Technologies, vol. 137, 2012, pp. 172-182.

Ryckman et al., "Proinflammatory Activities of S100: Proteins S100A8, S100A9, and S100A8/A9 Induce Neutrophil Chemotaxis and Adhesion", The Journal of Immunology, vol. 170, 2003, pp. 3233-3242.

Shepherd et al., "Inflammatory S100A9 and S100A12 proteins in Alzheimer's disease", Neurobiology of Aging, vol. 27, 2006, pp. 1554-1563.

Sinha et al., "Proinflammatory S100 Proteins Regulate the Ackcumulation of Myeloid-Derived Suppressor Cells", The Journal of Immunology, vol. 181, 2008, pp. 4666-4675.

Srikrishna, "S100A8 and S100A9: New insights into Their Roles in Malignancy", The Hournal of Innate Immunigy, vol. 4, 2012, pp. 31-40.

Van Lent et al., "Active Involvement of Alarmins S100A8 and S100A9 in the Regulation of Synovial Activation and Joint Destruction During Mouse and Human Osteoarthritis", Arthritis & Rheumatism, vol. 64, No. 5, May 2012, pp. 1-13.

Wang et al., "Increased Myeloid-Derived Suppressor Cells in Gastric Cancer Correlate with Cancer Stage and Plasma S100A8/A9 Proinflammatory Proteins", The Journal of Immunology, vol. 190, 2013, pp. 794-804.

Bradbury et al., "New Non-Peptide Endothelin-A Receptor Antagonists: Synthesis, Biological Properties, and Structure—Activity Relationships of 5-(Dimethylamino)-N-pyridyl-, -N-pyrimidinyl-, -N-pyridazinyl-, and -N-pyrazinyl-1-naphthalenesulfonamides", Journal of Medicinal Chemistry, vol. 40, No. 6, 1997, pp. 996-1004.

N-(HETEROARYL)-SULFONAMIDE DERIVATIVES USEFUL AS S100-INHIBITORS

This application is a continuation of U.S. application Ser. No. 14/890,938 filed on Nov. 13, 2015, which is a national phase of International Application No. PCT/EP2014/059829 filed May 14, 2014 and published in the English language, which claims priority to Application No. EP 13167680.1 filed May 14, 2013.

FIELD OF THE INVENTION

The present invention relates to sulfonamide derivatives, pharmaceutical compositions of these derivatives and their use as medicaments. More particularly the invention relates to sulfonamide derivatives for use in the treatment of cancer, autoimmune disorders, inflammatory disorders and neurodegenerative disorders.

BACKGROUND OF THE INVENTION

S100A9 belongs to the S100-family of calcium-binding proteins and has been recognized as an attractive novel therapeutic target for the treatment of e.g. autoimmunity, inflammatory disease, neurodegenerative disease and cancer. Other S100 proteins have distinct roles in many different biological processes and are connected to a number of diseases including cancer, cardiomyopathies, atherosclerosis, Alzheimer's disease and inflammatory diseases. Twenty-one of the human genes, including S100A9, are located at chromosomal region 1q21, which is frequently altered in tumors (Marenholz et al., 2004). Interestingly, although the primary sequence diverges between family members, the 3D-structures of the different proteins are very similar.

S100A9 is often co-expressed with S100A8, another member of the S100 protein family, and they are highly expressed in myeloid cells, such as neutrophils and monocytes, but can also be induced in other cells or tissues (Srikrishna 2012). They form non-covalent homo- and heterocomplexes that can be specifically released in response to cellular activation (Foell et al., 2007, Ryckman et al., 2003). S100A9 can functionally be described as a damage-associated molecular pattern (DAMP) molecule which is released in tissues and induces signaling by interacting with receptors such as RAGE and TLR4 (Foell et al., 2007, below). As for many other DAMP molecules, S100A9 also has intracellular roles in addition to its extracellular functions, e.g. by binding to the cytoskeleton and influencing cytoskeletal rearrangements and thereby cellular migration (Srikrishna 2012).

A pro-inflammatory role for S100A9 is supported by elevated S100A9 serum levels in inflammatory diseases and by high concentrations of S100A9 at local sites of inflammation, for example in the synovial fluid of rheumatoid arthritis patients (Foell & Roth, 2004) or osteoarthritis patients (van Lent 2012) where high levels correlate with joint destruction. Also, preclinical studies with S100A9 knock-out mice show an involvement of S100A9 in many inflammatory processes including synovial activation and cartilage destruction during osteoarthritis (van Lent 2012). High levels of S100A9 have also been found in several forms of cancer and a high expression level has been shown to correlate with poor tumor differentiation in some of these cancer forms (Arai et al., 2001). Elevated S100A9 levels in pathological conditions of chronic inflammation as well as in cancer argue for a possible role in inflammation-associated carcinogenesis.

A role for S100A9 in the coupling between the immune system and cancer is also supported by studies showing that S100A8 and S100A9 are highly expressed in and important for the function of myeloid-derived suppressor cells (MDSCs) (Cheng et al., 2008, Sinha et al., 2008, Wang et al., 2013), a mixture of immature myeloid cells that suppress T- and NK-cell activation and promote angiogenesis and tumor growth. By interfering with S100A9-regulated accumulation of tumor infiltrating MDSCs, the balance between these processes may change in favor of an anti-angiogenic and less immune suppressive milieu with inhibited tumor progression. Furthermore, there are data suggesting a role for S100A9 in recruiting both inflammatory cells and tumor cells to metastatic sites (Hiratsuka et al., 2006, Acharyya et al. 2012, Hibino et al., 2013). Thus, blocking the function of S100A9 may provide a new approach to prevention of metastasis.

Although a number of possible biological functions of S100A9 have been proposed, the exact role of S100A9 in inflammation, in cancer and in other diseases is still unknown. Members of the S100 protein family have been reported to interact with the pro-inflammatory molecule RAGE and studies showed that S100A9 is the strongest RAGE binder within the S100 family in the presence of physiological levels of $Ca^{2+}$ and $Zn^{2+}$ (Björk et al. 2009). These studies further demonstrated that S100A9 interacts with toll-like receptor 4 (TLR4). As for the S100A9-RAGE interaction, the S100A9-TLR4 interaction appears to be strictly dependent on the presence of physiological levels of both $Ca^{2+}$ and $Zn^{2+}$. Another receptor for S100A9 that may be important in cancer is EMMPRIN (CD147), this protein is expressed on different cell types and the S100A9-EMMPRIN interaction has been shown to be involved in melanoma metastasis (Hibino et al., 2013).

S100A8 and S100A9 proteins have predominantly been described as cytoplasmic proteins that are secreted from myeloid cells upon activation. It is generally believed that the major biological functions relevant to inflammation require the release of the S100 proteins to the extracellular space. In this model, extracellular S100A9 would bind to e.g. the pro-inflammatory receptors RAGE and TLR4 and result in an inflammatory response. This is supported by studies showing that S100A9 induces TNFα production in human monocytes via TLR4 (Riva et al. 2012, Cesaro et al. 2012). Also, S100A9 in complex with S100A8 has shown growth promoting activity directly on tumors cells via RAGE signaling (Ghavami et al., 2008). S100A9 also exists in a membrane-associated form on monocytes (Bhardwaj et al., 1992). Membrane associated S100A9 opens up for the possibility of cell-cell or cell-ECM signaling involving S100A9.

The collected data suggest that S100A9 have important roles in inflammation, cancer growth, cancer metastasis and in their connections. Novel compounds that inhibit the activity of S100A9 in these processes, and thereby disturb the tumor microenvironment, would be attractive in treatment of cancer of different types.

Besides cancer, inflammation and autoimmunity, S100A9 has strong connections to neurodegenerative disease. S100A9 is upregulated in the brain in Alzheimer's disease (AD) patients and in mouse disease models (Shepherd et al., 2006, Ha et al., 2010). Furthermore, knock-down or deletion of S100A9 in mice models of AD inhibits cognition decline and plaque burden in the brain (Ha et al., 2010, Chang et al., 2012). A role for RAGE is also evident in AD where inhibition of RAGE reduces disease in a mouse AD model (Deane et al., 2013). Inhibition of S100A9 and its interactions represents a new promising approach for therapeutic intervention in AD and other neurodegenerative diseases.

Sulfonamides are known in the prior art. Thus, e.g. in EP1661889 A1 N-[5-bromo-3-hydroxypyridin-2-yl]-4-methylbenzenesulfonamide is disclosed as a synthesis intermediate. The compounds N-(1,2-dihydro-2-oxo-3-pyridinyl)-2-(trifluoromethyl)-benzenesulfonamide and 4-chloro-N-(1,2-dihydro-2-oxo-3-pyridinyl)-3-(trifluoromethyl)-benzenesulfonamide are disclosed in a chemical database (Database Chemcats XP002698561) and Enamine Advanced HTS Collection. In Hsieh Jui-Hua et al, J Comp-Aid Mol Des, 22(9), 593, 2008, 4-chloro-N-(3-hydroxy-2-pyridinyl)-benzenesulfonamide is described. In Andersen K et al, J Org Chem, 53(20), 4667, 1988, 3-trifluoromethyl-N-(3-hydroxy-2-pyridinyl)-benzenesulfonamide is described. In Andersen K et al, J Org Chem, 47(10), 1884, 1982, 4-methyl-N-(3-hydroxy-2-pyridinyl)-benzenesulfonamide is described. In Koshiro A, Chem Pharm Bull, 7, 725, 1959, 4-methyl-N-(2-hydroxy-3-pyridinyl)-benzenesulfonamide is described. In Nakagone T et al, Chem Pharm Bull, 14(10), 1074, 1966, 4-methyl-N-(2,3-dihydro-3-oxo-4-pyridazinyl)-benzenesulfonamide and its tautomer 4-methyl-N-(3-hydroxy-4-pyridazinyl)-benzenesulfonamide are described.

SUMMARY OF THE INVENTION

In a first aspect, novel sulfonamide compounds are provided, according to formula (I)

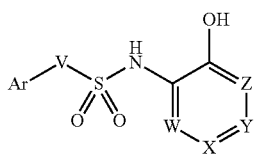

or a pharmaceutically acceptable salt thereof;
wherein
W is N or CH;
X is N or $CR_1$;
Y is N or $CR_2$;
Z is N or $CR_3$;
at least one and at most two of W, X, Y and Z are N;
$R_1$ is H, halogen, $S(O)_2$C1-C3 alkyl, cyano, or C1-C3 alkyl optionally substituted with one or more halogen(s);
$R_2$ is H, halogen, cyano, C(O)OH, C(O)OC1-C3 alkyl, C1-C3 alkyl optionally substituted with one or more F; hydroxy-C1-C3 alkyl, $S(O)_2$C1-C3 alkyl, $S(O)_2$C3-C6 cycloalkyl or $S(O)_2$C1-C3 hydroxyalkyl;
$R_3$ is H, halogen or cyano;
V is $(CHR_4)_m$;
m is 0 or 1;
$R_4$ is H or C1-C3 alkyl optionally substituted with one or more halogen(s);
Ar is

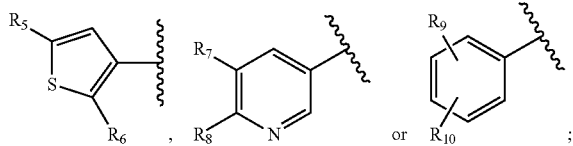

$R_5$ is H, halogen or cyano;
$R_6$ is H or halogen;
$R_7$ is H, halogen, C1-C3 alkyl, cyano, $S(O)_2$C1-C3 alkyl, or phenyl;
$R_8$ is H, halogen, C1-C3 alkyl optionally substituted with one or more F; C1-C3 alkoxy optionally substituted with one or more F; phenoxy, $NHR_{11}$, or $NR_{11}R_{12}$;
$R_9$ is H, halogen, cyano, C1-C3 alkyl optionally substituted with one or more F; C1-C3 alkylthio optionally substituted with one or more F; C1-C3 alkoxy optionally substituted with one or more F; or $C(O)NR_{13}R_{14}$;
$R_{10}$ is H, halogen, cyano, C1-C3 alkyl optionally substituted with one or more F; C1-C3 alkylthio optionally substituted with one or more F; C1-C3 alkoxy optionally substituted with one or more F; or $C(O)NR_{13}R_{14}$;
$R_{11}$ is C1-C3 alkyl;
$R_{12}$ is C1-C3 alkyl; or
$R_{11}$ and $R_{12}$, together with the nitrogen atom to which they are both attached, form a ring of formula

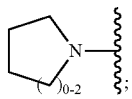

$R_{13}$ is H or C1-C3 alkyl; and
$R_{14}$ is H or C1-C3 alkyl;
provided that the compound is not selected from
3,4-difluoro-N-(2-hydroxypyridin-3-yl)benzene-1-sulfonamide,
N-[5-bromo-3-hydroxypyridin-2-yl]-4-methylbenzenesulfonamide,
N-(1,2-dihydro-2-oxo-3-pyridinyl)-2-(trifluoromethyl)-benzenesulfonamide,
4-chloro-N-(1,2-dihydro-2-oxo-3-pyridinyl)-3-(trifluoromethyl)-benzenesulfonamide,
4-chloro-N-(3-hydroxy-2-pyridinyl)-benzenesulfonamide,
3-trifluoromethyl-N-(3-hydroxy-2-pyridinyl)-benzenesulfonamide,
4-methyl-N-(3-hydroxy-2-pyridinyl)-benzenesulfonamide,
4-methyl-N-(2-hydroxy-3-pyridinyl)-benzenesulfonamide, and
4-methyl-N-(2,3-dihydro-3-oxo-4-pyridazinyl)-benzenesulfonamide or its tautomer
4-methyl-N-(3-hydroxy-4-pyridazinyl)-benzenesulfonamide.

The compounds of formula (I) as defined herein above are useful as inhibitors of interactions between S100A9 and interaction partners such as RAGE, TLR4 and EMMPRIN. Thus, according to a further aspect, compounds of formula (I) as defined herein above are provided for use as inhibitors of interactions of S100A9 and its interaction partners and for use in the treatment of disorders associated with functions of S100A9, e.g. inflammatory diseases, neurodegenerative diseases, autoimmune diseases and cancer.

According to one aspect, compounds of formula (I) are provided for use in therapy, e.g. for the treatment of of a disorder selected from inflammatory diseases, neurodegenerative diseases, autoimmune diseases and cancer.

According to one aspect, the use of compounds of formula (I) in the manufacturing of a medicament for use in the treatment of a disorder selected from inflammatory diseases, neurodegenerative diseases, autoimmune diseases and cancer.

According to a further aspect, a pharmaceutical composition is provided, comprising a compound of formula (I), or a pharmaceutically acceptable salt thereof, and at least one pharmaceutically acceptable excipient. The pharmaceutical composition of the invention is useful for the treatment of diseases selected from inflammatory diseases, autoimmune diseases, neurodegenerative diseases and cancer.

DETAILED DESCRIPTION OF THE INVENTION

Figure 1:
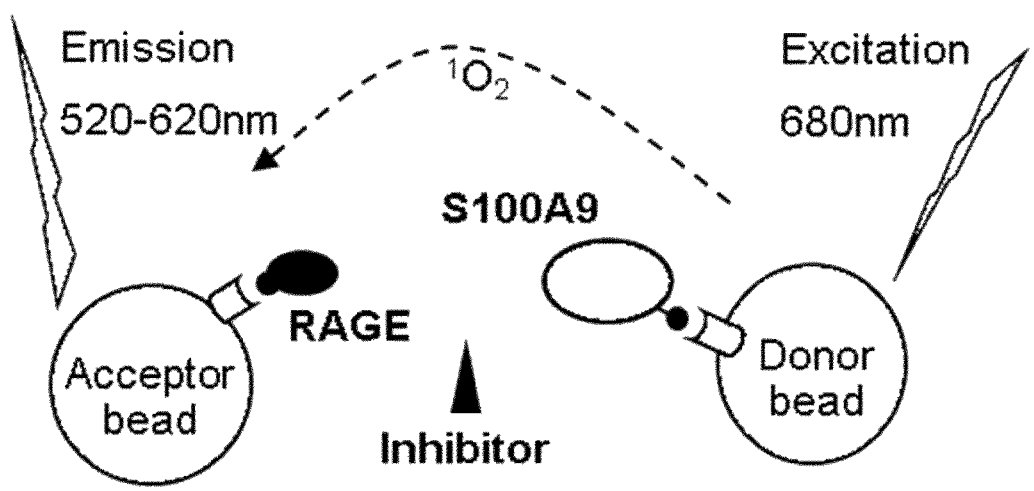
FIG. 1 is a schematic representation of an assay of the inhibition of the interaction between biotinylated human S100A9 and human RAGE-Fc using a small molecule S100A9 binder.

For the purpose of the present invention, the term alkyl, either alone or as part of a radical, includes straight or branched chain alkyl of the general formula $C_nH_{2n+1}$.

The term C1-C3 alkyl includes methyl, ethyl, n-propyl and isopropyl.

The term phenyl refers to a $C_6H_5$ radical of the formula

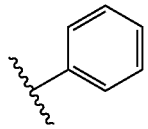

For the purpose of the present invention, the term halogen refers to F, Cl, Br and I.

The term hydroxy refers to a radical of the formula —OH.
The term hydroxy-C1-C3 alkyl refers to an alkyl radical substituted with a hydroxy, e.g. 1-hydroxypropan-2-yl.

The term C1-C3 alkylthio refers to a radical of the formula —SR, wherein R is C1-C3 alkyl.

The term C1-C3 alkoxy refers to a radical of the formula —OR, wherein R is C1-C3 alkyl.

The term phenoxy refers to a radical of the formula —OR wherein R is phenyl.

The term cyano refers to a radical of formula —C≡N (i.e. —CN).

The term $S(O)_2$C1-C3 alkyl refers to a radical of formula

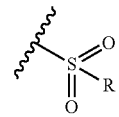

wherein R is C1-C3 alkyl.

The term $S(O)_2$C3-C6 cycloalkyl refers to a radical of formula

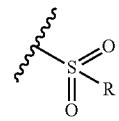

wherein R is C3-C6 cycloalkyl.

The term $S(O)_2$C1-C3 hydroxyalkyl refers to a radical of formula

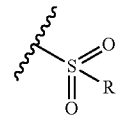

wherein R is C1-C3 hydroxyalkyl.

The term C(O)OC1-C3 alkyl refers to a radical of formula

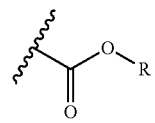

wherein R is C1-C3 alkyl.

"Optional" or "optionally" means that the subsequently described event or circumstance may but need not occur, and that the description includes instances where the event or circumstance occurs and instances in which it does not.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

The term pharmaceutically acceptable salt of a compound refers to a salt that is pharmaceutically acceptable, as defined herein, and that possesses the desired pharmacological activity of the parent compound. Pharmaceutically acceptable salts include acid addition salts formed with inorganic acids, e.g. hydrochloric acid, hydrobromic acid, sulfuric acid, nitric acid, phosphoric acid; or formed with organic acids, e.g. acetic acid, benzenesulfonic acid, benzoic acid, camphorsulfonic acid, citric acid, ethanesulfonic acid, fumaric acid, glucoheptonic acid, gluconic acid, glutamic acid, glycolic acid, hydroxynaphtoic acid, 2-hydroxyethanesulfonic acid, lactic acid, maleic acid, malic acid, malonic acid, mandelic acid, methanesulfonic acid, muconic acid, 2-naphthalenesulfonic acid, propionic acid, salicylic acid, succinic acid, tartaric acid, p-toluenesulfonic acid, trimethylacetic acid; or salts formed when an acidic proton present in the parent compound either is replaced by a metal ion, e.g., an alkali metal ion, an alkaline earth ion, or an aluminum ion; or coordinates with an organic or inorganic base. Acceptable organic bases include e.g. diethanolamine, ethanolamine, N-methylglucamine, triethanolamine, morpholine, and tromethamine. Acceptable inorganic bases include e.g. ammonia, aluminum hydroxide, calcium hydroxide, potassium hydroxide, sodium carbonate and sodium hydroxide.

Whenever a chiral carbon is present in a chemical structure, it is intended that all stereoisomers associated with that chiral carbon are encompassed by the structure, unless otherwise specified. Using the Cahn-Ingold-Prelog RS notational system, any asymmetric carbon atom may be present in the (R)- or (S)-configuration, and the compound may be present as a mixture of its stereoisomers, e.g. a racemic mixture, or one stereoisomer only.

Some of the compounds of the invention may exist in tautomeric forms, e.g. 2-hydroxypyridine and its tautomer 2-pyridone. Any such tautomer is contemplated to be within the scope of the invention.

Also, in a compound of formula (I) as defined herein, any hydrogen atom may be replaced by a deuterium ($^2$H), and any such deuterated compound of formula (I), comprising one or more deuteriums in place of the corresponding number of hydrogen atoms, is considered to be within the scope of the invention.

The compounds of formula (I) carry a hydroxy group on the ring containing W, X, Y and Z. It has been found that the corresponding alkoxy compounds, i.e. where said hydroxyl group is alkylated, are prodrugs of the compounds of formula (I).

"Therapeutically effective amount" means an amount of a compound that, when administered to a subject for treating a disease state, is sufficient to effect such treatment for the disease state. The "therapeutically effective amount" will vary depending on the compound, the disease state being treated, the severity of the disease treated, the age and relative health of the subject, the route and form of administration, the judgment of the attending medical or veterinary practitioner, etc.

As used herein the terms "treatment" or "treating" is an approach for obtaining beneficial or desired results including clinical results. Beneficial or desired clinical results can include, but are not limited to, alleviation or amelioration of one or more symptoms or conditions, diminishment of extent of disease, stabilized (i.e., not worsening) state of disease, preventing spread of disease, delay or slowing of disease progression, amelioration or palliation of the disease state, and remission (whether partial or total) whether detectable or undetectable. The term can also mean prolonging survival as compared to expected survival without the treatment.

The term mammal refers to a human or any mammalian animal, e.g. a primate, a farm animal, a pet animal, or a laboratory animal. Examples of such animals are monkeys, cows, sheep, horses, pigs, dogs, cats, rabbits, mice, rats etc. Preferably, the mammal is a human.

The term cancer refers to any malignant growth or tumor caused by abnormal and uncontrolled cell division; it may spread to other parts of the body through the lymphatic system or the blood stream and includes both solid tumors and blood-borne tumors. Exemplary cancers include adrenocortical carcinoma, AIDS-related cancers, AIDS-related lymphoma, anal cancer, anorectal cancer, appendix cancer, childhood cerebellar astrocytoma, childhood cerebral astrocytoma, basal cell carcinoma, biliary cancer, extrahepatic bile duct cancer, intrahepatic bile duct cancer, urinary bladder cancer, bone and joint cancer, osteosarcoma and malignant fibrous histiocytoma, brain tumor, brain stem glioma, cerebellar astrocytoma, cerebral astrocytoma/malignant glioma, ependymoma, medulloblastoma, visual pathway and hypothalamic glioma, breast cancer, bronchial adenomas/carcinoids, nervous system cancer, nervous system lymphoma, central nervous system cancer, central nervous system lymphoma, cervical cancer, childhood cancers, chronic lymphocytic leukemia, chronic myelogenous leukemia, chronic myeloproliferative disorders, colon cancer, colorectal cancer, cutaneous T-cell lymphoma, lymphoid neoplasm, mycosis fungoides, Sezary syndrome, endometrial cancer, esophageal cancer, extracranial germ cell tumor, extragonadal germ cell tumor, eye cancer, retinoblastoma, gallbladder cancer, gastric (stomach) cancer, gastrointestinal carcinoid tumor, gastrointestinal stromal tumor (GIST), germ cell tumor, ovarian germ cell tumor, gestational trophoblastic tumor glioma, head and neck cancer, hepatocellular (liver) cancer, Hodgkin's lymphoma, hypopharyngeal cancer, ocular cancer, Kaposi's sarcoma, renal cancer, laryngeal cancer, acute lymphoblastic leukemia, acute myeloid leukemia, hairy cell leukemia, lip and oral cavity cancer, lung cancer, non-small cell lung cancer, small cell lung cancer, non-Hodgkin's lymphoma, primary central nervous system lymphoma, Waldenstrom's macroglobulinemia, intraocular (eye) melanoma, Merkel cell carcinoma, malignant mesothelioma, metastatic squamous neck cancer, cancer of the tongue, multiple endocrine neoplasia syndrome, myelodysplastic syndromes, myelodysplastic/myeloproliferative diseases, nasopharyngeal cancer, neuroblastoma, oral cancer, oral cavity cancer, oropharyngeal cancer, ovarian cancer, ovarian epithelial cancer, ovarian low malignant potential tumor, pancreatic cancer, islet cell pancreatic cancer, paranasal sinus and nasal cavity cancer, parathyroid cancer, penile cancer, pheochromocytoma, pineoblastoma and supratentorial primitive neuroectodermal tumors, pituitary tumor, plasma cell neoplasm/multiple myeloma, pleuropulmonary blastoma, prostate cancer, rhabdomyosarcoma, salivary gland cancer, Ewing's sarcoma family of tumors, soft tissue sarcoma, uterine cancer, uterine sarcoma, skin cancer (non-melanoma), skin cancer (melanoma), small intestine cancer, squamous cell carcinoma, testicular cancer, throat cancer, thymoma, thymoma and thymic carcinoma, thyroid cancer, transitional cell cancer of the renal pelvis and ureter and other urinary organs, gestational trophoblastic tumor, urethral cancer, vaginal cancer, vulvar cancer, and Wilm's tumor.

The term autoimmune disorder (or autoimmune disease) refers to any disorder arising from an inappropriate immune response of the body against substances and tissues normally present in the body (autoimmunity). Such response may be restricted to certain organs or involve a particular tissue in different places. Exemplary autoimmune disorders are acute disseminated encephalomyelitis (ADEM), Addison's disease, agammaglobulinemia, alopecia areata, amyotrophic lateral sclerosis, ankylosing spondylitis, antiphospholipid syndrome, antisynthetase syndrome, atopic allergy, atopic dermatitis, autoimmune aplastic anemia, autoimmune cardiomyopathy, autoimmune enteropathy, autoimmune hemolytic anemia, autoimmune hepatitis, autoimmune inner ear disease, autoimmune lymphoproliferative syndrome, autoimmune peripheral neuropathy, autoimmune pancreatitis, autoimmune polyendocrine syndrome, autoimmune progesterone dermatitis, autoimmune thrombocytopenic purpura, autoimmune urticarial, autoimmune uveitis, Balo disease/Balo concentric sclerosis, Behcet's disease, Berger's disease, Bickerstaffs encephalitis, Blau syndrome, bullous pemphigoid, Castleman's disease, celiac disease, Chagas disease, chronic inflammatory demyelinating polyneuropathy, chronic recurrent multifocal osteomyelitis, chronic obstructive pulmonary disease, Churg-Strauss syndrome, cicatricial pemphigoid, Cogan syndrome, cold agglutinin disease, complement component 2 deficiency, contact dermatitis, cranial arteritis, CREST syndrome, Crohn's disease (one of two types of idiopathic inflammatory bowel disease "IBD"), Cushing's Syndrome, cutaneous leukocytoclastic angiitis, Dego's disease, Dercum's disease, dermatitis herpetiformis, dermatomyositis, diabetes mellitus type 1, diffuse cutaneous systemic sclerosis, Dressler's syndrome, drug-induced lupus, discoid lupus erythematosus, eczema, endometriosis, enthesitis-related arthritis, eosinophilic fasciitis, eosinophilic gastroenteritis, epidermolysis bullosa acquisita, erythema nodosum, erythroblastosis fetalis, essential mixed cryoglobulinemia, Evan's syndrome, fibrodysplasia ossificans progressive, fibrosing alveolitis (or Idiopathic pulmonary fibrosis), gastritis, gastrointestinal pemphigoid, glomerulonephritis, Goodpasture's syndrome, Graves' disease, Guillain-Barré syndrome (GBS), Hashimoto's encephalopathy, Hashimoto's thyroiditis, Henoch-Schonlein purpura, herpes gestationis (aka gestational pemphigoid), Hidradenitis suppurativa, Hughes-Stovin syndrome, hypogammaglobulinemia, idiopathic inflammatory demyelinating diseases, idiopathic pulmonary fibrosis, idiopathic thrombocytopenic purpura, IgA nephropathy, inclusion body myositis, chronic inflammatory demyelinating polyneuropathy, interstitial cystitis, juvenile idiopathic arthritis (aka juvenile rheumatoid arthritis), Kawasaki's disease, Lambert-Eaton myasthenic syndrome, leukocytoclastic vasculitis, lichen planus, lichen sclerosus, linear IgA disease (LAD), lupoid hepatitis (aka autoimmune hepatitis), lupus erythematosus, Majeed syndrome, Ménière's disease, microscopic polyangiitis, mixed connective tissue disease, morphea, Mucha-Habermann disease (aka pityriasis lichenoides et varioliformis acuta), multiple sclerosis, myasthenia gravis, myositis, narcolepsy, neuromyelitis optica (also Devic's disease), neuromyotonia, occular cicatricial pemphigoid, opsoclonus myoclonus syndrome, Ord's thyroiditis, palindromic rheumatism, PANDAS (pediatric autoimmune neuropsychiatric disorders associated with streptococcus), paraneoplastic cerebellar degeneration, paroxysmal nocturnal hemoglobinuria (PNH), Parry Romberg syndrome, Parsonage-Turner syndrome, pars planitis, pemphigus vulgaris, pernicious anaemia, perivenous encephalomyelitis, POEMS syndrome, polyarteritis nodosa, polymyalgia rheumatic, polymyositis, primary biliary cirrhosis, primary sclerosing cholangitis, progressive inflammatory neuropathy, psoriasis, psoriatic arthritis, pyoderma gangrenosum, pure red cell aplasia, Rasmussen's encephalitis, Raynaud phenomenon, relapsing polychondritis, Reiter's syndrome, restless leg syndrome, retroperitoneal fibrosis, rheumatoid arthritis, rheumatic fever, sarcoidosis, schizophrenia, Schmidt syndrome another form of APS, Schnitzler syndrome, Scleritis, Scleroderma, Serum Sickness, Sjögren's syndrome, spondyloarthropathy, stiff person syndrome, subacute bacterial endocarditis (SBE), Susac's syndrome, Sweet's syndrome, sympathetic ophthalmia, systemic lupus erythematosus, Takayasu's arteritis, temporal arteritis (also known as "giant cell arteritis"), thrombocytopenia, Tolosa-Hunt syndrome, transverse myelitis, ulcerative colitis (one of two types of idiopathic inflammatory bowel disease "IBD"), undifferentiated connective tissue disease different from mixed connective tissue disease, undifferentiated spondyloarthropathy, urticarial vasculitis, vasculitis, vitiligo, and Wegener's granulomatosis.

The term inflammatory disorder (or inflammatory disease) refers to a pathological state associated with inflammation, typically caused by leukocyte infiltration. The inflammatory disorder may be acute or chronic. Exemplary inflammatory disorders include inflammatory skin diseases, including, without limitation, psoriasis and atopic dermatitis, systemic scleroderma and sclerosis, responses associated with inflammatory bowel disease (IBD) (such as Crohn's disease and ulcerative colitis), ischemic reperfusion disorders including surgical tissue reperfusion injury, myocardial ischemic conditions such as myocardial infarction, cardiac arrest, reperfusion after cardiac surgery and constriction after percutaneous transluminal coronary angioplasty, stroke, and abdominal aortic aneurysms, cerebral edema secondary to stroke, cranial trauma, hypovolemic shock, asphyxia, adult respiratory distress syndrome, acute-lung injury, Behcet's Disease, dermatomyositis; polymyositis; multiple sclerosis (MS); dermatitis; meningitis; encephalitis; uveitis, osteoarthritis, lupus nephritis, autoimmune diseases such as rheumatoid arthritis (RA), Sjorgen's syndrome, vasculitis, diseases involving leukocyte diapedesis, central nervous system (CNS) inflammatory disorder, multiple organ injury syndrome secondary to septicemia or trauma, alcoholic hepatitis, bacterial pneumonia, antigen-antibody complex mediated diseases including glomerulonephritis, sepsis, sarcoidosis, immunopathologic responses to tissue or organ transplantation, inflammations of the lung, including pleurisy, alveolitis, vasculitis, pneumonia, chronic bronchitis, bronchiectasis, diffuse panbronchiolitis, hypersensitivity pneumonitis, idiopathic pulmonary fibrosis (IPF), and cystic fibrosis, etc.

The term neurogenerative disorder (or neurogenerative disease) refers to disorders associated with a progressive loss of structure or function of neurons affecting the structure or function of the brain, spinal cord or peripheral nervous system. Exemplary neurodegenerative disorders include mitochondrial encephalomyopathies and gut dysmotility syndromes, ataxia syndromes including Friedreich's ataxia and spinocerebellar ataxia (SCA), spinal cord injury, familial and sporadic amyotrophic lateral sclerosis (FALS and ALS, respectively), familial and sporadic Parkinson's disease, familial and sporadic Alzheimer's disease, Huntington's disease, olivopontocerebellar atrophy, multiple system atrophy, progressive supranuclear palsy, diffuse lewy body disease and synucleinopathies, Down Syndrome, corticodentatonigral degeneration, progressive familial myoclonic epilepsy, strionigral degeneration, torsion dystonia, familial tremor, Gilles de la Tourette syndrome, and Hallervorden-Spatz disease.

The term excipient refers to pharmaceutically acceptable chemicals, such as known to those of ordinary skill in the art of pharmacy to aid the administration of the medicinal agent. It a compound that is useful in preparing a pharmaceutical composition, generally safe, non-toxic and neither biologically nor otherwise undesirable, and includes excipients that are acceptable for veterinary use as well as human pharmaceutical use.

Exemplary excipients include binders, surfactants, diluents, disintegrants, antiadherents, and lubricants.

According to a first aspect, a compound of formula (I)

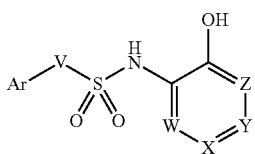

is provided, as defined herein above.
In some embodiments, in a compound of formula (I),
W is N or CH;
X is N or $CR_1$;
Y is N or $CR_2$;
Z is N or $CR_3$;
at least one and at most two of W, X, Y and Z are N;
$R_1$ is H or halogen;
$R_2$ is H, halogen, cyano, C(O)OH, C(O)OC1-C3 alkyl, C1-C3 alkyl, hydroxy-C1-C3 alkyl, or $S(O)_2$C1-C3 alkyl;
$R_3$ is H or halogen;
V is $(CHR_4)_m$;
m is 0 or 1;
$R_4$ is H or methyl;
Ar is

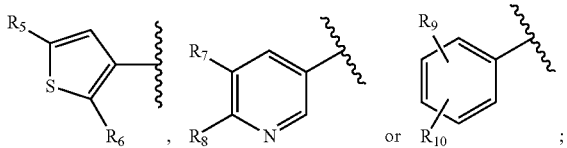

$R_5$ is H or halogen;
$R_6$ is H or halogen;
$R_7$ is H, halogen, C1-C3 alkyl, or phenyl;
$R_8$ is H, halogen, C1-C3 alkyl optionally substituted with one or more F; C1-C3 alkoxy optionally substituted with one or more F, phenoxy, $NHR_{11}$, or $NR_{11}R_{12}$;
$R_9$ is H, halogen, cyano, C1-C3 alkyl optionally substituted with one or more F, C1-C3 alkoxy optionally substituted with one or more F, or $C(O)NR_{13}R_{14}$;
$R_{10}$ is H, halogen, cyano, C1-C3 alkyl optionally substituted with one or more F, C1-C3 alkoxy optionally substituted with one or more F, or $C(O)NR_{13}R_{14}$;
$R_{11}$ is C1-C3 alkyl;
$R_{12}$ is C1-C3 alkyl; or
$R_{11}$ and $R_{12}$, together with the nitrogen atom to which they are both attached, form a ring of formula

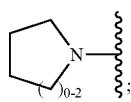

$R_{13}$ is H or C1-C3 alkyl; and
$R_{14}$ is H or C1-C3 alkyl.
In a compound of formula (I), W is N or CH; X is N or $CR_1$; Y is N or $CR_2$; and Z is N or $CR_3$; and at least one and at most two of W, X, Y and Z are N.
In a compound formula (I), $R_1$ is H, halogen, e.g. Cl or Br; $S(O)_2$C1-C3 alkyl, e.g. $CH_3S(O)_2$; cyano, or C1-C3 alkyl, e.g. methyl, optionally substituted with one or more F, such as $CF_3$; $R_2$ is H, halogen, cyano, C(O)OH, C(O)OC1-C3 alkyl, C1-C3 alkyl optionally substituted with one or more F, hydroxy-C1-C3 alkyl, $S(O)_2$C1-C3 alkyl, $S(O)_2$C3-C6 cycloalkyl or $S(O)_2$C1-C3 hydroxyalkyl; and $R_3$ is H, halogen or cyano.

In some embodiments, $R_1$ is H or halogen, e.g. H or Cl; $R_2$ is H, halogen, e.g. Cl or Br; cyano; C(O)OH; C(O)OC1-C3 alkyl, e.g. $C(O)OCH_3$; C1-C3 alkyl, e.g. $CH(CH_3)_2$; hydroxy-C1-C3 alkyl, e.g. $CH(CH_3)CH_2OH$; or $S(O)_2$C1-C3 alkyl, e.g. $SO_2CH_3$; and $R_3$ is H or halogen, e.g. H, Cl or Br, e.g. Cl or Br.

In some embodiments, the moiety $R_1$ is H, halogen, e.g. Cl or Br, e.g. Cl; $S(O)_2$C1-C3 alkyl, e.g. $CH_3S(O)_2$; cyano, or C1-C3 alkyl, e.g. methyl, optionally substituted with one or more F, e.g. $CF_3$.

In some embodiments, $R_1$ is H or halogen, e.g. H, Cl, or Br, in particular H or Cl. In some embodiments, $R_1$ is halogen, e.g. $R_1$ is Cl or Br, in particular Cl. In some other embodiments, $R_1$ is H.

In some embodiments, $R_1$ is selected from H, Cl, Br, $CH_3S(O)_2$, cyano and $CF_3$.

The moiety $R_2$ is H, halogen, cyano, C(O)OH, C(O)OC1-C3 alkyl, C1-C3 alkyl optionally substituted with one or more F, hydroxy-C1-C3 alkyl, $S(O)_2$C1-C3 alkyl, $S(O)_2$C3-C6 cycloalkyl or $S(O)_2$C1-C3 hydroxyalkyl.

When $R_2$ is halogen, it e.g. may be Cl, Br or I, in particular Cl or Br, more particularly Cl.

When $R_2$ is C(O)OC1-C3 alkyl, it e.g. may be C(O)OC1-C2 alkyl, e.g. $C(O)OCH_3$.

When $R_2$ is C1-C3 alkyl optionally substituted with one or more F, it e.g. may be $CF_3$.

When $R_2$ is hydroxy-C1-C3 alkyl, it e.g. may be $CH(CH_3)CH_2OH$.

When $R_2$ is $S(O)_2$C1-C3 alkyl, it e.g. may be $CH_3S(O)_2$, $CH_3CH_2S(O)_2$, $(CH_3)_2CHS(O)_2$ or $CH_3CH_2CH_2SO_2$.

When $R_2$ is $S(O)_2$C3-C6 cycloalkyl, it e.g. may be $S(O)_2$C4-C6 cycloalkyl, or $S(O)_2$C4-C5 cycloalkyl, e.g. cyclopentanesulfonyl.

When $R_2$ is $S(O)_2$C1-C3 hydroxyalkyl, it e.g. may be $OHCH_2CH_2CH_2S(O)_2$ (3-hydroxypropanesulfonyl).

In some embodiments, $R_2$ is H, halogen, C(O)OH, C(O)OC1-C3 alkyl, C1-C3 alkyl optionally substituted with one or more F, hydroxy-C1-C3 alkyl, $S(O)_2$C1-C3 alkyl, $S(O)_2$C3-C6 cycloalkyl or $S(O)_2$C1-C3 hydroxyalkyl.

In some embodiments, $R_2$ is H, halogen, C(O)OH, C(O)OC1-C3 alkyl, C1-C3 alkyl optionally substituted with one or more F, $S(O)_2$C1-C3 alkyl, $S(O)_2$C3-C6 cycloalkyl or $S(O)_2$C1-C3 hydroxyalkyl.

In some embodiments, $R_2$ is H, halogen, C(O)OC1-C3 alkyl, C1-C3 alkyl optionally substituted with one or more F, $S(O)_2$C1-C3 alkyl, $S(O)_2$C3-C6 cycloalkyl or $S(O)_2$C1-C3 hydroxyalkyl.

In some embodiments, $R_2$ is H, Cl, Br, I, cyano, C(O)OH, $C(O)OCH_3$, $CH(CH_3)_2$, CF3, $(CH_2OH)(CH_3)CH$—), $CH_3S(O)_2$, $CH_3CH_2S(O)_2$, $(CH_3)_2CHS(O)_2$, $CH_3CH_2CH_2S(O)_2$, cyclopentanesulfonyl, or $CH_2(OH)CH_2CH_2S(O)_2$.

In some embodiments, $R_2$ is H, halogen, cyano, C(O)OH, C(O)OC1-C3 alkyl, C1-C3 alkyl, hydroxy-C1-C3 alkyl, or $S(O)_2$C1-C3 alkyl. For example, $R_2$ may be selected from H, Cl, Br, cyano, COOH, $COOCH_3$, $CH_3$, $CH_3CH_2$, $CH(CH_3)_2$, $CH(CH_3)CH_2OH$, and $SO_2CH_3$.

In some embodiments, $R_2$ is H, halogen, cyano, C(O)OH, C(O)OC1-C3 alkyl, C1-C3 alkyl, hydroxy-C1-C3 alkyl, or $S(O)_2$C1-C3 alkyl. For example, $R_2$ may be selected from H, Cl, Br, cyano, COOH, $COOCH_3$, $CH_3$, $CH_3CH_2$, $CH(CH_3)_2$, $CH(CH_3)CH_2OH$, and $SO_2CH_3$.

In some embodiments, $R_2$ is selected from H, halogen, $C(O)OC1$-$C3$ alkyl, $C1$-$C3$ alkyl, hydroxy-$C1$-$C3$ alkyl, and $S(O)_2C1$-$C3$ alkyl. For example, $R_2$ may be selected from H, Cl, Br, $C(O)OCH_3$, $CH_3$, $CH_3CH_2$, $(CH_3)_2CH$, $CH(CH_3)CH_2OH$, and $SO_2CH_3$.

In some embodiments, $R_2$ is H, halogen, cyano, $C(O)OH$, $C(O)OC1$-$C3$ alkyl, hydroxy-$C1$-$C3$ alkyl, or $S(O)_2C1$-$C3$ alkyl, e.g. H, halogen, hydroxy-$C1$-$C3$ alkyl, or $S(O)_2C1$-$C3$ alkyl. For example, $R_2$ may be selected from H, Cl, Br, cyano, $C(O)OH$, $COOCH_3$, $CH(CH_3)CH_2OH$, and $SO_2CH_3$.

In some embodiments, $R_2$ is H, halogen, cyano, $S(O)_2C1$-$C3$ alkyl, $S(O)_2C3$-$C6$ cycloalkyl or $S(O)_2C1$-$C3$ hydroxyalkyl, e.g. $R_2$ is H, halogen, cyano or $S(O)_2C1$-$C3$ alkyl; e.g. H, halogen, or $S(O)_2C1$-$C3$ alkyl; or $S(O)_2C1$-$C3$ alkyl.

In some embodiments, $R_2$ is H, halogen, or $S(O)_2C1$-$C3$ alkyl, $S(O)_2C3$-$C6$ cycloalkyl or $S(O)_2C1$-$C3$ hydroxyalkyl, e.g. $R_2$ is H, $S(O)_2C1$-$C3$ alkyl, $S(O)_2C3$-$C6$ cycloalkyl or $S(O)_2C1$-$C3$ hydroxyalkyl.

In some embodiments, $R_2$ is H, cyano, $S(O)_2C1$-$C3$ alkyl, $S(O)_2C3$-$C6$ cycloalkyl or $S(O)_2C1$-$C3$ hydroxyalkyl, e.g. $R_2$ is H, cyano, or $S(O)_2C1$-$C3$ alkyl.

In some embodiments, $R_2$ is H or halogen or cyano, e.g. H or cyano.

In some embodiments, $R_2$ is H or halogen, e.g. $R_2$ is H, Cl or Br; or $R_2$ is H or Cl.

In some embodiments, $R_2$ is as defined herein, but $R_2$ is not H.

The moiety $R_3$ is H, halogen or cyano. In some embodiments, $R_3$ is H or halogen, e.g. H, Cl or Br, in particular H or Cl. In some embodiments, $R_3$ is H. In some other embodiments, $R_3$ is halogen, e.g. Cl or Br, in particular Cl.

In some embodiments, $R_1$ is H, $R_2$ is as defined herein, and $R_3$ is H.

In some embodiments, $R_1$, $R_2$ and $R_3$ are as defined herein, but at least one of $R_1$, $R_2$ and $R_3$ is not H. In some other embodiments, $R_1$, $R_2$ and $R_3$ are as defined herein, but at least one of $R_1$, $R_2$ and $R_3$ is H. In some other embodiments, $R_1$, $R_2$ and $R_3$ are as defined herein, but at least two of $R_1$, $R_2$ and $R_3$ are H. In some other embodiments, $R_1$, $R_2$ and $R_3$ are all H.

In some embodiments, W is N or CH; X is N or CH; Y is N or $CR_2$; and Z is N or CH; at least one and at most two of W, X, Y and Z are N; and $R_2$ is as defined herein.

In formula (I), at least one and at most two of W, X, Y and Z are N. In some embodiments, W is N; X is N or $CR_1$; Y is N or $CR_2$; and Z is N or $CR_3$, and at most one of X, Y and Z is N, and the compound may then be represented by formula (Ia)

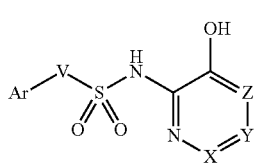
(Ia)

wherein Ar, V, X, Y and Z are as defined herein.

In some particular embodiments, W is N, Y is $CR_2$, and Z is CH; and the compound may then be represented by formula (Ia-1)

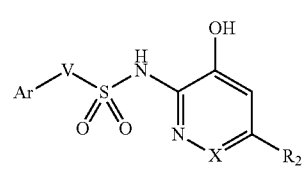
(Ia-1)

wherein Ar and V are as defined herein, X is N or $CR_1$, and $R_2$ is as defined herein, e.g. $R_2$ is halogen, cyano or $S(O)_2C1$-$C3$ alkyl, in particular $R_2$ is halogen or $S(O)_2C1$-$C3$ alkyl.

In some other embodiments, W is N or CH; X is N; Y is N or $CR_2$; and Z is N or $CR_3$, and at most one of W, Y and Z is N, and the compound may then be represented by formula (Ib)

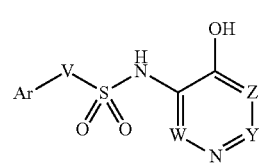
(Ib)

wherein Ar, V, W, Y and Z are as defined herein.

In still other embodiments, W is N or CH; X is N or $CR_1$; Y is N; and Z is N or $CR_3$, and at most one of W, X and Z is N, and the compound may then be represented by formula (Ic)

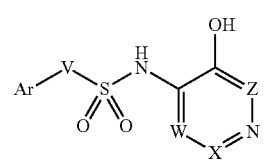
(Ic)

wherein Ar, V, W, X and Z are as defined herein.

In other embodiments, W is N or CH; X is N or $CR_1$; Y is N or $CR_2$; and Z is N, and at most one of W, X and Y is N, and the compound may then be represented by formula (Id)

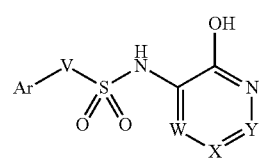
(Id)

wherein Ar, V, W, X and Y are as defined herein.

In some particular embodiments, W is CH or N, X is CH, Y is $CR_2$, and Z is N, and the compound may then be represented by formula (Id-1)

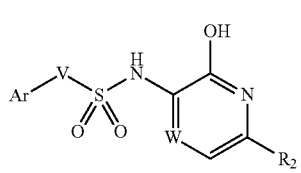
(Id-1)

wherein Ar, V, and $R_2$ are as defined herein, e.g $R_2$ is cyano, halogen or $S(O)_2C1-C3$ alkyl, e.g. $R_2$ is halogen or $S(O)_2C1-C3$ alkyl, In some other particular embodiments, W is CH, X is CH, Y is $CR_2$, and Z is N, and the compound may then be represented by formula (Id-2)

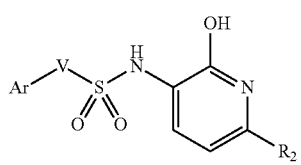
(Id-2)

wherein Ar, V, and $R_2$ are as defined herein, e.g $R_2$ is cyano, halogen or $S(O)_2C1-C3$ alkyl, e.g. $R_2$ is halogen or $S(O)_2C1-C3$ alkyl, In some other particular embodiments, W is CH, X is $CR_1$, Y is CH, and Z is N, and the compound may then be represented by formula (Id-3)

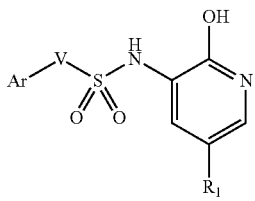
(Id-3)

wherein Ar, V, and $R_1$ are as defined herein, e.g $R_1$ is halogen.

In some embodiments, only one of W, X, Y and Z is N. For example, W is N; X is $CR_1$; Y is $CR_2$; and Z is $CR_3$, and the compound may then be represented by formula (Ie)

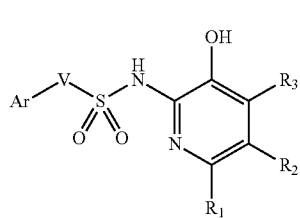
(Ie)

wherein Ar, V, $R_1$, $R_2$ and $R_3$ are as defined herein.

In some particular embodiments, W is N; X is CH; Y is $CR_2$; and Z is CH, and the compound may then be represented by formula (Ie-1)

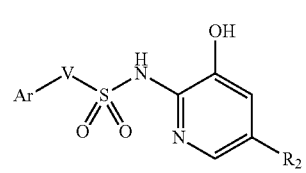
(Ie-1)

wherein Ar, V, $R_1$, $R_2$ and $R_3$ are as defined herein, e.g. $R_2$ is $S(O)_2C1-C3$ alkyl, In some other embodiments, when only one of W, X, Y and Z is N, X is N, W is CH, Y is $CR_2$, and Z is $CR_3$, and the compound may then be represented by formula (If)

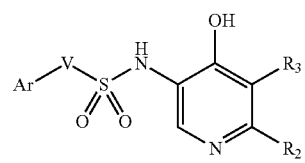
(If)

wherein Ar, V, $R_2$ and $R_3$ are as defined herein.

In some particular embodiments, X is N, W and Y are both CH, and Z is $CR_3$, and the compound may then be represented by formula (If-1)

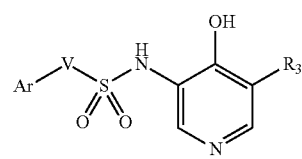
(If-1)

wherein Ar, V and $R_3$ are as defined herein, e.g. $R_3$ is halogen.

In some other particular embodiments, X is N, and W, Y and Z are all CH, and the compound may then be represented by formula (If-2)

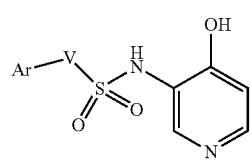
(If-2)

wherein Ar and V are as defined herein.

In other embodiments, when only one of W, X, Y and Z is N, W is CH, X is $CR_1$, Y is $CR_2$ and Z is N.

In some embodiments according to formulas (Ia), (Ib), and (Id) Y is $CR_2$, wherein $R_2$ is as defined herein.

In some embodiments, in a compound of formula (Ia), X is CH, Y is $CR_2$, and Z is CH;

the compound may then be represented by formula (Ig)

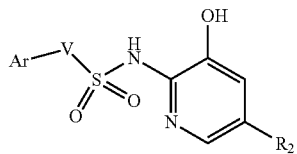
(Ig)

wherein Ar, V, and R$_2$ are as defined herein.

In some embodiments, two of W, X, Y and Z are N, e.g. W and X or W and Z are N. In some embodiments, the two N are adjacent, e.g. W and X are N. In some other embodiments, the two N are non-adjacent e.g. W and Z are N, or Z and X are N.

Thus, in some embodiments, W and X are N, and the compound of the invention may be represented by formula (Ih)

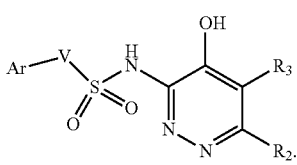
(Ih)

wherein Ar, V, R$_2$ and R$_3$ are as defined herein.

In some particular embodiments, W and X are N, Y is CR$_2$, and Z is CH, and the compound of the invention may be represented by formula (Ih-1)

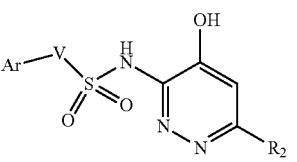
(Ih-1)

wherein Ar, V, and R$_2$ are as defined herein, e.g. R$_2$ is halogen or S(O)$_2$C1-C3 alkyl.

In some other embodiments, W and Z are N, and the compound of the invention may be represented by formula (Ij)

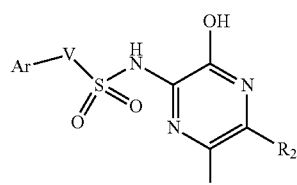
(Ij)

wherein Ar, V, R$_1$ and R$_2$ are as defined herein.

In some particular embodiments, W is N, X is CH, Y is CR$_2$ and Z is N, and the compound of the invention may be represented by formula (Ij-1)

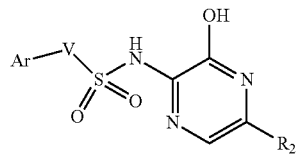
(Ij-1)

wherein Ar, V, R$_2$ are as defined herein, e.g. R$_2$ is halogen, S(O)$_2$C1-C3 alkyl or cyano.

In still other embodiments, W and Y are N, and the compound of the invention may be represented by formula (Ik)

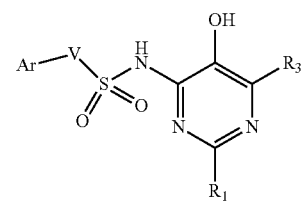
(Ik)

wherein Ar, V, R$_1$ and R$_3$ are as defined herein.

In still other embodiments, X and Z are N, and the compound of the invention may be represented by formula (Im)

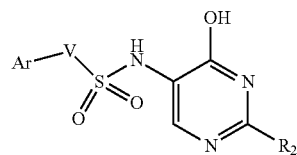
(Im)

wherein Ar, V and R$_2$ are as defined herein.

In some particular embodiments, the moiety

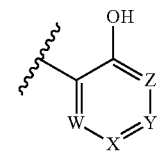

is selected from:

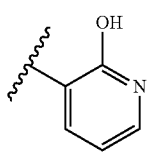 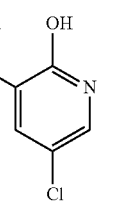 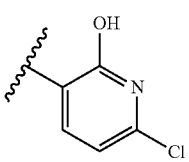

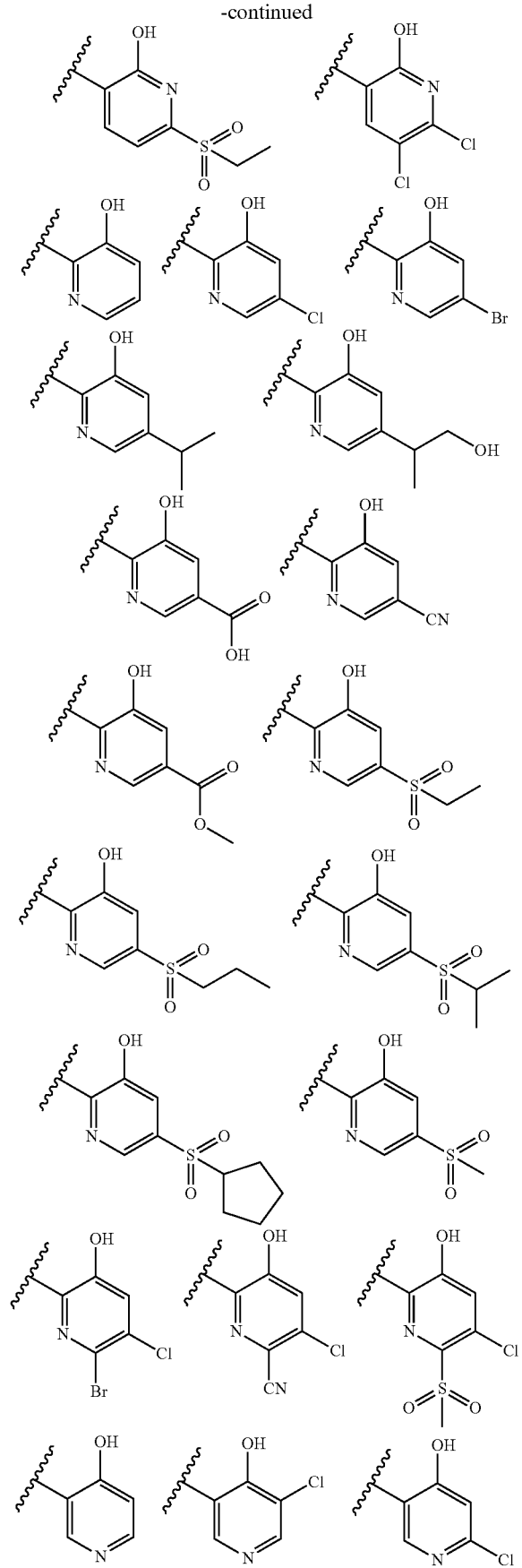
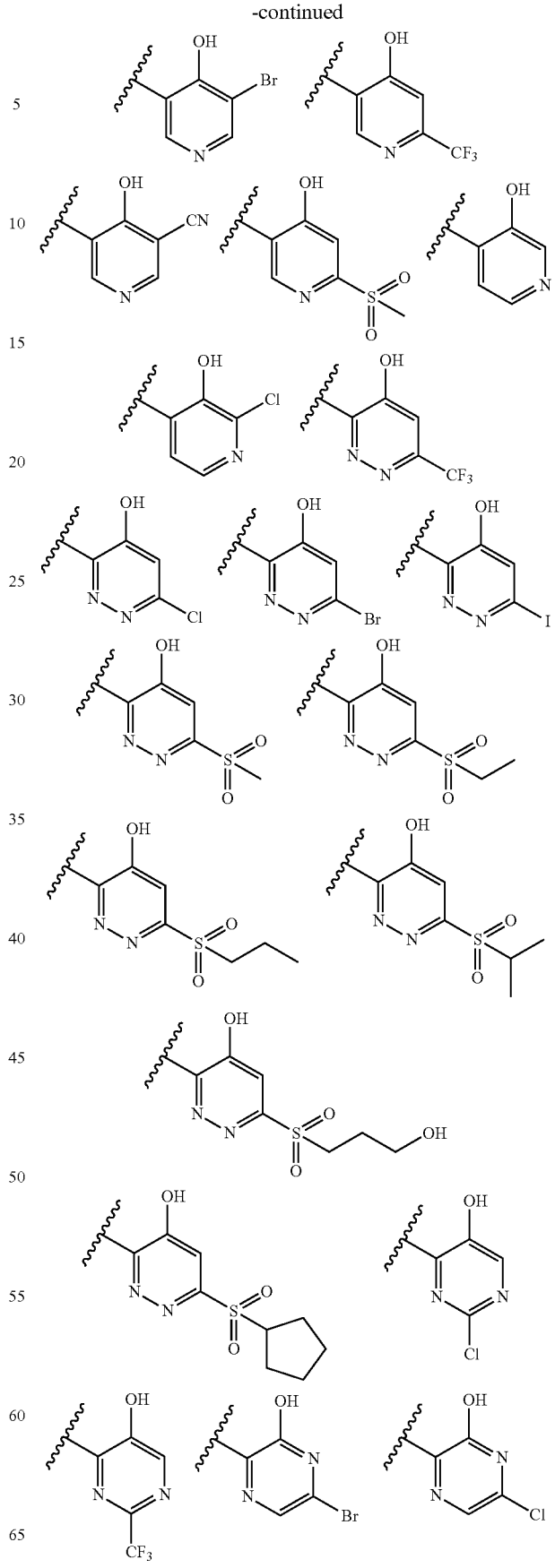

-continued

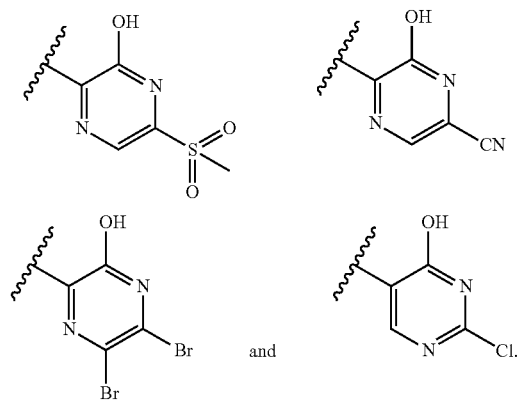

and

In a compound of formula (I) as defined herein, V is $(CHR_4)_m$, wherein m is 0 or 1, and $R_4$ is H or C1-C3 alkyl optionally substituted with one or more F. In some embodiments, $R_4$ is H or methyl, optionally substituted with one or more F, e.g $R_4$ is H or $CF_3$, or $R_4$ is H.

In some embodiments, m is 0, i.e. the compound may be represented by formula (In)

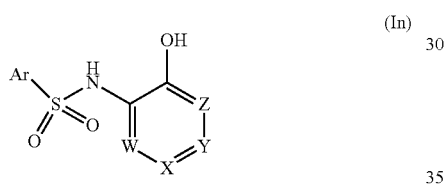

wherein Ar, W, X, Y and Z are as defined herein.

In some other embodiments, m is 1, i.e. the compound may be represented by formula (Io)

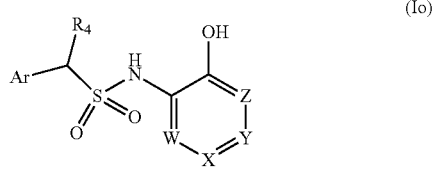

wherein Ar, $R_4$, W, X, Y and Z are as defined herein.

The moiety $R_4$ is H or C1-C3 alkyl optionally substituted with one or more F. In some embodiments $R_4$ is H or $CH_3$. In some embodiments, $R_4$ is H, and a compound of formula (Io) may then be represented by formula (Ip)

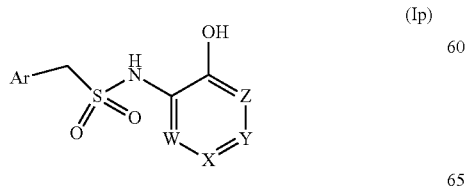

wherein Ar, W, X, Y and Z are as defined herein.

In formula (I), the moiety Ar is

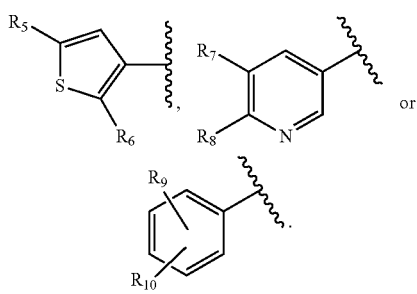

In some embodiments, Ar is

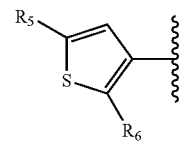

and the compound of formula (I) may then be represented by formula (Iq)

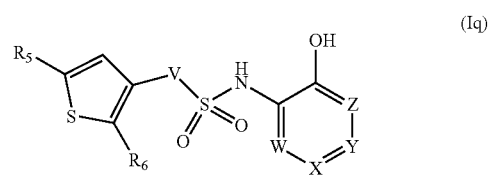

wherein $R_5$, $R_6$, V, W, X, Y and Z are as defined herein.

In a compound of formula (Iq), $R_5$ is H, halogen or cyano, e.g. $R_5$ is H or halogen, and $R_6$ is H or halogen. In some embodiments, $R_5$ is halogen or cyano and $R_6$ is H or halogen. In some embodiments, at least one of $R_5$ and $R_6$ is halogen. In some embodiments, both $R_5$ and $R_6$ are halogen, e.g. both $R_5$ and $R_6$ are Cl. In some embodiments, $R_5$ is cyano and $R_6$ is H or halogen, in particular H.

In some embodiments, in a compound of formula (Iq), the moiety

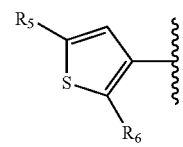

is 2,5-dichlorothiophen-3-yl or 5-cyanothiophen-3-yl.

In some embodiments, Ar is

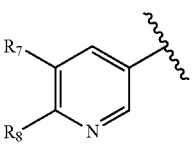

and the compound of formula (I) may then be represented by formula (Ir)

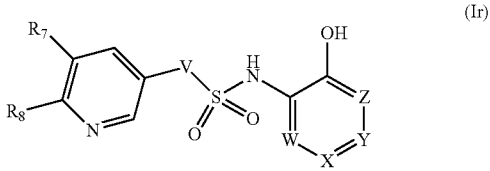

wherein $R_7$, $R_8$, V, W, X, Y and Z are as defined herein.

In a compound of formula (Ir), $R_7$ is H, halogen, C1-C3 alkyl, cyano, $S(O)_2$C1-C3 alkyl, or phenyl, e.g. H, halogen, C1-C3 alkyl or phenyl; and $R_8$ is H, halogen, C1-C3 alkyl optionally substituted with one or more F, C1-C3 alkoxy optionally substituted with one or more F, phenoxy, $NHR_{11}$, or $NR_{11}R_{12}$. For example, in some embodiments, $R_7$ is H, Cl, Br or $CH_3SO_2$; and $R_8$ is H, Cl, $CH_3$, $CF_3$, $CH_3O$, $CH_3CH_2O$, $(CH_3)_2CHO$, phenoxy, $((CH_3)_2CH)NH$, $(CH_3)_2N$, azetidin-1-yl, pyrrolidin-1-yl or piperidin-1-yl.

In some embodiments, $R_7$ is H, halogen, C1-C3 alkyl, cyano or $S(O)_2$C1-C3 alkyl; e.g. H, halogen, C1-C3 alkyl, or $S(O)_2$C1-C3 alkyl; or H, halogen, or $S(O)_2$C1-C3 alkyl.

When $R_7$ is halogen, it e.g. is Cl or Br, in particular Br.

When $R_7$ is $S(O)_2$C1-C3 alkyl, it e.g. is $CH_3S(O)_2$.

For example, in some embodiments, $R_7$ is H, halogen, methyl, phenyl or $S(O)_2$C1-C3 alkyl; e.g. H, halogen or $S(O)_2$C1-C3 alkyl; in particular H or halogen; and $R_8$ is H, halogen, methyl, ethyl, isopropyl, trifluoromethyl, methoxy, trifluoromethoxy, phenoxy, $NHR_{11}$, or $NR_{11}R_{12}$.

In some embodiments, $R_7$ is H or halogen, e.g. H, Cl or Br, in particular H or Br.

In some embodiments, $R_7$ is as defined herein, but $R_7$ is not H. In some other embodiments, $R_7$ is H.

The moiety $R_8$ is H, halogen, C1-C3 alkyl, optionally substituted with one or more F; C1-C3 alkoxy optionally substituted with one or more F; phenoxy, $NHR_{11}$, or $NR_{11}R_{12}$.

When $R_8$ is halogen, it e.g. may be Cl.

When $R_5$ is C1-C3 alkyl, optionally substituted with one or more F; it e.g. may be $CH_3$ or $CF_3$, in particular it may be $CF_3$.

When $R_5$ is C1-C3 alkoxy optionally substituted with one or more F; it e.g. may be $CH_3O$, $CH_3CH_2O$ or $(CH_3)_2CHO$, in particular $CH_3O$.

When $R_5$ is $NHR_{11}$, it e.g. may be $((CH_3)_2CH)NH$.

When $R_8$ is $NR_{11}R_{12}$, it e.g. may be $(CH_3)_2N$ or

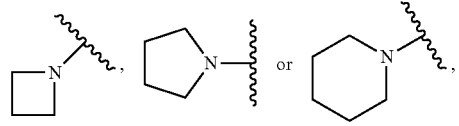

in particular

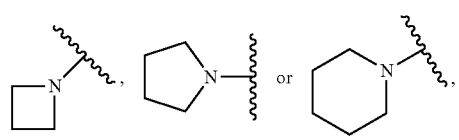 [SMILES: *N1CCC1 ; *N1CCCC1 ; *N1CCCCC1]

e.g.

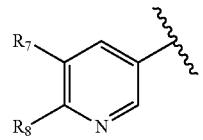

In some embodiments, $R_8$ is H, halogen, C1-C3 alkyl optionally substituted with one or more F; C1-C3 alkoxy optionally substituted with one or more F; $NHR_{11}$ or $NR_{11}R_{12}$; e.g. $R_8$ is H, Cl, methoxy, trifluoromethyl, $NHR_{11}$, or $NR_{11}R_{12}$.

For example, $R_7$ is H or Br; and $R_8$ is H, Cl, methoxy, trifluoromethyl, $NH(CH(CH_3)_2)$ or pyrrolidin-1-yl.

In $NR_{11}R_{12}$, the moieties $R_{11}$ and $R_{12}$ are independently selected from C1-C3 alkyl, e.g. both are methyl; or $R_{11}$ and $R_{12}$, together with the nitrogen atom to which they are both attached, form a ring of formula

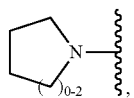

i.e. a ring selected from

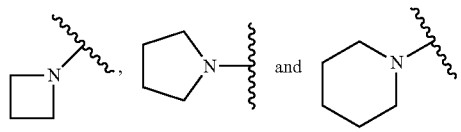

In some embodiments, when $NR_{11}R_{12}$ form a ring, the ring is 4- or 5-membered, i.e. it is azetidin-1-yl or pyrrolidin-1-yl. In some other embodiments, the when $NR_{11}R_{12}$ form a ring, the ring is 5- or 6-membered, i.e. it is pyrrolidin-1-yl or piperidin-1-yl, in particular pyrrolidin-1-yl.

In some embodiments, the moiety

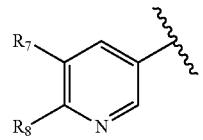

is selected from:

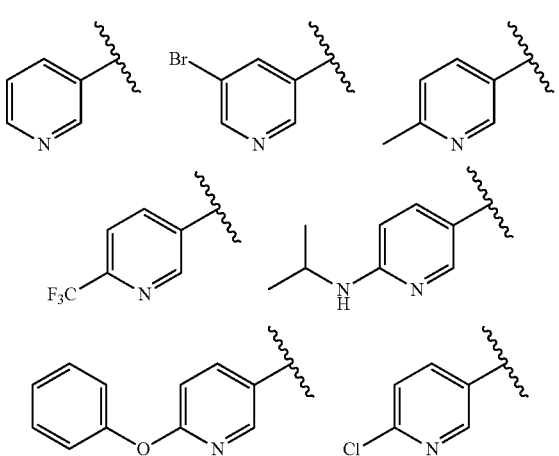

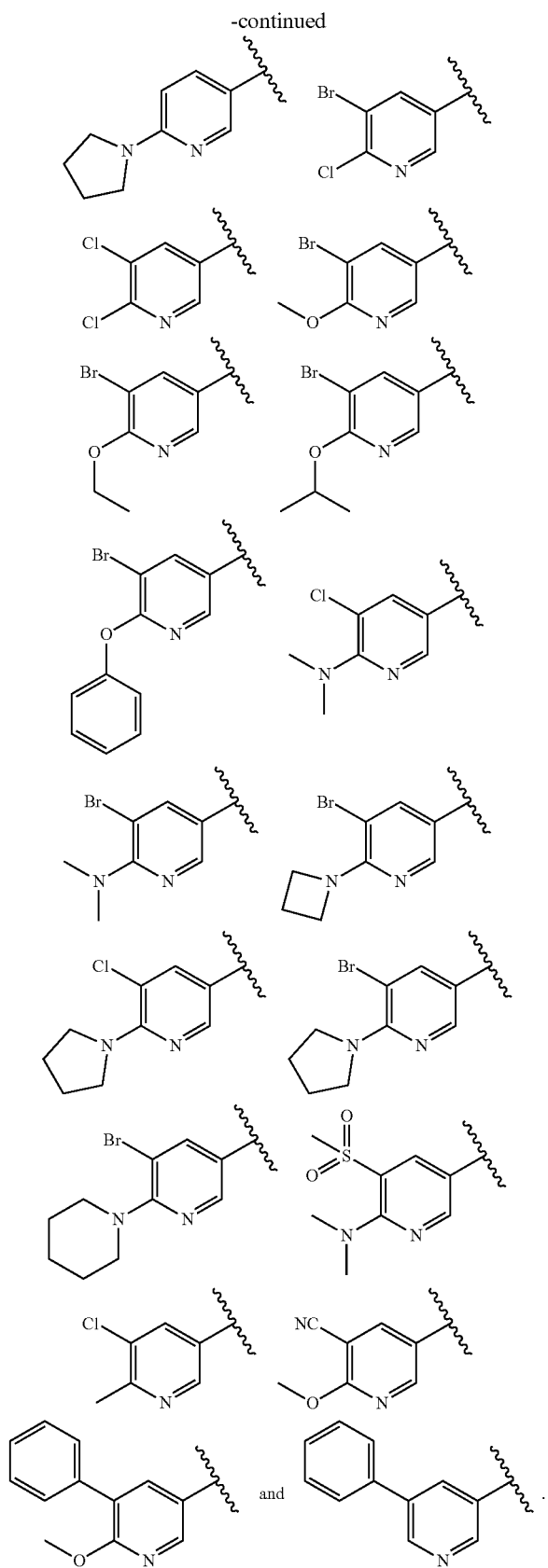
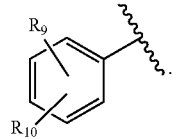

and the compound of formula (I) may then be represented by formula (Is)

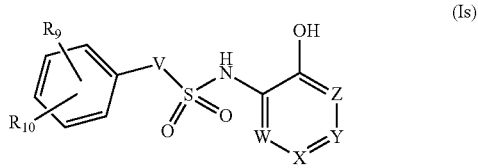

wherein $R_9$, $R_{10}$, V, W, X, Y and Z are as defined herein.

In a compound of formula (Is), $R_9$ and $R_{10}$ are independently selected from H, halogen, cyano, C1-C3 alkyl optionally substituted with one or more F; C1-C3 alkylthio optionally substituted with one or more F; C1-C3 alkoxy optionally substituted with one or more F; and C(O)NR$_{13}$R$_{14}$. For example, $R_9$ and $R_{10}$ may be independently selected from H, F, Cl, Br, CN, $CH_3$, $C_3H_7$ (e.g. $CH_3CH_2CH_2$), $CF_3$, $CH_3CH_2S$, $CH_3O$, $CF_3O$, $C(O)NH_2$, and $C(O)N(CH_2CH_3)_2$.

In some embodiments, $R_9$ and $R_{10}$ are independently selected from H, F, Cl, Br, CN, $CF_3$, $CF_3O$, and $C(O)NH_2$.

In some embodiments, $R_9$ and $R_{10}$ are independently selected from H, halogen, cyano, C1-C3 alkoxy optionally substituted with one or more F; and C(O)NR$_{13}$R$_{14}$.

In some embodiments, one of $R_9$ and $R_{10}$, is selected from H and halogen, e.g. from H, F, Cl and Br; or from H, F and Cl, e.g. H and Cl. In other embodiments, both $R_9$ and $R_{10}$ are selected from H and halogen, e.g. from H, F, Cl and Br; or from H, F and Cl, e.g. H and Cl. For example, both $R_9$ and $R_{10}$ are halogen, e.g. F, Cl or Br, such as F or Cl, in particular Cl.

In some embodiments, one of $R_9$ and $R_{10}$ is halogen and the other one is selected from H, halogen, cyano, C1-C3 alkyl optionally substituted with one or more F; C1-C3 alkylthio optionally substituted with one or more F; C1-C3 alkoxy optionally substituted with one or more F; and C(O)NR$_{13}$R$_{14}$. For example, one of $R_9$ and $R_{10}$ is halogen and the other one is a moiety as defined herein, i.e. selected from H, halogen, cyano, C1-C3 alkyl optionally substituted with one or more F; C1-C3 alkylthio optionally substituted with one or more F; C1-C3 alkoxy optionally substituted with one or more F; and C(O)NR$_{13}$R$_{14}$; such as from F, Cl, Br, CN, $CH_3$, $C_3H_7$ (e.g. $CH_3CH_2CH_2$), $CF_3$, $CH_3CH_2S$, $CH_3O$, $CF_3O$, $C(O)NH_2$, and $C(O)N(CH_2CH_3)_2$.

In some other embodiments, one of $R_9$ and $R_{10}$ is halogen and the other one is selected from H, halogen, cyano, C1-C3 alkyl optionally substituted with one or more F; C1-C3 alkoxy optionally substituted with one or more F; and C(O)NR$_{13}$R$_{14}$. For example, one of $R_9$ and $R_{10}$ is halogen and the other one is a moiety as defined herein, i.e. selected from H, halogen, cyano, C1-C3 alkyl optionally substituted with one or more F; C1-C3 alkoxy optionally substituted with one or more F; and C(O)NR$_{13}$R$_{14}$; such as from F, Cl, Br, CN, $CF_3$, $CF_3O$, and $C(O)NH_2$.

In some embodiments of a compound of formula (I), Ar is

In some embodiments, $R_9$ is as defined herein, but is different from H. For example, $R_9$ is different from H and is located in meta or para position.

In some embodiments, e.g. when at least $R_9$ is different from H, or both $R_9$ and $R_{10}$ are different from H, $R_9$ and $R_{10}$ are located in meta and meta' position, i.e. the compound of formula (I) may be represented by formula (It)

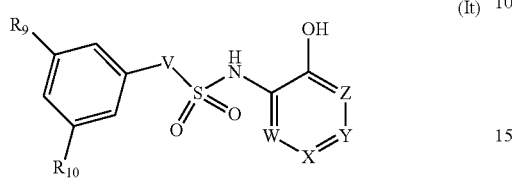

wherein $R_9$, $R_{10}$, V, W, X, Y and Z are as defined herein.

In some other embodiments, e.g. when at least $R_{10}$ is different from H, or both $R_9$ and $R_{10}$ are different from H, $R_9$ and $R_{10}$ are located in meta and para position, i.e. the compound of formula (I) may be represented by formula (Iu)

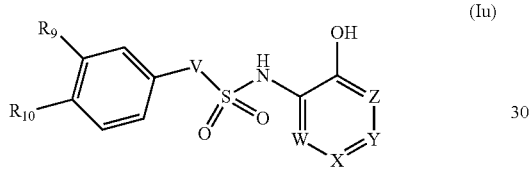

wherein $R_9$, $R_{10}$, V, W, X, Y and Z are as defined herein.

In still other embodiments, e.g. when at least $R_9$ is different from H, or both $R_9$ and $R_{10}$ are different from H, $R_9$ is in ortho position, i.e. the compound of formula (I) may be represented by formula (Iv)

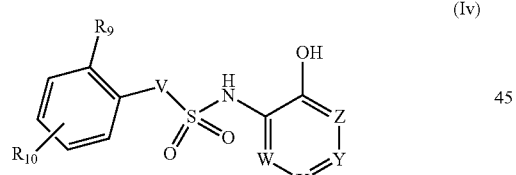

wherein $R_9$, $R_{10}$, V, W, X, Y and Z are as defined herein.

In the moiety $C(O)NR_{13}R_{14}$, $R_{13}$ and $R_{14}$ are independently selected from H and C1-C3 alkyl, e.g. from H, methyl and ethyl, or from H and methyl. In some embodiments, both $R_{13}$ and $R_{14}$ are H. In some other embodiments, both $R_{13}$ and $R_{14}$ are C1-C3 alkyl, e.g. methyl or ethyl. For example, both $R_{13}$ and $R_{14}$ may be ethyl.

In some embodiments the moiety

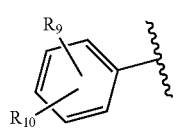

is selected from

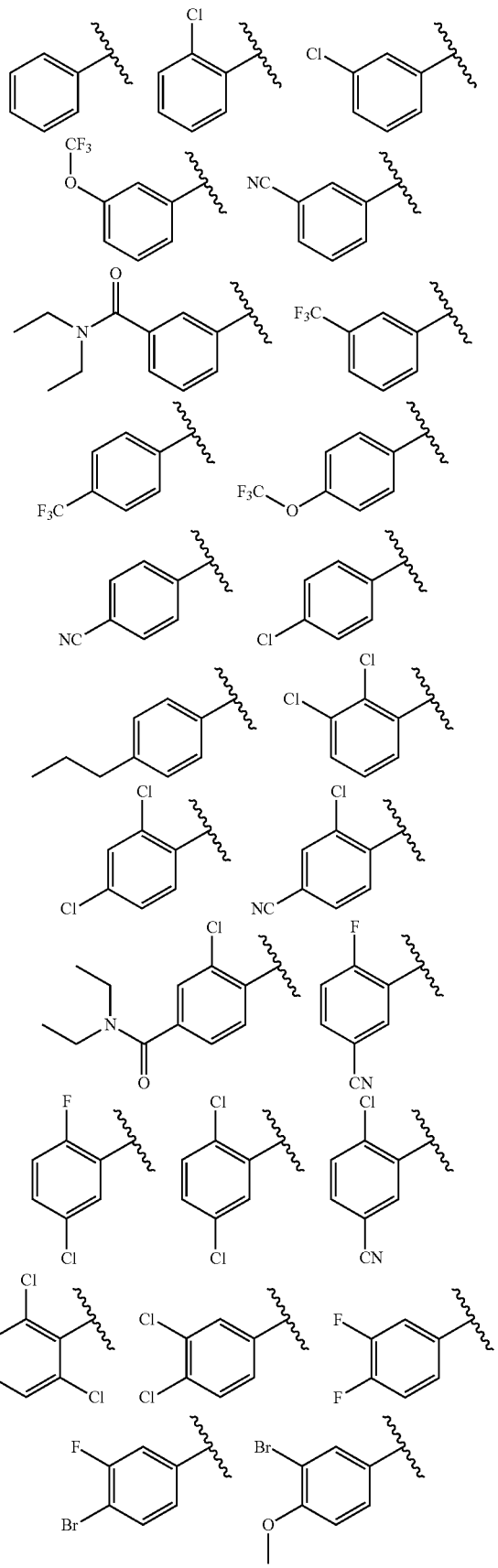

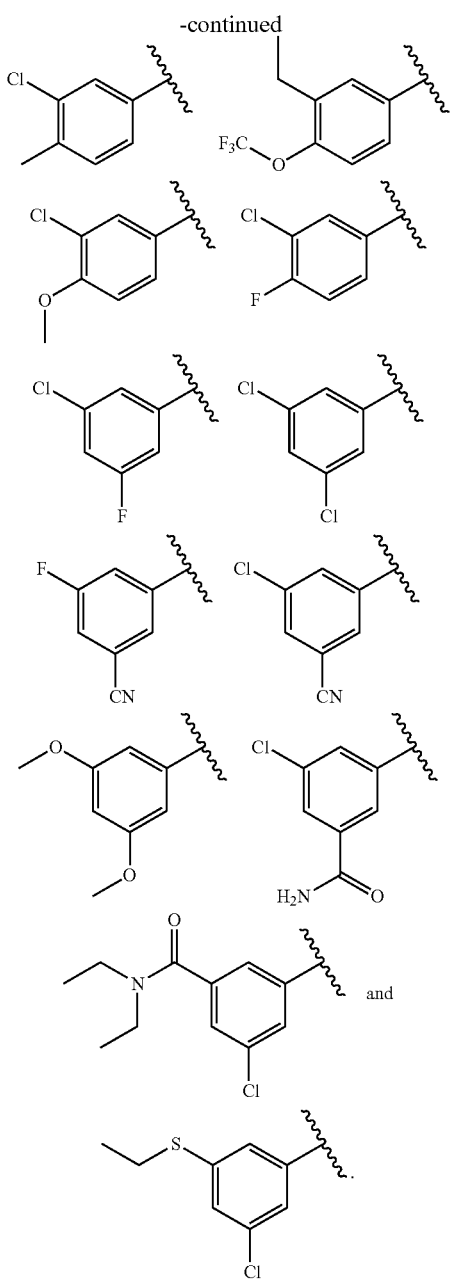

From the above, it appears that the compound of formula (I) may vary with respect to features of essentially three main parts of the compound of formula (I), i.e. the ring containing W, X, Y and Z, as e.g. represented by formulas (Ia), (Ib), (Ic), (Id), (Ie), (If), (Ig), (Ih), (Ij), (Ik) and (Im); the moiety V, as e.g. represented by formulas (In), (Io) and (Ip), and the moiety Ar, as e.g. represented by formulas (Iq), (Ir), (Is), (It), (Iu) and (Iv). It should be realized that any combination of the various embodiments relating to these three main parts is an embodiment within the scope of the invention and is covered by formula (I).

For example, in some embodiments, the compound is as represented by formula (Ia), in particular formula (Ie), or formula (Ig), or formula (Ih), (Ij) or (Ik), m is 0, and Ar is as generally defined in formula (I).

In some other embodiments, the compound is as represented by formula (Ia), in particular formula (Ie), or formula (Ig), or formula (Ih), (Ij) or (Ik), m is 1, and Ar is as generally defined in formula (I).

In still other embodiments, the compound is as represented by formula (Ib), in particular formula (If), (Ih) or (Im), m is 0, and Ar is as generally defined in formula (I).

In still other embodiments, the compound is as represented by formula (Ib), in particular formula (If), (Ih) or (Im), m is 1, and Ar is as generally defined in formula (I).

In still other embodiments, the compound is as represented by formula (Ic), m is 0, and Ar is as generally defined in formula (I).

In still other embodiments, the compound is as represented by formula (Ic), m is 1, and Ar is as generally defined in formula (I).

In other embodiments, the compound is as represented by formula (Id), in particular formula (Ij) or (Im), m is 0, and Ar is as generally defined in formula (I).

In still other embodiments, the compound is as represented by formula (Id), in particular formula (Ij) or (Im), m is 1, and Ar is as generally defined in formula (I).

In some embodiments, the compound is as represented by formula (Ia), in particular formula (Ie), or formula (Ig), or formula (Ih), (Ij) or (Ik), V is as generally defined in formula (I), and Ar is as represented in formula (Iq).

In other embodiments, the compound is as represented by formula (Ia), in particular formula (Ie), or formula (Ig), or formula (Ih), (Ij) or (Ik), V is as generally defined in formula (I), and Ar is as represented in formula (Ir).

In other embodiments, the compound is as represented by formula (Ia), in particular formula (Ie), or formula (Ig), or formula (Ih), (Ij) or (Ik), V is as generally defined in formula (I), and Ar is as represented in formula (Is).

In some embodiments, the compound is as represented by formula (Ib), in particular formula (If), V is as generally defined in formula (I), and Ar is as represented in formula (Iq).

In some embodiments, the compound is as represented by formula (Ib), in particular formula (If), (Ih) or (Im), V is as generally defined in formula (I), and Ar is as represented in formula (Ir).

In some embodiments, the compound is as represented by formula (Ib), in particular formula (If), (Ih) or (Im), V is as generally defined in formula (I), and Ar is as represented in formula (Is).

In still other embodiments, the compound is as represented by formula (Ic), V is as generally defined in formula (I), and Ar is as represented in formula (Iq).

In still other embodiments, the compound is as represented by formula (Ic), V is as generally defined in formula (I), and Ar is as represented in formula (Ir).

In still other embodiments, the compound is as represented by formula (Ic), V is as generally defined in formula (I), and Ar is as represented in formula (Is).

In still other embodiments, the compound is as represented by formula (Id), in particular formula (Ij) or (Im), V is as generally defined in formula (I), and Ar is as represented in formula (Iq).

In still other embodiments, the compound is as represented by formula (Id), in particular formula (Ij) or (Im), V is as generally defined in formula (I), and Ar is as represented in formula (Ir).

In still other embodiments, the compound is as represented by formula (Id), in particular formula (Ij) or (Im), V is as generally defined in formula (I), and Ar is as represented in formula (Is).

Furthermore, in some embodiments, the compound is as represented by formula (Ia), in particular formula (Ie), or formula (Ig), or formula (Ih), (Ij) or (Ik), m is 0, and Ar is as defined in formula (Iq).

In some embodiments, the compound is as represented by formula (Ia), in particular formula (Ie), or formula (Ig), or formula (Ih), (Ij) or (Ik), m is 0, and Ar is as defined in formula (Ir).

In some embodiments, the compound is as represented by formula (Ia), in particular formula (Ie), or formula (Ig), or formula (Ih), (Ij) or (Ik), m is 0, and Ar is as defined in formula (Is).

In some other embodiments, the compound is as represented by formula (Ia), in particular formula (Ie), or formula (Ig), or formula (Ih), (Ij) or (Ik), m is 1, and Ar is as defined in formula (Iq).

In some other embodiments, the compound is as represented by formula (Ia), in particular formula (Ie), or formula (Ig), or formula (Ih), (Ij) or (Ik), m is 1, and Ar is as defined in formula (Ir).

In some other embodiments, the compound is as represented by formula (Ia), in particular formula (Ie), or formula (Ig), or formula (Ih), (Ij) or (Ik), m is 1, and Ar is as defined in formula (Is).

In still other embodiments, the compound is as represented by formula (Ib), in particular formula (If), (Ih) or (Im), m is 0, and Ar is as defined in formula (Iq).

In still other embodiments, the compound is as represented by formula (Ib), in particular formula (If), (Ih) or (Im), m is 0, and Ar is as defined in formula (Ir).

In still other embodiments, the compound is as represented by formula (Ib), in particular formula (If), (Ih) or (Im), m is 0, and Ar is as defined in formula (Is).

In still other embodiments, the compound is as represented by formula (Ib), in particular formula (If), (Ih) or (Im), m is 1, and Ar is as defined in formula (Iq).

In still other embodiments, the compound is as represented by formula (Ib), in particular formula (If), (Ih) or (Im), m is 1, and Ar is as defined in formula (Ir).

In still other embodiments, the compound is as represented by formula (Ib), in particular formula (If), (Ih) or (Im), m is 1, and Ar is as defined in formula (Is).

In still other embodiments, the compound is as represented by formula (Ic), m is 0, and Ar is as defined in formula (Iq).

In still other embodiments, the compound is as represented by formula (Ic), m is 0, and Ar is as defined in formula (Ir).

In still other embodiments, the compound is as represented by formula (Ic), m is 0, and Ar is as defined in formula (Is).

In still other embodiments, the compound is as represented by formula (Id), in particular formula (Ij) or (Im), m is 1, and Ar is as defined in formula (Iq).

In still other embodiments, the compound is as represented by formula (Id), in particular formula (Ij) or (Im), m is 1, and Ar is as defined in formula (Ir).

In still other embodiments, the compound is as represented by formula (Id), in particular formula (Ij) or (Im), m is 1, and Ar is as defined in formula (Is).

Studies have shown efficacy of the compounds of the invention in vitro and in vivo in mice and, although the compounds have been developed toward S100A9 inhibition, they can also show activity to other S100 proteins. The present invention therefore relates to compounds as defined herein, as S100 protein inhibitors, mainly as S100A9 inhibitors and to their use in treatment or prevention of S100-protein related diseases, in particular diseases related to the activity of S100A9 protein.

In particular, the present invention relates to the compounds of formula (I) as defined herein, to pharmaceutical compositions comprising said compounds, to the use of such compositions in the therapeutic treatment of conditions selected from in particular cancer, but also autoimmune diseases, inflammatory diseases and neurodegenerative diseases, to a method of treatment of such conditions, and to said compounds for use in the treatment of conditions selected from in particular cancer, but also autoimmune diseases, inflammatory diseases and neurodegenerative diseases, as well as the use of said compounds in the manufacture of pharmaceutical compositions for the treatment of such conditions.

The present invention includes pharmaceutical compositions comprising at least one compound according to formula (I), or an individual isomer, racemic or non-racemic mixture of isomers or a pharmaceutically acceptable salt thereof, together with at least one pharmaceutically acceptable excipient, e.g. a carrier, and optionally other therapeutic and/or prophylactic ingredients.

A pharmaceutical composition according to the invention may be for topical (local) or systemic administration, e.g for enteral administration, such as rectal or oral administration, or for parenteral administration to a mammal (especially a human), and comprises a therapeutically effective amount of a compound according to the invention or a pharmaceutically acceptable salt thereof, as active ingredient, in association with a pharmaceutically acceptable excipient, e.g. a pharmaceutically acceptable carrier. The therapeutically effective amount of the active ingredient is as defined herein above and depends e.g. on the species of mammal, the body weight, the age, the individual condition, individual pharmacokinetic data, the disease to be treated and the mode of administration.

For enteral, e.g. oral, administration, the compounds of the invention may be formulated in a wide variety of dosage forms. The pharmaceutical compositions and dosage forms may comprise a compound or compounds of the present invention or pharmaceutically acceptable salt(s) thereof as the active component. The pharmaceutically acceptable carriers may be either solid or liquid. Solid form preparations include powders, tablets, pills, lozenges, capsules, cachets, suppositories, and dispersible granules. A solid carrier may be one or more substances which may also act as diluents, flavouring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatine, tragacanth, methylcellulose, sodium carboxymethylcellulose, a low melting wax, cocoa butter, and the like. The formulation of the active compound may comprise an encapsulating material as carrier, providing a capsule in which the active component, with or without carriers, is surrounded by a carrier, which is in association with it.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

Exemplary compositions for rectal administration include suppositories which can contain, for example, a suitable non-irritating excipient, such as cocoa butter, synthetic glyceride esters or polyethylene glycols, which are solid at ordinary temperatures, but liquefy and/or dissolve in the rectal cavity to release the drug.

The compounds of the invention also may be administered parenterally, e.g. by inhalation, injection or infusion, e.g. by intravenous, intraarterial, intraosseous, intramuscular, intracerebral, intracerebroventricular, intrasynovial, intrasternal, intrathecal, intralesional, intracranial, intratumoral, intracutaneous and subcutaneous injection or infusion.

Thus, for parenteral administration, the pharmaceutical compositions of the invention may be in the form of a sterile injectable or infusible preparation, for example, as a sterile aqueous or oleaginous suspension. This suspension may be formulated according to techniques known in the art using suitable dispersing or wetting agents (e.g., Tween 80), and suspending agents. The sterile injectable or infusible preparation may also be a sterile injectable or infusible solution or suspension in a non-toxic parenterally acceptable diluent or solvent. For example, the pharmaceutical composition may be a solution in 1,3-butanediol. Other examples of acceptable vehicles and solvents that may be employed in the compositions of the present invention include, but are not limited to, mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions may also contain a long-chain alcohol diluent or dispersant.

Solutions for parenteral use also may contain suitable stabilizing agents, and if necessary, buffer substances. Suitable stabilizing agents include antioxidizing agents, such as sodium bisulfate, sodium sulfite or ascorbic acid, either alone or combined, citric acid and its salts and sodium EDTA. Parenteral solutions may also contain preservatives, such as benzalkonium chloride, methyl- or propyl-paraben, and cholorobutanol.

For inhalation or nasal administration, suitable pharmaceutical formulations are as particles, aerosols, powders, mists or droplets, e.g. with an average size of about 10 µm in diameter or less. For example, compositions for inhalataion may be prepared as solutions in saline, employing benzyl alcohol or other suitable preservatives, absorption promoters to enhance bioavailability, fluorocarbons, and/or other solubilizing or dispersing agents known in the art.

The pharmaceutical compositions of the invention also may be administered topically, to the skin or to a mucous membrane. For topical application, the pharmaceutical composition may be e.g. a lotion, a gel, a paste, a tincture, a transdermal patch, a gel for transmucosal delivery. The composition may be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition may be formulated as a suitable lotion or cream containing the active compound suspended or dissolved in a carrier. Suitable carriers include, but are not limited to, mineral oil, sorbitan monostearate, polysorbate 60, cetyl esters wax, cetaryl alcohol, 2-octyldodecanol, benzyl alcohol and water. The pharmaceutical compositions of this invention may also be topically applied to the lower intestinal tract by rectal suppository formulation or in a suitable enema formulation.

Suitable pharmaceutical excipients, e.g. carriers, and methods of preparing pharmaceutical dosage forms are described in Remington's Pharmaceutical Sciences, Mack Publishing Company, a standard reference text in art of drug formulation.

The pharmaceutical compositions may comprise from approximately 1% to approximately 95%, preferably from approximately 20% to approximately 90% of a compound of formula (I), together with at least one pharmaceutically acceptable excipient. In general, the compounds of the invention will be administered in a therapeutically effective amount by any of the accepted modes of administration for agents that serve similar utilities. Suitable daily dosages typically ranges from 1 to 1000 mg, e.g. 1-500 mg daily, or 1-50 mg daily, depending upon numerous factors such as the severity of the disease to be treated, the age and relative health of the patient, the potency of the compound used, the route and form of administration, and the indication towards which the administration is directed, etc. One of ordinary skill in the art of treating such diseases will be able, without undue experimentation and in reliance upon personal knowledge and the disclosure of this application, to ascertain a therapeutically effective amount of the compounds of the present invention for a given disease. Compounds of the invention may be administered as pharmaceutical formulations including those suitable for enteral or parenteral administration. The preferred manner of administration is generally oral using a convenient daily dosage regimen which can be adjusted according to the degree of affliction.

According to one aspect, the present invention relates to a method of treatment of a disease that responds to inhibition of a member of the S100 protein family, e.g. S100A9, e.g. a cancer, an autoimmune disease, an inflammatory disease, or a neurodegenerative disease, which method comprises administering a therapeutically effective amount of a compound of formula (I), or pharmaceutically acceptable salt thereof, to a warm-blooded animal, e.g., a human, in need of such treatment.

In some embodiments, the disorder treated according to the present invention is a cancer, e.g. a cancer such as defined herein above.

In some other embodiments, the disorder treated according to the present invention is an automimmune disorder, e.g. and automimmune disorder such as defined herein above.

In some other embodiments, the disorder treated according to the present invention is an an inflammatory disorder, e.g. an inflammatory disorder such as defined herein above.

In some other embodiments, the disorder treated according to the present invention is an neurodegenerative disorder, e.g. a neurodegenerative disorder such as defined herein above.

The preparation of compounds within the scope of formula (I) is well within the capacity of the person of ordinary skill in the art. For example, a compound of formula (I) may be prepared by reacting a sulfonyl chloride 1 with an amine 2 in a suitable solvent medium, as as illustrated in the following reaction scheme:

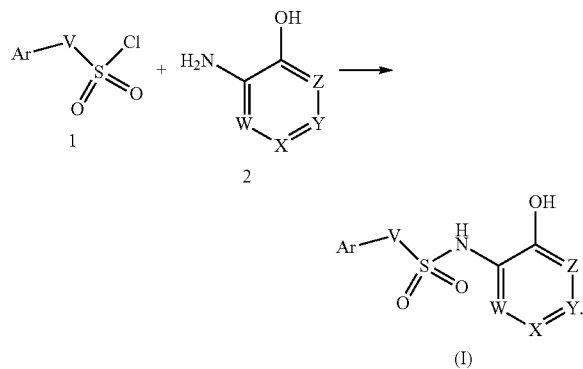

If necessary, the hydroxy group of amine 2 may be protected during the coupling reaction, e.g. as a methoxy group.

The following examples will enable a person skilled in the art to more clearly understand and practice the present invention. These examples, however, should not be considered as limiting the scope of the invention, but merely as being illustrative and representative thereof.

EXAMPLES

All pyridine used was stored over activated 4 Å mol sieves.

"Low pH method" refers to HPLC purification using a mobile phase consisting of 0.2% formic acid in a gradient of 0-100% MeCN in water. The stationary phase consisted of a Waters Sunfire C18 column, 10 m particle size, 30×100 mm.

"High pH method" refers to HPLC purification using a mobile phase consisting of 0.2% ammonia in a gradient of 0-100% MeCN in water. The stationary phase consisted of a Waters X-bridge C18 column, 10 m particle size, 30×100 mm.

SFC was carried out using a Chiralpak AD-H column with a mobile phase of supercritical $CO_2$ and methanol containing 0.1% formic acid.

General Procedure for Coupling Sulfonyl Chlorides to Methoxy- or Hydroxy Substituted Aminopyridines, Procedure A:

To an ice-cooled solution of the methoxy- or hydroxy substituted aminopyridine (1 mmol, in dichloromethane (4 mL) and pyridine (4 mmol), was added dropwise a solution of sulfonyl chloride (1.2 mmol) dissolved in dichloromethane (2 mL). The mixture was allowed to stir at room temperature until TLC (heptane/ethyl acetate/acetic acid 1:3:0.16) show complete disappearance of the aminopyridine (ususally 1-18 hours). Samples for TLC were taken out from the mixture and shaken with a mixture of ethyl acetate and water. TLC was run on the organic phase. When TLC indicated complete reaction the mixture was concentrated on a rotary evaporator, then dissolved in a mixture of ethanol (5 mL) and NaOH (1 M, 2 mL) and heated at 60° C. for 2 hours. The mixture was then cooled and acetic acid (0.5 mL) was added which usually results in precipitation of the desired product. If there was no precipitation the mixture was instead partitioned between ethyl acetate and water, the organic phase was concentrated and the residue was purified by flash chromatography (silica, ethyl acetate/heptane mixtures).

General Procedure for the Cleavage of the Methoxy Group to Prepare Hydroxy Substituted Sulfonamides, Procedure B:

To 1 mmol methoxy-substituted compound (achieved using procedure A) was added 4 mL dichloromethane under nitrogen, the mixture was cooled in an ice-bath and $BBr_3$ (1 M solution in $CH_2Cl_2$, 2 equiv., 2 mL) was added dropwise. The cooling bath was removed and the mixture was stirred until TLC (heptane/ethyl acetate/acetic acid 1:3:0.16) showed complete disappearance of methoxy compound (usually 2-4 hours). Eventually one extra equiv. $BBr_3$ was added to complete the reaction. When the reaction was complete the mixture was cooled in an ice bath and 1 mL 1,2-propanediol was added (exothermic!) followed by the addition of 5 mL n-propanol. The mixture was concentrated to remove dichloromethane, then diluted with n-propanol (5 mL) and 0.5 ml 5 M HCl and heated at 80° C. until the mixture gets clear. Then the mixture was cooled to room temp and water was added to precipitate the desired product. The precipitate was filtered, dried and recrystallized. Recrystallization was performed by dissolving the material in a mixture of 5 mL ethanol and approx. 2 mL 1M NaOH to pH>11, any insolubilities were filtered off and the mixture was acidified by addition of HCl or acetic acid. Eventually water was added to initiate the crystallization. Alternatively, recrystallization was achieved by dissolving in hot acetic acid and precipitation with water. If there was no solid precipitation after the heating step at 80° C. and addition of water the mixture was extracted with ethyl acetate and purified by flash chromatography (SiO2, ethyl acetate/heptane mixtures).

Non-commercial sulfonyl chlorides or methoxy- or hydroxy substituted aminopyridines were prepared using literature methods or the methods described in this patent application.

Intermediates 6-chloro-N-(5-chloro-3-methoxypyridin-2-yl)pyridine-3-sulfonamide

To a solution of 5-chloro-3-methoxypyridin-2-amine (1.50 g, 9.46 mmol), prepared according to literature (Int. Appl. No. PCT/US2011/020414; Publ. No. WO 2011085126) in pyridine (15 mL) was added 6-chloropyridine-3-sulfonyl chloride hydrochloride (2.35 g, 9.46 mmol) and the solution stirred at room temperature for 64 hrs. The solvent was evaporated and the mixture partitioned between DCM (60 mL) and water (20 mL). The phases were separated and the organic phase was washed with brine (20 mL), dried ($Na_2SO_4$), the mixture was filtered and the filtrate evaporated to dryness to afford a purple solid which was chromatographed on silica (100 g SNAP column, eluting with 15-40% EtOAc in heptane), affording 6-chloro-N-(5-chloro-3-methoxypyridin-2-yl)pyridine-3-sulfonamide as an orange oil (360 mg, 11%); m/z 333.8, 335.8 (MH)$^+$.

3-methoxy-2-nitro-5-(prop-1-en-2-yl)pyridine

To a solution of 5-bromo-3-methoxy-2-nitropyridine (1.30 g, 5.58 mmol), prepared by a literature method (Int. Appl. No. PCT/EP2010/052589; Publ. No. WO 2010100127) in a mixture of 1,4-dioxane (13 mL) and water (5 mL) were added potassium isopropenyl trifluoroborate (908 mg, 6.14 mmol), caesium carbonate (5.46 g, 16.7 mmol) and 1,1'-bis(diphenylphosphino)ferrocene-palladium (II) dichloride dichloromethane complex (70 mg, 0.086 mmol) and the mixture was stirred at 70° C. for 1 hr under a nitrogen atmosphere. Brine (10 mL) and EtOAc (50 mL) were then added. The phases were separated and the organic phase was washed with brine (5 mL), dried (Na$_2$SO$_4$), the mixture was filtered and the filtrate evaporated to dryness to afford an orange oil which was chromatographed on silica (heptane/EtOAc 4:1) to afford 3-methoxy-2-nitro-5-(prop-1-en-2-yl)pyridine as a yellow solid (740 mg, 68%); m/z=195.0 (MH)$^+$.

3-methoxy-5-(propan-2-yl)pyridin-2-amine

A solution of 3-methoxy-2-nitro-5-(prop-1-en-2-yl)pyridine (250 mg, 1.29 mmol) in EtOH (10 mL) was treated with 10% Pd/C (25 mg), degassed three times under nitrogen/vacuum and hydrogenated for 3 hrs at atmospheric pressure. The mixture was filtered through Celite and the filtrate evaporated to dryness to afford 3-methoxy-5-(propan-2-yl)pyridin-2-amine as a purple oil (240 mg at 78% purity, 87% yield); m/z=167.0 (MH)$^+$.

(+/−)-2-(5-methoxy-6-nitropyridin-3-yl)propan-1-ol

A solution of 3-methoxy-2-nitro-5-(prop-1-en-2-yl)pyridine (400 mg, 2.06 mmol) in THF (10 mL) was stirred at 0° C. Borane dimethylsulfide complex (2M in THF, 1.54 mL, 3.08 mmol) was added and the mixture was allowed to warm to room temperature and stirred for 1 hr. 30% hydrogen peroxide (2.3 mL, 20 mmol) was then added dropwise, followed by 5M sodium hydroxide solution (2.0 mL, 10 mmol), also dropwise. CAUTION-rapid effervesence and exotherm occurred. The mixture was stirred for 30 min and partitioned between EtOAc and further 5M NaOH. The phases were separated and the organic phase was washed with brine (20 mL), dried (Na$_2$SO$_4$), the mixture was filtered and the filtrate evaporated to dryness to afford an orange oil which was chromatographed on silica (heptane:EtOAc 1:1) to afford (+/−)-2-(5-methoxy-6-nitropyridin-3-yl)propan-1-ol as a colourless oil (170 mg, 39%); m/z=212.9 (MH)$^+$.

(+/−)-2-(6-amino-5-methoxypyridin-3-yl)propan-1-ol

A solution of (+/−)-2-(5-methoxy-6-nitropyridin-3-yl)propan-1-ol (170 mg, 0.801 mmol) in EtOH (10 mL) was treated with 10% Pd/C (30 mg), degassed three times under nitrogen/vacuum then hydrogenated for 16 hrs at room temperature. The mixture was filtered through Celite and the filtrate evaporated to dryness to afford (+/−)-2-(6-amino-5-methoxypyridin-3-yl)propan-1-ol as a yellow oil (130 mg, 89%); m/z=182.9 (MH)$^+$.

5-bromo-6-chloro-N-(5-chloro-3-methoxypyridin-2-yl)pyridine-3-sulfonamide

To a solution of 2-amino-5-chloro-3-methoxypyridine (1.00 g, 4.92 mmol) in pyridine (10 mL) was added 5-bromo-6-chloropyridine-3-sulfonyl chloride (2.00 g, 6.89 mmol) and the mixture was stirred at room temperature for 1 h. The solvent was evaporated and purification of the residue carried out by silica chromatography to afford 50% pure 5-bromo-6-chloro-N-(5-chloro-3-methoxypyridin-2-yl)pyridine-3-sulfonamide, contaminated with starting amine (1.84 g at 50% purity, 45%); m/z=411.6, 413.6.

1-{[(2,5-dichlorothiophen-3-yl)methyl]sulfanyl}ethan-1-one

To a solution of 3-(bromomethyl)-2,5-dichlorothiophene (3.60 g, 14.6 mmol), prepared by a literature procedure (Int. Appl. No. PCT/CA2010/000779; Publ. No. WO 2010132999) in acetone (150 mL) was added potassium carbonate (6.07 g, 43.9 mmol) and thioacetic acid (1.34 g, 17.6 mmol) and the mixture refluxed 45 min. The solvent was evaporated then DCM (100 mL) and water (15 mL) were added to the residue. The phases were separated and the organic phase was washed with brine (10 mL), dried (Na$_2$SO$_4$), the mixture was filtered and the filtrate evaporated to dryness to afford 1-{[(2,5-dichlorothiophen-3-yl)methyl]sulfanyl}ethan-1-one as a brown oil (3.53 g, 97%); $^1$H NMR (500 MHz, CDCl$_3$) δ 2.27 (s, 3H), 3.90 (s, 2H), 6.65 (s, 1H).

(2,5-dichlorothiophen-3-yl)methanesulfonyl Chloride

A solution of 1-{[(2,5-dichlorothiophen-3-yl)methyl]sulfanyl}ethan-1-one (130 mg, 0.518 mmol) in a mixture of AcOH (2.2 mL) and water (0.3 mL) at room temperature was saturated with chlorine gas and stirred until the disappearance of starting material was observed by TLC. The reaction mixture was diluted with EtOAc (50 mL) and brine (20 mL). The phases were separated and the organic phase was washed with brine (2×10 mL), dried (Na$_2$SO$_4$), the mixture was filtered and the filtrate evaporated to dryness to afford (2,5-dichlorothiophen-3-yl)methanesulfonyl chloride as a yellow oil (130 mg, 82%); $^1$H NMR (500 MHz, CDCl$_3$) δ 4.74 (s, 2H), 6.92 (s, 1H).

1-{[(3-chloro-5-fluorophenyl)methyl]sulfanyl}ethan-1-one

The procedure for the preparation of 1-{[(2,5-dichlorothiophen-3-yl)methyl]-sulfanyl}ethan-1-one was used, except that 1-(bromomethyl)-3-chloro-5-fluorobenzene was substituted for 3-(bromomethyl)-2,5-dichlorothiophene (97% yield); $^1$H NMR (250 MHz, CDCl$_3$) δ 2.37 (s, 3H), 4.05 (s, 2H), 6.94 (m, 2H), 7.08 (s, 1H).

(3-chloro-5-fluorophenyl)methanesulfonyl chloride

The procedure for the preparation of (2,5-dichlorothiophen-3-yl)methanesulfonyl chloride was used, except that 1-{[(3-chloro-5-fluorophenyl)methyl]sulfanyl}ethan-1-one was substituted for 1-{[(2,5-dichlorothiophen-3-yl)methyl]sulfanyl}ethan-1-one (80% yield); $^1$H NMR (500 MHz, CDCl$_3$) δ 4.83 (s, 2H), 7.16 (m, 1H), 7.25 (m, 1H), 7.31 (s, 1H).

3-methoxy-5-(methylsulfanyl)-2-nitropyridine

To a solution of 5-bromo-3-methoxy-2-nitropyridine (2.00 g, 8.58 mmol) in DMF (10 mL) was added sodium methanethiolate (541 mg, 7.72 mmol) in portions so that the temperature did not rise above 30° C. More sodium methanethiolate (155 mg, 2.21 mmol) was added in an attempt to drive the reaction to completion. Water (100 mL) was added followed by EtOAc (300 mL). The phases were separated and the organic phase was washed with water (2×20 mL) and brine (20 mL), dried (Na$_2$SO$_4$), the mixture was filtered and the filtrate evaporated to dryness to afford a brown oil which was chromatographed on silica (eluent: heptane:EtOAc 3:1 falling to 2:1) to afford 3-methoxy-5-(methylsulfanyl)-2-nitropyridine as an orange solid (307 mg, 18%); m/z=200.9.

3-methoxy-5-(methylsulfanyl)pyridin-2-amine

To a suspension of 3-methoxy-5-(methylsulfanyl)-2-nitropyridine (220 mg, 1.10 mmol) in EtOH (15 mL) was added anhydrous tin(II) chloride (870 mg, 4.40 mmol) and the mixture heated at 90° C. for 2 hrs. The solvent was evaporated and the residue was partitioned between DCM (100 mL) and 2M NaOH (60 mL). The phases were separated and the organic phase was washed with more 2M NaOH (20 mL), brine (20 mL), dried (Na$_2$SO$_4$), the mixture was filtered and the filtrate evaporated to dryness to afford 3-methoxy-5-(methylsulfanyl)pyridin-2-amine as a yellow oil which crystallized on standing (96% yield); m/z=170.9.

1-{[(5-chloro-2-fluorophenyl)methyl]sulfanyl}ethan-1-one

The procedure for the preparation of 1-{[(2,5-dichlorothiophen-3-yl)methyl]sulfanyl})-ethan-1-one was used, except that 1-(bromomethyl)-5-chloro-2-fluorobenzene was substituted for 3-(bromomethyl)-2,5-dichlorothiophene (82%); $^1$H NMR (400 MHz, CDCl$_3$) δ 2.36 (s, 3H), 4.09 (d, 2H), 6.97 (m, 1H), 7.18 (ddd, 1H), 7.35 (dd, 1H).

(5-chloro-2-fluorophenyl)methanesulfonyl chloride

To a stirred solution of N-chlorosuccinimide (855 mg, 6.44 mmol) in acetonitrile (5 mL) was added 2M HCl (5 drops) and the reaction mixture cooled to 0° C. To this mixture was added a solution of 1-{[(5-chloro-2-fluorophenyl)methyl]sulfanyl}ethan-1-one (350 mg, 1.60 mmol) in acetonitrile (1 mL) and the resultant reaction mixture was stirred at 0° C. On disappearance of starting material (as judged by TLC), the solvent was evaporated and (5-chloro-2-fluorophenyl)methanesulfonyl chloride was used crude in the next step (98%).

(+/−)-1-(3,5-dichlorophenyl)ethan-1-ol

To a solution of 1-(3,5-dichlorophenyl)ethan-1-one (1.00 g, 5.29 mmol) in EtOH (10 mL) at room temperature was added solid NaBH$_4$ (100 mg, 2.64 mmol) in three portions over 5 min with stirring. The solvent was evaporated and the resultant white solid treated with 1M HCl (20 mL) and DCM (70 mL). The phases were separated and the organic phase was washed with brine (20 mL), dried (Na$_2$SO$_4$), the mixture was filtered and the filtrate evaporated to dryness to afford (+/−)-1-(3,5-dichlorophenyl)ethan-1-ol as a cloudy oil (1025 mg, 100%); $^1$H NMR (250 MHz, CDCl$_3$) δ 1.47 (d, 3H), 4.85 (q, 1H), 7.24-7.28 (m, 3H).

(+/−)-1-{[1-(3,5-dichlorophenyl)ethyl]sulfanyl}ethan-1-one

To a solution of (+/−)-1-(3,5-dichlorophenyl)ethan-1-ol (650 mg, 3.40 mmol) in DCM (5 mL) was added phosphorus tribromide (967 mg, 3.57 mmol) and the mixture was stirred for 15 min. More DCM was added (30 mL) followed by saturated NaHCO$_3$ (15 mL). The phases were separated and the organic phase was washed with brine (5 mL), dried (Na$_2$SO$_4$), the mixture was filtered and the filtrate evaporated to dryness to afford the crude bromide which was immediately dissolved in acetone (15 mL), thioacetic acid added (285 mg, 3.74 mmol) followed by K$_2$CO$_3$ (705 mg, 5.10 mmol) and the mixture was stirred at 50° C. for 1 h. The solvent was evaporated and DCM (60 mL) and saturated K$_2$CO$_3$ was added (15 mL). The phases were separated and the organic phase was washed with brine (5 mL), dried (Na$_2$SO$_4$), the mixture was filtered and the filtrate evaporated to dryness to afford a brown oil which was chromatographed (heptane:EtOAc 12:1) to afford (+/−)-1-{[1-(3,5-dichlorophenyl)ethyl]sulfanyl}ethan-1-one as an orange oil (310 mg, 37%); $^1$H NMR (250 MHz, CDCl$_3$) δ 1.54 (d, 3H), 2.24 (s, 3H), 4.58 (q, 1H), 7.13-7.18 (m, 3H).

(+/−)-1-(3,5-dichlorophenyl)ethane-1-sulfonyl chloride

The procedure for the preparation of (2,5-dichlorothiophen-3-yl)methanesulfonyl chloride was used, except that (+/−)-1-{[1-(3,5-dichlorophenyl)ethyl]sulfanyl}ethan-1-one was substituted for 1-{[(2,5-dichlorothiophen-3-yl)methyl]sulfanyl}ethan-1-one (245 mg, 75%); no data taken as material was used immediately in the next step.

5-bromo-N-(5-chloro-3-methoxypyridin-2-yl)pyridine-3-sulfonamide 5-chloro-3-methoxypyridin-2-amine (200 mg, 1.26 mmol) and 5-bromopyridine-3-sulfonyl chloride (350 mg, 1.39 mmol) were combined in a sealed tube and heated at 110° C. for 16 hrs. The reaction mixture was dissolved in 10% methanol in DCM (10 mL) and the solvent evaporated to yield a brown residue which was chromatographed on silica (eluent: acetone:DCM, 1:9) to afford 5-bromo-N-(5-chloro-3-methoxypyridin-2-yl)-pyridine-3-sulfonamide (60 mg, 12%) as an off-white solid; m/z=378.3, 380.3 (MH)$^+$.

N-(5-chloro-3-methoxypyridin-2-yl)-3-(trifluoromethoxy)benzene-1-sulfonamide The procedure for preparation of N-(5-chloro-3-methoxypyridin-2-yl)-1-methyl-1H-imidazole-4-sulfonamide was used, except that 3-(trifluoromethoxy)benzenesulfonyl chloride was substituted for 1-methyl-1H-imidazole-4-sulfonyl chloride. Chromatography on silica (eluent: MeOH:DCM, 1:19 containing 1% aq. ammonia) afforded N-(5-chloro-3-methoxypyridin-2-yl)-3-(trifluoromethoxy)benzene-1-sulfonamide (100 mg, 28%) as a white solid; m/z=383.3, 385.3 (MH)$^+$.

5-bromo-3-methoxypyridin-2-amine

To a solution of 3-methoxypyridin-2-amine (1.00 g, 8.06 mmol) in acetic acid (10 mL) was added bromine (0.414 mL, 8.06 mmol) over 30 min. The reaction mixture was then stirred at room temperature for 18 hrs. Acetic acid was evaporated in vacuo and the pH of the residue was adjusted to 7-8 by slow addition of a saturated aqueous solution of sodium bicarbonate. The mixture was extracted with ethyl acetate (2×50 mL) and the combined organic phases dried ($Na_2SO_4$), filtered and concentrated to afford a crude residue which was triturated in ethyl acetate and n-pentane to afford 5-bromo-3-methoxy-pyridin-2-amine (750 mg, 46%) as a red solid. $^1$H NMR (400 MHz, $CDCl_3$) δ 3.85 (d, 3H), 4.69 (s, 2H), 7.00 (d, 1H), 7.71 (d, 1H).

N-(5-bromo-3-methoxypyridin-2-yl)benzene sulfonamide

The procedure for preparation of N-(5-chloro-3-methoxypyridin-2-yl)-2,4-dimethyl-1,3-thiazole-5-sulfonamide was used except that benzenesulfonyl chloride was substituted for dimethyl-1,3-thiazole-5-sulfonyl chloride and 5-bromo-3-methoxypyridin-2-amine substituted for 5-chloro-3-methoxypyridin-2-amine. The crude product was purified by trituration in ethyl acetate and n-hexane to yield N-(5-bromo-3-methoxypyridin-2-yl)-benzene sulfonamide (100 mg, 60%) as an off-white solid; $^1$H NMR (400 MHz, $CDCl_3$) δ 3.85 (s, 3H), 7.14 (d, 1H), 7.50 (dd, 2H), 7.54-7.62 (m, 2H), 7.89 (d, J=1H), 8.11-8.17 (m, 2H).

N-(5-bromo-3-methoxypyridin-2-yl)-2,5-dichlorothiophene-3-sulfonamide

The procedure for preparation of N-(5-bromo-3-methoxypyridin-2-yl)benzene sulfonamide was used except that 2,5-dichlorothiophene-3-sulfonyl chloride was substituted for benzenesulfonyl chloride.

N-(5-bromo-3-methoxypyridin-2-yl)-3-(trifluoromethoxy)benzene-1-sulfonamide

The procedure for preparation of N-(5-chloro-3-methoxypyridin-2-yl)-1-methyl-1H-imidazole-4-sulfonamide was used, except that 3-(trifluoromethoxy)benzenesulfonyl chloride was substituted for 1-methyl-1H-imidazole-4-sulfonyl chloride and 5-bromo-3-methoxypyridin-2-amine substituted for 5-chloro-3-methoxypyridin-2-amine. Purification was carried out by chromatography on silica (eluent: MeOH:DCM, 1:9 containing 1% aq. ammonia) to afford N-(5-bromo-3-methoxypyridin-2-yl)-3-(trifluoromethoxy)benzene-1-sulfonamide (44%) as a brown solid; m/z=427.3, 429.3 $(MH)^+$.

N-(5-bromo-3-methoxypyridin-2-yl)-6-(trifluoromethyl)pyridine-3-sulfonamide

The procedure for preparation of N-(5-chloro-3-methoxypyridin-2-yl)-2,4-dimethyl-1,3-thiazole-5-sulfonamide was used except that 6-(trifluoromethyl)pyridine-3-sulfonyl chloride was substituted for dimethyl-1,3-thiazole-5-sulfonyl chloride and 5-bromo-3-methoxypyridin-2-amine substituted for 5-chloro-3-methoxypyridin-2-amine. The crude compound was chromatographed on silica (eluent: EtOAc:Hexane, 3:7) to yield N-(5-bromo-3-hydroxypyridin-2-yl)-6-(trifluoromethyl)pyridine-3-sulfonamide (58%) as an off-white solid; m/z=412.3, 414.3 $(MH)^+$.

5-bromo-N-(5-bromo-3-methoxypyridin-2-yl)-6-chloropyridine-3-sulfonamide

The procedure for preparation of N-(5-chloro-3-methoxypyridin-2-yl)-2,4-dimethyl-1,3-thiazole-5-sulfonamide was used except that 5-bromo-6-chloropyridine-3-sulfonyl chloride was substituted for dimethyl-1,3-thiazole-5-sulfonyl chloride and 5-bromo-3-methoxypyridin-2-amine substituted for 5-chloro-3-methoxypyridin-2-amine. The crude compound was chromatographed on silica (eluent: EtOAc:Hexane, 3:7) to yield 5-bromo-N-(5-bromo-3-methoxypyridin-2-yl)-6-chloropyridine-3-sulfonamide (41%) as an off-white solid; m/z=458.0, 460.0 $(MH)^+$.

N-(3-methoxypyridin-2-yl)-6-(trifluoromethyl)pyridine-3-sulfonamide

The procedure for preparation of N-(5-chloro-3-methoxypyridin-2-yl)-1-methyl-1H-imidazole-4-sulfonamide was used, except that 6-(trifluoromethyl)pyridine-3-sulfonyl chloride was substituted for 1-methyl-1H-imidazole-4-sulfonyl chloride and 3-methoxy-pyridin-2-amine substituted for 5-chloro-3-methoxypyridin-2-amine. Chromatography on silica (eluent: Methanol:DCM, 3:97) afforded N-(3-methoxypyridin-2-yl)-6-(trifluoro-methyl)pyridine-3-sulfonamide (13%) as an off-white solid; m/z=334.4 $(MH)^+$.

Methyl 6-amino-5-methoxypyridine-3-carboxylate

In a sealable tube, 5-hydroxypyridine-3-carboxylic acid (1.00 g, 5.95 mol) was dissolved in concentrated $H_2SO_4$ (1.34 mL). Then fuming nitric acid (1.35 mL) was added drop wise at 0-5° C. and the reaction mixture brought to room temperature slowly and stirred for 16 hrs before being poured onto ice cold water. The pH was adjusted to 3 with 50% NaOH solution and then extracted with isopropyl alcohol:chloroform (1:19, 4×45 mL). After separation of layers and removal of solvent under reduced pressure, a pale yellow solid was obtained (1.2 g), consisting of a mixture of starting material and 5-hydroxy-6-nitropyridine-3-carboxylic acid in a 2:3 ratio.

This mixture was dissolved in DMF (7 mL) and $K_2CO_3$ (1.50 g, 10.9 mmol) was added. The reaction mixture was stirred at room temperature for 15 min, cooled to 5-10° C. and methyl iodide (0.680 mL, 10.9 mmol) as a solution in DMF (3 mL) was added slowly. The reaction mixture was stirred at room temperature for 3 more hours, then poured into ice cold water. A yellow solid precipitated, which was filtered and washed sequentially with water then hexanes and dried under vacuum to afford methyl 5-methoxy-6-nitropyridine-3-carboxylate (0.5 g, 43%) as a yellow solid.

To a solution of methyl 5-methoxy-6-nitropyridine-3-carboxylate (1 g, 4.71 mmol) in methanol, iron powder (390 mg, 7.07 mmol) and acetic acid (3.8 mL) were added and the reaction mixture was stirred for 3 hrs. The resultant mixture was concentrated to near dryness, 30% ammonium hydroxide solution (18 mL) was added and the aqueous phase was extracted with ethyl acetate (3×50 mL). The combined organic phases were dried ($Na_2SO_4$), concentrated and the crude compound triturated with n-pentane to afford methyl 6-amino-5-methoxypyridine-3-carboxylate (0.5 g, 58%) as a red solid, m/z 183.3 $(MH)^+$.

Methyl 6-(2,5-dichlorothiophene-3-sulfonamido)-5-methoxypyridine-3-carboxylate

The procedure used to prepare N-(5-chloro-3-methoxypyridin-2-yl)-2,4-dimethyl-1,3-thiazole-5-sulfonamide was used, except that 2,5-dichlorothiophene-3-sulfonyl chloride was substituted for dimethyl-1,3-thiazole-5-sulfonyl chloride and methyl 6-amino-5-methoxypyridine-3-carboxylate was substituted for 5-chloro-3-methoxypyridin-2-amine.

The crude product was chromatographed on silica (eluent: EtOAc:Hexane, 2:8) to yield methyl 6-(2,5-dichlorothiophene-3-sulfonamido)-5-methoxypyridine-3-carboxylate (40%) as a grey solid; m/z=397.3, 399.3 (MH)+.

Methyl 6-benzenesulfonamido-5-methoxypyridine-3-carboxylate

The procedure used to prepare N-(5-chloro-3-methoxypyridin-2-yl)-1-methyl-1H-pyrazole-4-sulfonamide was used, except that benzenesulfonyl chloride was substituted for 1-methyl-1H-pyrazole-4-sulfonyl chloride and methyl 6-amino-5-methoxypyridine-3-carboxylate substituted for 5-chloro-3-methoxypyridin-2-amine. The crude compound was chromatographed on silica (eluent: EtOAc:Hexane, 2:8) to afford methyl 6-benzenesulfonamido-5-methoxypyridine-3-carboxylate (68%) as a grey solid; $^1$H NMR (400 MHz, CDCl$_3$) δ 3.89 (s, 3H), 3.91 (s, 3H), 7.46-7.61 (m, 5H), 8.17 (d, 2H), 8.46 (s, 1H).

N-(5-chloro-2-methoxypyridin-3-yl)-3-(trifluoromethoxy)benzene-1-sulfonamide

The procedure to prepare N-(5-chloro-3-methoxypyridin-2-yl)-1-methyl-1H-imidazole-4-sulfonamide was used, except that 5-chloro-2-methoxypyridin-3-amine, prepared according to literature (Int. Appl. No. PCT/EP2010/062300; Publ. No. WO 2011023677), was substituted for 5-chloro-3-methoxypyridin-2-amine and 3-(trifluoromethoxy)-benzenesulfonyl chloride was substituted for 1-methyl-1H-imidazole-4-sulfonyl chloride. The crude product was chromatographed on silica (eluent: MeOH:DCM, 1:19 containing 1% aq. ammonia) to afford N-(5-chloro-2-methoxypyridin-3-yl)-3-(trifluoromethoxy)benzene-1-sulfonamide (28%) as a white solid; m/z=381.3, 383.3 (MH)+.

N-(5-chloro-2-methoxypyridin-3-yl)-6-(trifluoromethyl)pyridine-3-sulfonamide

The procedure to prepare N-(5-chloro-3-methoxypyridin-2-yl)-2,4-dimethyl-1,3-thiazole-5-sulfonamide was used, except that 5-chloro-2-methoxypyridin-3-amine was substituted for 5-chloro-3-methoxypyridin-2-amine and 6-(trifluoromethyl)pyridine-3-sulfonyl chloride was substituted for dimethyl-1,3-thiazole-5-sulfonyl chloride. The crude product was chromatographed on silica (eluent: MeOH:DCM, 1:19) to yield N-(5-chloro-2-methoxypyridin-3-yl)-6-(trifluoromethyl)pyridine-3-sulfonamide (42%) as a grey solid; m/z=368.3, 370.3 (MH)+.

5-bromo-6-chloro-N-(5-chloro-2-methoxypyridin-3-yl)pyridine-3-sulfonamide

The procedure used to prepare N-(5-chloro-3-methoxypyridin-2-yl)-2,4-dimethyl-1,3-thiazole-5-sulfonamide was used, except that 5-bromo-6-chloropyridine-3-sulfonyl chloride was substituted for dimethyl-1,3-thiazole-5-sulfonyl chloride and 5-chloro-2-methoxypyridin-3-amine was substituted for 5-chloro-3-methoxypyridin-2-amine. The crude product was chromatographed on silica (eluent: 0-30% EtOAc in hexanes) to afford 5-bromo-6-chloro-N-(5-chloro-2-methoxypyridin-3-yl)pyridine-3-sulfonamide as an off-white solid; m/z 412.2, 414.2 (MH)+.

5-iodo-3-methoxypyridin-2-amine

To a solution of 3-methoxypyridin-2-amine (20 g, 160 mmol) in a mixture of acetic acid (200 mL) and water (20 mL) was added solid I$_2$ (41 g, 160 mmol) and the mixture heated at 50° C. for 1 hr. Another 20 g of iodine was added and the mixture heated for a further 4 hrs. To the cooled reaction mixture was added EtOAc (1 L) and 1M sodium thiosulfate (3×400 mL). The phases were separated and the organic phase was washed with brine (3×200 mL), dried (Na$_2$SO$_4$), the mixture filtered and the filtrate evaporated to dryness to afford a brown oil containing the desired product, which was purified by flash silica chromatography (eluent 3:7 EtOAc:hexane) to obtain the title compound as a yellow solid (5.5 g, 14%); $^1$H NMR (400 MHz, DMSO) δ 3.76 (s, 3H), 5.91 (s, 2H), 7.20 (d, 1H), 7.65 (d, 1H).

1-(3,5-dichlorophenyl)-N-(5-iodo-3-methoxypyridin-2-yl)methanesulfonamide

To a stirred solution of 5-iodo-3-methoxypyridin-2-amine (4.8 g, 0.019 mol) in pyridine (50 mL) was added (3,5-dichlorophenyl)methanesulfonyl chloride (5.0 g, 0.019 mol) and the reaction mixture stirred for 16 hrs then diluted with water and extracted with EtOAc (3×150 mL). The combined organic layers were washed with water and brine, the organic layer was dried (Na$_2$SO$_4$), the mixture was filtered and the filtrate concentrated to dryness to obtain the crude product which was purified by silica chromatography (eluent: 20% EtOAc in hexane) to afford the title compound as a yellow solid (5.5 g, 60%); m/z=471.3, 473.3 (MH)+.

1-(3,5-dichlorophenyl)-N-[3-methoxy-5-(propan-2-ylsulfanyl)pyridin-2-yl]methane-sulfonamide A stirred solution of 1-(3,5-dichlorophenyl)-N-(5-iodo-3-methoxypyridin-2-yl)methane-sulfonamide (1.00 g, 2.11 mmol), propane-2-thiol (161 mg, 2.11 mmol), (9,9-dimethyl-9H-xanthene-4,5-diyl)bis(diphenylphosphane) (123 mg, 0.211 mmol) in 1,4-dioxane (30 mL) was degassed for 15 min by running a stream of nitrogen through the solution. DIPEA (547 mg, 4.23 mmol) was added followed by (1E, 4E)-1,5-diphenylpenta-1,4-dien-3-one-palladium (3:2) (61 mg, 0.05 mmol) and the mixture degassed for a further 5 min before being heated at 90° C. for 16 hrs. The mixture was cooled and filtered then the filtrate was concentrated to obtain crude product which was dissolved in EtOAc and washed with water then saturated brine. The organic layer was dried (Na$_2$SO$_4$), the mixture was filtered and the filtrate concentrated to dryness to obtain the title compound as a brown solid (790 mg, 89%). m/z=421.4, 423.4 (MH)+.

1-(3,5-dichlorophenyl)-N-[3-methoxy-5-(propane-2-sulfonyl)pyridin-2-yl]methane-sulfonamide To a stirred solution of 1-(3,5-dichlorophenyl)-N-[3-methoxy-5-(propan-2-ylsulfanyl)pyridin-2-yl]methanesulfonamide (750 mg, 1.78 mmol) in CHCl$_3$ (5 mL) was added portionwise solid mCPBA (523 mg, 3.03 mmol). And the reaction mixture stirred at room temperature for 16 hrs. The mixture was then diluted with CHCl$_3$ (50 mL), washed with water (25 mL) and sat. NaHCO$_3$ (2×25 mL) and the organic layer was dried over sodium sulfate, the mixture filtered and the filtrate evaporated to dryness to afford the crude product which was purified by flash silica chromatography, (eluent 10-50% EtOAc in hexane to remove the benzoic acid products followed by 1% MeOH in DCM, to elute the compound which was isolated as an off white solid (550 mg, 68%); $^1$H NMR (400 MHz, CDCl$_3$) δ 1.36 (d, J=6.9 Hz, 6H), 3.26 (m, 1H), 3.95 (s, 3H), 4.86 (s, 2H), 7.22 (d, 2H), 7.38 (s, 1H), 7.44 (s, 1H), 7.51 (d, J=8.2 Hz, 1H), 8.49 (s, 1H).

4,6-dibromopyridazin-3-amine and 4-bromo-6-iodopyridazin-3-amine

To a mixture of 6-iodopyridazin-3-amine (500 mg, 2.26 mmol), NaHCO$_3$ (230 mg, 2.71 mmol) in MeOH (5 mL) was added bromine (117 μl, 2.26 mmol) dropwise. The resulting mixture was stirred at room temperature for 16 hrs. The solution was filtered and the filtrate concentrated in vacuo. The residue was dissolved in water, and the product extracted with EtOAc (3 times). The organic layers were combined, dried (Na$_2$SO$_4$) and concentrated in vacuo to give a dark red solid which was purified by flash silica chromatography (eluent: 20% EtOAc:Hexane) to give a 60:40 mixture of the title compounds as an off white solid (250 mg); H NMR (400 MHz, CDCl$_3$) δ 5.49 (s, 4H), 7.66 (s, 1H), 7.81 (s, 1H).

6-bromo-4-methoxypyridazin-3-amine and 6-iodo-4-methoxypyridazin-3-amine

To a stirred solution of a mixture of 4,6-dibromopyridazin-3-amine and 4-bromo-6-iodopyridazin-3-amine (10 g, compounds not separated in previous step, estimated 34 mmol) in methanol (90 mL) was added solid sodium methoxide (3.6 g, 67 mmol) at room temperature and the reaction mixture stirred at 90° C. for 16 hrs. More sodium methoxide was added regularly until all starting material had been consumed. The cooled solution was concentrated in vacuo and the residue poured into water (200 mL). The resulting solution was extracted with EtOAc three times and the organic layers were combined, dried (MgSO$_4$), and concentrated in vacuo. The residue was purified by silica column chromatography (eluent: chloroform:methanol (98:0.2 to 90:10) to afford the title mixture of methoxy ethers (3.0 g, taken into next steps without further purification); $^1$H NMR (400 MHz, CDCl$_3$) δ 3.90 (s, 3H), 3.92 (s, 3H), 5.05 (m, 3H), 6.75 (s, 1H), 6.91 (s, 1H).

4-chloro-3-(hydroxymethyl)benzonitrile

To a stirring solution of 4-chloro-3-formylbenzonitrile (5.00 g, 30.2 mmol) in ethanol (50 mL), NaBH4 (571 mg, 15.1 mmol) was added batch-wise over 1 minute under stirring at room temperature. After 1 hr, the reaction mixture was concentrated in vacuo to afford an off-white solid, treated with 2M HCl (200 mL) and DCM (260 mL), effervescence and dissolution occurred. The layers were separated, the organic layer was dried over Na$_2$SO$_4$, the mixture filtered and concentrated in vacuo to afford the title compound (4.86 g, 96%) as an off-white solid; $^1$H NMR (500 MHz, DMSO) δ 4.58 (d, 2H), 5.63 (t, 1H), 7.65 (d, 1H), 7.78 (dd, 1H), 7.85-7.94 (m, 1H).

3-(bromomethyl)-4-chlorobenzonitrile

To a stirred solution of 4-chloro-3-(hydroxymethyl)benzonitrile (4.86 g, 29.0 mmol) in DCM (100 mL) at room temperature, PBr$_3$ (3.35 mL, 35.3 mmol) was added in portions and stirring continued for 1 hr. The reaction mixture was quenched with slow additions of saturated NaHCO$_3$ until the aqueous phase was neutral. The organic phase obtained by phase separation was washed with water (100 mL), dried over Na$_2$SO$_4$, filtered and the filtrate concentrated in vacuo to afford the title compound as an off white solid (3.36 g, 50%) of an off-white solid; $^1$H NMR (500 MHz, CDCl$_3$) δ 4.56 (s, 2H), 7.52 (d, 1H), 7.54 (d, 1H), 7.75 (d, 1H).

3-[(acetylsulfanyl)methyl]-4-chlorobenzonitrile

To a stirring solution of 3-(bromomethyl)-4-chlorobenzonitrile (3.36 g, 14.6 mmol) in acetone (30 mL) was added potassium thioacetate (2.0 g, 17.5 mmol) and the mixture was left under stirring at room temperature for 1 hr. The orange reaction mixture was concentrated in vacuo before it was diluted in DCM (130 mL) and washed with water (100 mL). The organic phase obtained was dried over Na$_2$SO$_4$, filtered and concentrated in vacuo to afford the title compound as an orange solid 2.79 g, 85%); $^1$H NMR (500 MHz, DMSO) δ 2.36 (s, 3H), 4.22 (s, 2H), 7.71 (d, 1H), 7.79 (d, 1H), 7.94 (d, 1H).

(2-chloro-5-cyanophenyl)methanesulfonyl chloride

A stirring suspension of 3-[(acetylsulfanyl)methyl]-4-chlorobenzonitrile (500 mg, 2.22 mmol) in AcOH:water (30:3 mL) at room temperature was saturated with chlorine gas three times and left stirring for 30 mins. The reaction mixture was degassed with N$_2$ (to remove excess chlorine), diluted with EtOAc (60 mL), washed with water (2×40 mL), dried over Na$_2$SO$_4$, filtered and concentrated in vacuo to afford the title compound as a yellow oil (358 mg, 65%); $^1$H NMR (500 MHz, DMSO) δ 3.94 (s, 2H), 7.62 (d, 1H), 7.71 (dd, 1H), 7.92 (d, 1H).

N-(6-chloro-4-methoxypyridazin-3-yl)-1-(2-chloro-5-cyanophenyl)methane-sulfonamide To a stirring solution of 6-chloro-4-methoxypyridazin-3-amine (319 mg, 2.00 mmol) in pyridine (5 mL) at room temperature under N$_2$ was added (2-chloro-5-cyanophenyl)-methanesulfonyl chloride (500 mg, 2.00 mmol) and the mixture stirred 30 mins. The reaction mixture was concentrated in vacuo to afford viscous orange oil which was diluted in EtOAc (100 mL) and washed with water (2×80 mL). The aqueous layers were combined and more product was extracted with EtOAc (3×100 mL). The organic layers were combined, dried over Na$_2$SO$_4$ and concentrated in vacuo to afford the title compound as an orange solid (649 mg, 42%); m/z=372.8, 374.8 (MH)$^+$.

6-chloro-4-methoxypyridin-3-amine

To a suspension of 2-chloro-4-methoxy-5-nitropyridine (300 mg, 1.59 mmol), prepared according to a literature procedure (PCT Int. Appl. (2003), WO 2003080610 A1 20031002) in EtOH (3 mL) was added SnCl$_2$.2H$_2$O (1.44 g, 6.36 mmol) and the the mixture heated at 90° C. for 1 hr. The solvents were evaporated and the residue partitioned between 3M NaOH (50 mL) and DCM (100 mL). The phases were separated and the organic phase was washed with brine (20 mL), dried (Na$_2$SO$_4$), the mixture filtered and the filtrate evaporated to dryness to afford the title compound as a yellow oil (174 mg, 69%); m/z=158.9, 160.8 (MH)$^+$.

N-(5-bromo-3-methoxypyrazin-2-yl)-1-(3-chlorophenyl)methanesulfonamide

To a solution of 5-bromo-3-methoxypyrazin-2-amine (500 mg, 2.45 mmol) in pyridine (5 mL) at room temperature was added 3-chlorophenyl)methanesulfonyl chloride (552 mg, 2.45 mol) over 5 min. The mixture was stirred 10 mins, the pyridine evaporated, then DCM (60 mL) and water (10 mL) was added. The phases were separated and the organic phase was washed with brine (5 mL), dried (Na$_2$SO$_4$), the mixture filtered and the filtrate evaporated to dryness to afford an orange oil which was chromatographed on silica (Heptane:EtOAc 1:1) to afford the title compound as a light brown solid (483 mg, 48%); m/z=393.7, 395.7 (MH)$^+$.

1-(3-chlorophenyl)-N-[5-(ethylsulfanyl)-3-methoxy-pyrazin-2-yl]methanesulfonamide The procedure to prepare 1-(3,5-dichlorophenyl)-N-[3-methoxy-5-(propan-2-ylsulfanyl)-pyridin-2-yl]methanesulfonamide was used except that N-(5-bromo-3-methoxy-pyrazin-2-yl)-1-(3-chlorophenyl)methanesulfonamide was substituted for 1-(3,5-dichlorophenyl)-N-(5-iodo-3-methoxypyridin-2-yl)methanesulfonamide and sodium thioethoxide was substituted for propane-2-thiol (77%); m/z=373.8, 376.9 (MH)$^+$.

1-(3-chlorophenyl)-N-[5-(ethanesulfonyl)-3-methoxypyrazin-2-yl]methane-sulfonamide To a solution of 1-(3-chlorophenyl)-N-[5-(ethylsulfanyl)-3-methoxypyrazin-2-yl]-methanesulfonamide (285 mg, 0.732 mmol) in acetone (12 mL) and water (2 mL) was added OXONE® (1.34 g, 2.20 mmol) and the reaction mixture stirred at room temperature overnight. The acetone was evaporated, water added (10 mL) followed by DCM (80 mL). The phases were separated and the organic phase was washed with brine (5 mL), dried (Na$_2$SO$_4$), the mixture filtered and the filtrate evaporated to dryness to afford a yellow solid (333 mg at 81% purity, 91% yield) which could be used without further purification; m/z=406.1, 408.1 (MH)$^+$.

6-bromo-3-methoxypyridin-2-amine

To a stirred suspension of 6-bromo-3-methoxy-2-nitropyridine, which can be prepared by literature methods (e.g. M. Lawson et al, Organic & Biomolecular Chemistry, 11(22), 3664-3673; 2013), (3.90 g, 16.7 mmol) in EtOH:Water 1:1 (100 mL) was added iron powder (4.67 g, 83.7 mmol) and solid ammonium chloride (4.48 g, 83.7 mmol). The mixture was then heated at 75° C. for 30 mins and mixture filtered while hot. The black filter cake was washed with more hot ethanol (2×50 mL) and the combined filtrates were evaporated to near dryness then slurried with water. Filtration gave a tan solid that containing mostly the title compound (1.67 g, 44%); $^1$H NMR (500 MHz, DMSO) δ 3.76 (bs, 3H), 6.16 (bs, 2H), 6.62 (bs, 1H), 6.94 (bs, 1H).

6-bromo-5-chloro-3-methoxypyridin-2-amine

To a solution of 6-bromo-3-methoxypyridin-2-amine (1.54 g, 6.83 mmol) in AcOH (10 mL) was added N-chlorosuccinimide (1.00 g, 7.51 mmol) and the brown mixture stirred overnight. The solvent was evaporated and DCM (20 mL) and saturated NaHCO$_3$ (20 mL) were added. The phases were separated and the organic phase was washed with brine (3 mL), dried (Na$_2$SO$_4$), the mixture filtered and the filtrate evaporated to dryness to afford a brown solid which was chromatographed on silica (eluent heptane:EtOAc 5:1 then 5:3) to afford mainly the title compound as a yellow solid (570 mg, 35%) m/z=238.8 (MH)$^+$.

N-(6-bromo-5-chloro-3-methoxypyridin-2-yl)-1-(3,5-dichlorophenyl)methane-sulfonamide The procedure to prepare 1-(3,5-dichlorophenyl)-N-(5-iodo-3-methoxypyridin-2-yl)-methanesulfonamide was used, except that 6-bromo-5-chloro-3-methoxypyridin-2-amine was substituted for 5-iodo-3-methoxypyridin-2-amine (34%); m/z=460.7 (MH)$^+$.

5-chloro-3-(hydroxymethyl)benzonitrile

The procedure to prepare 4-chloro-3-(hydroxymethyl)benzonitrile was used except that 5-chloro-3-formylbenzonitrile was substituted for 4-chloro-3-formylbenzonitrile (62%); $^1$H NMR (500 MHz, CDCl$_3$) δ 4.77 (s, 2H), 7.55-7.61 (m, 2H), 7.63 (d, 1H).

3-[(acetylsulfanyl)methyl]-5-chlorobenzonitrile

To a solution of 5-chloro-3-(hydroxymethyl)benzonitrile (1.25 g, 7.48 mmol) in DCM (100 mL) was added neat PBr$_3$ (2.43 g, 7.48 mmol) and the mixture stirred 1 hr. The mixture was quenched by the addition of saturated NaHCO$_3$ until the aqueous phase was neutral or slightly basic. The phases were separated and the organic phase was washed with brine (20 mL), dried (Na$_2$SO$_4$), the mixture filtered and the filtrate evaporated to dryness to afford the intermediate bromide as a colourless oil. This was dissolved in acetone (100 mL), thioacetic acid (569 mg, 7.48 mmol) and K$_2$CO$_3$ (1.55 g, 11.2 mmol) added and the mixture stirred 1 hr. DCM (100 mL) and saturated brine (30 mL) were then added. The phases were separated and the organic phase was washed with more brine (10 mL), dried (Na$_2$SO$_4$), the mixture filtered and the filtrate evaporated to dryness to afford a brown oil, containing the desired title compound (880 mg, 44%); $^1$H NMR (500 MHz, CDCl$_3$) δ 2.41 (s, 3H), 4.09 (s, 2H), 7.47-7.59 (m, 3H).

(3-chloro-5-cyanophenyl)methanesulfonyl chloride

The procedure to prepare (2-chloro-5-cyanophenyl)methanesulfonyl chloride was used except that 3-[(acetylsulfanyl)methyl]-5-chlorobenzonitrile was substituted for 3-[(acetyl-sulfanyl)methyl]-4-chlorobenzonitrile (54%); $^1$H NMR (500 MHz, CDCl$_3$) δ 4.87 (s, 2H), 7.71 (s, 1H), 7.76 (s, 1H), 7.80 (s, 1H).

1-(2-chlorophenyl)-N-(6-iodo-4-methoxypyridazin-3-yl)methanesulfonamide

To a solution of 6-iodo-4-methoxypyridazin-3-amine (614 mg, 2.34 mmol) in pyridine (3 mL) at 80° C. was added (2-chlorophenyl)methanesulfonyl chloride (500 mg, 2.21 mmol) over 5 min. The mixture was stirred 10 min, the pyridine evaporated and the residue chromatographed on silica (eluent: EtOAc:Heptane 2:1) to afford the title compound as a light brown solid (180 mg, 15%); m/x 439.7 (MH)$^+$. Note: starting material and product also contained the bromo pyridazine (see above).

1-(2-chlorophenyl)-N-[4-methoxy-6-(methylsulfanyl)pyridazin-3-yl]methane-sulfonamide The procedure to prepare 1-(3,5-dichlorophenyl)-N-[3-methoxy-5-(propan-2-ylsulfanyl)-pyridin-2-yl]methanesulfonamide was used except that 1-(2-chlorophenyl)-N-(6-iodo-4-methoxypyridazin-3-yl)methanesulfonamide was substituted for 1-(3,5-dichlorophenyl)-N-(5-iodo-3-methoxypyridin-2-yl)methanesulfonamide and sodium thiomethoxide was substituted for propane-2-thiol (25%); m/z=359.8, 361.9 (MH)+.

1-(2-chlorophenyl)-N-(6-methanesulfonyl-4-methoxypyridazin-3-yl)methane-sulfonamide The procedure to prepare 1-(3-chlorophenyl)-N-[5-(ethanesulfonyl)-3-methoxypyrazin-2-yl]methanesulfonamide was used except that 1-(2-chlorophenyl)-N-[4-methoxy-6-methylsulfanyl)pyridazin-3-yl]methanesulfonamide was substituted for 1-(3-chloro-phenyl)-N-[5-(ethanesulfonyl)-3-methoxypyrazin-2-yl]methanesulfonamide (57%); m/z=391.9, 393.8 (MH)+.

Methyl 3-[(5-chloro-4-hydroxypyridin-3-yl)sulfamoyl]benzoate

To a stirred solution of 3-amino-5-chloropyridin-4-ol (500 mg, 3.46 mmol) in pyridine (3 mL) was added DMAP (10 mg, 0.08 mmol) and methyl 3-(chlorosulfonyl)benzoate (812 mg, 3.46 mmol). The reaction was stirred at 40° C. under nitrogen for 4 hrs. The reaction mixture was concentrated in vacuo, diluted in EtOAc (140 mL), the organic layer washed with water (2×100 mL) and washed with brine. The organic layer was dried over $Na_2SO_4$ and concentrated in vacuo to afford the title compound as an orange solid (185 mg, 14%); m/z=342.8, 344.9 (MH)+.

3-[(5-chloro-4-hydroxypyridin-3-yl)sulfamoyl]benzoic acid

To a stirred solution of methyl 3-[(5-chloro-4-hydroxypyridin-3-yl)sulfamoyl]benzoate, 203 mg, 0.59 mmol) in ethanol (10 mL) at room temperature was added aqueous sodium hydroxide (2 M, 1.5 mL) and the reaction stirred at 40° C. under nitrogen for 1 hr. The reaction mixture was concentrated in vacuo before being acidified with 2 M HCl until a pH of 1 was achieved. The precipitated solid was collected by vacuum filtration to afford the title compound as an orange solid (108 mg, 57%); m/z=328.8 (MH)+.

1-(3,4-difluorophenyl)-N-(6-iodo-4-methoxypyridazin-3-yl)methanesulfonamide

The procedure to prepare N-(6-chloro-4-methoxypyridazin-3-yl)-1-(2-chloro-5-cyano-phenyl)methanesulfonamide was used except that (3,4-difluorophenyl)methanesulfonyl chloride was substituted for (2-chloro-5-cyanophenyl) methanesulfonyl chloride and 6-iodo-4-methoxypyridazin-3-amine was substituted for 6-chloro-4-methoxypyridazin-3-amine; (57%); $^1$H NMR (500 MHz, DMSO) δ 3.92 (d, 3H), 4.88 (br.s, 2H), 7.19 (s, 1H), 7.44 (qd, 2H), 7.50-7.68 (m, 1H), 10.55 (br.s, 1H).

1-(3,4-difluorophenyl)-N-[4-methoxy-6-(methylsulfanyl)pyridazin-3-yl]methane-sulfonamide 1-(3,4-difluorophenyl)-N-(6-iodo-4-methoxypyridazin-3-yl)methanesulfonamide (680 mg, 1.43 mmol), sodium methanethiolate (121 mg, 1.72 mmol) (1E,4E)-1,5-diphenylpenta-1,4-dien-3-one-palladium (3:2) (65 mg, 0.07 mmol), (9,9-dimethyl-9H-xanthene-4,5-diyl)bis(diphenylphosphane) (85 mg, 0.14 mmol) and anhydrous dioxane (12 mL) were charged to a round bottom flask, DIPEA (498 µL, 2.87 mmol) was added and the mixture was degassed by bubbling with nitrogen for approximately 5 min. The mixture was sealed under nitrogen and stirred at 75° C. for 1 h. EtOAc (70 mL) and water (20 mL) were added and the phases were separated. The aqueous was back extracted with EtOAc (2×10 mL). The combined organic phases were washed with brine (20 mL), dried over anhydrous $Na_2SO_4$, filtered and the filtrate was concentrated in vacuo. The residue obtained was purified by flash column chromatography over silica (Biotage 25 g SNAP cartridge) eluted with heptane:EtOAc 1:0 to 6:4 to 2:8 to afford the title compound (518 mg, 99%) as an off white solid. $^1$H NMR (500 MHz, $CDCl_3$) δ 2.50 (s, 3H), 3.93 (s, 3H), 4.44 (s, 2H), 6.47 (s, 1H), 7.10 (dt, 1H), 7.14-7.20 (m, 1H), 7.29 (ddd, 1H).

1-(3,4-difluorophenyl)-N-(6-methanesulfonyl-4-methoxypyridazin-3-yl)methane-sulfonamide The procedure to prepare 1-(3,5-dichlorophenyl)-N-[3-methoxy-5-(propane-2-sulfonyl)-pyridin-2-yl]methanesulfonamide was used except that 1-(3,4-difluorophenyl)-N-[4-methoxy-6-(methylsulfanyl)pyridazin-3-yl] methanesulfonamide was substituted for 1-(3,5-dichlorophenyl)-N-[3-methoxy-5-(propan-2-ylsulfanyl) pyridin-2-yl]methane-sulfonamide and the pH of the solution was brought to 1 with 1M HCl prior to extraction; (44%)$^1$H NMR (500 MHz, $CDCl_3$) δ 3.36 (s, 3H), 4.06 (s, 3H), 4.81 (d, 2H), 7.10-7.19 (m, 2H), 7.27-7.31 (m, 1H), 7.37 (s, 1H).

N-(5-bromo-3-methoxypyrazin-2-yl)-1-(3,5-dichlorophenyl)methanesulfonamide

To a stirring solution of 5-bromo-3-methoxypyrazin-2-amine (1.50 g, 7.35 mmol) in pyridine (15 mL), DMAP (15 mg, 0.12 mmol) and (3,5-dichlorophenyl)methanesulfonyl chloride (1.91 g, 7.34 mmol) was added. The reaction was left stirring at room temperature under nitrogen for 2 hrs. A further addition of (3,5-dichlorophenyl)methanesulfonyl chloride (0.20 g, 0.77 mmol) was added to the reaction mixture which was then left stirring for 1 hr at room temperature. The reaction mixture was concentrated in vacuo resulting in a viscous orange mixture which was then diluted with EtOAc (100 mL), washed with water (2×80 mL), the organic layer was dried over $Na_2SO_4$ and concentrated in vacuo to afford an orange solid. This was dissolved in EtOAc (30 mL) and acidified with HCl (2M, 20 mL) which resulted in the precipitation of the title compound as a white solid. The organic and aqueous layer were subsequently separated, the organic layer was washed with water (3×30 mL), dried over $Na_2SO_4$ and concentrated in vacuo to afford a second crop of the title compound as an orange solid (combined yield 1.73 g, 54%); $^1$H NMR (500 MHz, DMSO) δ 3.93 (s, 3H), 4.88 (s, 2H), 7.36 (d, 2H), 7.63 (m, 1H), 8.12 (s, 1H), 10.80 (s, 1H).

N-(5-cyano-3-methoxypyrazin-2-yl)-1-(3,5-dichlorophenyl)methanesulfonamide

To a solution of N-(5-bromo-3-methoxypyrazin-2-yl)-1-(3,5-dichlorophenyl)methane-sulfonamide (250 mg, 0.585 mol) in NMP (10 mL) was added solid copper(I) cyanide (262 mg, 2.93 mmol) and the mixture heated at 170° C. for 1 hr. The cooled reaction mixture was then treated with EtOAc (50 mL) and dilute ammonia (15 mL). The phases were separated and the organic phase was washed with brine (5 mL), dried (Na$_2$SO$_4$), the mixture filtered and the filtrate evaporated to dryness to afford a brown oil containing NMP and desired product. Carried over into next step without further purification; m/z=372.8, 374.9 (MH)$^+$.

1-(3,5-dichlorophenyl)-N-[4-methoxy-6-(propylsulfanyl)pyridazin-3-yl]methane-sulfonamide A stirred solution of N-(6-chloro-4-methoxypyridazin-3-yl)-1-(3,5-dichlorophenyl)-methanesulfonamide (800 mg, 2.09 mmol), propane-1-thiol (159 mg, 2.09 mmol), (9,9-dimethyl-9H-xanthene-4,5-diyl)bis(diphenylphosphane) (121 mg, 0.21 mmol) in 1,4-Dioxane (18 mL) was degassed for 15 min, then followed dropwise addition of DIPEA (540 mg, 4.18 mmol) then (1E,4E)-1,5-diphenylpenta-1,4-dien-3-one-palladium (3:2) (72 mg, 0.08 mmol). The mixture was degassed for a further 5 mins then stirred at at 90° C. for a 3.5 hrs. The cooled mixture was filtered, the filtrate was concentrated and the residue dissolved in EtOAc, and the resultant layer washed with water and brine. The organic layer was concentrated and the residues purified by flash silica chromatography (eluent 25% EtOAc in hexane) to afford the title compound as a yellow solid (450 mg, 51%); $^1$H NMR (400 MHz, DMSO) δ 0.98 (t, 3H), 1.68 (m, 2H), 3.14 (t, 2H), 3.88 (s, 3H), 4.68 (s, 2H), 7.09 (s, 1H), 7.41 (m, 2H), 7.57 (s, 1H).

1-(3,5-dichlorophenyl)-N-[4-methoxy-6-(propane-1-sulfonyl)pyridazin-3-yl]-methanesulfonamide The method used to prepare 1-(3,5-dichlorophenyl)-N-[3-methoxy-5-(propane-2-sulfonyl)pyridin-2-yl]methanesulfonamide was used except that 1-(3,5-dichlorophenyl)-N-[4-methoxy-6-(propylsulfanyl)pyridazin-3-yl]methanesulfonamide was substituted for 1-(3,5-dichlorophenyl)-N-[3-methoxy-5-(propan-2-ylsulfanyl)pyridin-2-yl]methane-sulfonamide (51%); $^1$H NMR (400 MHz, DMSO) δ 0.97 (t, 3H), 1.68 (m, 2H), 3.49-3.62 (m, 2H), 4.03 (s, 3H), 4.97 (s, 2H), 7.41 (s, 2H), 7.62 (s, 2H), 11.21 (s, 1H).

5-chloro-2-nitropyridin-3-ol 5-chloropyridin-3-ol (2.00 g, 15.4 mmol) was dissolved in concentrated H$_2$SO$_4$ (15 mL) at 5° C. Concentrated nitric acid (1.0 mL) was then added. The reaction was allowed to warm to room temperature over 3 hrs. The reaction solution was poured onto ice water (25 mL). The resultant precipitate was filtered, washed with water and dried overnight at 40° C. in vacuo to afford was obtained as a yellow powder, (1.80 g, 67%); $^1$H NMR (400 MHz, CDCl$_3$) δ 7.68 (d, 1H), 8.15 (d, 1H), 10.29 (s, 1H).

5-chloro-2-nitro-3-(prop-2-en-1-yloxy)pyridine

To a solution of 5-chloro-2-nitropyridin-3-ol (1.5 g, 8.59 mmol) in acetonitrile (30 mL) was added K$_2$CO$_3$ (2.38 g, 17.2 mmol) and the mixture stirred for 15 mins followed by dropwise addition of 3-bromoprop-1-ene (1.25 g, 10.31 mmol). The reaction mixture was refluxed for 16 hrs, cooled and filtered. The filtrate was concentrated and the residue purified by flash silica chromatography (eluent 1:9 EtOAc) to afford the title compound as a yellow solid (1.40 g, 76%); $^1$H NMR (400 MHz, CDCl$_3$) δ 4.72 (dt, 2H), 5.45 (m, 2H), 6.01 (m, 1H), 7.50 (d, 1H), 8.04 (d, 1H).

5-chloro-3-(prop-2-en-1-yloxy)pyridin-2-amine

To a stirred solution of 5-chloro-2-nitro-3-(prop-2-en-1-yloxy)pyridine (1.40 g, 6.52 mmol) in ethanol (150 mL) was added iron powder (3.64 g, 65.2 mmol) and 1 mL of conc. HCl at room temperature for 1 hr. The cooled mixture was filtered through Celite and the filtrate concentrated to dryness. 1M NaOH was added to make the mixture basic and this was then extracted with EtOAc. The organic layer was dried (MgSO$_4$), filtered and the filtrate concentrated to obtain the title compound as a brown solid (0.800 g, 66%); $^1$H NMR (400 MHz, CDCl$_3$) δ 4.55 (d, 2H), 4.72 (s, 2H), 5.49-5.26 (m, 2H), 6.03 (ddd, 1H), 6.89 (d, 1H), 7.64 (d, J=1.7 Hz, 1H).

N-[5-chloro-3-(prop-2-en-1-yloxy)pyridin-2-yl]-1-(3,5-dimethoxyphenyl)methane-sulfonamide To 1-(bromomethyl)-3,5-dimethoxybenzene (1.00 g, 4.33 mmol) in acetone (18 mL) was added disodium sulfite (0.55 g, 4.33 mmol) in water (5 mL) and the mixture refluxed. After completion of the reaction, as judged by disappearance of starting material on TLC, the mixture was cooled to room temperature and concentrated. The resulting white precipitate was filtered off and the solid washed with DCM (30 mL) then dried under high vacuum to give the sodium (3,5-dimethoxyphenyl)methanesulfonate (780 mg, 71%)

A stirred solution of sodium (3,5-dimethoxyphenyl)methanesulfonate (800 mg, 3.15 mmol) in DCM (25 mL) and a few drops of DMF was cooled to −20° C. then oxalyl chloride (26901, 31.4 mmol) was added The mixture was stirred for 30 min at this temperature then allowed to warm to room temperature and stirred for 2 hrs. DCM was added and organic phase washed with water and brine (2×40 mL). The organic layer was dried (Na$_2$SO$_4$) and concentrated to obtain of (3,5-dimethoxyphenyl)methanesulfonyl chloride as a yellow liquid which was used immediately (678 mg).

To a stirred solution of 5-chloro-3-(prop-2-en-1-yloxy)pyridin-2-amine (500 mg, 2.71 mmol) in DCM (15 mL), was added DIPEA (1050 mg, 8.12 mmol). After 10-15 mins (3,5-dimethoxyphenyl)methanesulfonyl chloride (678 mg, 2.71 mmol) was added and the reaction mixture stirred at room temperature for 16 hrs. It was then concentrated and the residue suspended in water and extracted with EtOAc (3×50 mL). The organic layer was dried (Na$_2$SO$_4$), filtered and the filtrate concentrated. The residue was purified by automated reverse-phase HPLC (low pH method) to afford the title (35 mg, 3%) as an off white solid; m/z=399 (MH)$^+$.

5,6-dichloro-N-(5-chloro-3-methoxypyridin-2-yl)pyridine-3-sulfonamide 5-chloro-3-methoxypyridin-2-amine (250 mg, 1.58 mmol) was dissolved in pyridine (2 mL). The solution was cooled to 0-5° C. To this cold solution 5,6-dichloropyridine-3-sulfonyl chloride (389 mg, 1.58 mmol) was added and the resultant reaction mixture was stirred at room temperature overnight. To this reaction mixture water was added and it was extracted with DCM. The combined organic layer was dried over Na$_2$SO$_4$ and evaporated under reduced pressure. The residue was purified using flash silica chromatography (20% EtOAc in hexane) to afford the title compound as an off white solid (70 mg, 11%); m/z=368.3, 370.3 (MH)$^+$.

5-chloro-N-(5-chloro-3-methoxypyridin-2-yl)-6-(dimethylamino)pyridine-3-sulfonamide A solution of 5,6-dichloro-N-(5-chloro-3-methoxypyridin-2-yl)pyridine-3-sulfonamide (150 mg, 0.41 mmol) and 40% aqueous dimethylamine (50 mg, 0.45 mmol) in THF (5 mL) was mixed in a sealable tube. The tube was sealed and heated 12 hrs at 90° C. To this reaction mixture water (3 mL) was added and it was extracted with DCM (3×5 mL). The combined organic layers were dried over $Na_2SO_4$ and evaporated under reduced pressure to afford the title compound as an off white solid (145 mg, 95%); $^1$H NMR (400 MHz, $CDCl_3$) δ 3.18 (s, 6H), 3.86 (s, 3H), 7.03 (d, 1H), 7.84 (m, 1H), 8.17 (d, 1H), 8.73 (d, 1H).

2-chloro-4-methoxypyrimidin-5-amine 5.4M sodium methoxide (100 μL, 0.54 mmol) was added dropwise to a stirring solution of 2,4-dichloropyrimidin-5-amine (89 mg, 0.54 mmol) in methanol (2 mL) at 0° C. under nitrogen. The reaction was allowed to warm to room temperature and stirred for 1 hr. The reaction was treated with more 5.4M sodium methoxide (10 μL) and stirred for a further 1 hr, then left to stand at room temperature for 64 hrs. The reaction was quenched with acetic acid (1 mL) and concentrated in vacuo. The residue was dissolved in EtOAc (20 mL) and washed with saturated aqueous $NaHCO_3$ (2×6 mL), brine (6 mL), dried over $Na_2SO_4$, filtered and the filtrate was concentrated in vacuo. The residue obtained was purified by flash column chromatography over silica (Biotage 10 g SNAP cartridge) eluting with heptane:EtOAc, smooth gradient 1:0 to 7:3 to afford the title compound as a white solid (80 mg, 83%); $^1$H NMR (500 MHz, DMSO) δ 3.93 (s, 3H), 5.31 (s, 2H), 7.72 (s, 1H).

N-(2-chloro-4-methoxypyrimidin-5-yl)-1-(3,5-dichlorophenyl)methanesulfonamide (3,5-dichlorophenyl)methanesulfonyl chloride (128 mg, 0.49 mmol) was added to a solution of 2-chloro-4-methoxypyrimidin-5-amine (75 mg, 0.47 mmol) and DIPEA (123 μL, 0.71 mmol) in DCM (2 mL). The reaction was allowed to stir at room temperature for 18 hrs. The reaction was treated with more (3,5-dichlorophenyl)methanesulfonyl chloride (20 mg, 0.08 mmol) and stirred for a further 4 hrs. The reaction was diluted with DCM (15 mL), washed with saturated aqueous citric acid (2×6 mL), sat. aq. $NaHCO_3$ (2×6 mL), brine (6 mL), dried over anhydrous sodium sulfate, filtered and the filtrate was concentrated in vacuo. The residue obtained was purified by flash column chromatography over silica (Biotage 10 g SNAP cartridge) eluting with Heptane:EtOAc constant gradient 1:0 to 7:3 to afford the title compound (108 mg, 60%) as a white solid; m/z=381.8, 383.9 $(MH)^+$.

1-(3,5-dichlorophenyl)-N-[5-(ethanesulfanyl)-3-methoxypyridin-2-yl]methane-sulfonamide The procedure to prepare 1-(3,5-dichlorophenyl)-N-[3-methoxy-5-(propan-2-yl-sulfanyl)pyridin-2-yl]methanesulfonamide was used except that ethanethiol was substituted for propan-2-thiol (59%); m/z=407.3, 405.3 $(MH)^+$.

1-(3,5-dichlorophenyl)-N-[5-(ethanesulfonyl)-3-methoxypyridin-2-yl]methane-sulfonamide The procedure to prepare 1-(3,5-dichlorophenyl)-N-[3-methoxy-5-(propane-2-sulfonyl)-pyridin-2-yl]methanesulfonamide was used except that 1-(3,5-dichlorophenyl)-N-[5-(ethanesulfanyl)-3-methoxypyridin-2-yl]methanesulfonamide was substituted for 1-(3,5-dichlorophenyl)-N-[3-methoxy-5-(propan-2-ylsulfanyl)pyridin-2-yl]methanesulfonamide (70%); m/z=439.4, 441.4 $(MH)^+$.

1-(3,5-dichlorophenyl)-N-[6-(ethylsulfanyl)-4-methoxypyridazin-3-yl]methane-sulfonamide The procedure for the preparation of 1-(3,5-dichlorophenyl)-N-[4-methoxy-6-(propyl-sulfanyl)pyridazin-3-yl] methanesulfonamide was used except that ethanethiol was substituted for propane-1-thiol. Purification was carried out after workup using ether/pentane recrystallisation (65%); $^1$H NMR (400 MHz, $CDCl_3$), δ 1.34 (t, 3H), 3.01-3.04 (m, 2H), 3.94 (s, 3H), 4.34 (s, 2H), 6.40 (s, 1H), 7.25-7.29 (m, 1H), 7.34 (d, 2H). 2

1-(3,5-dichlorophenyl)-N-[6-(ethanesulfonyl)-4-methoxypyridazin-3-yl]methane sulfonamide The procedure for the preparation of 1-(3,5-dichlorophenyl)-N-[3-methoxy-5-(propane-2-sulfonyl)pyridin-2-yl] methanesulfonamide was used except that 1-(3,5-dichlorophenyl)-N-[6-(ethylsulfanyl)-4-methoxypyridazin-3-yl] methanesulfonamide was substituted for 1-(3,5-dichlorophenyl)-N-[3-methoxy-5-(propan-2-ylsulfanyl) pyridin-2-yl]methane-sulfonamide (51%); $^1$H NMR (400 MHz, DMSO), δ 1.21 (t, 3H), 3.57-3.62 (m, 2H), 4.03 (s, 3H), 4.97 (s, 2H), 7.41 (s, 2H), 7.63 (s, 2H).

1-(3,5-dichlorophenyl)-N-(5-methanesulfanyl-3-methoxypyrazin-2-yl)methane-sulfonamide The procedure for preparation of 1-(3,5-dichlorophenyl)-N-[4-methoxy-6-(propyl-sulfanyl)pyridazin-3-yl]methane-sulfonamide was used except that N-(5-bromo-3-methoxypyrazin-2-yl)-1-(3,5-dichlorophenyl)methanesulfonamide was substituted for N-(6-chloro-4-methoxypyridazin-3-yl)-1-(3,5-dichlorophenyl)methanesulfonamide and sodium methanethiolate was substituted for propane-1-thiol; (94%); m/z=393.8, 395.9 $(MH)^+$.

1-(3,5-dichlorophenyl)-N-(5-methanesulfonyl-3-methoxypyrazin-2-yl)methane-sulfonamide To a solution of 1-(3,5-dichlorophenyl)-N-(5-methanesulfanyl-3-methoxypyrazin-2-yl)methanesulfonamide (418 mg, 1.06 mmol) in DCM (15 mL) was added mCPBA (522 mg, 70%, 2.12 mmol) and the reaction stirred at room temperature for 3 hrs. More mCPBA was added every hour (200 mg each time) until all the sulfoxide intermediate had converted to sulfone, as judgded by LCMS. The solvent was evaporated and the solid chromatographed on silica (eluent: heptane:EtOAc 3:1 then 1:1 then neat EtOAc) to afford the title compound as a colourless oil (213 mg, 47%); m/z=425.8, 427.9 $(MH)^+$.

2,5-dichloro-N-(6-chloro-4-methoxypyridazin-3-yl) thiophene-3-sulfonamide

A mixture of 6-chloro-4-methoxypyridazin-3-amine (200 mg, 1.25 mmol) and 2,5-dichlorothiophene-3-sulfonyl chloride (347 mg, 1.38 mmol) was dissolved in DCM (5 mL). To that solution pyridine (991 mg, 13 mmol) was added and reaction mixture was stirred at room temperature for 12 h. Water was added and the mixture was extracted with EtOAc (3×30 mL). The combined organic layers were washed with brine, dried ($Na_2SO_4$), filtered and the filtrate evaporated to give the crude title compound as an off white solid which was used without further purification (180 mg at 51%, 19%); m/z=374.1, 376.1 $(MH)^+$.

5-bromo-6-chloro-N-(6-chloro-4-methoxypyridazin-3-yl)pyridine-3-sulfonamide

To a suspension of 6-chloro-4-methoxypyridazin-3-amine (3.00 g, 18.8 mmol) in dry dimethoxyethane (60 mL) was added sodium hydride (752 mg, 60%, 18.8 mmol) and the mixture stirred 5 mins. 5-bromo-6-chloropyridine-3-sulfonyl chloride (4.92 g, 16.9 mmol) was then added and the mixture stirred 1 hr. EtOAc was added (100 mL) followed by water (15 mL) and the phases were separated. The aqueous phase was then acidified (1M HCl) resulting in a white emulsion. More EtOAc (50 mL) was added. The phases were separated and the organic phase was washed with brine (15 mL), dried ($Na_2SO_4$), the mixture filtered and the filtrate evaporated to dryness to afford an off white solid containing the title compound (1.03 g, 13%); m/z=412.7, 414.7 (MH)$^+$.

N-(6-chloro-4-methoxypyridazin-3-yl)-3-(trifluoromethoxy)benzene-1-sulfonamide Excess NaH (301 mg, low purity) was added to a stirred solution of 6-chloro-4-methoxy-pyridazin-3-amine (200 mg, 1.26 mmol) in DME (6 mL) under nitrogen at room temperature. After 1 hr 3-(trifluoromethoxy)benzene-1-sulfonyl chloride (359 mg, 1.38 mmol) was added and the resultant mixture was stirred for 2 hrs at room temperature. Aqueous citric acid was added and the aqueous phase was extracted with EtOAc (3×30 mL). The combined organic layers were dried on $Na_2SO_4$ filtered and the filtrate evaporated to afford the crude title compound as a brown solid (210 mg at 81% purity, 35%); m/z=384.2, 386.2 (MH)$^+$.

1-(3,5-dichlorophenyl)-N-[4-methoxy-6-(propan-2-ylsulfanyl)pyridazin-3-yl]-methanesulfonamide The method to prepare 1-(3,5-dichlorophenyl)-N-[4-methoxy-6-(propylsulfanyl)-pyridazin-3-yl]methanesulfonamide was used except that propan-2-thiol was substituted for propan-1-thiol (51%); m/z=422.4, 424.4 (MH)$^+$.

1-(3,5-dichlorophenyl)-N-[4-methoxy-6-(propane-2-sulfonyl)pyridazin-3-yl]-methanesulfonamide The method to prepare 1-(3,5-dichlorophenyl)-N-[3-methoxy-5-(propane-2-sulfonyl)-pyridin-2-yl]methanesulfonamide was used except that 1-(3,5-dichlorophenyl)-N-[4-methoxy-6-(propan-2-ylsulfanyl)pyridazin-3-yl]methanesulfonamide was substituted for 1-(3,5-dichlorophenyl)-N-[3-methoxy-5-(propane-2-sulfanyl)pyridin-2-yl]methane-sulfonamide (52%); m/z=454.4, 456.4 (MH)$^+$.

5-bromo-N-(5-chloro-3-methoxypyridin-2-yl)-6-(dimethylamino)pyridine-3-sulfonamide The procedure to prepare 5-chloro-N-(5-chloro-3-methoxypyridin-2-yl)-6-(dimethyl-amino)pyridine-3-sulfonamide was used except that 5-bromo-6-chloro-N-(5-chloro-3-methoxypyridin-2-yl)pyridine-3-sulfonamide was substituted for 5,6-dichloro-N-(5-chloro-3-methoxypyridin-2-yl)pyridine-3-sulfonamide (81%); m/z=421.3, 423.3 (MH)$^+$.

N-(6-chloro-4-methoxypyridazin-3-yl)-3-cyanobenzene-1-sulfonamide

To a suspension of potassium 2-methylpropan-2-olate (70 mg, 0.63 mmol) in THF (4 mL) at 0° C. was added 6-chloro-4-methoxypyridazin-3-amine (100 mg, 0.63 mmol) and stirred for 30 mins. 3-cyanobenzene-1-sulfonyl chloride (126 mg, 0.63 mmol) was added to the reaction mixture and was stirred for 18 hrs at room temperature. The reaction mixture was diluted with EtOAc (15 mL) and washed with 1M aqueous HCl (10 mL). The organic phase was dried using $Na_2SO_4$, filtered and concentrated. The crude residue was purified using silica column chromatography (DCM:MeOH 90:10) to yield the title compound (63 mg, 30%); m/z=323.0, 325.0 (MH)$^+$.

1-(3,5-dichlorophenyl)-N-[3-methoxy-5-(propylsulfanyl)pyridin-2-yl]methane-sulfonamide The procedure to prepare 1-(3,5-dichlorophenyl)-N-[3-methoxy-5-(propan-2-ylsulfanyl)-pyridin-2-yl]methanesulfonamide was used except that propane-1-thiol was substituted for propane-2-thiol (65%); $^1$H NMR (400 MHz, DMSO) δ 0.97 (t, 3H), 1.58 (m, 2H), 2.97 (t, 2H), 3.81 (s, 3H), 4.90 (s, 2H), 7.34 (d, 2H), 7.41 (d, 1H), 7.61 (s, 1H), 7.91 (d, 1H), 9.97 (s, 1H).

1-(3,5-dichlorophenyl)-N-[3-methoxy-5-(propane-1-sulfonyl)pyridin-2-yl]methane-sulfonamide The procedure to prepare 1-(3,5-dichlorophenyl)-N-[3-methoxy-5-(propane-2-sulfonyl)-pyridin-2-yl]methanesulfonamide was used except that 1-(3,5-dichlorophenyl)-N-[3-methoxy-5-(propylsulfanyl)pyridin-2-yl]methanesulfonamide was substituted for 1-(3,5-dichlorophenyl)-N-[3-methoxy-5-(propan-2-ylsulfanyl)pyridin-2-yl]methanesulfonamide (61%); m/z=453.0, 455.0 (MH)$^+$.

1-(3,5-dichlorophenyl)-N-(6-methanesulfanyl-4-methoxypyridazin-3-yl)methane-sulfonamide The procedure to prepare 1-(3,5-dichlorophenyl)-N-[4-methoxy-6-(propylsulfanyl)-pyridazin-3-yl]methanesulfonamide was used except that sodium methanethiolate was substituted for propane-1-thiol (56%); $^1$H NMR (400 MHz, $CDCl_3$) δ 2.45 (s, 3H), 3.95 (s, 3H), 4.31 (s, 2H), 6.42 (s, 1H), 7.26-7.39 (m, 3H).

1-(3,5-dichlorophenyl)-N-(6-methanesulfonyl-4-methoxypyridazin-3-yl)methane-sulfonamide To a solution of 1-(3,5-dichlorophenyl)-N-(6-methanesulfanyl-4-methoxypyridazin-3-yl)methanesulfonamide (800 mg, 2.03 mmol) in chloroform (25 mL) was added mCPBA (1.05 g, 6.09 mmol) and the reaction mixture stirred for 16 hrs at room temperature. The chloroform was evaporated and the crude residue purified directly by silica chromatography (eluent DCM:MeOH (95:5) to afford the title compound (500 mg at 64% purity, 37%) as a white solid. $^1$H NMR (400 MHz, DMSO) δ 3.39 (s, 3H), 3.97 (s, 3H), 4.82 (s, 2H), 7.39 (s, 1H), 7.59 (s, 1H), 7.72 (s, 1H), 7.91 (s, 2H).

4-(bromomethyl)thiophene-2-carbonitrile 4-methylthiophene-2-carbonitrile (900 mg, 7.31 mmol) was dissolved in carbon tetrachloride (20 mL) then N-bromosuccinimide (1.43 g, 8.03 mmol) and AIBN (120 mg, 0.73 mmol) were added and the resulting reaction mixture was refluxed for 8 hrs. To the cooled reaction mixture was added water and the product was extracted with EtOAc (3×10 mL). The combined organic layers were dried on Na$_2$SO$_4$, the mixture filtered and the solvent evaporated. The residue was purified by silica chromatography (eluent: 2% EtOAc in n-hexane) to afford the title compound as a white solid (810 mg, 49%); (400 MHz, CDCl$_3$) δ 4.44 (s, 2H), 7.53 (m, 1H), 7.61-7.67 (m, 1H).

4-[(acetylsulfanyl)methyl]thiophene-2-carbonitrile 4-(bromomethyl)thiophene-2-carbonitrile (800 mg, 3.96 mmol) was dissolved in acetone then potassium thioacetate (1.13 g, 9.91 mmol) was added and the reaction mixture stirred at room temperature for 2 hrs. Water was added to the reaction mixture and the compound was extracted with EtOAc (3×30 mL). The combined organic layers were dried on Na$_2$SO$_4$, the solvents evaporated. The crude residue was purified by silica chromatography (eluent 2% EtOAc in n-hexane) to afford the title compound as a brown oil (710 mg, 86%); (400 MHz, CDCl$_3$) δ 2.37 (s, 3H), 4.07 (s, 2H), 7.42 (s, 1H), 7.52 (s, 1H).

N-(5-chloro-3-methoxypyridin-2-yl)-1-(5-cyanothiophen-3-yl)methanesulfonamide

A solution of 4-[(acetylsulfanyl)methyl]thiophene-2-carbonitrile (400 mg, 2.03 mmol) in a mixture of acetic acid (16 mL) and water (4 mL) was treated with gaseous chlorine and stirred until the colour changed from brown to pale yellow. Excess chlorine was removed by passing a stream of N$_2$ gas through the solution. The reaction mixture was diluted with EtOAc and brine. The phases were separated and the organic phase was washed with brine, dried on Na$_2$SO$_4$ and evaporated to afford the intermediate sulfonyl chloride which was dissolved in DCM then 5-chloro-3-methoxypyridin-2-amine (354 mg, 2.22 mmol) was added to it followed by pyridine (3 mL). The reaction mixture was then stirred at room temperature for 12 hrs. The solvents were evaporated and the residue purified by preparative TLC (eluent 2% MeOH in DCM) twice to afford the title compound (190 mg, 26%) as an off white solid; m/z=343.0, 345.0 (MH)$^+$.

5-amino-2-(trifluoromethyl)pyridin-4-ol

To a stirred solution of 5-nitro-2-(trifluoromethyl)pyridin-4-ol, made by a literature method (U.S. Pat. No. 7,767,687, 2010) (720 mg, 3.46 mmol) in MeOH (5 mL) at room temperature was added ammonium chloride (925 mg, 17.3 mmol) in water (25 mL). Iron powder (966 mg, 17.3 mmol) was then added to the stirred suspension and the reaction heated at 80° C. overnight. The solvent was removed and the residual crude solid sonicated sequentially with dichloromethane (20 mL) then 1:1 CHCl$_3$/propan-2-ol (30 mL). The combined solutions were evaporated to give the title compound as a brown solid (528 mg, 85%); $^1$H NMR (500 MHz, DMSO-d6) δ 5.31 (s, 2H), 6.99 (s, 1H), 7.88 (s, 1H), 10.81 (s, 1H).

N-(5-chloro-6-cyano-3-methoxypyridin-2-yl)-1-(3,5-dichlorophenyl)methane-sulfonamide A solution of N-(6-bromo-5-chloro-3-methoxypyridin-2-yl)-1-(3,5-dichlorophenyl)-methanesulfonamide (220 mg at 70% purity, 0.334 mmol) in NMP (1 mL) was treated with solid CuCN (150 mg, 1.67 mmol) and the mixture stirred at 165° C. for 2 hrs. The cooled reaction mixture was then partitioned between EtOAc (50 mL) and 0.5M NH$_3$ (50 mL). The phases were separated and the organic phase was washed with water (2×5 mL), brine (5 mL), dried (Na$_2$SO$_4$), the mixture filtered and the filtrate evaporated to dryness to afford a brown oil containing some title compound which was taken onto final step without further purification 135 mg at 36% purity, 66% yield); m/z=405.8, 407.8 (MH)$^+$.

N-[5-(cyclopentanesulfanyl)-3-methoxypyridin-2-yl]-1-(3,5-dichlorophenyl)methane-sulfonamide The procedure to prepare 1-(3,5-dichlorophenyl)-N-[3-methoxy-5-(propan-2-ylsulfanyl)-pyridin-2-yl]methanesulfonamide was used except that cyclopentanethiol was substituted for propane-2-thiol (60%); m/z=447.4, 449.4 (MH)$^+$.

N-[5-(cyclopentanesulfonyl)-3-methoxypyridin-2-yl]-1-(3,5-dichlorophenyl)methane-sulfonamide The procedure to prepare 1-(3,5-dichlorophenyl)-N-[3-methoxy-5-(propane-2-sulfonyl)pyridin-2-yl]methanesulfonamide was used except that N-[5-(cyclopentanesulfanyl)-3-methoxypyridin-2-yl]-1-(3,5-dichlorophenyl)methanesulfonamide was substituted for 1-(3,5-dichlorophenyl)-N-[3-methoxy-5-(propan-2-ylsulfanyl)pyridin-2-yl]methanesulfonamide (76%); m/z=479.4, 481.4 (MH)$^+$.

N-(5-chloro-6-methanesulfanyl-3-methoxypyridin-2-yl)-1-(3,5-dichlorophenyl)-methanesulfonamide To a stirring solution of N-(6-bromo-5-chloro-3-methoxypyridin-2-yl)-1-(3,5-dichlorophenyl)methanesulfonamide (1.48 g, 3.20 mmol) in 1,4-dioxane (40 mL), NaSMe (898 mg, 12.8 mmol), (1E,4E)-1,5-diphenylpenta-1,4-dien-3-one-palladium (3:2) (293 mg, 0.32 mmol), (9,9-dimethyl-9H-xanthene-4,5-diyl)bis(diphenylphosphane) (371 mg, 0.64 mmol) and DIPEA (1.66 g, 12.8 mmol) were all added to the reaction mixture under stirring at room temperature. The reaction mixture was degassed with N$_2$ for 2 mins before being left stirring for 2 hrs at 80° C. The reaction mixture was retreated with all the reagents at the same quantities and left stirring for a further 2 hrs at 80° C. Finally, the reaction mixture was retreated with all the reagents at half the quantities originally used and left under stirring for a further 2 hrs at 100° C. The reaction mixture was diluted with EtOAc (120 mL) and washed with brine (2×80 mL). The aqueous layers were combined and extracted with EtOAc (5×120 mL). The combined organic layers were dried over Na$_2$SO$_4$, filtered and concentrated in vacuo. The brown solid residue was purified via column chromatography (eluent 15-30% EtOAc in heptane), to afford the title compound as a yellow solid (586 mg, 39%); $^1$H NMR (500 MHz, DMSO) δ 2.56 (s, 3H), 3.80 (s, 3H), 4.85 (s, 2H), 7.34 (d, 2H), 7.62 (dd, 2H), 10.25 (s, 1H).

N-(5-chloro-6-methanesulfonyl-3-methoxypyridin-2-yl)-1-(3,5-dichlorophenyl)-methanesulfonamide The method to prepare 1-(3-chlorophenyl)-N-[5-(ethanesulfonyl)-3-methoxypyrazin-2-yl]methanesulfonamide was used except that N-(5-chloro-6-methanesulfanyl-3-methoxy-pyridin-2-yl)-1-(3,5-dichlorophenyl)methanesulfonamide was substituted for 1-(3-chloro-phenyl)-N-[5-(ethyl sulfanyl)-3-methoxypyrazin-2-yl] methanesulfonamide (80%); $^1$H NMR (500 MHz, DMSO) δ 3.42 (s, 3H), 3.94 (s, 3H), 4.94 (s, 2H), 7.38 (d, 2H), 7.63 (m, 1H), 7.78 (s, 1H), 10.80 (s, 1H).

5-bromo-N-(5-chloro-3-methoxypyridin-2-yl)-6-(dimethylamino)pyridine-3-sulfonamide A solution of 5-bromo-6-chloro-N-(5-chloro-3-methoxy-pyridin-2-yl)pyridine-3-sulfonamide (1.40 g, 3.39 mmol) and 40% aqueous dimethylamine (0.573 g, 5.08 mmol) in THF (10 mL) was heated for 12 hrs at 90° C. in a sealed tube. The cooled mixture was diluted with water (5 mL) and extracted with DCM (3×15 mL). The combined organic fraction was dried over $Na_2SO_4$ and evaporated under reduced pressure to afford the title compound as an off white solid (1.3 g, 86%); $^1$H NMR (400 MHz, $CDCl_3$) δ 3.17 (s, 6H), 3.86 (s, 3H), 7.03 (d, 1H), 7.84 (d, 1H), 8.38 (d, 1H), 8.77 (d, 1H).

N-(5-chloro-3-methoxypyridin-2-yl)-6-(dimethylamino)-5-(methylsulfanyl)pyridine-3-sulfonamide A mixture of 5-bromo-N-(5-chloro-3-methoxypyridin-2-yl)-6-(dimethylamino)pyridine-3-sulfonamide (150 mg, 0.356 mmol), sodium methanethiolate (38 mg, 0.534 mmol) and K2CO3 (73 mg, 0.534 mmol) in a mixture of dioxane (3 mL) and water (1 mL) was degassed for 15 mins using argon. 1,1'-bis(diphenylphosphanyl)ferrocene-dichloropalladium (1:1) (25 mg, 0.034 mmol) was added and the reaction mixture was heated in a sealed tube at 90° C. overnight. The cooled reaction mixture was diluted with more water and EtOAc added. The organic phase was separated and dried over $Na_2SO_4$, filtered and concentrated under reduced pressure. The crude product was purified using flash silica chromatography (eluent 35% EtOAc in hexane) to afford the title compound as an off white solid (40 mg, 26%); $^1$H NMR (400 MHz, $CDCl_3$) δ 2.47 (s, 3H), 3.09 (s, 6H), 3.86 (s, 3H), 7.02 (m, 1H), 7.58 (s, 1H), 7.82 (m, 1H), 8.10 (d, 1H), 8.65 (d, 1H).

N-(5-chloro-3-methoxypyridin-2-yl)-6-(dimethylamino)-5-methanesulfonylpyridine-3-sulfonamide N-(5-chloro-3-methoxypyridin-2-yl)-6-(dimethylamino)-5-(methylsulfanyl)pyridine-3-sulfonamide (60 mg, 0.15 mmol) was dissolved in DCM (3 mL) and mCPBA (143 mg, 77% purity, 0.46 mmol) was added. The reaction mixture was stirred at room temperature overnight. The reaction mixture was concentrated and it was made basic using aqueous $NaHCO_3$. The aqueous layer was extracted with EtOAc (3×15 mL). The combined organic phases were dried ($MgSO_4$), filtered and the filtrate evaporated to dryness. The residue was purified using silica column chromatography (eluent 45% EtOAc in hexane) to afford the title compound as an off white solid (60 mg at 29% purity, 13%); m/z=421.3, 421.5 (MH)$^+$.

1-(3,5-dichlorophenyl)-N-{4-methoxy-6-[(3-methoxypropyl)sulfanyl]pyridazin-3-yl}methanesulfonamide The procedure to prepare 1-(3,5-dichlorophenyl)-N-[4-methoxy-6-(propylsulfanyl)-pyridazin-3-yl]methanesulfonamide was used except that 3-methoxypropane-1-thiol was substituted for propane-1-thiol (39%); $^1$H NMR (400 MHz, $CDCl_3$), δ 1.88-1.94 (m, 2H), 3.10 (t, 2H), 3.35 (s, 3H), 3.47 (t, 2H), 3.94 (s, 3H), 4.33 (s, 2H), 6.42 (s, 1H), 7.26 (s, 1H), 7.34 (s, 2H).

1-(3,5-dichlorophenyl)-N-[4-methoxy-6-(3-methoxypropanesulfonyl)pyridazin-3-yl]methanesulfonamide The procedure to prepare 1-(3,5-dichlorophenyl)-N-[3-methoxy-5-(propane-2-sulfonyl)-pyridin-2-yl]methanesulfonamide was used except that 1-(3,5-dichlorophenyl)-N-{4-methoxy-6-[(3-methoxypropyl)sulfanyl]pyridazin-3-yl}methanesulfonamide was substituted for 1-(3,5-dichlorophenyl)-N-[3-methoxy-5-(propan-2-ylsulfanyl)pyridin-2-yl]methanesulfonamide (52%); $^1$H NMR (400 MHz, DMSO), δ 1.86-1.93 (m, 2H), 3.19 (s, 3H), 3.39 (t, 2H), 3.59 (t, 2H), 4.03 (s, 3H), 4.95 (s, 2H), 7.41 (s, 2H), 7.63 (s, 2H).

N-[6-(cyclopentylsulfanyl)-4-methoxypyridazin-3-yl]-1-(3,5-dichlorophenyl)-methanesulfonamide The procedure to prepare 1-(3,5-dichlorophenyl)-N-[4-methoxy-6-(propylsulfanyl)pyridazin-3-yl]methanesulfonamide was used except that cyclopentanethiol was substituted for propan-1-thiol (59%); m/z=448.4, 450.4 (MH)$^+$.

N-[6-(cyclopentanesulfonyl)-4-methoxypyridazin-3-yl]-1-(3,5-dichlorophenyl)-methanesulfonamide The procedure to prepare 1-(3,5-dichlorophenyl)-N-[3-methoxy-5-(propane-2-sulfonyl)-pyridin-2-yl]methanesulfonamide was used except that N-[6-(cyclopentyl-sulfanyl)-4-methoxypyridazin-3-yl]-1-(3,5-dichlorophenyl)methanesulfonamide was substituted for 1-(3,5-dichlorophenyl)-N-[3-methoxy-5-(propan-2-ylsulfanyl)pyridin-2-yl]methane-sulfonamide (65%); $^1$H NMR (400 MHz, DMSO-d6), δ 1.63 (m, 4H), 1.93 (dt, 4H), 4.03 (s, 3H), 4.13 (d, 1H), 4.94 (s, 2H), 7.40 (s, 2H), 7.62 (d, 2H).

(+/−)-1-(3,5-dichlorophenyl)-2,2,2-trifluoroethan-1-ol 2M (Methylsulfanyl)methane-borane (1:1) (3.12 mL, 6.24 mmol) was added slowly to a stirring solution of 1-(3,5-dichlorophenyl)-2,2,2-trifluoroethanone (1.52 g, 6.24 mmol) in anhydrous THF (18 mL) under nitrogen. The reaction was allowed to stir at room temperature for 1 hr. The reaction was quenched by the careful addition of MeOH (5 mL) at 0° C., then concentrated in vacuo and the residue was purified by flash column chromatography over silica (Biotage 25 g SNAP cartridge, eluent: a gradient of heptane: EtOAc 1:0 to 8.5:1.5) to afford the title compound (1.44 g, 88%) as a colourless liquid. $^1$H NMR (500 MHz, $CDCl_3$) δ 4.99 (dt, 1H), 7.34-7.46 (m, 3H).

(+/−)-1-(1-bromo-2,2,2-trifluoroethyl)-3,5-dichlorobenzene

N-bromo succinimide (1.99 g, 0.01 mol) was added portionwise at 0° C. to a stirring solution of (+/−)-1-(3,5-dichlorophenyl)-2,2,2-trifluoroethan-1-ol (1.44 g, 0.01 mol) and triphenyl phosphite (2.93 mL, 0.01 mol) in DCM (15 mL). The reaction was sealed under nitrogen, allowed to warm to room temperature and stirred for 18 hrs. The reaction was concentrated in vacuo and the residue slurried in $Et_2O$ (50 mL), filtered over glass fibre filter paper and the filter pad was washed with $Et_2O$ (4×30 mL). The combined filtrates were concentrated in vacuo and the residue was purified by flash column chromatography over silica (Biotage 25 g SNAP cartridge, eluent: gradient of heptane: EtOAc 1:0 to 8.5:1.5) to afford the title compound as a pale brown liquid (1.35 g, 79%); $^1$H NMR (500 MHz, $CDCl_3$) δ 5.03 (q, 1H), 7.37-7.45 (m, 3H).

(+/−)-1-{[1-(3,5-dichlorophenyl)-2,2,2-trifluoroethyl]sulfanyl}ethan-1-one

The procedure to prepare 4-[(acetylsulfanyl)methyl]thiophene-2-carbonitrile was used except that (+/−)-1-(1-bromo- 2,2,2-trifluoroethyl)-3,5-dichlorobenzene was substituted for 4-(bromomethyl)thiophene-2-carbonitrile; $^1$H NMR (500 MHz, CDCl$_3$) δ 2.43 (s, 3H), 5.15 (q, 1H), 7.27 (d, 2H), 7.37 (t, 1H).

(+/−)-1-(3,5-dichlorophenyl)-2,2,2-trifluoroethane-1-sulfonyl chloride

The procedure to prepare (2-chloro-5-cyanophenyl)methanesulfonyl chloride was used except that (+/−)-1-{[1-(3,5-dichlorophenyl)-2,2,2-trifluoroethyl]sulfanyl}-ethan-1-one was substituted for 3-[(acetylsulfanyl)methyl]-4-chlorobenzonitrile; $^1$H NMR (250 MHz, CDCl$_3$) δ 5.20 (q, 1H), 7.50 (d, 2H), 7.59 (t, 1H).

(+/−)-N-(5-bromo-3-methoxypyrazin-2-yl)-1-(3,5-dichlorophenyl)-2,2,2-trifluoro-ethane-1-sulfonamide (+/−)-1-(3,5-dichlorophenyl)-2,2,2-trifluoroethane-1-sulfonyl chloride (165 mg, 0.48 mmol) was added to a solution of 5-bromo-3-methoxypyrazin-2-amine (107 mg, 0.53 mmol) in anhydrous pyridine (5 mL) The reaction was sealed under nitrogen and stirred at room temperature for 60 min then at 60° C. for 45 min. The reaction was allowed to cool to room temperature then concentrated in vacuo. The residue was purified over silica (Biotage 10 g SNAP cartridge) eluted with Heptane:EtOAc 1:0 to 8:2 to 6:4 to 4:6 to afford the title compound (20 mg, 7%) as a light brown solid. $^1$H NMR (500 MHz, CDCl$_3$) δ 4.06 (s, 3H), 5.71 (q, 1H), 7.36 (br.s, 1H), 7.46 (d, 2H), 7.49 (m, 1H), 8.03 (s, 1H).

Methyl 3-[(5-bromo-3-methoxypyrazin-2-yl)sulfamoyl]benzoate

The procedure to prepare N-(5-bromo-3-methoxypyrazin-2-yl)-1-(3-chlorophenyl)-methanesulfonamide was used except that methyl 3-(chlorosulfonyl)benzoate was substituted for 3-chlorophenyl)methanesulfonyl chloride. In addition, the reaction was carried out at 60° C. rather than at room temperature (15%); m/z=401.9, 403.9 (MH)$^+$.

3-[(5-bromo-3-hydroxypyrazin-2-yl)sulfamoyl]benzoic acid

To a stirred solution of methyl 3-[(5-bromo-3-methoxypyrazin-2-yl)sulfamoyl]benzoate (300 mg, 0.75 mmol) in DCM (30 mL) was added BBr$_3$ (1M in DCM, 3.0 mL, 2.99 mmol) and the reaction mixture was left stirring at room temperature for 2 hrs. Further additions of BBr$_3$ were made every 2 hrs until both methoxy groups had been removed, as judged by LCMS. The reaction mixture was quenched with water (60 mL) and diluted with DCM (120 mL). The organic and aqueous layers were separated and the combined aqueous layers were washed with DCM (2×100 mL). The aqueous later was concentrated in vacuo to half its volume before it was extracted with EtOAc (2×120 mL). The EtOAc organic layers were combined, dried over Na$_2$SO$_4$ and concentrated in vacuo to afford the title compound as a beige solid (150 mg, 49%); $^1$H NMR (500 MHz, DMSO) δ 7.72 (m, 1H), 8.02-8.32 (m, 3H), 8.51 (s, 1H).

N-(2-chloro-5-methoxypyrimidin-4-yl)-1-(3,5-dichlorophenyl)methanesulfonamide

To a stirring solution of 2,4-dichloro-5-methoxypyrimidine (295 mg, 1.65 mmol) in MeCN (10 mL), (3,5-dichlorophenyl)methanesulfonamide (a literature compound, Bioorganic & Medicinal Chemistry Letters (2005), 15(4), 1235-1238, 396 mg, 1.65 mmol) and K$_2$CO$_3$ (273 mg, 1.98 mmol) were added and the mixture heated under reflux for 18 hrs. The solvent was removed under reduced pressure and the residue taken up in DCM (50 mL). Water (15 mL) was added and acidified to approx. pH 2 (2M HCl). The phases were separated, and the aqueous phase extracted using more DCM (4×50 mL). The organic layers were combined, dried using Na$_2$SO$_4$, filtered and concentrated in vacuo to yield the title compound as yellow solid (450 mg at 40% purity, 29%; m/z=381.9, 383.9 (MH)$^+$.

3,4-dichloro-N-(2-chloro-5-methoxypyrimidin-4-yl)benzene-1-sulfonamide

A microwave tube containing 2,4-dichloro-5-methoxypyrimidine (350 mg, 1.96 mmol) and 3,4-dichlorobenzene-1-sulfonamide (442 mg, 1.96 mmol) in MeCN (2 mL) was heated at 80° C. in a CEM Discover microwave for 1 min. The solvent was removed in vacuo and the residue dissolved in DCM then washed with 0.5M HCl solution, dried over MgSO$_4$, filtered and the filtrate evaporated. Silica chromatography (EtOAc in heptane as eluent, 20-100%) gave the title compound (400 mg, 55%) m/z=367.8, 369.7 (MH)$^+$.

3,5-dichloro-N-(2-chloro-5-methoxypyrimidin-4-yl)benzene-1-sulfonamide

The procedure to prepare 3,4-dichloro-N-(2-chloro-5-methoxypyrimidin-4-yl)benzene-1-sulfonamide was used except that 3,5-dichlorobenzene-1-sulfonamide was substituted for 3,4-dichlorobenzene-1-sulfonamide. Microwave heating was at 130° C. for 2×1 hr (37%); m/z=367.8, 369.7 (MH)$^+$.

Methyl 3-[(6-chloro-4-methoxypyridazin-3-yl)sulfamoyl]benzoate

To a suspension of 6-chloro-4-methoxypyridazin-3-amine (1.00 g, 6.27 mmol) in dry DME (30 mL) was added sodium hydride (60%, 238 mg, 5.85 mmol) and the mixture stirred 5 mins. Methyl 3-(chlorosulfonyl)benzoate (1.47 g, 6.27 mmol) was then added and the mixture stirred 1 hr. EtOAc was added (100 mL) followed by 1M HCl (30 mL) and the phases were separated. The organic phase was washed with brine (15 mL), dried (Na$_2$SO$_4$), the mixture filtered and the filtrate evaporated to dryness to afford an off white solid containing the title compound (1.84 g at 47% purity, 38% yield); m/z=357.8, 359.9 (MH)$^+$.

Methyl 3-[(6-chloro-4-hydroxypyridazin-3-yl)sulfamoyl]benzoate

To a stirred solution of methyl 3-[(6-chloro-4-methoxypyridazin-3-yl)sulfamoyl]benzoate (1.3 g, 1.82 mmol) in DCM (30 mL) was added 1M BBr$_3$ in DCM (3.0 mL, 3.0 mmol) and the reaction mixture left under stirring at room temperature for 3 hrs. The reaction mixture was diluted with DCM (30 mL) and washed with water (2×50 mL). The organic layer was dried over Na$_2$SO$_4$ and concentrated in vacuo to afford a yellow solid which was a mixture of the title compound and 3-[(6-chloro-4-hydroxypyridazin-3-yl)sulfamoyl]benzoic acid (480 mg, roughly 1:2 mixture) m/z=343.8, 345.8 (MH)$^+$.

3-[(6-chloro-4-hydroxypyridazin-3-yl)sulfamoyl]benzoic acid

To a stirring solution of methyl 3-[(6-chloro-4-hydroxypyridazin-3-yl)sulfamoyl]-benzoate (481 mg, 0.70 mmol) in EtOH (50 mL) was added NaOH solution (5 M, 0.42 mL, 2.10 mmol) and the mixture stirred at room temperature for 15 mins. The reaction mixture was concentrated in vacuo and the residue acidified with 1M HCl and extracted with EtOAc (120 mL). The organic phase was washed with water (2×80 mL), dried over $Na_2SO_4$, filtered and the filtrate concentrated in vacuo to afford the title compound (311 mg, 97%) as a yellow solid m/z=329.8, 331.8 $(MH)^+$.

N-(6-chloro-4-methoxypyridazin-3-yl)-1-(4-cyanophenyl)methanesulfonamide

The procedure to prepare N-(6-chloro-4-methoxypyridazin-3-yl)-1-(2-chloro-5-cyano-phenyl)methanesulfonamide was used except that (4-cyanophenyl)methanesulfonyl chloride was substituted for (2-chloro-5-cyanophenyl) methanesulfonyl chloride (40%); $^1$H NMR (500 MHz, DMSO) δ 3.93 (s, 3H), 5.00 (s, 2H), 7.49 (s, 1H), 7.54 (d, 2H), 7.84 (d, 2H).

3-(bromomethyl)-4-fluorobenzonitrile

To a solution 4-fluoro-3-(hydroxymethyl)benzonitrile (1.10 g, 7.0 mmol) in DCM (10 mL) was added $PBr_3$ (0.76 mL, 7.0 mmol). The reaction mixture stirred for 4 hrs and was then quenched by the slow addition of saturated $NaHCO_3$ until the aqueous phase was neutral. The organic phase was washed with brine (30 mL), dried ($Na_2SO_4$), the mixture filtered and the filtrate evaporated to dryness to afford 3-(bromomethyl)-4-fluorobenzonitrile as a yellow solid (800 mg, 50%); $^1$H NMR (250 MHz, $CDCl_3$) δ 4.48 (s, 2H), 7.20 (t, 1H), 7.60-7.67 (m, 1H), 7.75 (dd, 1H).

3-[(acetylsulfanyl)methyl]-4-fluorobenzonitrile

The procedure to prepare 3-[(acetylsulfanyl)methyl]-4-chlorobenzonitrile was used except that 3-(bromomethyl)-4-fluorobenzonitrile was substituted for 3-(bromomethyl)-4-chlorobenzonitrile (94%); $^1$H NMR (500 MHz, DMSO) δ 2.36 (s, 3H), 4.16 (s, 2H), 7.45 (dd, 1H), 7.86 (ddd, 1H), 7.92 (dd, 1H).

(5-cyano-2-fluorophenyl)methanesulfonyl chloride

To a stirred solution of N-chlorosuccinimide (2.04 g, 15.3 mmol) in acetonitrile (10 mL) at 0° C. was added 2M HCl (2 mL) followed by a solution of 3-[(acetylsulfanyl)methyl]-4-fluorobenzonitrile (800 mg, 3.82 mmol) in acetonitrile (2 mL). The reaction mixture was stirred at 0° C. for 30 mins then concentrated under reduced pressure to give a white solid. Diethyl ether (20 mL) was added and the mixture sonicated, then filtered. The filtrate was then concentrated to afford the title compound as a white solid (84%); $^1$H NMR (500 MHz, DMSO) δ 3.79 (s, 2H), 7.27-7.46 (m, 1H), 7.78 (ddd, 1H), 7.87 (dd, 1H).

N-(6-chloro-4-methoxypyridazin-3-yl)-1-(5-cyano-2-fluorophenyl)methanesulfonamide The procedure to prepare N-(6-chloro-4-methoxypyridazin-3-yl)-1-(2-chloro-5-cyanophenyl)methanesulfonamide was used except that (5-cyano-2-fluorophenyl)methanesulfonyl chloride was substituted for (2-chloro-5-cyanophenyl) methanesulfonyl chloride (15%); m/z 356.6, 358.6 $(MH)^+$.

3-fluoro-5-(hydroxymethyl)benzonitrile

To a solution of 3-cyano-5-fluorobenzoic acid (2 g, 0.01 mol) stirring in anhydrous THF (40 mL) was added carbonyl diimidazole (2.16 g, 0.01 mol) and the reaction mixture left to stir at room temperature for 3 hrs under a nitrogen atmosphere.

The reaction mixture was cooled to 0° C. and $NaBH_4$ (1.37 g, 0.04 mol) was added portion wise over 30 mins and the reaction mixture stirred for a further 1 hr at 0° C. before being allowed to warm to room temperature and stirred for another 1 hr. It was then cooled to 0° C. and quenched with saturated ammonium chloride. The mixture was concentrated under reduced pressure to remove the THF and the resultant aqueous suspension extracted into EtOAc (3×25 mL). The organics were combined and washed with brine (3×15 mL), dried over $MgSO_4$ and concentrated to afford a yellow oil which was purified by silica chromatography (heptane:EtOAc, eluent: 35% EtOAc), to afford the title compound as a white solid (1.22 g, 65%); $^1$H NMR (500 MHz, DMSO) δ 4.56 (d, 2H), 5.53 (t, 1H), 7.48-7.54 (m, 1H), 7.61 (s, 1H), 7.68-7.73 (m, 1H).

3-(bromomethyl)-5-fluorobenzonitrile

The procedure to prepare 3-(bromomethyl)-4-chlorobenzonitrile was used except that 3-fluoro-5-(hydroxymethyl)benzonitrile was substituted for 4-chloro-3-(hydroxymethyl)benzonitrile (50%); $^1$H NMR (500 MHz, DMSO) δ 4.73 (s, 2H), 7.70-7.75 (m, 1H), 7.80-7.84 (m, 2H).

3-[(acetylsulfanyl)methyl]-5-fluorobenzonitrile

The procedure to prepare 3-[(acetylsulfanyl)methyl]-4-chlorobenzonitrile was used except that 3-(bromomethyl)-5-fluorobenzonitrile was substituted for 3-(bromomethyl)-4-chlorobenzonitrile (89%); $^1$H NMR (500 MHz, DMSO) δ 2.37 (s, 3H), 4.17 (s, 2H), 7.50-7.57 (m, 1H), 7.64 (s, 1H), 7.69-7.82 (m, 1H).

(3-cyano-5-fluorophenyl)methanesulfonyl chloride

The procedure to prepare (5-cyano-2-fluorophenyl)methanesulfonyl chloride was used except that 3-[(acetylsulfanyl)methyl]-5-fluorobenzonitrile was substituted for 3-[(acetylsulfanyl)methyl]-4-fluorobenzonitrile (73%); $^1$H NMR (500 MHz, DMSO) δ 3.81 (s, 2H), 7.52 (d, 1H), 7.59 (s, 1H), 7.68 (ddd, 1H).

N-(6-chloro-4-methoxypyridazin-3-yl)-1-(3-cyano-5-fluorophenyl)methanesulfonamide The procedure to prepare N-(6-chloro-4-methoxypyridazin-3-yl)-1-(2-chloro-5-cyanophenyl)methanesulfonamide was used except that (3-cyano-5-fluorophenyl)methanesulfonyl chloride was substituted for (2-chloro-5-cyanophenyl) methanesulfonyl chloride (15%); m/z 356.6, 358.6 $(MH)^+$.

(2-chloro-5-cyanophenyl)methanesulfonamide

To a stirring solution of (2-chloro-5-cyanophenyl)methanesulfonyl chloride (500 mg, 2.0 mmol) in DCM (15 mL)

was added ammonium hydroxide (0.76 mL, 20 mmol) the mixture stirred at room temperature for 16 hrs. Water (20 mL) was added and the solution acidified to approx. pH 2 using 1M HCl. The mixture was extracted using DCM (3×30 mL), dried (Na$_2$SO$_4$), filtered and the filtrate concentrated in vacuo to yield the title compound as a white solid (400 mg, 70%); $^1$H NMR (250 MHz, DMSO) δ 4.51 (s, 2H), 7.11 (s, 2H), 7.74 (d, 1H), 7.87 (dd, 1H), 7.93 (d, 1H).

1-(2-chloro-5-cyanophenyl)-N-(2-chloro-5-methoxypyrimidin-4-yl)methanesulfonamide The procedure to prepare 3,4-dichloro-N-(2-chloro-5-methoxypyrimidin-4-yl)benzene-1-sulfonamide was used except that (2-chloro-5-cyanophenyl)methanesulfonamide was substituted for 3,4-dichlorobenzene-1-sulfonamide and microwave heating was at 135° C. for 2.5 hrs (30%); m/z=372.8, 374.8 (MH)$^+$.

2-chloro-N-(6-chloro-4-methoxypyridazin-3-yl)-4-cyanobenzene-1-sulfonamide

The procedure to prepare N-(6-chloro-4-methoxypyridazin-3-yl)-1-(2-chloro-5-cyanophenyl)methanesulfonamide was used except that 2-chloro-4-cyanobenzenesulfonyl chloride was substituted for (2-chloro-5-cyanophenyl)methanesulfonyl chloride (38%); m/z=358.9, 360.9 (MH)$^+$.

3-chloro-N-(6-chloro-4-methoxypyridazin-3-yl)-4-fluorobenzene-1-sulfonamide

To a suspension of NaH (60%, 25 mg, 0.63 mmol) in THF (5 mL) at 0° C. was added 6-chloro-4-methoxypyridazin-3-amine (100 mg, 0.63 mmol) was added and stirred for 30 minutes, 3-chloro-4-fluorobenzenesulfonyl chloride (144 mg, 0.63 mmol) was added and the reaction mixture was stirred for 3 hrs at room temperature. The THF was removed under reduced pressure and the residue was taken up in EtOAc and washed with 1M HCl (2×10 mL). The organic layer was dried using Na$_2$SO$_4$, filtered and concentrated in vacuo to yield a brown residue which was purified using silica column chromatography (Gradient: EtOAc in heptane, 0 to 100% EtOAc) to yield the title compound as an off white solid (19%); m/z=351.8, 353.8 (MH)$^+$.

3-chloro-N-(6-chloro-4-methoxypyridazin-3-yl)-5-fluorobenzene-1-sulfonamide

The procedure to prepare 3-chloro-N-(6-chloro-4-methoxypyridazin-3-yl)-4-fluorobenzene-1-sulfonamide was used except that 3-chloro-5-fluorobenzenesulfonyl chloride was substituted for 3-chloro-4-fluorobenzenesulfonyl chloride (21%); m/z=351.8, 353.8 (MH)$^+$.

4-methoxy-2-(methylsulfanyl)-5-nitropyridine

To a solution of 2-chloro-4-methoxy-5-nitropyridine (500 mg, 2.65 mmol) in anhydrous DMF (10 mL) at 0° C. was added sodium methanethiolate (220 mg, 3.18 mmol) portion-wise over 5 mins. The reaction mixture was allowed to warm to room temperature and then stirred for a further 2 hrs. A further portion of sodium methanethiolate (110 mg, 1.59 mmol) was added and the mixture left to stir for a further 1 hr. Water (50 mL) was added followed by DCM (100 mL). The phases were separated and the organic phase was washed with water (2×20 mL) brine (20 mL) and dried over Na$_2$SO$_4$. The filtrate was evaporated to dryness to afford the title compound as an off white solid (512 mg, 96%); $^1$H NMR (500 MHz, DMSO-d6) δ 2.60 (s, 3H), 4.01 (s, 3H), 7.24 (s, 1H), 8.90 (s, 1H).

2-methanesulfonyl-4-methoxy-5-nitropyridine

To a solution of 4-methoxy-2-(methylsulfanyl)-5-nitropyridine (510 mg, 2.55 mmol) in methanol (12 mL) was added OXONE (5:1:1:2) (1.56 g, 2.55 mmol) as a solution in water (15 mL) drop-wise. The resulting reaction mixture (which formed a white precipitate on addition) was stirred at 50° C. for 1 hr. A further portion of Oxone (1.56 g, 2.55 mmol) was added and the mixture was stirred for a further 1 hr at 50° C. The solvent was partially evaporated and the aqueous residue extracted with DCM (50 mL). The organic phase was dried (Na$_2$SO$_4$), filtered and concentrated under reduced pressure to obtain the title compound as an off-white solid (650 mg, 109%); m/z=232.9 (MH)$^+$.

6-methanesulfonyl-4-methoxypyridin-3-amine

To a solution of 2-methanesulfonyl-4-methoxy-5-nitropyridine (650 mg, 2.80 mmol) in a mixture of MeOH (4 mL), water (4 mL) and concentrated HCl (0.3 mL) was added iron powder (630 mg, 11.2 mmol). The resulting suspension was stirred at 80° C. for 2 hrs then cooled to room temperature and filtered through a pad of Celite. The solid was washed further with MeOH and the collected filtrate evaporated to dryness to afford a light yellow solid containing the title compound (599 mg, >100% due to presence of iron residues); m/z=202.9 (MH)$^+$.

3,5-dichloro-N-(6-methanesulfonyl-4-methoxypyridin-3-yl)benzene-1-sulfonamide

To a solution of 6-methanesulfonyl-4-methoxypyridin-3-amine (400 mg, 1.98 mmol) in pyridine (10 mL) was added 3,5-dichlorobenzene-1-sulfonyl chloride (243 mg, 0.99 mmol) portionwise. The resulting reaction mixture was stirred at room temperature under nitrogen for 2 hrs then evaporated to dryness, the residue re-dissolved in EtOAc (50 mL) and washed with water (25 mL) followed by saturated NaHCO$_3$ (25 mL) (to remove sulfonic acid residues). The combined aqueous layers were back-extracted and combined organics were dried over MgSO$_4$ and evaporated to dryness. The resulting crude residue was purified by silica chromatography (eluent: heptane:EtOAc 20-50%) to afford the title compound as a yellow solid (185 mg, 22%); $^1$H NMR (500 MHz, DMSO-d6) δ 3.26 (s, 3H), 3.81 (s, 3H), 7.58 (s, 1H), 7.81 (d, 2H), 8.00 (t, 1H), 8.45 (s, 1H).

3,5-dichloro-N-(6-chloro-4-methoxypyridin-3-yl)benzene-1-sulfonamide

The procedure to prepare 3,5-dichloro-N-(6-methanesulfonyl-4-methoxypyridin-3-yl)benzene-1-sulfonamide was used except that 6-chloro-4-methoxypyridin-3-amine was substituted for 6-methanesulfonyl-4-methoxypyridin-3-amine; m/z=366.7, 368.7 (MH)$^+$.

1-(3,5-dichlorophenyl)-N-[5-methoxy-2-(trifluoromethyl)pyrimidin-4-yl]methanesulfonamide The procedure to prepare 3,4-dichloro-N-(2-chloro-5-methoxypyrimidin-4-yl)benzene-1-sulfonamide was used except that (3,5-dichlorophenyl)methanesulfonamide was substituted for 3,4-dichlorobenzene-1-sulfonamide, 4-chloro-5-methoxy-2-(trifluoromethyl)pyrimidine was substituted for 2,4-dichloro-5-methoxypyrimidine and microwave heating was at 120° C. for 2 hrs (66%); m/z=415.8, 417.8 (MH)+.

3-chloro-5-fluorobenzene-1-sulfonamide 3-chloro-5-fluorobenzene-1-sulfonyl chloride (100 mg, 0.437 mmol) was suspended in DCM (5 mL) and stirred at room temperature. Ammonium hydroxide (0.165 mL) was added and the solution was stirred at room temperature for 2 hrs. Saturated ammonium chloride (5 mL) added. The layers were separated and the aqueous was extracted with DCM (2×20 mL). The combined organics were dried ($Na_2SO_4$), filtered and concentrated to a solid containing the title compound; m/z=208.0, 210.0 (MH)+.

3-chloro-5-fluoro-N-[5-methoxy-2-(trifluoromethyl)pyrimidin-4-yl]benzene-1-sulfonamide The procedure to prepare 3,4-dichloro-N-(2-chloro-5-methoxypyrimidin-4-yl)benzene-1-sulfonamide was used except that that 3-chloro-5-fluorobenzene-1-sulfonamide was substituted for 3,4-dichlorobenzene-1-sulfonamide, 4-chloro-5-methoxy-2-(trifluoromethyl)pyrimidine was substituted for 2,4-dichloro-5-methoxypyrimidine and microwave heating was at 120° C. for 2 hrs (66%); m/z=385.8, 387.8 (MH)+.

N-(5-bromo-3-hydroxypyrazin-2-yl)-3,5-dichlorobenzene-1-sulfonamide

To a stirred suspension of sodium hydride (60%, 196 mg, 4.9 mmol) and THF (10 mL) at 0° C., under $N_2$, was added 5-bromo-3-methoxypyrazin-2-amine (1.00 g, 4.9 mmol) in one portion. This was stirred at 0° C. for 30 min before the addition of 3,5-dichlorobenzene-1-sulfonyl chloride (120 mg, 0.49 mmol) in one portion. The reaction was allowed to warm to room temperature and stirred for 2 hrs. The reaction was acidified to pH 2 with 2 M HCl, diluted with water (100 mL) and extracted with EtOAc (100 ml×3). The combined organic extracts were washed with water (100 ml), brine (100 ml), dried ($Na_2SO_4$), filtered and concentrated to give the crude product as a brown oil, which was purified using silica chromatography (eluent 12% to 50% EtOAc in heptane) to give the title compound as a white solid (866 mg, 39%); m/z=411.7, 413.6 (MH)+

3,5-dichloro-N-[3-methoxy-5-(methylsulfanyl)pyrazin-2-yl]benzene-1-sulfonamide

The procedure for preparation of 1-(3,5-dichlorophenyl)-N-[4-methoxy-6-(propyl sulfanyl)pyridazin-3-yl]methanesulfonamide was used except that N-(5-bromo-3-hydroxypyrazin-2-yl)-3,5-dichlorobenzene-1-sulfonamide was substituted for N-(6-chloro-4-methoxypyridazin-3-yl)-1-(3,5-dichlorophenyl)methanesulfonamide and sodium methanethiolate was substituted for propane-1-thiol; (94% $^1$H NMR (500 MHz, DMSO-d6) δ 3.93 (s, 3H), 7.73 (s, 1H), 7.89-7.92 (m, 2H), 7.95-7.99 (m, 1H).

3,5-dichloro-N-(5-methanesulfonyl-3-methoxypyrazin-2-yl)benzene-1-sulfonamide

The procedure to prepare 2-methanesulfonyl-4-methoxy-5-nitropyridine was used except that 3,5-dichloro-N-[3-methoxy-5-(methylsulfanyl)pyrazin-2-yl]benzene-1-sulfonamide was substituted for 4-methoxy-2-(methylsulfanyl)-5-nitropyridine. Extraction was with EtOAc rather than DCM (65%); $^1$H NMR (250 MHz, DMSO-d6) δ 3.18 (s, 3H), 3.97 (s, 3H), 7.90-7.99 (m, 3H), 8.14 (s, 1H).

2-chloro-4-cyanobenzene-1-sulfonyl Chloride

Thionyl chloride (15 mL) was dropped into water (60 mL) with stirring and cooling so that the temperature did not rise above −5° C. Copper(I) chloride (19 mg) was then added.

In parallel, 4-amino-3-chlorobenzonitrile (1.50 g, 9.83 mmol) was dissolved in conc. HCl (30 mL), cooled to −5° C. whereupon a solution of sodium nitrite (746 mg, 10.8 mmol) in water (15 mL) was added. After complete addition the solution of diazonium salt was added in over 2 mins to the first solution, both at −5 to 0° C. (gas evolution was observed) and a foam formed on top of the solution. The temperature was allowed to come to room temperature and the aqueous phase was then extracted with DCM (3×70 ml). The combined organic phase was washed with brine (5 mL), dried ($Na_2SO_4$), the mixture filtered and the filtrate evaporated to dryness to afford a yellow solid containing the title compound (1.88 g, 88%); $^1$H NMR (500 MHz, $CDCl_3$) δ 7.83 (dd, 1H), 7.97 (d, 1H), 8.31 (d, 1H).

2-chloro-N-(6-chloro-4-methoxypyridazin-3-yl)-4-cyanobenzene-1-sulfonamide

The procedure to prepare 5-bromo-6-chloro-N-(6-chloro-4-methoxypyridazin-3-yl)pyridine-3-sulfonamide was used except that 2-chloro-4-cyanobenzene-1-sulfonyl chloride was substituted for 5-bromo-6-chloropyridine-3-sulfonyl chloride (46%); m/z=359.0, 361.0 (MH)+.

3-chloro-4-[(6-chloro-4-hydroxypyridazin-3-yl)sulfamoyl]benzoic acid

A suspension of 2-chloro-N-(6-chloro-4-methoxypyridazin-3-yl)-4-cyanobenzene-1-sulfonamide (480 mg, 1.34 mmol) was refluxed for 2 hrs in concentrated HCl. The cooled reaction mixture was diluted with water (25 mL) and filtered. The solid was washed in more water and dried in air to afford the title compound as a tan solid (62%); m/z=363.8, 365.8 (MH)+.

Methyl 3-chloro-5-(diethylcarbamoyl)benzoate

To a solution of 1,3-dimethyl 5-chlorobenzene-1,3-dicarboxylate (4.00 g, 17.5 mmol) in dioxane (50 mL) and water (50 mL) was added NaOH (700 mg, 17.5 mmol). The resulting suspension was stirred vigorously at 40° C. for 2 hrs and then for a further 16 hrs at room temperature. The reaction mixture was evaporated to dryness, re-dissolved in water (~200 mL) and acidified to pH 3 using 1M HCl. The resulting white precipitate was sonicated for 2 mins and filtered. The white solid was washed further with water and then dried in a vacuum oven overnight. This afforded a white solid (3.6 g) which was a mixture of 3 products including 3-chloro-5-(methoxycarbonyl)benzoic acid.

This solid was dissolved in DMF (150 mL) at 0° C. and diethylamine (2.56 g, 0.03 mol), DIPEA (6.09 ml, 0.03 mol) and HATU (6.64 g, 0.02 mol) were added. The reaction mixture was then stirred at room temperature for 6 hrs then evaporated to dryness, re-dissolved in EtOAc (200 mL) and washed with water (3×200 mL) and brine (2×200 mL). The combined organics were then dried over $MgSO_4$ and evaporated to dryness to afford the crude product. This was purified by silica chromatography (Biotage: 100 g SNAP cartridge) eluting with 0-80% EtOAc in heptane to afford the title compound as a colourless oil (880 mg (28%); $^1$H NMR (500 MHz, CDCl$_3$) δ 1.13 (br. s, 3H), 1.26 (t, 3H), 3.24 (br.s, 2H), 3.54 (br. s, 2H), 3.93 (s, 3H), 7.55 (m, 1H), 7.92 (m, 1H), 8.04 (m, 1H).

3-chloro-N,N-diethyl-5-(hydroxymethyl)benzamide

To a solution of methyl 3-chloro-5-(diethylcarbamoyl) benzoate (880 mg, 3.26 mmol) in DCM (50 mL) and MeOH (50 mL) at 0° C. under nitrogen was added NaBH$_4$ (247 mg, 6.53 mmol). The resulting solution was allowed to warm to room temperature and then stirred for 4 hrs. More NaBH$_4$ (247 mg, 6.53 mmol) was added and the reaction mixture was left to stir at ambient temperature for 48 hrs then quenched at 0° C. with saturated NH$_4$Cl (10 mL) and then extracted into EtOAc (3×50 mL). Combined organics were dried over MgSO$_4$ and evaporated to dryness.

The residue (a mixture of starting material and desired product) was re-dissolved in THF (50 mL) and MeOH (10 mL). More NaBH$_4$ (247 mg, 6.53 mmol) was added at 0° C. and then the reaction mixture was heated at 50° C. for 2 hrs. A final portion of NaBH$_4$ (247 mg, 6.53 mmol) was added and the mixture was stirred for a further 2 hrs at 50° C.

The reaction mixture was cooled to 0° C., quenched with saturated NH$_4$Cl (20 mL) and evaporated to approx. 20 mL. The resulting solution was diluted with water (50 mL) and extracted into EtOAc (3×50 mL). Combined organics were dried over MgSO$_4$ and evaporated to dryness to afford the title compound as a yellow oil (741 mg, 94%); $^1$H NMR (500 MHz, CDCl$_3$) δ 1.11 (br. s, 3H), 1.25 (br. s, 3H), 3.23 (s, 2H), 3.53 (s, 2H), 4.66 (s, 2H), 7.20 (s, 1H), 7.24 (s, 1H), 7.37 (s, 1H).

3-(bromomethyl)-5-chloro-N,N-diethylbenzamide

The procedure to prepare 3-(bromomethyl)-4-chlorobenzonitrile was used except that 3-chloro-N,N-diethyl-5-(hydroxymethyl)benzamide was substituted for 4-chloro-3-(hydroxymethyl)benzonitrile (79%); $^1$H NMR (500 MHz, CDCl$_3$) δ 1.13 (br.s, 3H), 1.25 (br.s, 4H), 3.24 (s, 2H), 3.53 (s, 2H), 4.43 (s, 2H), 7.27-7.29 (m, 2H), 7.41 (d, 1H).

3-[(acetylsulfanyl)methyl]-5-chloro-N,N-diethylbenzamide

The procedure to prepare 3-[(acetylsulfanyl)methyl]-4-chlorobenzonitrile was used except that 3-(bromomethyl)-5-chloro-N,N-diethylbenzamide was substituted for 3-(bromomethyl)-4-chlorobenzonitrile (98%); $^1$H NMR (500 MHz, CDCl$_3$) δ 1.11 (br. s, 3H), 1.17-1.30 (br. m, 3H), 2.36 (s, 3H), 3.22 (br. s, 2H), 3.52 (br. s, 2H), 4.07 (s, 2H), 7.17 (m, 1H), 7.23 (m, 1H), 7.31 (m, 1H).

3-chloro-5-{[(6-chloro-4-methoxypyridazin-3-yl) sulfamoyl]methyl}-N,N-diethylbenzamide A solution of 3-[(acetylsulfanyl)methyl]-5-chloro-N,N-diethylbenzamide (695 mg, 2.32 mmol) in acetic acid (10 mL) and water (2 mL) at room temperature was saturated with chlorine gas with stirring until the disappearance of starting material was observed by TLC (1:1 EtOAc/heptane). The reaction mixture was diluted with EtOAc (50 mL) and brine (50 mL). The phases were separated and the organic phase was washed with brine (2×25 mL), dried (Na$_2$SO$_4$) and the mixture filtered and the filtrate evaporated to dryness to afford the intermediate sulfonyl chloride as a yellow oil which was used immediately in the following reaction (700 mg, 93%).

To a solution of 6-chloro-4-methoxypyridazin-3-amine (344 mg, 2.16 mmol) in anhydrous THF (30 mL) at 0° C. under nitrogen was added NaH (60%, 104 mg, 2.59 mmol). The resulting solution was stirred at 0° C. for 30 mins and then the intermediate sulfonyl chloride (700 mg, 2.16 mmol) in anhydrous THF (2 mL) was added. The resulting reaction mixture was stirred at room temperature for 16 hrs then quenched with saturated NH$_4$Cl (approx. 10 mL), diluted with water (50 mL), acidified to pH 5 using 1M HCl and extracted into EtOAc (3×50 mL). The combined organics were dried over MgSO4 and evaporated to dryness to afford the title compound as a dark yellow solid (360 mg, 37%); m/z=446.9, 448.9 (MH)$^+$.

N-(6-chloro-4-methoxypyridazin-3-yl)-3-cyano-5-fluorobenzene-1-sulfonamide

The procedure to prepare 5-bromo-6-chloro-N-(6-chloro-4-methoxypyridazin-3-yl)pyridine-3-sulfonamide was used except that 3-cyano-5-fluorobenzene-1-sulfonyl chloride was substituted for 5-bromo-6-chloropyridine-3-sulfonyl chloride (yield not determined). 4-bromo-6-(trifluoromethyl)pyridazin-3-amine To a solution of 6-(trifluoromethyl)pyridazin-3-amine (480 mg, 0.003 mol)) and sodium hydrogencarbonate (297 mg, 0.004 mol) in MeOH (10 mL) was added bromine (0.159 mL, 0.003 mol). The reaction mixture was stirred at room temperature for 2 hrs before the solvent was evaporated, water (30 mL) added and the solid produced isolated by filtration. The solid obtained was dried under vacuum to afford the title compound as a brown solid (671 mg, 89%); $^1$H NMR (500 MHz, CDCl$_3$) 5.69 (s, 2H), 7.73 (s, 1H).

4-methoxy-6-(trifluoromethyl)pyridazin-3-amine

To a solution of 4-bromo-6-(trifluoromethyl)pyridazin-3-amine (671 mg, 2.63 mmol) in MeOH (10 mL) was added sodium methoxide (5.4M in MeOH, 3.16 mmol) and the solution stirred at 90° C. for 1.5 hrs. The MeOH was evaporated, water (100 mL) added and the mixture filtered. The crude brown solid was purified using silica chromatography (0-100% ethyl acetate in heptane) to afford the title compound (230 mg, 45%); $^1$H NMR (500 MHz, CDCl$_3$) δ 4.03 (s, 3H), 5.49 (s, 2H), 6.91 (s, 1H).

(3,4-dichlorophenyl)methanesulfonamide

The procedure to prepare 3-chloro-5-fluorobenzene-1-sulfonamide was used except that (3,4-dichlorophenyl) methanesulfonyl chloride was substituted for 3-chloro-5-fluorobenzene-1-sulfonyl chloride (94%); $^1$H NMR (250 MHz, DMSO) δ 4.32 (s, 2H), 6.93 (s, 2H), 7.36 (dd, 1H), 7.60-7.69 (m, 2H).

1-(3,4-dichlorophenyl)-N-[5-methoxy-2-(trifluoromethyl)pyrimidin-4-yl]methanesulfonamide The procedure to prepare 3,4-dichloro-N-(2-chloro-5-methoxypyrimidin-4-yl)benzene-1-sulfonamide was used except that that (3,4-dichlorophenyl)methanesulfonamide was substituted for 3,4-dichlorobenzene-1-sulfonamide, 4-chloro-5-methoxy-2-(trifluoromethyl)pyrimidine was substituted for 2,4-dichloro-5-methoxypyrimidine and microwave heating was at 140° C. for 2 hrs (83%); m/z=415.8, 417.8 (MH)+.

N-(6-chloro-4-methoxypyridazin-3-yl)-1-(2,5-dichlorothiophen-3-yl)methane-sulfonamide The procedure to prepare N-(6-chloro-4-methoxypyridazin-3-yl)-1-(2-chloro-5-cyanophenyl)methanesulfonamide was used except that (2,5-dichlorothiophen-3-yl) methanesulfonyl chloride was substituted for (2-chloro-5-cyanophenyl)methane-sulfonyl chloride (27%); $^1$H NMR (500 MHz, DMSO) δ 3.94 (s, 3H), 4.84 (s, 2H), 7.11 (s, 1H), 7.46 (s, 1H).

3,5-dichloro-N-(6-iodo-4-methoxypyridazin-3-yl)benzene-1-sulfonamide

To a solution of 6-iodo-4-methoxypyridazin-3-amine (1.35 g, 5.38 mmol, but containing large amounts of the bromo byproduct) stirring in anhydrous THF (10 mL) at 0° C. was added NaH (60%, 215 mg, 5.38 mmol). The reaction mixture was allowed to stir for 30 mins. After this time 3,5-dichlorobenzenesulfonyl chloride (1.32 g, 5.38 mmol) was added portion wise and the mixture stirred for 2 hrs. It was then cooled to 0° C. and quenched with saturated ammonium chloride. Once effervescence had ceased the mixture was allowed to warm to room temperature and stirred for a further 15 min then extracted with EtOAc (3×25 mL). The combined organics were washed with brine (20 mL) and dried over MgSO$_4$ then concentrated under reduced pressure. Purification was successfully achieved by silica chromatography (0-100% EtOAc in heptane) to afford the title compound (also containing the bromo analogue) as a grey solid (300 mg, 12%); m/z=413.6, 459.7 (MH)+.

3,5-dichloro-N-[4-methoxy-6-(methylsulfanyl)pyridazin-3-yl]benzene-1-sulfonamide The procedure for preparation of 1-(3,5-dichlorophenyl)-N-[4-methoxy-6-(propyl sulfanyl)pyridazin-3-yl]methanesulfonamide was used except that 3,5-dichloro-N-(6-iodo-4-methoxypyridazin-3-yl)benzene-1-sulfonamide was substituted for N-(6-chloro-4-methoxypyridazin-3-yl)-1-(3,5-dichlorophenyl)methanesulfonamide and sodium methanethiolate was substituted for propane-1-thiol (35%); 1H NMR (500 MHz, DMSO) δ 2.53 (s, 3H), 3.87 (s, 3H), 7.28 (s, 1H), 7.80-7.95 (m, 3H).

3,5-dichloro-N-(6-methanesulfonyl-4-methoxypyridazin-3-yl)benzene-1-sulfonamide The procedure to prepare 2-methanesulfonyl-4-methoxy-5-nitropyridine was used except that 3,5-dichloro-N-[4-methoxy-6-(methylsulfanyl)pyridazin-3-yl]benzene-1-sulfonamide was substituted for 4-methoxy-2-(methylsulfanyl)-5-nitropyridine. Heating was at 60° C. for 2 hrs (54%); m/z=411.8, 413.8 (MH)+.

4-amino-2-chloro-3-methoxypyridine

The procedure for preparation of 3-amino-5-chloro-4-hydroxy-pyridine was used except that 2-chloro-3-methoxy-4-nitropyridine was substituted for 3-chloro-4-hydroxy-5-nitropyridine. $^1$H NMR (500 mHz, DMSO) δ 3.68 (s, 3H), 6.3 (bs, 2H), 6.59 (d, 1H), 7.60 (d, 1H).

3-amino-5-chloropyridin-4-ol

A solution of 3-chloro-4-hydroxy-5-nitropyridine (7.31 g, 42 mmol) in MeOH (400 mL) was treated with RaneyNi (1 teaspoon) and hydrogenated for 8 hrs at atmospheric pressure. The mixture was filtered through Celite carefully without drying out the celite/residue and the filtrate evaporated to dryness to afford 3-amino-5-chloro-4-hydroxy-pyridine as a dark purple solid (5.8 g at 95% purity, 96% yield); $^1$H NMR (500 mHz, DMSO) δ 4.79 (bs, 2H), 7.13 (s, 1H), 7.76 (s, 1H), 11.50 (bs, 1H).

3-amino-6-chloro-2-methoxypyridine

The title compound was prepared from commercial 2,6-dichloropyridine by the following sequence; nitration at 120° C. in a mixture of fuming nitric acid and conc. sulfuric acid (½) followed by reaction with 1.0 equiv. methanol and sodium hydride in THF. Reduction of the nitro group was accomplished using hydrogen gas and Raney nickel in THF. H-nmr for 3-amino-6-chloro-2-methoxypyridine; (500 mHz, DMSO) δ 3.88 (s, 3H), 5.09 (bs, 2H), 6.79 (d, 1H), 6.93 (d, 1H).

3-amino-6-ethanesulfonyl-2-methoxypyridine

The title compound was prepared from commercial 2,6-dichloropyridine using the following sequence; nitration at 120° C. in a mixture of fuming nitric acid and conc. sulfuric acid (½) followed by reaction with sodium ethanethiolate in THF and oxidation with Oxone in ethanol/water. Reduction of the nitro group was accomplished using hydrogen and Raney nickel in THF. H-nmr for 3-amino-6-ethanesulfonyl-2-methoxypyridine; (500 mHz, DMSO) δ 1.12 (t, 3H), 3.26 (q, 2H), 3.96 (s, 3H), 6.07 (bs, 2H), 6.98 (d, 1H), 7.44 (d, 1H).

1-(5,6-dichloropyridin-3-yl)methanesulfonylchloride

The title compound was prepared as a crystalline solid from comm. 5,6-dichloronicotinic acid using the sequence; formation of the carboxylic acid chloride using oxalyl chloride and cat. DMF in dichloromethane followed by reduction with sodium borohydride in water, then reaction with phosphorus oxychloride/DMF in chloroform to give the chloromethylpyridine followed by substitution with thioacetic acid/potassium carbonate in acetone and finally chlorosulfonylation using NCS in acetonitrile/water/hydrochloric acid. H-nmr for 1-(5,6-dichloropyridin-3-yl) methanesulfonylchloride; (500 mHz, DMSO) δ 3.83 (s, 2H), 8.07 (s, 1H), 8.30 (s, 1H).

3-amino-5,6-dichloro-2-methoxypyridine

The title compound was prepared from 3-amino-5-chloro-2-methoxypyridine (commercial) by chlorination with 1 equiv. NCS in DMF. After stirring for 18 h at room temperature the mixture was partitioned between dichloromethane and water, the organic phase was concentrated and purified by flash chromatography (SiO$_2$, ethyl acetate/heptane; 1:10) which gave the title compound in 15% yield. H-nmr for 3-amino-5,6-dichloro-2-methoxypyridine; (500 mHz, DMSO) δ 3.84 (s, 3H), 5.44 (bs, 2H), 7.04 (s, 1H).

4-fluoro-3-(hydroxymethyl)benzonitrile

A solution of 5-cyano-2-fluorobenzoic acid (1.90 g, 11.5 mmol) in thionyl chloride (7 mL, 96.5 mmol) was refluxed for 3 hrs. The excess thionyl chloride was evaporated. The residue was dissolved in EtOH (20 ml) and THF (15 ml). Sodium borohydride (1.31 g, 34.5 mmol) was added slowly at 0° C. The reaction mixture was stirred for 1 hr at 0° C. and then for 3 days at room temperature. The reaction was quenched by the addition of water (50 mL) and was extracted with EtOAc (3×50 mL). The combined organic extracts were washed with water (50 mL) and brine (50 mL), dried (Na$_2$SO$_4$), the mixture filtered and the filtrate evaporated to dryness. The crude product was purified using silica chromatography (eluent 0% to 10% MeOH in DCM) to give 4-fluoro-3-(hydroxymethyl)benzonitrile as a yellow solid (1.10 g, 60%); $^1$H NMR (500 MHz, CDCl$_3$) δ 4.81 (s, 2H), 7.13-7.17 (m, 1H), 7.58-7.62 (m, 1H), 7.84 (dd, 1H).

N-(5-cyano-3-methoxypyridin-2-yl)-1-(3,5-dichlorophenyl)methanesulfonamide

A suspension of 1-(3,5-dichlorophenyl)-N-(5-iodo-3-methoxypyridin-2-yl)methanesulfonamide (200 mg, 0.42 mmol) and copper(I) cyanide (189 mg, 2.11 mmol) in NMP (4 mL) was heated at 145° C. for 3 hrs. The cooled reaction mixture was partitioned between EtOAc (100 mL) and water (30 mL). The phases were separated and the organic phase was washed with water (3×15 mL) and brine (5 mL), dried (Na$_2$SO$_4$), the mixture filtered and the filtrate evaporated to dryness to afford N-(5-cyano-3-methoxypyridin-2-yl)-1-(3,5-dichlorophenyl)methanesulfonamide as a brown oil which was used in the next step without further purification (183 mg, 91%); m/z=371.8, 373.8 (MH)$^+$.

5-chloro-6-methylpyridine-3-sulfonyl chloride

Thionyl chloride (3 mL) was added dropwise into water with mixing and cooling so that the temperature did not rise above −5° C. Copper(I) chloride (3 mg, 0.04 mmol) was then added. In parallel, 5-chloro-6-methylpyridin-3-amine (250 mg, 1.75 mmol), prepared by a literature method (PCT Int. Appl., 2006067445, 29 Jun. 2006) was dissolved in conc. HCl (6 mL), cooled to −5° C. whereupon a solution of sodium nitrite (133 mg, 1.93 mmol) in water (4 mL) was added to form the diazonium salt. With both solutions cooled at −5 to 0° C., the solution of diazonium salt was added to the first solution over 2 min. After stirring for 30 min, the reaction mixture was taken to pH 7 by addition of NaHCO$_3$. The aqueous phase was extracted with DCM (3×70 mL). The combined organic phases were washed with brine (5 mL), dried (Na$_2$SO$_4$), the mixture filtered and the filtrate evaporated to dryness to afford 5-chloro-6-methylpyridine-3-sulfonyl chloride as a green oil (256 mg, 58%); $^1$H NMR (500 MHz, CDCl$_3$) δ 2.71 (s, 3H), 8.16 (d, 1H), 8.92 (d, 1H).

N-(5-chloro-3-methoxypyridin-2-yl)-5-phenylpyridine-3-sulfonamide

A flask charged with 5-bromo-N-(5-chloro-3-methoxypyridin-2-yl)pyridine-3-sulfonamide (300 mg, 0.79 mmol), phenylboronic acid (97 mg, 0.79 mmol) 1,4-dioxane (5 mL) and 2M Na$_2$CO$_3$ (0.6 mL) and tetrakis(triphenylphosphane)palladium(0) (10 mg, 0.01 mmol) was degassed with argon and then heated at 80° C. for 3 hrs. The mixture was then diluted with EtOAc (10 mL) and water (10 mL). The organic layer was washed with brine, dried (Na$_2$SO$_4$), the mixture was filtered and the filtrate evaporated to dryness. The crude product was purified using silica chromatography (eluent 10% MeOH in DCM) to give N-(5-chloro-3-methoxypyridin-2-yl)-5-phenylpyridine-3-sulfonamide (150 mg, 50%); m/z=376.4 (MH)$^+$.

Example 1

5-bromo-6-chloro-N-(5-chloro-2-hydroxypyridin-3-yl)pyridine-3-sulfonamide

ABR-238823

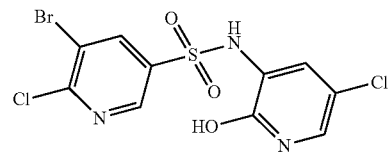

5-bromo-6-chloro-N-(5-chloro-2-methoxypyridin-3-yl)pyridine-3-sulfonamide (250 mg, 0.605 mmol) was dissolved in DCM (15 mL) and the reaction mixture cooled to −10° C. followed by addition of neat BBr$_3$ (454 mg, 1.82 mmol) drop wise. The reaction mixture was then stirred at room temperature for 16 hrs, diluted with DCM (5 mL) and neutralized with sodium bicarbonate to pH 7-8. More DCM (5 mL) was added, the phases were separated, the organic phase was washed with brine (15 mL), dried (Na$_2$SO$_4$) filtered and the filtrate concentrated under vacuum to afford the crude compound which was chromatographed on silica (5% Methanol in DCM) to afford 5-bromo-6-chloro-N-(5-chloro-2-hydroxypyridin-3-yl)pyridine-3-sulfonamide (90 mg, 37%) as a white solid.

Example 2

N-(4-hydroxypyridin-3-yl)benzenesulfonamide

ABR-238066

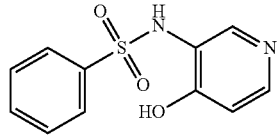

To a stirred solution of 3-amino-pyridin-4-ol (94 mg, 0.850 mmol) in DCM (4 mL) and DIPEA (220 mg, 1.70 mmol) at 0° C., was added dropwise a solution of benzenesulfonyl chloride (150 mg, 0.85 mmol) in DCM (4 mL) under nitrogen. The reaction mixture was warmed to room temperature and stirred for 16 hrs, before being washed with 3M HCl solution (2×10 mL) and water (2×10 mL). The combined aqueous phases were re-extracted with DCM (10 mL), then the combined organic layers were dried (Na$_2$SO$_4$) and concentrated under vacuum. The residue was recrystallized (EtOH/water) and further purification carried out by chromatography on silica (eluent: 10% MeOH in DCM) to afford N-(4-hydroxypyridin-3-yl)benzenesulfonamide (7 mg, 3%).

Example 3

N-(4-hydroxypyridin-3-yl)-4-(trifluoromethyl)benzene-1-sulfonamide

ABR-238845

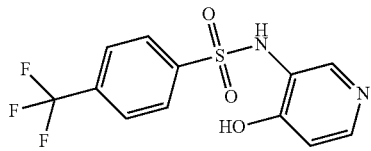

A mixture of 3-amino-pyridin-4-ol (100 mg, 0.908 mmol) and 4-trifluoromethyl)-benzene-1-sulfonyl chloride (222 mg, 0.908 mmol) was heated at 120° C. for 2 hrs under nitrogen. The cooled residue was partitioned between water and EtOAc and the organic phase was washed with a saturated solution of NaHCO₃ (5 mL) followed by brine (5 mL). It was then dried (MgSO₄), the mixture was filtered and the filtrate concentrated in vacuo. Purification was carried out by automated preparative HPLC (low pH method) to afford N-(4-hydroxypyridin-3-yl)-4-(trifluoromethyl)benzene-1-sulfonamide as a pink solid (22 mg, 8%).

Example 4

N-(4-hydroxypyridin-3-yl)-4-(trifluoromethoxy)benzene-1-sulfonamide

ABR-238846

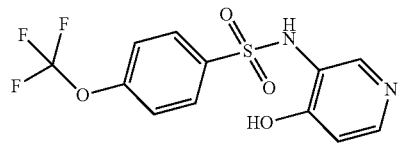

The procedure to prepare N-(4-hydroxypyridin-3-yl)-4-(trifluoromethyl)benzene-1-sulfonamide was used except that 4-(trifluoromethoxy)benzene-1-sulfonyl chloride was used instead of 4-trifluoromethyl)-benzene-1-sulfonyl chloride (14%).

Example 5

N-(5-chloro-3-hydroxypyridin-2-yl)-1-phenylmethanesulfonamide

ABR-239202

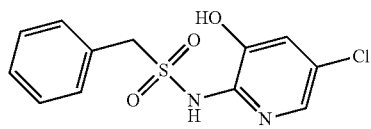

To a solution of 2-amino-5-chloro-3-methoxypyridine (100 mg, 0.631 mmol), prepared according to literature (Int. Appl. WO 2011085126) in pyridine (0.5 mL) benzyl sulfonyl chloride (120 mg, 0.631 mmol) was added and the solution was stirred at 50° C. for 1 h. The pyridine was evaporated, DCM was added (10 mL) followed by a solution of 1M BBr₃ in DCM dropwise (0.95 mL, 0.95 mmol). After 1 hr the mixture was quenched with 5M NaHCO₃ (10 mL), and more DCM was added (30 mL). The phases were separated and the organic phase was washed with brine (2 mL), dried (Na₂SO₄), the mixture was filtered and the filtrate evaporated to dryness to afford an orange oil which was chromatographed on silica (eluent: heptane:EtOAc 1:1) to afford the product as an off-white solid. Further purification was achieved by slurrying the solid in DCM/heptane 1:5 (5 mL) followed by filtration (66 mg, 35%).

Example 6

N-(5-chloro-3-hydroxypyridin-2-yl)-6-(pyrrolidin-1-yl)pyridine-3-sulfonamide

ABR-239224

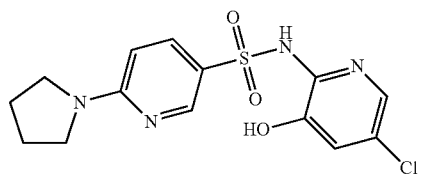

A solution of 6-chloro-N-(5-chloro-3-methoxypyridin-2-yl)pyridine-3-sulfonamide (100 mg, 0.299 mmol) in pyrrolidine (1 mL) was heated at 80° C. for 2 hrs. The pyrrolidine was evaporated and DCM was added (3 mL). 1M BBr₃ in DCM (3 mL, 3 mmol) was then added and the mixture was stirred for 3 hrs before being made alkaline with saturated NaHCO₃. The phases were separated and the organic phase was washed with brine (2 mL), dried (Na₂SO₄), the mixture was filtered and the filtrate evaporated to dryness to afford a dark blue oil which was subjected to automated reverse phase HPLC (low pH method) to afford N-(5-chloro-3-hydroxypyridin-2-yl)-6-(pyrrolidin-1-yl)pyridine-3-sulfonamide as the formate salt (29 mg, 27%).

Example 7

N-(5-chloro-3-hydroxypyridin-2-yl)pyridine-3-sulfonamide

ABR-239225

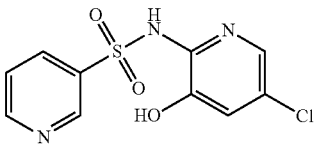

To a solution of 5-chloro-3-methoxypyridin-2-amine (100 mg, 0.631 mmol) in pyridine (1 mL) pyridine-3-sulfonyl chloride hydrochloride (135 mg, 0.631 mmol) was added and the solution was stirred at room temperature for 1 hr. The pyridine was evaporated, DCM was added (5 mL) followed by 1M BBr₃ in DCM (0.95 mL, 0.95 mmol) and the solution was stirred overnight. Saturated NaHCO₃ (5 mL) and more DCM (30 mL) were added. The phases were separated and the organic phase was washed with brine (2 mL), dried (Na₂SO₄), the mixture was filtered and the filtrate evaporated to dryness to afford an orange oil which was chromatographed on silica (eluent: heptane:EtOAc 2:1 then EtOAc:MeOH 9:1) to afford the product as a green oil. Further purification was achieved using automated reverse phase HPLC (high pH method) to afford N-(5-chloro-3-hydroxypyridin-2-yl) pyridine-3-sulfonamide as a brown solid (29 mg, 16%).

Example 8

6-chloro-N-(5-chloro-3-hydroxypyridin-2-yl)pyridine-3-sulfonamide

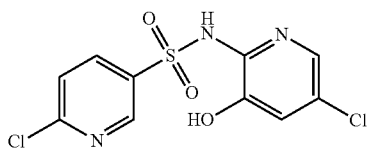

ABR-239226

6-chloro-N-(5-chloro-3-methoxypyridin-2-yl)pyridine-3-sulfonamide was deprotected with 1M BBr₃ in DCM and the resultant 6-chloro-N-(5-chloro-3-hydroxypyridin-2-yl)pyridine-3-sulfonamide was purified as described in the procedure for the preparation of N-(5-chloro-3-hydroxypyridin-2-yl) pyridine-3-sulfonamide, except that HPLC using the low pH method was used, affording the formate salt (5%).

Example 9

N-(5-chloro-3-hydroxypyridin-2-yl)-1-(3,5-dichlorophenyl)methanesulfonamide

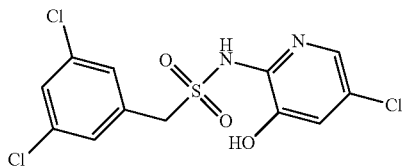

ABR-239247

To a solution of 5-chloro-3-methoxypyridin-2-amine (167 mg, 0.821 mmol) in pyridine (3 mL) (3,5-dichlorophenyl)methanesulfonyl chloride (213 mg, 0.821 mmol) was added and the mixture was stirred at room temperature over 64 hrs. The solvent was evaporated and a rough purification was carried out by silica chromatography (eluent: heptane:EtOAc 2:1). Product-containing fractions were combined, evaporated, dissolved in DCM (5 mL), then treated with 1M BBr₃ in DCM (0.82 mL, 0.82 mmol) and the solution stirred for 3 hrs. The reaction was quenched with excess saturated NaHCO₃ and more DCM added (15 mL). The phases were separated and the organic phase was washed with brine (3 mL), dried (Na₂SO₄), the mixture was filtered and the filtrate evaporated to dryness to afford a purple grey solid which was purified by slurrying in heptane:EtOAc to afford N-(5-chloro-3-hydroxypyridin-2-yl)-1-(3,5-dichlorophenyl)methanesulfonamide as a white solid (55 mg, 18%).

Example 10

N-(5-chloro-3-hydroxypyridin-2-yl)-6-[(propan-2-yl)amino]pyridine-3-sulfonamide

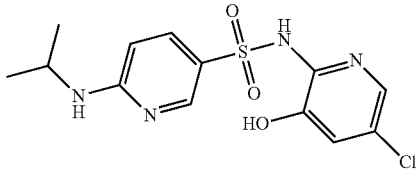

ABR-239248

A solution of 6-chloro-N-(5-chloro-3-methoxypyridin-2-yl)pyridine-3-sulfonamide (60 mg, 0.180 mmol) in isopropylamine (1 mL) was heated at 145° C. in a CEM discover microwave for 4 hrs (about 50% conversion). The solvent was evaporated and the residue was dissolved in DCM (5 mL), then treated with 1M BBr₃ in DCM (0.18 mL, 0.18 mmol) and the solution stirred overnight. The reaction was quenched with excess saturated NaHCO₃ and more DCM was added (15 mL). The phases were separated and the organic phase was washed with brine (3 mL), dried (Na₂SO₄), the mixture was filtered and the filtrate evaporated to dryness to afford an orange oil which was purified by automated reverse phase HPLC (high pH method) to afford N-(5-chloro-3-hydroxypyridin-2-yl)-6-[(propan-2-yl)amino]pyridine-3-sulfonamide as a brown oil (5 mg, 8%).

Example 11

5-bromo-6-chloro-N-[3-hydroxy-5-(propan-2-yl)pyridin-2-yl]pyridine-3-sulfonamide

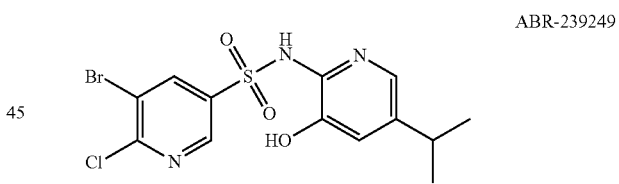

ABR-239249

To a solution of 3-methoxy-5-(propan-2-yl)pyridin-2-amine (117 mg, 0.549 mmol) in pyridine (1 mL) was added 5-bromo-6-chloropyridine-3-sulfonyl chloride (160 mg, 0.549 mmol) and the mixture was stirred for 1 hr at room temperature. The solvent was evaporated and rudimentary purification carried out by silica chromatography (eluent: heptane:EtOAc 2:1). Product-containing fractions were combined, evaporated, dissolved in DCM (5 mL), then treated with 1M BBr₃ in DCM (2.2 mL, 2.2 mmol) and the solution stirred for 3 hrs. The reaction was quenched with excess saturated NaHCO₃ and more DCM was added (15 mL). The phases were separated and the organic phase was washed with brine (3 mL), dried (Na₂SO₄), the mixture was filtered and the filtrate evaporated to dryness to afford an orange oil which was purified by automated reverse phase HPLC (high pH method) to afford 5-bromo-6-chloro-N-[3-hydroxy-5-(propan-2-yl)pyridin-2-yl]pyridine-3-sulfonamide as a green solid (28 mg, 12%).

Example 12

N-(5-chloro-3-hydroxypyridin-2-yl)-1-(3-cyanophenyl)methanesulfonamide

ABR-239254

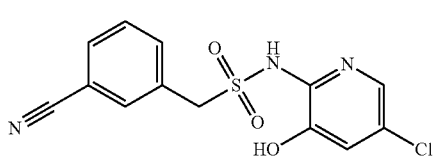

The procedure for preparation of N-(5-chloro-3-hydroxypyridin-2-yl)-1-(3,5-dichloro-phenyl)methanesulfonamide was used except that (3-cyanophenyl)methanesulfonyl chloride was substituted for (3,5-dichlorophenyl)methanesulfonyl chloride (18%).

Example 13

(+/−)-5-bromo-6-chloro-N-[3-hydroxy-5-(1-hydroxypropan-2-yl)pyridin-2-yl]pyridine-3-sulfonamide

ABR-239269

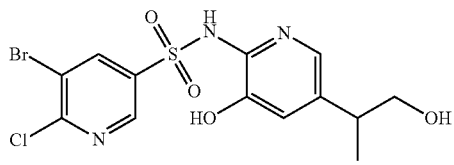

The procedure for preparation of 5-bromo-6-chloro-N-[3-hydroxy-5-(propan-2-yl)-pyridin-2-yl]pyridine-3-sulfonamide was used, except that (+/−)-2-(6-amino-5-methoxypyridin-3-yl)propan-1-ol was substituted for 3-methoxy-5-(propan-2-yl)pyridin-2-amine (3%).

Example 14

5-bromo-6-chloro-N-(3-hydroxypyridin-2-yl)pyridine-3-sulfonamide

ABR-239270

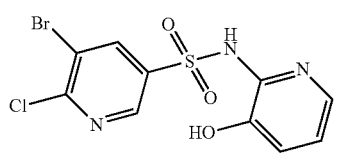

The procedure for preparation of 5-bromo-6-chloro-N-[3-hydroxy-5-(propan-2-yl)pyridin-2-yl]pyridine-3-sulfonamide was used, except that 2-amino-3-methoxy-pyridine was substituted for 3-methoxy-5-(propan-2-yl)pyridin-2-amine. No chromatographic purification of the intermediate methoxy ether was carried out (7%).

Example 15

N-(5-chloro-3-hydroxypyridin-2-yl)-1-(2,4-dichlorophenyl)methanesulfonamide

ABR-239271

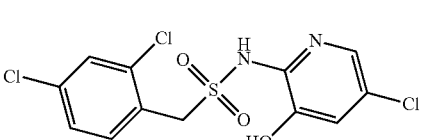

The procedure for preparation of N-(5-chloro-3-hydroxypyridin-2-yl)-1-(3,5-dichloro-phenyl)methanesulfonamide was used except that (2,4-dichlorophenyl)-methanesulfonyl chloride was substituted for (3,5-dichlorophenyl)methanesulfonyl chloride. No chromatographic purification of the intermediate methoxy ether was carried out and the target compound was purified by automated reverse phase HPLC (low pH method) (18%).

Example 16

N-(5-chloro-3-hydroxypyridin-2-yl)-1-(4-cyanophenyl)methanesulfonamide

ABR-239272

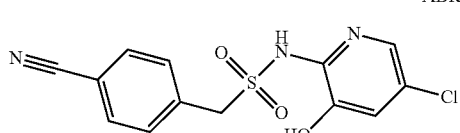

The procedure for preparation of N-(5-chloro-3-hydroxypyridin-2-yl)-1-(3,5-dichloro-phenyl)methanesulfonamide was used except that (4-cyanophenyl)methanesulfonyl chloride was substituted for (3,5-dichlorophenyl)methanesulfonyl chloride. No chromato-graphic purification of the intermediate methoxy ether was carried out and the target compound was purified by automated reverse phase HPLC (high pH method) (27%).

Example 17

N-(5-chloro-3-hydroxypyridin-2-yl)-1-pyridin-3-ylmethanesulfonamide

ABR-239290

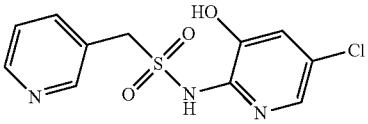

The procedure for preparation of N-(5-chloro-3-hydroxypyridin-2-yl)-1-(3,5-dichloro-phenyl)methanesulfonamide was used except that pyridin-3-ylmethanesulfonyl chloride, trifluoroacetate salt was substituted for (3,5-dichlorophenyl)methanesulfonyl chloride. No chromatographic purification of the intermediate methoxy ether was carried out and the target compound was purified by automated reverse phase HPLC (low pH method) (7%).

Example 18

5-bromo-N-(5-chloro-3-hydroxypyridin-2-yl)-6-(pyrrolidin-1-yl)pyridine-3-sulfonamide

ABR-239291

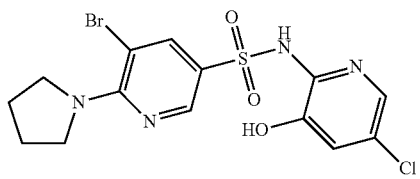

The procedure for preparation of N-(5-chloro-3-hydroxy-pyridin-2-yl)-6-(pyrrolidin-1-yl)pyridine-3-sulfonamide was used except that 5-bromo-6-chloro-N-(5-chloro-3-methoxypyridin-2-yl)pyridine-3-sulfonamide was substituted for 6-chloro-N-(5-chloro-3-methoxypyridin-2-yl)pyridine-3-sulfonamide. In addition, several ineffective attempts were made to purify the intermediate methoxy compound by chromatography (7%).

Example 19

N-(5-chloro-3-hydroxypyridin-2-yl)-1-(3,5-difluoro-phenyl)methanesulfonamide

ABR-239314

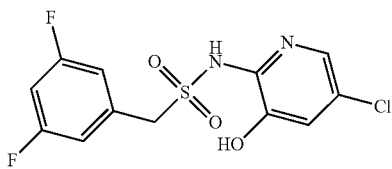

The procedure for preparation of N-(5-chloro-3-hydroxy-pyridin-2-yl)-1-(3,5-dichloro-phenyl)methanesulfonamide was used except that (3,5-difluorophenyl)methanesulfonyl chloride was substituted for (3,5-dichlorophenyl)methanesulfonyl chloride. No chromato-graphic purification of the intermediate methoxy ether was carried out and the target compound was purified by automated reverse phase HPLC (high pH method) (14%).

Example 20

N-(5-chloro-3-hydroxypyridin-2-yl)-1-(2,5-dichloro-thiophen-3-yl)methane-sulfonamide

ABR-239315

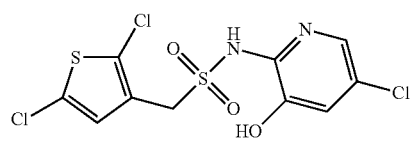

The procedure for preparation of N-(5-chloro-3-hydroxy-pyridin-2-yl)-1-(3,5-dichloro-phenyl)methanesulfonamide was used except that (2,5-dichlorothiophen-3-yl)methane-sulfonyl chloride was substituted for (3,5-dichlorophenyl)methanesulfonyl chloride. No chromatographic purification of the intermediate methoxy ether was carried out and the target compound was purified by automated reverse phase HPLC (low pH method) (35%).

Example 21

N-(5-chloro-3-hydroxypyridin-2-yl)-1-(3,4-dichloro-phenyl)methanesulfonamide

ABR-239316

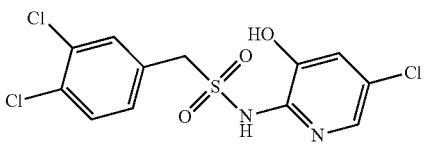

The procedure for preparation of N-(5-chloro-3-hydroxy-pyridin-2-yl)-1-(3,5-dichloro-phenyl)methanesulfonamide was used except that (3,4-dichlorophenyl)methanesulfonyl chloride was substituted for (3,5-dichlorophenyl)methane-sulfonyl chloride. An extra charge of sulfonyl chloride (0.3 mol equivalents) was added 16 hrs after initial addition and stirring continued for a further 30 min. No chromatographic purification of the intermediate methoxy ether was carried out and the target compound was purified by automated reverse phase HPLC (low pH method) (17%).

Example 22

N-(5-chloro-3-hydroxypyridin-2-yl)-1-(3-chloro-5-fluorophenyl)methane-sulfonamide

ABR-239317

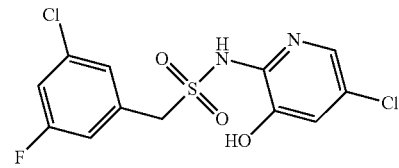

The procedure for preparation of N-(5-chloro-3-hydroxy-pyridin-2-yl)-1-(3,5-dichloro-phenyl)methanesulfonamide was used except that (3-chloro-5-fluorophenyl)methane-sulfonyl chloride was substituted for (3,5-dichlorophenyl)methanesulfonyl chloride. An extra charge of sulfonyl chloride (0.3 mol equivalents) was added 16 hrs after the initial addition and stirring continued for a further 30 min. No chromatographic purification of the intermediate methoxy ether was carried out and the target compound was purified by automated reverse phase HPLC (low pH method) (23%).

Example 23

1-(2,4-dichlorophenyl)-N-(4-hydroxypyridin-3-yl)methanesulfonamide

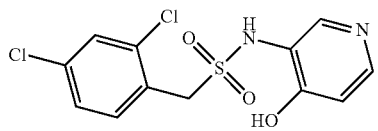

ABR-239318

To a solution of 3-amino-4-methoxypyridine (120 mg, 0.754 mmol) in pyridine (3 mL) at 50° C. (2,4-dichlorophenyl)methanesulfonyl chloride was added and the mixture was stirred for 2 hrs at this temperature. The pyridine was evaporated, DCM (60 mL) was added followed by 1M HCl (20 mL). The phases were separated and the organic phase was washed with brine (20 mL), dried (Na$_2$SO$_4$), the mixture was filtered and the filtrate evaporated to dryness to afford a brown oil which was dissolved in DCM (10 mL) and 1M BBr$_3$ in DCM (2.26 mL, 2.26 mmol) was added. The mixture was stirred for 1 hr before being quenched with excess saturated NaHCO$_3$. The phases were separated and the organic phase was washed with brine (20 mL), dried (Na$_2$SO$_4$), the mixture was filtered and the filtrate evaporated to dryness to afford a brown oil which was purified by preparative automated reverse phase HPLC (low pH method) (6 mg, 2%).

Example 24

1-(3,5-dichlorophenyl)-N-(4-hydroxypyridin-3-yl)methanesulfonamide

ABR-239321

The procedure for the preparation of 1-(2,4-dichlorophenyl)-N-(4-hydroxypyridin-3-yl)methanesulfonamide was used, except that (3,5-dichlorophenyl)methanesulfonyl chloride was substituted for (2,4-dichlorophenyl)methanesulfonyl chloride. HPLC purification was carried out using the high pH method (1%).

Example 25

3,5-dichloro-N-(5-chloro-3-hydroxypyridin-2-yl)benzene-1-sulfonamide

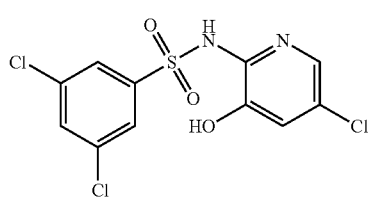

ABR-239331

To a solution of 2-amino-5-chloro-3-methoxypyridine (150 mg, 0.738 mmol) in pyridine (3 mL) at room temperature 3,5-dichlorobenzene-1-sulfonyl chloride (181 mg, 0.738 mmol) was added and the mixture was stirred for 2 hrs. The pyridine was evaporated, DCM (60 mL) was added followed by 1M HCl (20 mL). The phases were separated and the organic phase was washed with brine (20 mL), dried (Na$_2$SO$_4$), the mixture was filtered and the filtrate evaporated to dryness to afford a brown oil which was dissolved in DCM (10 mL) and 1M BBr$_3$ in DCM (2.21 mL, 2.21 mmol) was added. The mixture was stirred for 1 hr before being quenched with saturated NaHCO$_3$. The phases were separated and the organic phase was washed with brine (20 mL), dried (Na$_2$SO$_4$), the mixture was filtered and the filtrate evaporated to dryness to afford a brown oil which was purified by preparative automated reverse phase HPLC (low pH method) (120 mg, 46%).

Example 26

3,4-dichloro-N-(5-chloro-3-hydroxypyridin-2-yl)benzene-1-sulfonamide

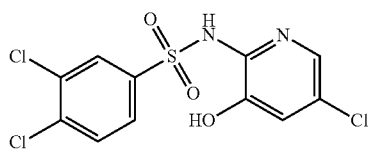

ABR-239332

The procedure for the preparation of 3,5-dichloro-N-(5-chloro-3-hydroxypyridin-2-yl)-benzene-1-sulfonamide was used, except that 3,4-dichlorobenzene-1-sulfonyl chloride was substituted for 3,5-dichlorobenzene-1-sulfonyl chloride (51%).

Example 27

N-(5-chloro-3-hydroxypyridin-2-yl)-1-(3-chlorophenyl)methanesulfonamide

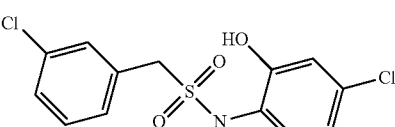

ABR-239333

The procedure for preparation of N-(5-chloro-3-hydroxy-pyridin-2-yl)-1-(3,5-dichloro-phenyl)methanesulfonamide was used except that (3-chlorophenyl)methanesulfonyl chloride was substituted for (3,5-dichlorophenyl)methanesulfonyl chloride. An extra charge of sulfonyl chloride (0.2 mol equivalents) was added 2 hrs after initial addition and stirring continued for a further 30 min. No chromatographic purification of the intermediate methoxy ether was carried out and the target compound was purified by automated reverse phase HPLC (low pH method) (19%).

Example 28

N-(5-chloro-3-hydroxypyridin-2-yl)-1-(4-chlorophenyl)methanesulfonamide

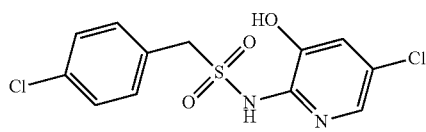

ABR-239334

The procedure for preparation of N-(5-chloro-3-hydroxy-pyridin-2-yl)-1-(3,5-dichloro-phenyl)methanesulfonamide was used except that (4-chlorophenyl)methane-sulfonyl chloride was substituted for (3,5-dichlorophenyl)methane-sulfonyl chloride. An extra charge of sulfonyl chloride (0.2 mol equivalents) was added 2 hrs after initial addition and stirring continued for a further 30 min. No chromatographic purification of the intermediate methoxy ether was carried out and the target compound was purified by automated reverse phase HPLC (low pH method) (22%).

Example 29

N-(5-chloro-3-hydroxypyridin-2-yl)-1-(2-chlorophenyl)methanesulfonamide

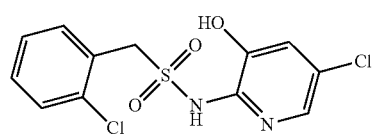

ABR-239335

The procedure for preparation of N-(5-chloro-3-hydroxy-pyridin-2-yl)-1-(3,5-dichloro-phenyl)methanesulfonamide was used except that (2-chlorophenyl)methane-sulfonyl chloride was substituted for (3,5-dichlorophenyl)methane-sulfonyl chloride. An extra charge of sulfonyl chloride (0.2 mol equivalents) was added 2 hrs after initial addition and stirring continued for a further 30 min. No chromatographic purification of the intermediate methoxy ether was carried out and the target compound was purified by automated reverse phase HPLC (low pH method) (33%).

Example 30

N-(5-chloro-3-hydroxypyridin-2-yl)-1-(2,5-dichloro-phenyl)methanesulfonamide

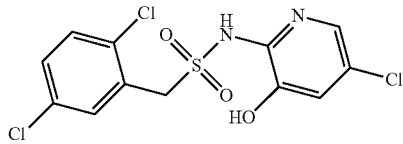

ABR-239336

The procedure for preparation of N-(5-chloro-3-hydroxy-pyridin-2-yl)-1-(3,5-dichloro-phenyl)methanesulfonamide was used except that (2,5-dichlorophenyl)methanesulfonyl chloride was substituted for (3,5-dichlorophenyl)methanesulfonyl chloride. An extra charge of sulfonyl chloride (0.2 mol equivalents) was added 2 hrs after initial addition and stirring continued for a further 30 min. No chromatographic purification of the intermediate methoxy ether was carried out and the target compound was purified by automated reverse phase HPLC (low pH method) (36%).

Example 31

N-(5-chloro-3-hydroxypyridin-2-yl)-1-(3,4-difluoro-phenyl)methanesulfonamide

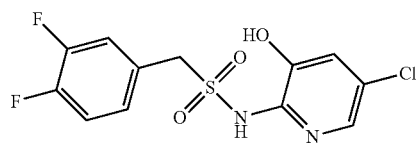

ABR-239337

The procedure for preparation of N-(5-chloro-3-hydroxy-pyridin-2-yl)-1-(3,5-dichloro-phenyl)methanesulfonamide was used except that (3,4-difluorophenyl)methanesulfonyl chloride was substituted for (3,5-dichlorophenyl)methane-sulfonyl chloride. An extra charge of sulfonyl chloride (0.2 mol equivalents) was added 2 hrs after initial addition and stirring continued for a further 30 min. No chromatographic purification of the intermediate methoxy ether was carried out and the target compound was purified by automated reverse phase HPLC (low pH method) (47%).

Example 32

1-(3,5-dichlorophenyl)-N-(3-hydroxy-5-methanesulfonylpyridin-2-yl)methane-sulfonamide

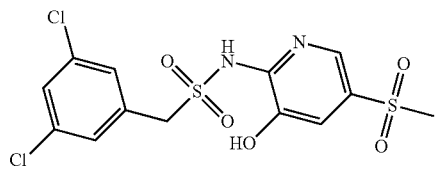

ABR-239338

To a solution of 3-methoxy-5-(methylsulfanyl)pyridin-2-amine (191 mg, 0.875 mmol) in pyridine (3 mL) was added (3,5-dichlorophenyl)methanesulfonyl chloride (227 mg, 0.875 mmol) and the mixture was stirred for 1 hr. The solvent was evaporated and the residue dissolved in DCM (25 mL), then treated with m-chloroperbenzoic acid (70% purity, 367 mg, 1.49 mmol) in three portions. After 15 min, 1M BBr$_3$ in DCM (2.62 mL, 2.62 mmol) was added and the solution stirred for 3 hrs. The reaction was quenched with excess saturated NaHCO$_3$ and more DCM was added (15 mL). The phases were separated and the organic phase was washed with brine (3 mL), dried (Na$_2$SO$_4$), the mixture was filtered and the filtrate evaporated to dryness to afford a brown oil which was purified by automated reverse-phase HPLC (low pH method) (17 mg, 5%).

Example 33

N-(5-chloro-3-hydroxypyridin-2-yl)-1-(3-chloro-5-cyanophenyl)methanesulfonamide

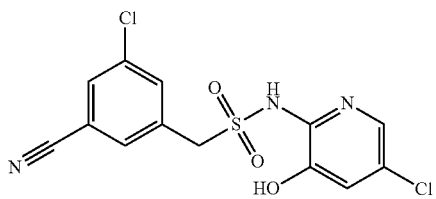

ABR-239514

The procedure to prepare N-(6-chloro-4-hydroxypyridazin-3-yl)-1-(3,4-difluorophenyl)-methanesulfonamide was used except that (3-chloro-5-cyanophenyl)methanesulfonyl chloride was substituted for (3,4-difluorophenyl)methanesulfonyl chloride and 5-chloro-3-methoxypyridin-2-amine was substituted for 6-chloro-4-methoxypyridazin-3-amine (21%).

Example 34

3-chloro-5-{[(5-chloro-3-hydroxypyridin-2-yl)sulfamoyl]methyl}benzamide

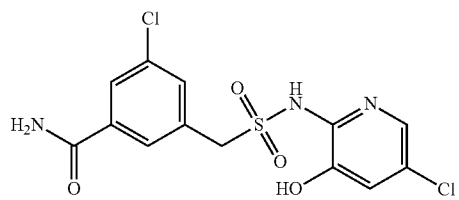

239520

To a solution of N-(5-chloro-3-hydroxypyridin-2-yl)-1-(3-chlorocyanophenyl)-methanesulfonamide (35 mg, 0.098 mmol) in DMSO (1.5 mL) was added K$_2$CO$_3$ (14 mg, 0.098 mmol) and 27% H$_2$O$_2$ (aq, 36 µL, 0.293 mmol). The mixture was stirred for 3 hrs at 45° C. then purified by automated reverse phased HPLC (low pH method) to afford the title compound as a white solid (3 mg, 7%).

Example 35

1-(5-chloro-2-fluorophenyl)-N-(5-chloro-3-hydroxypyridin-2-yl)methane-sulfonamide

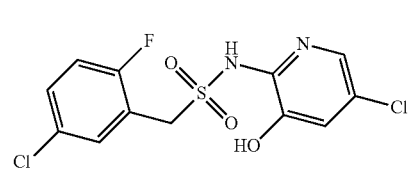

ABR-239359

The procedure for preparation of N-(5-chloro-3-hydroxypyridin-2-yl)-1-(3,5-dichloro-phenyl)methanesulfonamide was used except that (5-chloro-2-fluorophenyl)methane-sulfonyl chloride was substituted for (3,5-dichlorophenyl)methanesulfonyl chloride. The intermediate methoxy ether was isolated by EtOAc/water workup and purified by silica chromatography (eluent: DCM:MeOH 9:1). After the usual deprotection (5 equivalents of BBr$_3$ at 0° C.) and workup, the target compound was purified by automated reverse phase HPLC (low pH method) (26%).

Example 36

N-(6-chloro-4-hydroxypyridazin-3-yl)-1-(3,5-dichlorophenyl)methanesulfonamide

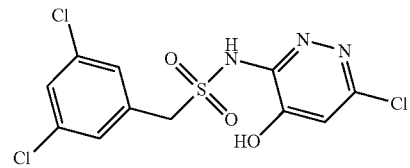

ABR-239372

To a solution of 6-chloro-4-methoxypyridazin-3-amine, prepared using a literature procedure (WO2004108690A1) (403 mg, 1.97 mmol), in pyridine (3 mL) was added (3,5-dichlorophenyl)methanesulfonyl chloride (511 mg, 1.97 mmol) and the mixture was stirred for 1 hr. The solvent was evaporated and the residue dissolved in DCM (100 mL), then treated with 1M BBr$_3$ in DCM (3.9 mL, 3.9 mmol) and the solution stirred 3 hrs. A further 2 mL of the BBr$_3$ solution was added with further stirring for 3 hrs. The reaction was quenched with excess saturated NaHCO$_3$ and more DCM was added (15 mL) A significant amount of solid precipitated, so the mixture was filtered and the filtrate reserved. The solid was treated with 3M HCl until effervescence stopped and was carefully added back to the DCM/NaHCO$_3$ mixture, ensuring the pH did not fall to below 7.

The phases were separated and the aqueous phase re-extracted with EtOAc (3×40 mL). The combined organic phases were dried (Na$_2$SO$_4$), the mixture was filtered and the filtrate evaporated to dryness to afford brown oil which was purified by reverse-phase HPLC (low pH method). After removal of solvent the residue was slurried with hot EtOAc/Heptane (1:1, 5 mL) and filtered to afford N-(6-chloro-4-hydroxypyridazin-3-yl)-1-(3,5-dichlorophenyl)methanesulfonamide as a tan solid (90 mg, 12%).

Example 37

N-(5-chloro-3-hydroxypyridin-2-yl)-1-(2,3-dichlorophenyl)methanesulfonamide

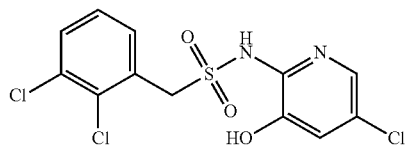

ABR-239373

The procedure for preparation of N-(5-chloro-3-hydroxypyridin-2-yl)-1-(3,5-dichloro-phenyl)methanesulfonamide was used except that (2,3-dichlorophenyl)methanesulfonyl chloride was substituted for (3,5-dichlorophenyl)methanesulfonyl chloride. The initial reaction was complete in 1 hr. No chromatographic purification of the intermediate methoxy ether was carried out and the target compound was purified by automated reverse phase HPLC (low pH method).

Example 38

N-(5-chloro-3-hydroxypyridin-2-yl)-1-(2,6-dichlorophenyl)methanesulfonamide

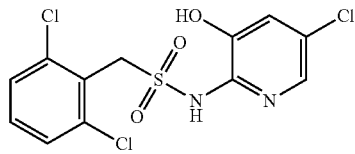

ABR-239374

The procedure for preparation of N-(5-chloro-3-hydroxypyridin-2-yl)-1-(3,5-dichloro-phenyl)methanesulfonamide was used except that (2,6-dichlorophenyl)methanesulfonyl chloride was substituted for (3,5-dichlorophenyl)methanesulfonyl chloride. The initial reaction was complete in 1 hr. No chromatographic purification of the intermediate methoxy ether was carried out and the target compound was purified by automated reverse phase HPLC (low pH method) (34%).

Example 39

(a) (1R)—N-(5-chloro-3-hydroxypyridin-2-yl)-1-(3,5-dichlorophenyl)ethane-1-sulfonamide, and (b) (1S)—N-(5-chloro-3-hydroxypyridin-2-yl)-1-(3,5-dichlorophenyl)-ethane-1-sulfonamide

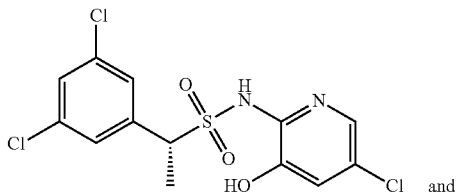

ABR-239405 and

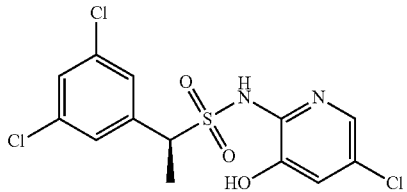

ABR-239406

The procedure for preparation of N-(5-chloro-3-hydroxypyridin-2-yl)-1-(3,5-dichloro-phenyl)methanesulfonamide was used except that (+/−)-1-(3,5-dichlorophenyl)ethane-1-sulfonyl chloride was substituted for (3,5-dichlorophenyl)methanesulfonyl chloride. The initial reaction was complete in 1 hr. No chromatographic purification of the intermediate methoxy ether was carried out and the racemic mixture was purified by automated reverse phase HPLC (low pH method) (29%).

The racemate was resolved by SFC to afford separate enantiomers (1R)—N-(5-chloro-3-hydroxypyridin-2-yl)-1-(3,5-dichlorophenyl)ethane-1-sulfonamide and (1S)—N-(5-chloro-3-hydroxypyridin-2-yl)-1-(3,5-dichlorophenyl)ethane-1-sulfonamide, stereochemistry not assigned.

Example 40

5-bromo-N-(5-chloro-3-hydroxypyridin-2-yl)pyridine-3-sulfonamide

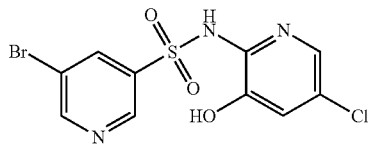

ABR-239183

5-bromo-N-(5-chloro-3-methoxypyridin-2-yl)pyridine-3-sulfonamide (50 mg, 0.13 mmol) was dissolved in DCM (2 mL) and the reaction mixture cooled to −10° C. followed by dropwise addition of $BBr_3$ (1.50 mL, 1.50 mmol) as a 1M DCM solution and stirring at room temperature for 16 hrs. The reaction mixture was diluted with DCM (5 mL) and quenched with saturated sodium bicarbonate. More DCM (10 mL) was added, the phases were separated and the organic phase washed with brine (2 mL), dried ($Na_2SO_4$), the mixture was filtered and the filtrate concentrated under vacuum and the residue purified by preparative TLC (eluent: 10% acetone in DCM) to afford 5-bromo-N-(5-chloro-3-hydroxypyridin-2-yl)pyridine-3-sulfonamide (5 mg, 10%) as a brown solid.

Example 41

N-(5-chloro-3-hydroxypyridin-2-yl)-6-(trifluoromethyl)pyridine-3-sulfonamide

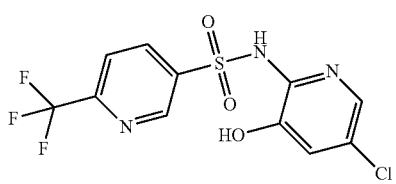

ABR-239239

The procedure to prepare 5-bromo-N-(5-chloro-3-hydroxypyridin-2-yl)pyridine-3-sulfonamide was used, except that 6-(trifluoromethyl)pyridine-3-sulfonyl chloride was substituted for 5-bromo-N-(5-chloro-3-methoxypyridin-2-yl)pyridine-3-sulfonamide. Crude compound was purified by preparative TLC (eluent: 30% MeOH in DCM) to afford N-(5-chloro-3-hydroxypyridin-2-yl)-6-(trifluoromethyl)pyridine-3-sulfonamide (30%) as an off-white solid.

Example 42

N-(5-chloro-3-hydroxypyridin-2-yl)-3-(trifluoromethoxy)benzene-1-sulfonamide

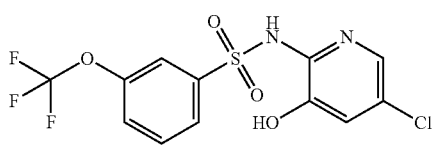

ABR-239262

The procedure to prepare 5-bromo-N-(5-chloro-3-hydroxypyridin-2-yl)pyridine-3-sulfonamide was used, except that N-(5-chloro-3-methoxypyridin-2-yl)-3-(trifluoromethoxy)benzene-1-sulfonamide was substituted for 5-bromo-N-(5-chloro-3-methoxy-pyridin-2-yl)pyridine-3-sulfonamide (yield 44%, brown oil).

Example 43

N-(5-bromo-3-hydroxypyridin-2-yl)benzene sulfonamide

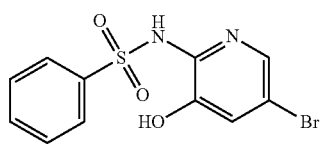

ABR-239049

The procedure to prepare 5-bromo-N-(5-chloro-3-hydroxypyridin-2-yl)pyridine-3-sulfon-amide was used, except that N-(5-bromo-3-methoxypyridin-2-yl)benzene sulfonamide was substituted for 5-bromo-N-(5-chloro-3-methoxypyridin-2-yl)pyridine-3-sulfonamide. The crude product was purified by preparative TLC (eluent: 2% MeOH in DCM) to afford N-(5-bromo-3-hydroxypyridin-2-yl)benzene sulfonamide (21%) as an off-white solid.

Example 44

N-(5-bromo-3-hydroxypyridin-2-yl)-2,5-dichlorothiophene-3-sulfonamide

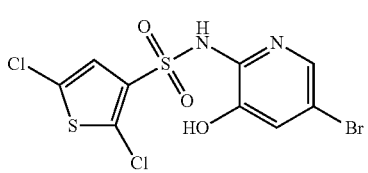

ABR-239050

The procedure to prepare 5-bromo-N-(5-chloro-3-hydroxypyridin-2-yl)pyridine-3-sulfon-amide was used, except that N-(5-bromo-3-methoxypyridin-2-yl)-2,5-dichlorothiophene-3-sulfonamide was substituted for 5-bromo-N-(5-chloro-3-methoxypyridin-2-yl)pyridine-3-sulfonamide. The crude product was purified by preparative TLC (eluent: 2% MeOH in DCM) to afford N-(5-bromo-3-hydroxypyridin-2-yl)-2,5-dichlorothiophene-3-sulfonamide (24%) as an off-white solid.

Example 45

N-(5-bromo-3-hydroxypyridin-2-yl)-3-(trifluoromethoxy)benzene-1-sulfonamide

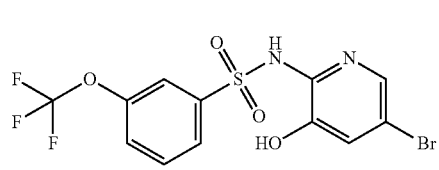

ABR-239275

The procedure to prepare 5-bromo-N-(5-chloro-3-hydroxypyridin-2-yl)pyridine-3-sulfon-amide was used, except that N-(5-bromo-3-methoxypyridin-2-yl)-3-(trifluoromethoxy)-benzene-1-sulfonamide was substituted for 5-bromo-N-(5-chloro-3-methoxy-pyridin-2-yl)pyridine-3-sulfonamide. The crude product was purified by preparative TLC eluting with 10% MeOH in DCM to afford N-(5-bromo-3-hydroxy-pyridin-2-yl)-3-(trifluoro-methoxy)benzene-1-sulfonamide (25%) as a brown oil.

Example 46

5-bromo-N-(5-bromo-3-hydroxypyridin-2-yl)-6-chloropyridine-3-sulfonamide

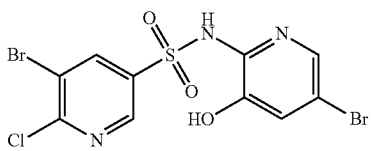

ABR-239304

A solution of 5-bromo-N-(5-bromo-3-methoxypyridin-2-yl)-6-chloropyridine-3-sulfon-amide (230 mg, 0.500 mmol) in DCM (2 mL) was cooled to 0° C. followed by addition of neat BBr$_3$ (3850 µL, 24.5 mmol) drop wise. The reaction mixture was then stirred at room temperature for 16 hrs. The reaction mixture was diluted with 5 mL DCM and the reaction mixture brought to pH 7-8 with sodium bicarbonate. More DCM (5 mL) was added, the phases were separated and the organic phase washed with brine (2 mL), dried (Na$_2$SO$_4$), the mixture was filtered and the filtrate concentrated under vacuum. The residue was chromatographed on silica (10% MeOH in DCM) to afford 5-bromo-N-(5-bromo-3-hydroxypyridin-2-yl)-6-chloropyridine-3-sulfonamide (50 mg, 22%) as an off-white solid.

Example 47

N-(5-bromo-3-hydroxypyridin-2-yl)-6-(trifluoromethyl)pyridine-3-sulfonamide

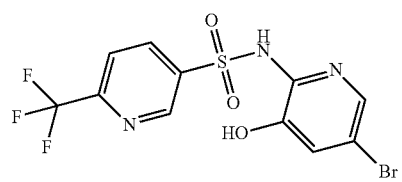

ABR-239327

The procedure to prepare 5-bromo-N-(5-chloro-3-hydroxypyridin-2-yl)pyridine-3-sulfonamide was used, except that N-(5-bromo-3-methoxypyridin-2-yl)-6-(trifluoromethyl)pyridine-3-sulfonamide was substituted for 5-bromo-N-(5-chloro-3-methoxy-pyridin-2-yl)pyridine-3-sulfonamide. The crude product was purified by preparative TLC eluting with 10% MeOH in DCM to afford N-(5-bromo-3-hydroxy-pyridin-2-yl)-6-(trifluoromethyl)pyridine-3-sulfonamide (16%) as an off-white solid.

Example 48

5-bromo-N-(5-bromo-3-hydroxypyridin-2-yl)-6-methoxypyridine-3-sulfonamide

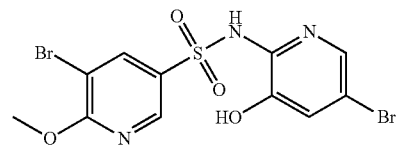

ABR-239345

To a solution of 5-bromo-N-(5-bromo-3-hydroxypyridin-2-yl)-6-chloropyridine-3-sulfonamide (30 mg, 0.068 mmol) in MeOH (2 mL) sodium methoxide (183 mg, 3.38 mmol) was slowly added at room temperature and the reaction mixture was stirred at room temperature for 16 hrs. It was then concentrated under vacuum and the residue dissolved in water (5 mL), with the pH adjusted to about 4 by addition of 1N HCl and extracted with ethyl acetate (2×10 mL). The combined organic layers were dried (Na$_2$SO$_4$) and concentrated to afford the crude product which was purified by preparative TLC in 8% methanol in DCM to afford 5-bromo-N-(5-bromo-3-hydroxypyridin-2-yl)-6-methoxypyridine-3-sulfonamide (5 mg, 17%) as a red solid.

Example 49

N-(3-hydroxypyridin-2-yl)-6-(trifluoromethyl)pyridine-3-sulfonamide

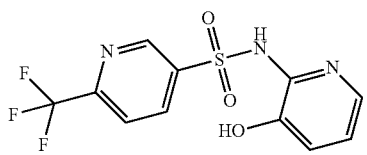

ABR-239238

The procedure to prepare 5-bromo-N-(5-chloro-3-hydroxypyridin-2-yl)pyridine-3-sulfonamide was used, except that N-(3-methoxypyridin-2-yl)-6-(trifluoromethyl)-pyridine-3-sulfonamide was substituted for 5-bromo-N-(5-chloro-3-methoxypyridin-2-yl)-pyridine-3-sulfonamide. The crude product was purified by preparative TLC eluting with 20% MeOH in DCM to afford N-(3-hydroxypyridin-2-yl)-6-(trifluoromethyl)-pyridine-3-sulfonamide (2%) as a brown oil.

Example 50

Methyl 6-(2,5-dichlorothiophene-3-sulfonamido)-5-hydroxypyridine-3-carboxylate

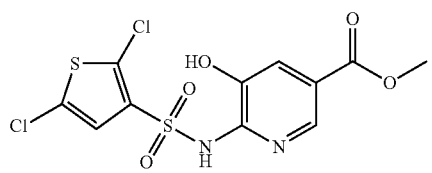

ABR-239215

The procedure to prepare 5-bromo-N-(5-chloro-3-hydroxypyridin-2-yl)pyridine-3-sulfonamide was used, except that methyl 6-(2,5-dichlorothiophene-3-sulfonamido)-5-methoxypyridine-3-carboxylate was substituted for 5-bromo-N-(5-chloro-3-methoxy-pyridin-2-yl)pyridine-3-sulfonamide. Only 3 equivalents of BBr$_3$ were added and the reaction time was 45 min. The crude product was chromatographed on silica (eluent: 30% EtOAc in hexanes) to afford methyl 6-(2,5-dichlorothiophene-3-sulfonamido)-5-hydroxypyridine-3-carboxylate (34%) as an off-white solid.

Example 51

Methyl 6-benzenesulfonamido-5-hydroxypyridine-3-carboxylate

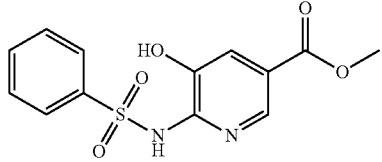

ABR-239216

The procedure to prepare 5-bromo-N-(5-chloro-3-hydroxypyridin-2-yl)pyridine-3-sulfonamide was used, except that methyl 6-benzenesulfonamido-5-methoxypyridine-3-carboxylate was substituted for 5-bromo-N-(5-chloro-3-methoxypyridin-2-yl)pyridine-3-sulfonamide. Only 3 equivalents of BBr$_3$ were added and reaction time was 45 min. The crude product was chromatographed on silica (eluent: 30% EtOAc in hexanes) to afford methyl 6-benzenesulfonamido-5-hydroxypyridine-3-carboxylate (61%) as an off-white solid.

Example 52

4-bromo-3-fluoro-N-(4-hydroxypyridin-3-yl)benzene-1-sulfonamide

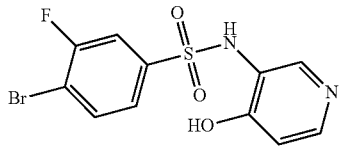

ABR-238979

The procedure for preparation of 5-chloro-N-(4-hydroxypyridin-3-yl)thiophene-2-sulfonamide was used, except that 4-bromo-3-fluorobenzene-1-sulfonyl chloride was substituted for 5-chlorothiophene-2-sulfonyl chloride A final purification was carried out after preparative TLC using automated reverse-phase HPLC (low pH method) which afforded 4-bromo-3-fluoro-N-(4-hydroxypyridin-3-yl)benzene-1-sulfonamide (68%) as a white solid.

Example 53

N-(5-chloro-2-hydroxypyridin-3-yl)-3-(trifluoromethoxy)benzene-1-sulfonamide

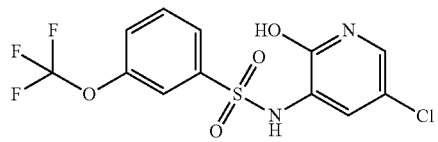

ABR-239323

The procedure to prepare 5-bromo-N-(5-chloro-3-hydroxypyridin-2-yl)pyridine-3-sulfonamide was used, except that N-(5-chloro-2-methoxypyridin-3-yl)-3-(trifluoromethoxy)benzene-1-sulfonamide was substituted for 5-bromo-N-(5-chloro-3-methoxy-pyridin-2-yl)pyridine-3-sulfonamide. The crude product was purified by preparative TLC eluting with 20% MeOH in DCM to afford N-(5-chloro-2-hydroxypyridin-3-yl)-3-(trifluoromethoxy)benzene-1-sulfonamide (25%) as a brown oil.

Example 54

N-(5-chloro-2-hydroxypyridin-3-yl)-6-(trifluoromethyl)pyridine-3-sulfonamide

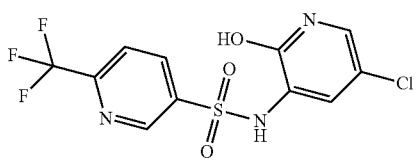

ABR-239324

The procedure to prepare 5-bromo-N-(5-chloro-3-hydroxypyridin-2-yl)pyridine-3-sulfonamide was used, except that N-(5-chloro-2-methoxypyridin-3-yl)-6-(trifluoromethyl)pyridine-3-sulfonamide was substituted for 5-bromo-N-(5-chloro-3-methoxy-pyridin-2-yl)pyridine-3-sulfonamide. The crude product was purified by silica chromatography eluting with 5% MeOH in DCM to afford N-(5-chloro-2-hydroxy-pyridin-3-yl)-6-(trifluoromethyl)pyridine-3-sulfonamide (36%) as an off-white solid.

Example 55

5-bromo-N-(5-chloro-2-hydroxypyridin-3-yl)-6-methoxypyridine-3-sulfonamide

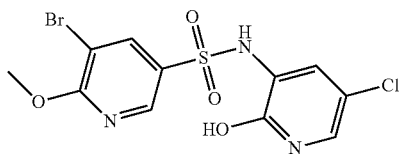

ABR-239326

To a solution of 5-bromo-6-chloro-N-(5-chloro-2-hydroxypyridin-3-yl)pyridine-3-sulfonamide (50 mg, 0.13 mmol) in MeOH (2 mL) sodium methoxide (338 mg, 6.26 mmol) was added at room temperature and the reaction mixture was stirred at room temperature for 16 hrs. The solvent was evaporated and the residue dissolved in water (5 mL), the pH adjusted to about 4 with 1N HCl and the mixture extracted with ethyl acetate (2×10 mL). The combined organic layers were dried (Na$_2$SO$_4$), the mixture was filtered and the filtrate concentrated. The residue was purified by preparative TLC eluting with 8% methanol in DCM to afford 5-bromo-N-(5-chloro-2-hydroxypyridin-3-yl)-6-methoxypyridine-3-sulfonamide (16 mg, 32%) as a white solid.

Example 56

2,5-dichloro-N-(5-chloro-3-hydroxypyridin-2-yl)thiophene-3-sulfonamide

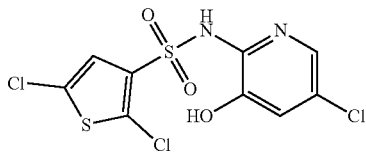

ABR-238857

To a solution of 2-amino-5-chloro-3-methoxypyridine (1.6 g, 10 mmol) in DCM (20 mL) pyridine (1.8 mL, 20.6 mmol) and 2,5-dichlorothiophene-3-sulfonyl chloride (3.6 g, 12.7 mmol) were added. The mixture was stirred at room temperature for 64 h. The solvent was evaporated and the residue was dissolved in hot EtOH. The mixture was allowed to cool to room temperature. The intermediate product was collected by filtration, dried in vacuum, suspended in DCM (60 mL), then treated with 1M $BBr_3$ in DCM (33 mL, 33.0 mmol) and the solution stirred at room temperature for 18 h. The reaction was quenched with water and ice and the resulting precipitate was collected by filtration, washed with water and dried in vacuum to afford 2,5-dichloro-N-(5-chloro-3-hydroxypyridin-2-yl)thiophene-3-sulfonamide as an off-white solid (1.4 g, 39%).

Example 57

N-(5-chloro-4-hydroxypyridin-3-yl)-6-(trifluoromethyl)pyridine-3-sulfonamide

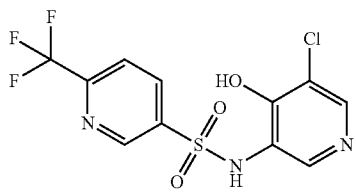

ABR-238733

A mixture of 3-amino-5-chloropyridin-4-ol (80 mg, 0.55 mmol) and 6-trifluoromethyl-pyridine-3-sulfonyl chloride (136 mg, 0.55 mmol) was heated at 140° C. for 0.5 h. The mixture was allowed to cool to 60° C. and MeOH (2 drops) and acetone (2 mL) were added. The decanted solution was allowed to pass through an NH2-column, eluted with acetone and then evaporated. The residue was chromatographed on silica (EtOAc/(MeOH/HOAc/$H_2O$ 3:3:2) 40:1, 20:1, 10:1), evaporated, washed with water and dried in vacuum to afford 6-trifluoromethyl-N-(5-chloro-4-hydroxypyridin-3-yl)pyridine-3-sulfonamide (2.1 mg, 1.1%).

Example 58

5-bromo-6-chloro-N-(5-chloro-4-hydroxypyridin-3-yl)pyridine-3-sulfonamide

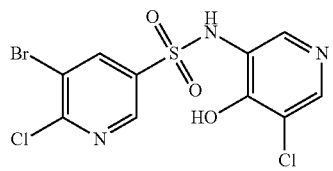

ABR-238734

A mixture of 3-amino-5-chloropyridin-4-ol (65 mg, 0.45 mmol) and 5-bromo-6-chloropyridine-3-sulfonyl chloride (131 mg, 0.45 mmol) was melted at 180° C. and then heated at 160° C. for 0.5 h. The mixture was allowed to cool to 60° C. and MeOH (2 mL) was added. After stirring for 0.5 h at 60° C. the precipitate was filtered off, washed with large volumes of methanol and water and dried in vacuum to afford 5-bromo-6-chloro-N-(5-chloro-4-hydroxypyridin-3-yl)pyridine-3-sulfonamide as a grey solid (46 mg, 26%).

Example 59

5-bromo-N-(5-chloro-4-hydroxypyridin-3-yl)-6-methoxypyridine-3-sulfonamide

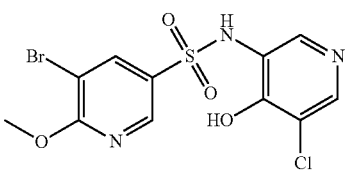

ABR-238901

To a solution of 5-bromo-6-chloro-N-(5-chloro-4-hydroxypyridin-3-yl)pyridine-3-sulfon-amide (60 mg, 0.15 mmol) in MeOH (3 mL) NaOMe was added in portions until the solution was saturated. The mixture was heated at 60° C. for 4 h and stirred at room temperature overnight. The mixture was evaporated and water (5 mL) and MeOH (0.2 mL) were added. The mixture was acidified with aqueous HCl and the precipitate was collected by filtration and washed with methanol to afford 5-bromo-6-methoxy-N-(5-chloro-4-hydroxypyridin-3-yl)pyridine-3-sulfonamide as a brown-grey solid (45 mg, 76%).

Example 60

5-bromo-N-(5-chloro-4-hydroxypyridin-3-yl)pyridine-3-sulfonamide

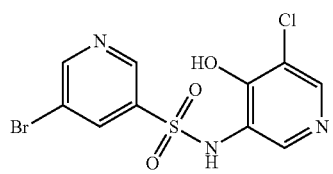

ABR-239044

The procedure for preparation of 5-bromo-6-chloro-N-(5-chloro-4-hydroxypyridin-3-yl)-pyridine-3-sulfonamide was used except that 5-bromopyridine-3-sulfonyl chloride was substituted for 5-bromo-6-chloro-pyridine-3-sulfonyl chloride.

Example 61

5-bromo-6-chloro-N-(4-hydroxypyridin-3-yl)pyridine-3-sulfonamide

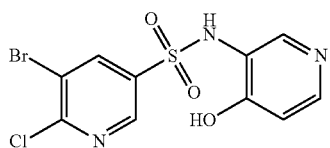

ABR-238580

A mixture of 3-amino-4-methoxypyridine (124 mg, 1.0 mmol) and 5-bromo-6-chloro-pyridine-3-sulfonyl chloride (291 mg, 1.0 mmol) was heated at 130° C. for 2 h. 2M HCl in EtOH (200 μl) was added to the warm mixture to complete hydrolysis of the methoxy group and heated at 130° C. for one additional hour. The mixture was allowed to cool to 60° C. and MeOH (2 mL) was added. After stirring for 0.5 h at 60° C., the decanted solution was allowed to pass through an $NH_2$-column, eluted with acetone/MeOH (1:0 to 1:1) and fractions containing product were evaporated. The residue was chromatographed on silica (EtOAc/(MeOH/HOAc/$H_2O$ 3:3:2) 40:1, 20:1, 10:1), evaporated and dried in vacuum to afford 5-bromo-6-chloro-N-(4-hydroxypyridin-3-yl)pyridine-3-sulfonamide (70 mg, 19%).

Example 62

5-bromo-N-(4-hydroxypyridin-3-yl)-6-methoxypyridine-3-sulfonamide

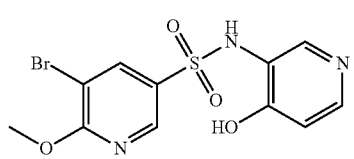

ABR-238868

The procedure for preparation of 5-bromo-6-methoxy-N-(5-chloro-4-hydroxypyridin-3-yl)pyridine-3-sulfonamide was used except that 5-bromo-6-chloro-N-(4-hydroxypyridin-3-yl)pyridine-3-sulfonamide was substituted for 5-bromo-6-chloro-N-(5-chloro-4-hydroxypyridin-3-yl)pyridine-3-sulfonamide.

Example 63

2,5-dichloro-N-(4-hydroxypyridin-3-yl)thiophene-3-sulfonamide

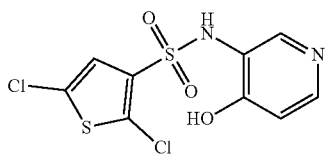

ABR-238581

A mixture of 3-amino-pyridin-4-ol (110 mg, 1.0 mmol) and 2,5-dichlorothiophene-3-sulfonyl chloride (245 mg, 1.0 mmol) was heated at 120° C. for 1.5 h. The mixture was allowed to cool to 60° C. and MeOH (2 mL) was added. After stirring for 0.5 h at 60° C., the decanted solution was allowed to pass through a $NH_2$-column, eluted with acetone/MeOH (1:0 to 1:1) and fractions containing product were evaporated. The residue was chromatographed on silica (EtOAc/(MeOH/HOAc/$H_2O$ 3:3:2) 40:1, 20:1, 10:1), evaporated and dried in vacuum to afford 2,5-dichloro-N-(4-hydroxypyridin-3-yl)thiophene-3-sulfonamide (78 mg, 25%).

Example 64

N-(4-hydroxypyridin-3-yl)-6-(trifluoromethyl)pyridine-3-sulfonamide

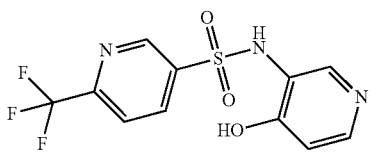

ABR-238582

The procedure for preparation of 2,5-dichloro-N-(4-hydroxypyridin-3-yl)thiophene-3-sulfonamide was used except that 6-trifluoromethylpyridine-3-sulfonyl chloride was substituted for 2,5-dichlorothiophene-3-sulfonyl chloride.

Example 65

3,4-difluoro-N-(4-hydroxypyridin-3-yl)benzene-1-sulfonamide

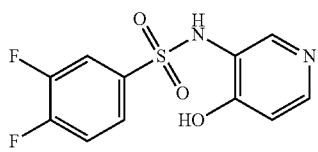

ABR-238615

The procedure for preparation of 2,5-dichloro-N-(4-hydroxypyridin-3-yl)thiophene-3-sulfonamide was used except that 3,4-difluorobenzene-1-sulfonyl chloride was substituted for 2,5-dichlorothiophene-3-sulfonyl chloride.

Example 66

3,4-dichloro-N-(4-hydroxypyridin-3-yl)benzene-1-sulfonamide

ABR-239168

The procedure for preparation of 2,5-dichloro-N-(4-hydroxypyridin-3-yl)thiophene-3-sulfonamide was used except that 3,4-dichlorobenzene-1-sulfonyl chloride was substituted for 2,5-dichlorothiophene-3-sulfonyl chloride.

Example 67

N-(2-hydroxypyridin-3-yl)-6-(trifluoromethyl)pyridine-3-sulfonamide

ABR-238612

The procedure for preparation of 2,5-dichloro-N-(4-hydroxypyridin-3-yl)thiophene-3-sulfonamide was used except that 6-trifluoromethylpyridine-3-sulfonyl chloride was substituted for 2,5-dichlorothiophene-3-sulfonyl chloride and 3-amino-2-hydroxy-pyridine was substituted for 3-amino-pyridin-4-ol.

Example 68

5-bromo-6-chloro-N-(2-hydroxypyridin-3-yl)pyridine-3-sulfonamide

ABR-238610

A mixture of 3-amino-2-hydroxypyridine (50 mg, 0.45 mmol) and 5-bromo-6-chloro-pyridine-3-sulfonyl chloride (131 mg, 0.45 mmol) was heated at 120° C. for 1.5 h. The mixture was allowed to cool to 60° C. and MeOH (2 mL) was added. After stirring for 0.5 h at 60° C. the solid residue was collected by filtration, boiled in hot MeOH (2 mL), filtrated, washed with water and dried in vacuum to afford 5-bromo-6-chloro-N-(2-hydroxypyridin-3-yl)pyridine-3-sulfonamide (28 mg, 17%).

Example 69

2,5-dichloro-N-(2-hydroxypyridin-3-yl)thiophene-3-sulfonamide

ABR-238611

The procedure for preparation of 5-bromo-6-chloro-N-(2-hydroxypyridin-3-yl)pyridine-3-sulfonamide was used except that 3-amino-2-hydroxy-pyridine was substituted for 3-amino-pyridin-4-ol.

Example 70

N-(6-chloro-4-hydroxypyridin-3-yl)-1-(3,4-dichlorophenyl)methanesulfonamide

ABR-239286

To a solution of 6-chloro-4-methoxypyridin-3-ylamine (0.95 mmol, 160 mg) in dichloromethane (1 mL) and pyridine (2 mmol, 165 microliter) (3,4-dichlorophenyl)-methanesulfonyl chloride ((275 mg, 0.95 mmol) was added and the mixture was stirred overnight and then concentrated on a rotary evaporator. To the residue ethanol (99.5%, 5 mL) and NaOH (1 M, 2 mL) were added and the mixture was heated at 60° C. until all material went into solution (took less than 5 min). The mixture was cooled, water (5 mL) and glacial acetic acid were added to pH 3-4 (checked with pH sticks). The precipitate was collected by filtration and dried to afford the intermediate N-(6-chloro-4-methoxy-pyridin-3-yl)-3,4-dichlorophenyl-methanesulfon-amide which was dissolved in dichloromethane (2 mL), cooled on an ice-bath and boron tribromide (1M solution in dichloromethane, 2 mmol, 2 mL) was added dropwise. The mixture was stirred at room temperature overnight. The mixture was then partitioned between dichloromethane and aqueous sodium hydroxide at pH 13. The aqueous phase was collected, pH was adjusted to approx. 3-4 with acetic acid and the mixture was extracted with ethylacetate (20 mL). The organic phase was collected and evaporated and the residue was crystallized from methanol/water to afford the title compound (158 mg, 43%).

Example 71

5-bromo-N-(5-chloro-3-hydroxypyridin-2-yl)-6-methoxypyridine-3-sulfonamide

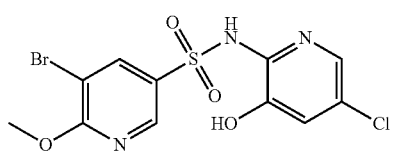

ABR-238942

5-chloro-3-methoxypyridin-2-ylamine (1 mmol) and 5-bromo-6-chloropyridine-3-sulfonyl chloride (1 mmol) were melted together at 130° C. for 3 hours. The mixture was cooled and partitioned between dichloromethane and aqueous sodium hydroxide at pH 13. The aqueous phase was separated, and acetic acid was added to pH 3-4, and then extracted with ethyl acetate. The organic phase was concentrated, heptane was added and the precipitate was collected to furnish N-(5-chloro-3-methoxypyridin-2-yl)-5-bromo-6-methoxypyridine-3-sulfonamide (90 mg). Subsequent treatment with boron tribromide was as described for the preparation of N-(6-chloro-4-hydroxypyridin-3-yl)-3,4-dichlorophenyl-methanesulfonamide except for purifying the intermediate N-(5-chloro-3-hydroxypyridin-2-yl)-5-bromo-6-chloropyridine-3-sulfonamide by chromatography (SiO$_2$, ethyl acetate). This material was then stirred in a high pressure reaction vessel in 0.5 M NaOMe/MeOH (10 mL) at 80° C. for 4 hours. The mixture was cooled and evaporated and methanol (1 mL), water (1 mL) and acetic acid (0.5 mL) were added. The precipitate was collected and dried to afford the title compound (90 mg, 22%).

Example 72

3,4-dichloro-N-(3-hydroxypyridin-4-yl)benzene-1-sulfonamide

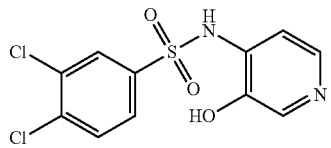

ABR-239281

3,4-dichlorobenzenesulfonyl chloride (1 mmol) and 3-methoxypyridin-4-ylamine (1 mmol) were reacted without solvent at 130° C. for 4 hours, then cooled and dissolved in a mixture of NaOH (1 M, 10 mL) and methanol (10 mL). Then water and dichloromethane were added and the aqueous phase was collected. The aqueous phase was adjusted to pH 3-4 with acetic acid and then extracted with ethyl acetate. The organic phase was evaporated and the residue was subjected to column chromatography (SiO2, ethyl acetate) to give N-(3-methoxypyridin-4-yl)-3,4-dichlorobenzenesulfonamide. The reaction of this intermediate with boron tribromide was as described for N-(6-chloro-4-hydroxypyridin-3-yl)-3,4-dichlorophenyl-methanesulfonamide except that a precipitate formed during the partition between dichloromethane and aqueous sodium hydroxide at pH 13. Without separating the phases, pH was adjusted to 3 with 1 M HCl and the two-phase mixture was filtered in order to collect the precipitate. The precipitate (30 mg, 9%) was the title compound according to nmr and mass spectroscopy.

Example 73

2,5-dichloro-N-(6-chloro-4-hydroxypyridin-3-yl)thiophene-3-sulfonamide

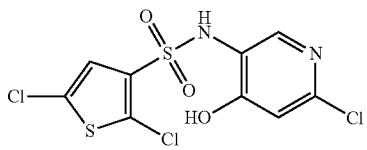

ABR-239167

Commercial 2-chloro-4-methoxy-5-nitropyridine (1.0 g) was hydrogenated using Raney nickel catalyst in THF until the consumption of hydrogen ceased. The mixture was filtered and evaporated to give 6-chloro-4-methoxypyridin-3-ylamine (813 mg). This amine (190 mg) was reacted with 2,5-dichlorothiophene-3-sulfonyl chloride (259 mg) according to the procedure described for N-(6-chloro-4-hydroxypyridin-3-yl)-3,4-dichlorophenyl-methanesulfonamide except that after treatment with boron tribromide the mixture underwent chromatography (SiO2, EtOAc/MeOH/HOAc/water, 10:1:1:0.5) to afford the title compound (55 mg, 15%)

Example 74

2,5-dichloro-N-(5-chloro-2-hydroxypyridin-3-yl)thiophene-3-sulfonamide

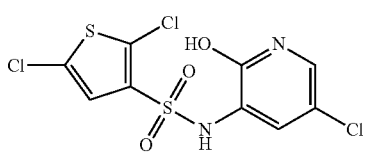

ABR-239417

5-Chloro-2-methoxypyridin-3-ylamine (10 mmol, 1.6 g) and 2,5-dichlorothiophene-3-sulfonyl chloride (12 mmol, 3.2 g) were reacted according to the procedure for N-(6-chloro-4-hydroxypyridin-3-yl)-3,4-dichlorophenyl-methanesulfonamide to afford the title compound (1.02 g, 33%).

Example 75

N-(5-bromo-3-hydroxypyrazin-2-yl)-1-(3,4-dichlorophenyl)methanesulfonamide

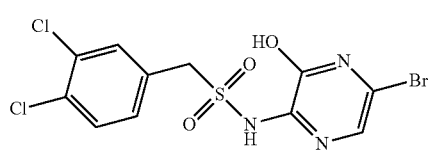

ABR-239417

3,4-dichlorophenyl-methanesulfonyl chloride (2.4 mmol, 650 mg) was added to a solution of 5-bromo-3-methoxy-pyrazine-2-ylamine (2 mmol, 410 mg) and pyridine (5 mmol, 411 microliter). The mixture was stirred for 72 hours and then partitioned between ethyl acetate, water and acetic acid. The organic phase was collected and evaporated and the residue was crystallized from ethyl acetate and heptane to afford the intermediate N-(5-bromo-3-methoxypyrazine-2-yl)-3,4-dichlorophenyl-methanesulfonamide (1.1 mmol, 470 mg). This was dissolved in dichloromethane (2 mL), cooled on an ice-bath, and boron tribromide (1 M solution in dichloromethane, 2 mmol) was added. The mixture was stirred for 3 hours, then poured onto NaHCO$_3$(s)/ice and stirred for additional 3 hours. The precipitate was collected and dissolved in hot ethanol (99.5%), the mixture was filtered while hot, and water was added to the filtrate. The precipitate was collected to afford the title compound (175 mg, 20%).

Example 76

N-(6-chloro-4-hydroxypyridazin-3-yl)-1-(3,4-difluorophenyl)methanesulfonamide

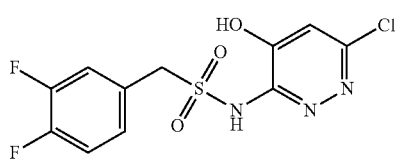

ABR-239462

To a solution of 6-chloro-4-methoxypyridazin-3-amine (150 mg, 0.733 mmol) in pyridine (4 mL) was added (3,4-difluorophenyl)methanesulfonyl chloride (190 mg, 0.733 mmol) in 5 portions over 10 min and the mixture stirred for 1 hr. The pyridine was evaporated and the residue dissolved in DCM (15 mL) and treated with 1M BBr$_3$ in DCM (0.733 mL, 0.733 mmol). Stirring was continued for 3 hrs at room temperature whereupon EtOAc was added (50 mL) and saturated NaHCO$_3$ (10 mL). The phases were separated and the organic phase was washed with brine (20 mL), dried (Na$_2$SO$_4$), the mixture filtered and the filtrate evaporated to dryness to afford a brown oil which was purified by automated reverse phase HPLC (low pH method) to afford the title compound as a tan solid (17 mg, 7%).

Example 77

1-(3,5-dichlorophenyl)-N-[3-hydroxy-5-(propane-2-sulfonyl)pyridin-2-yl]methanesulfonamide

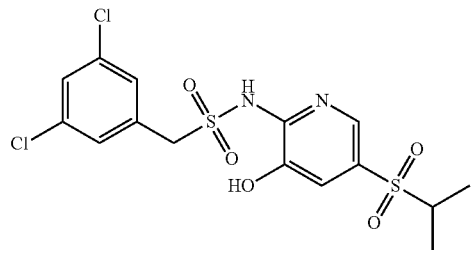

ABR-239468

To a stirred solution of 1-(3,5-dichlorophenyl)-N-[3-methoxy-5-(propane-2-sulfonyl)pyridin-2-yl]methanesulfonamide (100 mg, 0.22 mmol) in CHCl$_3$ (10 mL) under nitrogen was added neat boron tribromide (166 mg, 0.662 mmol) at 0° C. The reaction mixture was allowed to warm to room temperature and stirred 16 h. The mixture was diluted with more chloroform and quenched with water. The aqueous layer was brought to pH 7 by the addition of saturated NaHCO$_3$ and extracted with more CHCl$_3$ followed by EtOAc. The combined organic layers were concentrated to obtain a crude residue which was purified by flash silica chromatography (eluent 1.5% MeOH:DCM). Further purification was achieved by crystallisation from a mixture of CHCl$_3$, MeOH and pentane followed by automated reverse phase HPLC (high pH method) to afford the title compound as an off white solid (55 mg, 57%).

Example 78

N-(5-chloro-3-hydroxypyrazin-2-yl)-1-(3,5-dichlorophenyl)methanesulfonamide

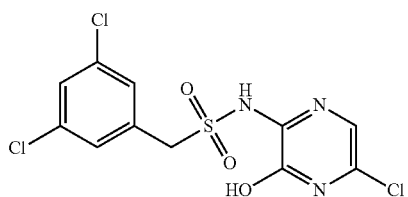

ABR-239604

To 5-chloro-3-methoxypyrazin-2-amine (150 mg, 0.94 mmol) in pyridine:DCM 1:1 (4 mL) at room temperature was added (3,5-dichlorophenyl)methanesulfonyl chloride (220 mg, 0.846 mmol) was added over 1 min. The mixture was stirred for 1 hr at this temperature then the pyridine was evaporated. The residue was dissolved in DCM (6 mL) and 1M BBr$_3$ in DCM (1.5 mL, 1.5 mmol)) was added and the mixture stirred for 2 hrs. Another 1.5 mL of BBr$_3$ in DCM was added and stirring continued for a further 1 hr. The reaction was quenched carefully with water, EtOAc was added and the phases separated. The EtOAc layer was evaporated and the residue was purified by automated preparative HPLC (low pH method) to afford the title compound as a white solid. Further purification was achieved by recrystallisation from MeOH (51 mg, 15%).

Example 79

5-bromo-N-(5-chloro-4-hydroxypyridin-3-yl)-6-phenoxypyridine-3-sulfonamide

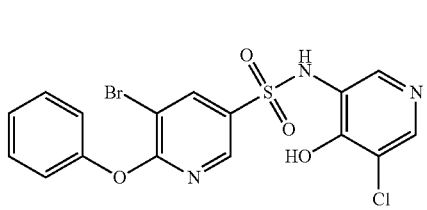

ABR-239614

To a stirred solution of phenol (24 mg, 0.25 mmol) in DMF (1 mL) at room temperature was added sodium hydride (29 mg, 1.2 mmol) and stirred for 5 min. To this was added a solution of 5-bromo-6-chloro-N-(5-chloro-4-hydroxypyridin-3-yl)pyridine-2-sulfonamide (50 mg, 0.13 mmol) in DMF (1 mL) and the reaction was heated using a Biotage microwave for 40 mins at 150° C. The mixture was acidified to pH 5 (0.2M HCl) and extracted with EtOAc (3×10 mL). The organics were combined and washed with brine (2×10 mL), dried (MgSO$_4$), the mixture filtered and the filtrate concentrated to dryness to yield purple oil which was purified by automated reverse phase HPLC (high pH method). Further purification was achieved by trituration with heptane to yield the title compound as an off-white solid (7 mg, 12%).

Example 80

N-(5-bromo-3-hydroxypyrazin-2-yl)-1-(3,5-dichlorophenyl)methanesulfonamide

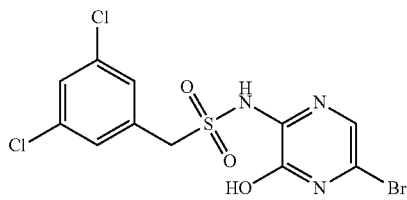

ABR-239618

The procedure to prepare N-(6-chloro-4-hydroxypyridazin-3-yl)-1-(3,4-difluorophenyl)-methanesulfonamide was used except that 5-bromo-3-methoxypyrazin-2-amine was substituted for 5-chloro-3-methoxypyrazin-2-amine and (3,5-dichlorophenyl)methane-sulfonyl chloride was substituted for (3,4-difluorophenyl)methanesulfonyl chloride (25%).

Example 81

N-(6-chloro-4-hydroxypyridazin-3-yl)-1-(2,4-dichlorophenyl)methanesulfonamide

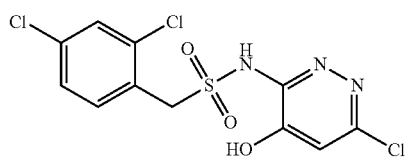

ABR-239494

The procedure to prepare N-(6-chloro-4-hydroxypyridazin-3-yl)-1-(3,4-difluorophenyl)-methanesulfonamide was used except that (2,4-dichlorophenyl)methanesulfonyl chloride was substituted for (3,4-difluorophenyl) methanesulfonyl chloride (5%).

Example 82

1-(3,5-dichlorophenyl)-N-(4-hydroxy-6-iodopyridazin-3-yl)methanesulfonamide

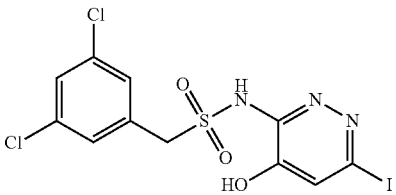

ABR-239498 and

Example 83

N-(6-bromo-4-hydroxypyridazin-3-yl)-1-(3,5-dichlorophenyl)methanesulfonamide

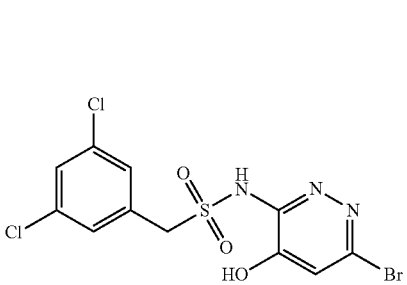

ABR-239497

To a stirred solution of (6-bromo-4-methoxypyridazin-3-amine and 6-iodo-4-methoxy-pyridazin-3-amine (0.8 g, mixture not separated in previous step, estimated 3.92 mmol) in pyridine (9 mL) was added (3,5-dichlorophenyl) methanesulfonyl chloride (1.02 g, 3.92 mmol) at room temperature and the mixture stirred for 16 hrs. Water was then added and the mixture extracted with EtOAc (3×150 mL). The combined organic layers were washed with more water and brine, then concentrated and purified by flash silica chromatography (eluent: 1% MeOH:DCM) to afford a mixture of methoxy ethers (250 mg).

To this mixture in DCM (5 mL) was added neat boron tribromide (166 μl, 1.76 mmol) and the mixture stirred for 3 h before being diluted with DCM and neutralised with saturated NaHCO$_3$ (pH 7). The phases were separated and the aqueous phase extracted with DCM and EtOAc. The combined organic layers were dried (MgSO$_4$), the mixture filtered and the filtrate concentrated to dryness to yield an oil which was purified by automated reverse phase HPLC (low pH method) to afford 1-(3,5-dichlorophenyl)-N-(4-hydroxy-6-iodopyridazin-3-yl)methanesulfonamide (22 mg, 16%) and N-(6-bromo-4-hydroxypyridazin-3-yl)-1-(3,5)-dichlorophenyl)methanesulfonamide (22 mg, 18%).

Example 84

3-bromo-N-(5-bromo-4-hydroxypyridin-3-yl)-4-methoxybenzene-1-sulfonamide

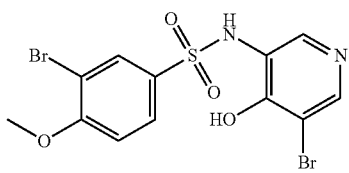

ABR-239570

To a stirred solution of 3-amino-5-bromopyridin-4-ol (200 mg, 1.06 mmol) in pyridine (15 mL) at 80° C. was added DMAP (5 mg, 0.04 mmol) followed by 4-bromo-3-methoxy-benzene-1-sulfonyl chloride (302 mg, 1.06 mmol) and the mixture stirred for 1 hr at 80° C. The reaction mixture was concentrated in vacuo, partitioned between EtOAc (60 mL) and water (40 mL). The organic layer was dried over Na$_2$SO$_4$ and concentrated in vacuo to afford a brown solid which was purified by automated reverse phase HPLC (low pH method) to afford the title compound as an off-white solid (50 mg, 10%).

Example 85

N-(6-chloro-4-hydroxypyridazin-3-yl)-1-(2-chloro-5-cyanophenyl)methane-sulfonamide

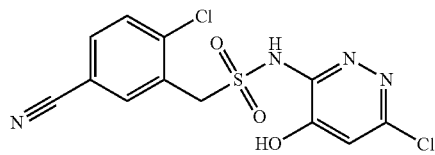

ABR-239571

To a stirring solution of N-(6-chloro-4-methoxypyridazin-3-yl)-1-(2-chloro-5-cyanophenyl)methanesulfonamide (649 mg, 1.74 mmol) in DCM (60 mL) was added BBr$_3$ (0.68 mL, 6.96 mmol) and the mixture stirred 30 mins. The reaction mixture was periodically re-treated with the same amount of BBr$_3$ over a 6 hr period until starting material had been fully converted (as judged by LCMS). The reaction mixture was quenched with water (30 mL), the layers were separated, the aqueous layer was extracted with DCM (2×60 mL), all organic layers were combined and were concentrated in vacuo to afford a yellow solid which was purified by automated reverse phase HPLC (low pH method) to afford the title compound as an off white solid (62 mg, 10%).

Example 86

N-(5-chloro-4-hydroxypyridin-3-yl)-6-phenoxypyridine-3-sulfonamide

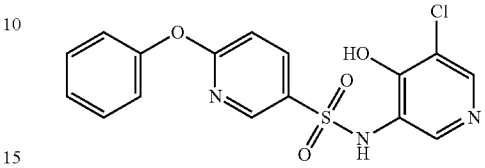

ABR-239593

To a stirring solution of 3-amino-5-chloropyridin-4-ol (250 mg, 1.73 mmol) in pyridine (3 mL) was added DMAP (10 mg, 0.08 mmol) and 6-phenoxypyridine-3-sulfonyl chloride (466 mg, 1.73 mmol). The reaction was left stirring at 40° C. under nitrogen for 3 hr. The reaction mixture was concentrated in vacuo, diluted with EtOAc (60 mL), washed twice with water (40 mL) and washed with saturated brine (40 mL). The organic layer was dried over Na$_2$SO$_4$ and concentrated in vacuo to afford a purple solid which was purified by automated reverse phase HPLC (low pH method) to afford the title compound as an off white solid (48 mg, 7%).

Example 87

N-(6-chloro-4-hydroxypyridin-3-yl)-1-(3,5-dichlorophenyl)methanesulfonamide

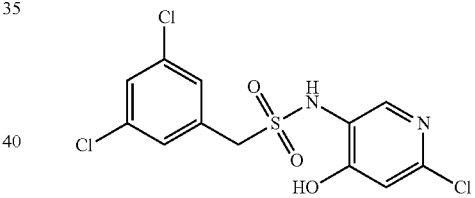

ABR-239522

The procedure to prepare N-(6-chloro-4-hydroxypyridazin-3-yl)-1-(3,4-difluorophenyl)-methanesulfonamide was used except 6-chloro-4-methoxypyridin-3-amine was substituted for 6-chloro-4-methoxypyridazin-3-amine and (3,5-dichlorophenyl)methane-sulfonyl chloride was substituted for (3,4-difluorophenyl)methanesulfonyl chloride (11%).

Example 88

1-(3-chlorophenyl)-N-[5-(ethanesulfonyl)-3-hydroxypyrazin-2-yl]methane-sulfonamide

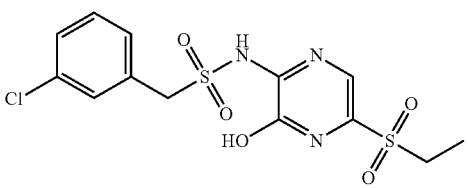

ABR-239676

To a solution of 1-(3-chlorophenyl)-N-[5-(ethanesulfonyl)-3-methoxypyrazin-2-yl]-methanesulfonamide (330 mg, 0.660 mmol) in DCM (12 mL) was added BBr$_3$ (1M in DCM, 1.98 mL, 1.98 mmol) and the solution stirred 3 hrs, then quenched by the addition of water (8 mL) and more DCM (50 mL) was added. The phases were separated and the organic phase was washed with brine (5 mL), dried (Na$_2$SO$_4$), the mixture filtered and the filtrate evaporated to dryness to afford a red oil which was purified by automated reverse-phase HPLC (high pH method) to afford the title compound as a white solid (28 mg, 11%).

Example 89

3,5-dichloro-N-(5-chloro-4-hydroxypyridin-3-yl)benzene-1-sulfonamide

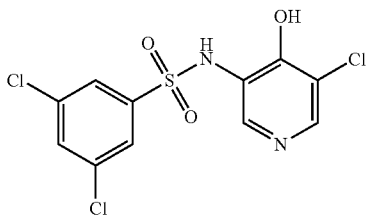

ABR-239610

To a stirred solution of 3-amino-5-chloropyridin-4-ol (150 mg, 1.04 mmol) and N,N-dimethylpyridin-4-amine (6 mg, 0.05 mmol) in pyridine (3 mL) at 0° C. was added 3,5-dichlorobenzene-1-sulfonyl chloride (255 mg, 1.04 mmol) and the mixture was stirred at room temperature for 2 hrs. The pyridine was evaporated under reduced pressure, the residue re-dissolved in water (10 mL), extracted with EtOAc (4×10 mL), the combined organics washed with brine (3×5 mL), dried (MgSO$_4$), filtered and concentrated to yield a crude purple solid which was purified by automated reverse-phase HPLC (high pH method) to afford the title compound as a white solid (19 mg, 5%).

Example 90

N-(6-chloro-4-hydroxypyridazin-3-yl)-1-(2-chlorophenyl)methanesulfonamide

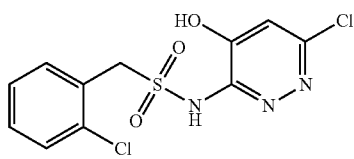

ABR-239486

The procedure to prepare N-(6-chloro-4-hydroxypyridazin-3-yl)-1-(3,4-difluorophenyl)-methanesulfonamide was used except that 2-chlorophenyl)methanesulfonyl chloride was substituted for (3,4-difluorophenyl)methanesulfonyl chloride (11% yield).

Example 91

5-bromo-N-(5-bromo-4-hydroxypyridin-3-yl)-6-methoxypyridine-3-sulfonamide

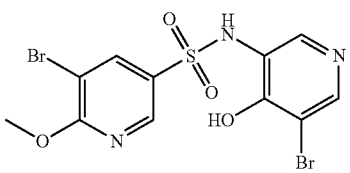

ABR-239567

To a solution of 3-amino-5-bromopyridin-4-ol (250 mg, 0.926 mmol) in pyridine (3 mL) at 80° C. was added a crystal of DMAP, and the solution stirred at this temperature for 10 min. Then 5-bromo-6-chloropyridine-3-sulfonyl chloride (269 mg, 0.926 mmol) was added in portions over 3 min. The mixture was stirred for 1 hr at this temperature then the pyridine was evaporated. The residue was suspended in MeOH (10 mL), methanolic sodium methoxide solution added via syringe (5.4M, 1.2 mL, 6.5 mmol) and the mixture heated at 75° C. for 3 h. The solvent was evaporated and the residue acidified with 0.5M HCl. EtOAc (50 mL) was added, the phases were separated and the organic phase was washed with brine (20 mL), dried (Na$_2$SO$_4$), the mixture filtered and the filtrate evaporated to dryness to afford a red solid which was purified by automated reverse-phase HPLC (low pH method) to afford the title compound as a pink solid (10 mg, 2%).

Example 92

N-(6-bromo-5-chloro-3-hydroxypyridin-2-yl)-1-(3,5-dichlorophenyl)methane-sulfonamide

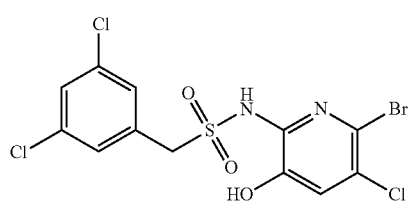

ABR-239637

The procedure to prepare N-(6-chloro-4-hydroxypyridazin-3-yl)-1-(2-chloro-5-cyano-phenyl)methanesulfonamide was used except that N-(6-bromo-5-chloro-3-methoxy-pyridin-2-yl)-1-(3,5-dichlorophenyl)methanesulfonamide was substituted for N-(6-chloro-4-methoxypyridazin-3-yl)-1-(2-chloro-5-cyanophenyl)methanesulfonamide (14%).

Example 93

1-(2-chlorophenyl)-N-(4-hydroxy-6-methanesulfonylpyridazin-3-yl)methane-sulfonamide

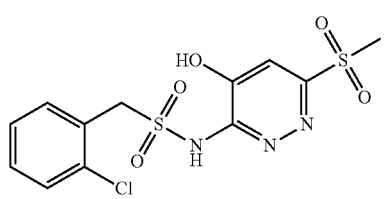

ABR-239654

The procedure to prepare 1-(3-chlorophenyl)-N-[5-(ethanesulfonyl)-3-hydroxypyrazin-2-yl]methanesulfonamide was used except that 1-(2-chlorophenyl)-N-(6-methanesulfonyl-4-methoxypyridazin-3-yl)methanesulfonamide was substituted for 1-(3-chlorophenyl)-N-[5-(ethanesulfonyl)-3-methoxypyrazin-2-yl]methanesulfonamide. Further purification was achieved after HPLC with a DCM/heptane recrystallisation (21%).

Example 94

N-(6-chloro-4-hydroxypyridazin-3-yl)-1-(3-chloro-5-fluorophenyl)methane-sulfonamide

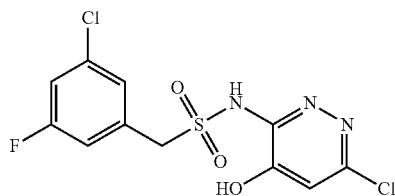

ABR-239532

The procedure to prepare N-(6-chloro-4-hydroxy-pyridazin-3-yl)-1-(3,4-difluorophenyl)-methanesulfonamide was used except that (3-chloro-5-fluorophenyl)methanesulfonyl chloride was substituted for (3,4-difluorophenyl)methanesulfonyl chloride (14%).

Example 95

3,5-dichloro-N-(6-chloro-4-hydroxypyridazin-3-yl)benzene-1-sulfonamide

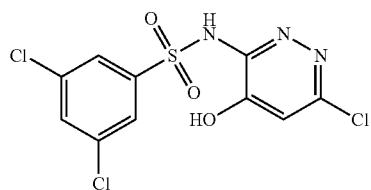

ABR-239477

To a solution of 6-chloro-4-methoxypyridazin-3-amine (250 mg, 1.22 mmol) in pyridine (3 mL), pre-heated to 80° C. was added 3,5-dichlorobenzene sulfonyl chloride (300 mg, 1.22 mmol) and the mixture stirred at this temperature for 2 hrs. The pyridine was evaporated and the residue chromatographed on silica (eluent: heptane:EtOAc 1:2). Product containing fractions were combined, the solvent evaporated and dissolved in DCM (15 mL). 1M BBr$_3$ in DCM (2.00 mL, 2.00 mmol) was added and the solution stirred 1 hr, before being quenched with saturated NaHCO$_3$ (10 mL). The phases were separated and the organic phase was washed with brine (3 mL), dried (Na$_2$SO$_4$), the mixture filtered and the filtrate evaporated to dryness to afford a yellow oil which was purified by automated reverse phase HPLC (low pH method) to afford the title compound as an off-white solid (36 mg, 8%).

Example 96

N-(6-chloro-4-hydroxypyridazin-3-yl)-1-(3-chlorophenyl)methanesulfonamide

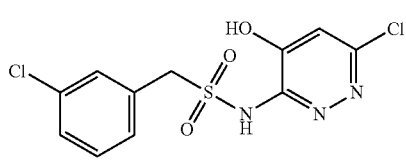

ABR-239485

The procedure to prepare N-(6-chloro-4-hydroxypyridazin-3-yl)-1-(3,4-difluorophenyl)-methanesulfonamide was used except that (3-chlorophenyl)methanesulfonyl chloride was substituted for (3,4-difluorophenyl)methanesulfonyl chloride (18%).

Example 97

N-(5-bromo-4-hydroxypyridin-3-yl)-1-(3,5-dichlorophenyl)methanesulfonamide

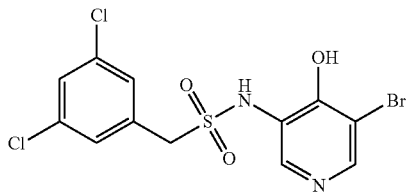

ABR-239565

To 3-amino-5-bromopyridin-4-ol (250 mg, 1.32 mmol) in pyridine (3 mL) at 80° C. was added a crystal of DMAP then (3,5-dichlorophenyl)methanesulfonyl chloride was added in portions over 3 min. The mixture was stirred for 1 hr at this temperature then the pyridine was evaporated. The residue was dissolved in DMSO and precipitated by addition of MeOH. The mixture was filtered and the solid washed with MeOH followed by water and dried in air to afford the title compound as a white solid (82 mg, 15%).

Example 98

3-[(5-chloro-4-hydroxypyridin-3-yl)sulfamoyl]-N,N-diethylbenzamide

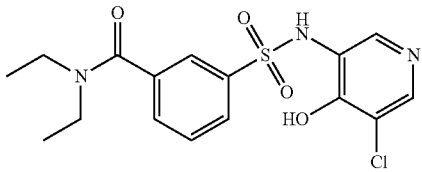 [SMILES: CCN(CC)C(=O)c1cccc(S(=O)(=O)Nc2cncc(Cl)c2O)c1]

To a stirred solution of 3-[(5-chloro-4-hydroxypyridin-3-yl)sulfamoyl]benzoic acid (54 mg, 0.15 mmol) in DMF (3 mL), HATU (83 mg, 0.22 mmol) and DIPEA (0.08 mL, 0.44 mmol) were added and left to stir for 30 mins at room temperature under nitrogen. Diethylamine (0.03 mL, 0.29 mmol) was added to the reaction mixture, the reaction was left stirring and under a nitrogen atmosphere for 15 hrs.

The reaction mixture was concentrated in vacuo (with addition of heptane (2 mL) to aid DMF evaporation) affording a viscous brown mixture. This was purified by automated reverse phase HPLC (low pH method) to afford the title compound as a pale pink solid (37 mg, 65%).

Example 99

1-(3,4-difluorophenyl)-N-(4-hydroxy-6-methanesulfonylpyridazin-3-yl)methane-sulfonamide

ABR-239635

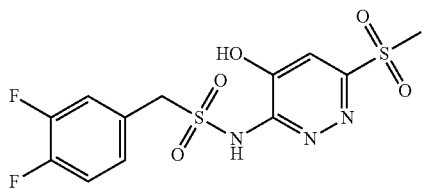

1M BBr$_3$ in DCM (583 μL, 0.583 mmol) was added dropwise under nitrogen to a stirring solution of 1-(3,4-difluorophenyl)-N-(6-methanesulfonyl-4-methoxypyridazin-3-yl)-methanesulfonamide (30% pure, 85 mg, 0.06 mmol) in DCM (2 mL). The reaction was stirred for 1 hr then concentrated in vacuo. The residue was purified by flash column chromatography over silica (Biotage 10 g SNAP cartridge) eluting with DCM:MeOH gradient 1:0 to 8.5:2.5 to the title compound as a white solid (16 mg, 62%).

Example 100

3-chloro-N-(5-chloro-4-hydroxypyridin-3-yl)-4-methylbenzene-1-sulfonamide

ABR-239591

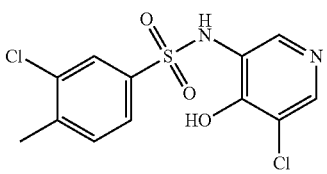

The procedure to prepare 3,5-dichloro-N-(5-chloro-4-hydroxypyridin-3-yl)benzene-1-sulfonamide was used, except that 3-chloro-4-methylbenzene-1-sulfonyl chloride was substituted for 3,5-dichlorobenzene-1-sulfonyl chloride, no DMAP was used and the temperature was 60° C. (8%).

Example 101

5-bromo-N-(5-chloro-4-hydroxypyridin-3-yl)-6-(propan-2-yloxy)pyridine-3-sulfonamide

ABR-239612

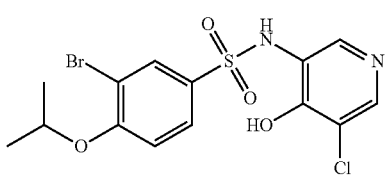

To a stirred solution of propan-2-ol (1 mL, 13.1 mmol) in DMF (1 mL) at room temperature was added sodium hydride (29 mg, 1.2 mmol) and stirred for 5 mins. To this was added a solution of 5-bromo-6-chloro-N-(5-chloro-4-hydroxypyridin-3-yl)pyridine-2-sulfonamide (50 mg, 0.13 mmol) in DMF (1 mL) and the reaction mixture heated using a Biotage microwave for 40 mins at 150° C. then acidified to pH5 (0.2M HCl) and extracted with EtOAc (3×10 mL). Organics were combined and washed with brine (2×10 mL), dried (MgSO4), filtered and concentrated to dryness to yield a deep purple oil which was purified by automated reverse phase HPLC (high pH method) to yield the title compound as an off white solid (7 mg, 12%).

Example 102

3-chloro-N-(5-chloro-4-hydroxypyridin-3-yl)-4-(trifluoromethoxy)benzene-1-sulfonamide

ABR-239607

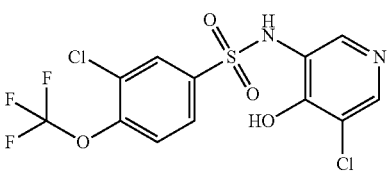

The procedure to prepare 3,5-dichloro-N-(5-chloro-4-hydroxypyridin-3-yl)benzene-1-sulfonamide was used, except that 3-chloro-4-(trifluoromethoxy)benzene-1-sulfonyl chloride was substituted for 3,5-dichlorobenzene-1-sulfonyl chloride, no DMAP was used and the temperature was 60° C. Further purification was achieved by re-crystallisation from MeOH/water (5%).

Example 103

N-(5-cyano-3-hydroxypyrazin-2-yl)-1-(3,5-dichlorophenyl)methanesulfonamide

ABR-239613

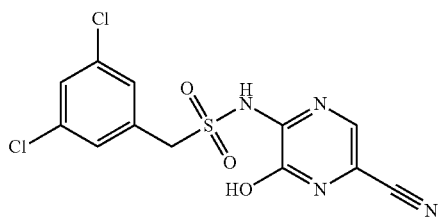

The procedure to prepare N-(6-chloro-4-hydroxypyridazin-3-yl)-1-(2-chloro-5-cyano-phenyl)methanesulfonamide was used except that N-(5-cyano-3-methoxypyrazin-2-yl)-1-(3,5-dichlorophenyl)methanesulfonamide was substituted for N-(6-chloro-4-methoxy-pyridazin-3-yl)-1-(2-chloro-5-cyanophenyl)methanesulfonamide (9%).

Example 104

1-(3,5-dichlorophenyl)-N-[4-hydroxy-6-(propane-1-sulfonyl)pyridazin-3-yl]methanesulfonamide

ABR-239512

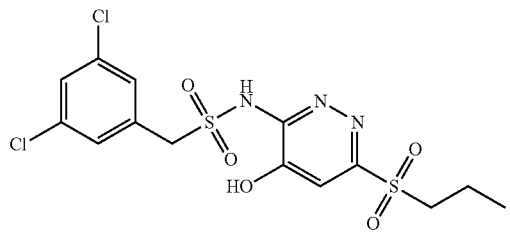

The procedure to prepare N-(6-chloro-4-hydroxypyridazin-3-yl)-1-(2-chloro-5-cyano-phenyl)methanesulfonamide was used except that 1-(3,5-dichlorophenyl)-N-[4-methoxy-6-(propane-1-sulfonyl)pyridazin-3-yl] methanesulfonamide was substituted for N-(6-chloro-4-methoxypyridazin-3-yl)-1-(2-chloro-5-cyanophenyl)methanesulfonamide (9%).

Example 105

N-(5-chloro-3-hydroxypyridin-2-yl)-1-(3,5-dimethoxyphenyl)methanesulfonamide

ABR-239413

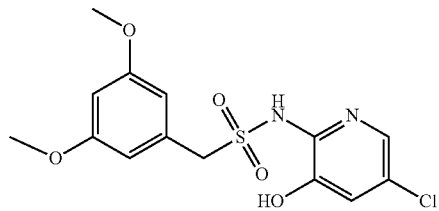

To a stirred solution of N-[5-chloro-3-(prop-2-en-1-yloxy)pyridin-2-yl]-1-(3,5-dimethoxyphenyl)methanesulfonamide (30 mg, 0.08 mmol) in MeOH (1 mL) was added bis[3-(diphenylphosphinyl)cyclopenta-2,4-dien-1-yl]iron; dichloromethane; dichloropalladium (61 mg, 0.08 mmol) at room temperature. After 10 min $K_2CO_3$ (32 mg, 0.23 mmol) was added and the reaction mixture was stirred at room temperature for 3.5 hrs. The cooled reaction mixture was filtered and the filtrate was concentrated. The residue was purified by preparative TLC (eluent 7:30 MeOH:DCM) to afford the title compound as a brown solid (8 mg, 30%).

Example 106

5-chloro-N-(5-chloro-3-hydroxypyridin-2-yl)-6-(dimethylamino)pyridine-3-sulfonamide

ABR-239428

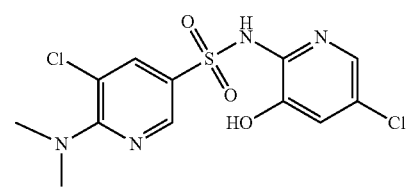

The procedure to prepare N-(6-chloro-4-hydroxypyridazin-3-yl)-1-(2-chloro-5-cyano-phenyl)methanesulfonamide was used except that 5-chloro-N-(5-chloro-3-methoxy-pyridin-2-yl)-6-(dimethylamino)pyridine-3-sulfonamide was substituted for N-(6-chloro-4-methoxypyridazin-3-yl)-1-(2-chloro-5-cyanophenyl) methanesulfonamide (28%).

Example 107

N-(2-chloro-4-hydroxypyrimidin-5-yl)-1-(3,5-dichlorophenyl)methanesulfonamide

ABR-239553

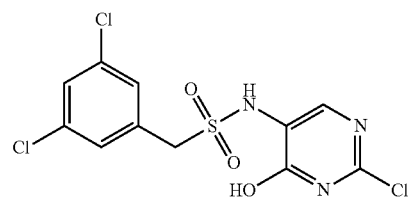

1M $BBr_3$ in DCM (575 µL, 0.575 mmol) was added to a stirring solution of N-(2-chloro-4-methoxypyrimidin-5-yl)-1-(3,5-dichlorophenyl)methanesulfonamide (55 mg, 0.14 mmol) in DCM (2 mL) under nitrogen. The reaction was stirred at room temperature for 2 hrs then partitioned between DCM (15 mL) and saturated aq. $NaHCO_3$ (15 mL). The aqueous was re-extracted with DCM (15 mL). The aqueous phase was then brought to pH ~2 by the careful addition of concentrated HCl. A white precipitate formed which was isolated by filtration. The solid obtained was suspended in MeOH (1 mL), filtered and the filter pad was washed with DCM (2×1 mL), water (2×1 mL), then dried in vacuo to afford the title compound (34 mg, 64%) as an off white solid.

Example 108

1-(3,5-dichlorophenyl)-N-[5-(ethanesulfonyl)-3-hydroxypyridin-2-yl]methanesulfonamide

ABR-239467

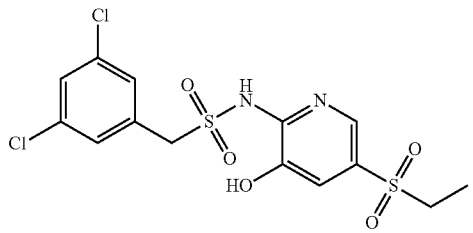

The procedure to prepare N-(6-chloro-4-hydroxypyridazin-3-yl)-1-(2-chloro-5-cyano-phenyl)methanesulfonamide was used except that 1-(3,5-dichlorophenyl)-N-[5-(ethane-sulfonyl)-3-methoxypyridin-2-yl]methanesulfonamide was substituted for N-(6-chloro-4-methoxypyridazin-3-yl)-1-(2-chloro-5-cyanophenyl)methanesulfonamide (22%).

Example 109

3,4-dichloro-N-(6-chloro-4-hydroxypyridazin-3-yl)benzene-1-sulfonamide

ABR-239478

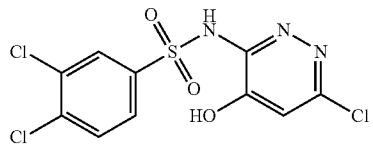

The procedure to prepare 3,5-dichloro-N-(6-chloro-4-hydroxypyridazin-3-yl)benzene-1-sulfonamide was used except that 3,4-dichlorobenzene sulfonyl chloride was substituted for 3,5-dichlorobenzene sulfonyl chloride (5%).

Example 110

N-(5-chloro-4-hydroxypyridin-3-yl)-1-(3,5-dichlorophenyl)methanesulfonamide

ABR-239568

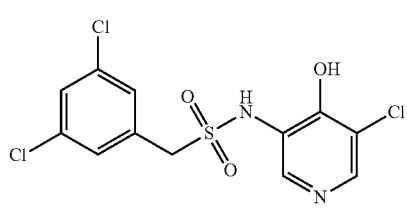

To a stirred solution of 3-amino-5-chloropyridin-4-ol (150 mg, 1.04 mmol) and N,N-dimethylpyridin-4-amine (6 mg, 0.05 mmol) in pyridine (3 mL) at 0° C. was added (3,5-dichlorophenyl)methanesulfonyl chloride (135 mg, 0.52 mmol) and the mixture stirred overnight. More sulfonyl chloride (67 mg, 0.26 mmol) was added to the reaction mixture and stirring was continued overnight. The mixture was acidified to pH3 with 1M HCl and extracted with EtOAc (3×15 mL). The organic layers contained substantial amounts of a pink solid so the mixture was filtered. The solid was washed with HCl (1M) and dried in air to yield the title compound as a pale pink solid (30 mg, 7%).

Example 111

1-(3,5-dichlorophenyl)-N-[6-(ethanesulfonyl)-4-hydroxypyridazin-3-yl]methanesulfonamide

ABR-239524

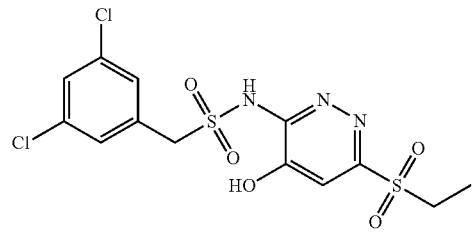

A stirred mixture of 1-(3,5-dichlorophenyl)-N-[6-(ethanesulfonyl)-4-methoxypyridazin-3-yl]methanesulfonamide (400 mg, 0.91 mmol) in 1,4-Dioxane-HCl (10%) was kept at 90° C. for an 3.5 hrs then concentrated in vacuo. The residue was treated with aqueous NaHCO$_3$ and extracted with EtOAc twice. The combined organic layers were dried (Na$_2$SO$_4$), filtered and the filtrate concentrated. The residue was purified by silica chromatography followed by automated preparative HPLC (high pH method) to afford the title compound as a white solid (90 mg, 23%).

Example 112

1-(3,5-dichlorophenyl)-N-(3-hydroxy-5-methanesulfonylpyrazin-2-yl)methane-sulfonamide

ABR-239619

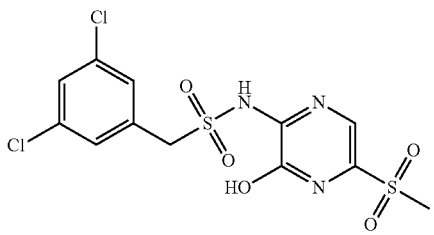

The procedure to prepare N-(6-chloro-4-hydroxypyridazin-3-yl)-1-(2-chloro-5-cyano-phenyl)methanesulfonamide was used except that 1-(3,5-dichlorophenyl)-N-(5-methane-sulfonyl-3-methoxypyrazin-2-yl)methanesulfonamide was substituted for N-(6-chloro-4-methoxypyridazin-3-yl)-1-(2-chloro-5-cyanophenyl)methanesulfonamide (28%).

Example 113

2,5-dichloro-N-(6-chloro-4-hydroxypyridazin-3-yl)thiophene-3-sulfonamide

ABR-239491

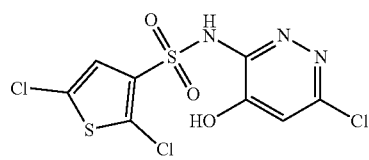

The procedure to prepare N-(6-chloro-4-hydroxypyridazin-3-yl)-1-(2-chloro-5-cyano-phenyl)methanesulfonamide was used except that 2,5-dichloro-N-(6-chloro-4-methoxy-pyridazin-3-yl)thiophene-3-sulfonamide was substituted for N-(6-chloro-4-methoxy-pyridazin-3-yl)-1-(2-chloro-5-cyanophenyl)methanesulfonamide. Purification was by silica chromatography (eluent: 1% MeOH in DCM) rather than HPLC (32%).

Example 114

5-bromo-N-(6-chloro-4-hydroxypyridazin-3-yl)-6-methoxypyridine-3-sulfonamide

ABR-239502

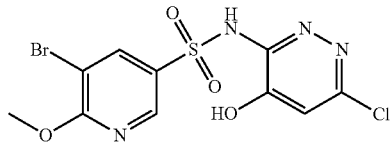

To a suspension of 5-bromo-6-chloro-N-(6-chloro-4-hydroxypyridazin-3-yl)pyridine-3-sulfonamide (740 mg, 1.85 mmol) in MeOH (38 mL) was added sodium methoxide solution (5.4M in MeOH, 1.7 mL, 9.2 mmol) and the solution heated at 80° C. for 1 hr. The solvent was evaporated, EtOAc added (80 mL) followed by 1M HCl (30 mL). A pink solid that did not dissolve in either was filtered off and then the solid was slurried with hot MeOH/water. Filtration and drying in air yielded the title compound as a pink solid (450 mg, 61%).

Example 115

N-(6-chloro-4-hydroxypyridazin-3-yl)-1-(2,3-dichlorophenyl)methanesulfonamide

ABR-239461

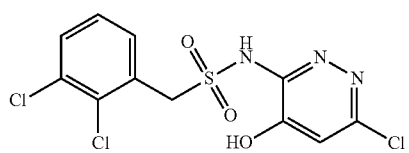

The procedure to prepare N-(6-chloro-4-hydroxypyridazin-3-yl)-1-(3,4-difluorophenyl)-methanesulfonamide was used except that (2,3-dichlorophenyl)methanesulfonyl chloride was substituted for (3,4-difluorophenyl)methanesulfonyl chloride (24%).

Example 116

N-(6-chloro-4-hydroxypyridazin-3-yl)-3-(trifluoromethoxy)benzene-1-sulfonamide

ABR-239501

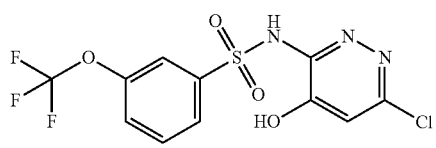

The procedure used to prepare N-(6-chloro-4-hydroxypyridazin-3-yl)-1-(2-chloro-5-cyanophenyl)methanesulfonamide was used except that N-(6-chloro-4-methoxypyridazin-3-yl)-3-(trifluoromethoxy)benzene-1-sulfonamide was substituted for N-(6-chloro-4-methoxypyridazin-3-yl)-1-(2-chloro-5-cyanophenyl)methanesulfonamide. Purification was by silica chromatography (eluent: 1-2% MeOH in DCM) rather than HPLC (28%).

Example 117

6-(azetidin-1-yl)-5-bromo-N-(5-chloro-4-hydroxypyridin-3-yl)pyridine-3-sulfonamide

ABR-239600

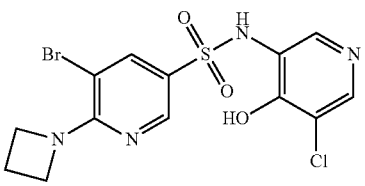

To 3-amino-5-chloropyridin-4-ol (150 mg, 1.04 mmol) in pyridine (2 mL) in a sealable tube at 60° C. was added 5-bromo-6-chloropyridine-3-sulfonyl chloride (272 mg, 0.934 mmol) in portions over 1 min. The mixture was stirred for 1 hr at this temperature then the pyridine was evaporated and the residue dissolved in DMSO (2 mL). Azetidine hydrochloride (291 mg, 3.11 mmol) and sodium carbonate (330 mg, 3.11 mmol) were added, the vessel sealed and the mixture heated at 60° C. for 1 hr. The cooled reaction mixture was diluted with MeOH (4 mL), filtered and subjected to low pH preparative HPLC. Product containing fractions were combined, the solvent evaporated and the residue slurried with MeOH (4 mL) followed by filtration to afford the title compound as a pink solid (51 mg, 12%).

Example 118

1-(3,5-dichlorophenyl)-N-[4-hydroxy-6-(propane-2-sulfonyl)pyridazin-3-yl]methane-sulfonamide

ABR-239525

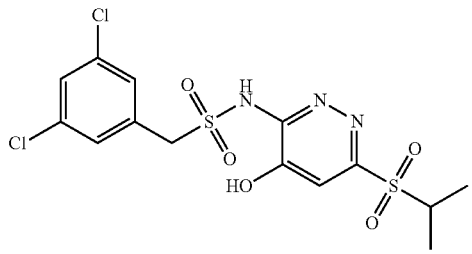

The procedure to prepare 1-(3,5-dichlorophenyl)-N-[6-(ethanesulfonyl)-4-hydroxy-pyridazin-3-yl]methanesulfonamide was used except that 1-(3,5-dichlorophenyl)-N-[4-methoxy-6-(propane-2-sulfonyl)pyridazin-3-yl] methanesulfonamide was substituted for 1-(3,5-dichlorophenyl)-N-[6-(ethanesulfonyl)-4-methoxypyridazin-3-yl]methane sulfonamide (10%).

Example 119

5-bromo-N-(5-chloro-4-hydroxypyridin-3-yl)-6-ethoxypyridine-3-sulfonamide

ABR-239611

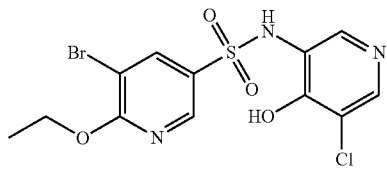

To a solution of 5-bromo-6-chloro-N-(5-chloro-4-hydroxypyridin-3-yl)pyridine-2-sulfonamide (40 mg, 0.10 mmol) in DMF (1 mL) and EtOH (1 mL) was added NaH (14 mg, 0.60 mmol) and the mixture heated at 150° C. for 40 mins in a Biotage microwave. The cooled reaction mixture was acidified to pH5 (0.2M HCl), extracted with EtOAc (3×10 mL), the organics combined and washed with brine (2×10 mL), dried (MgSO4), filtered and concentrated under reduced pressure to afford a crude purple oil which was purified by automated reverse phase HPLC to afford the title compound as an off white solid, (4.8 mg, 11%).

Example 120

5-bromo-N-(5-chloro-3-hydroxypyridin-2-yl)-6-(dimethylamino)pyridine-3-sulfonamide

ABR-239411

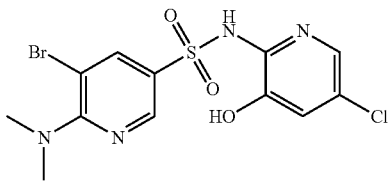

The procedure to prepare N-(6-chloro-4-hydroxypyridazin-3-yl)-1-(2-chloro-5-cyano-phenyl)methanesulfonamide was used except that 5-bromo-N-(5-chloro-3-methoxy-pyridin-2-yl)-6-(dimethylamino)pyridine-3-sulfonamide was substituted for N-(6-chloro-4-methoxypyridazin-3-yl)-1-(2-chloro-5-cyanophenyl)methanesulfonamide (25%).

Example 121

N-(6-chloro-4-hydroxypyridazin-3-yl)-3-cyanobenzene-1-sulfonamide

ABR-239628

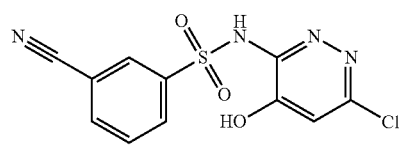

The procedure to prepare N-(6-chloro-4-hydroxypyridazin-3-yl)-1-(2-chloro-5-cyano-phenyl)methanesulfonamide was used except that N-(6-chloro-4-methoxypyridazin-3-yl)-3-cyanobenzene-1-sulfonamide was substituted for N-(6-chloro-4-methoxypyridazin-3-yl)-1-(2-chloro-5-cyanophenyl)methanesulfonamide (31%).

Example 122

3-chloro-N-(5-chloro-4-hydroxypyridin-3-yl)-4-methoxybenzene-1-sulfonamide

ABR-239554

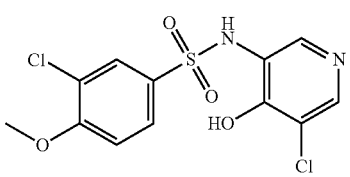

The procedure to prepare N-(5-chloro-4-hydroxypyridin-3-yl)-1-(3,5-dichlorophenyl)-methanesulfonamide was used except that 3-chloro-4-methoxybenzene-1-sulfonyl chloride was substituted for (3,5-dichlorophenyl)methanesulfonyl chloride (18%).

Example 123

3-bromo-N-(5-chloro-4-hydroxypyridin-3-yl)-4-methoxybenzene-1-sulfonamide

ABR-239555

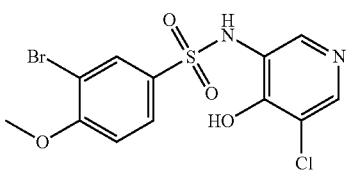

The procedure to prepare N-(5-chloro-4-hydroxypyridin-3-yl)-1-(3,5-dichlorophenyl)-methanesulfonamide was used except that 3-bromo-4-methoxybenzene-1-sulfonyl chloride was substituted for (3,5-dichlorophenyl)methanesulfonyl chloride (32%).

Example 124

1-(3,5-dichlorophenyl)-N-[3-hydroxy-5-(propane-1-sulfonyl)pyridin-2-yl]methanesulfonamide

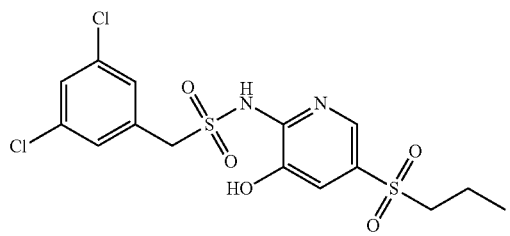

ABR-239457

The procedure to prepare 1-(3,5-dichlorophenyl)-N-[3-hydroxy-5-(propane-2-sulfonyl)-pyridin-2-yl]methanesulfonamide was used except that 1-(3,5-dichlorophenyl)-N-[3-methoxy-5-(propane-1-sulfonyl)pyridin-2-yl]methanesulfonamide was substituted for 1-(3,5-dichlorophenyl)-N-[3-methoxy-5-(propane-2-sulfonyl)pyridin-2-yl]methane-sulfonamide (34%).

Example 125

N-(6-chloro-4-hydroxypyridazin-3-yl)-1-(3,4-dichlorophenyl)methanesulfonamide

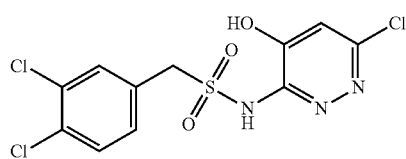

ABR-239449

The procedure to prepare N-(6-chloro-4-hydroxy-pyridazin-3-yl)-1-(3,4-difluorophenyl)-methanesulfonamide was used except that (3,4-dichlorophenyl)methanesulfonyl was substituted for (3,4-difluorophenyl)methanesulfonyl chloride (7%).

Example 126

1-(3,5-dichlorophenyl)-N-(4-hydroxy-6-methanesulfonylpyridazin-3-yl)methane-sulfonamide

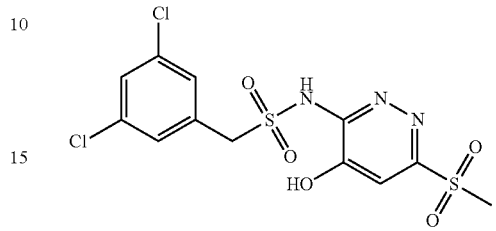

ABR-239450

The procedure to prepare 1-(3,5-dichlorophenyl)-N-[6-(ethanesulfonyl)-4-hydroxy-pyridazin-3-yl]methanesulfonamide was used except that 1-(3,5-dichlorophenyl)-N-(6-methanesulfonyl-4-methoxypyridazin-3-yl) methanesulfonamide was substituted for 1-(3,5-dichlorophenyl)-N-(6-ethanesulfonyl-4-methoxypyridazin-3-yl)methanesulfonamide. Purification was by prep TLC (eluent 7% MeOH in DCM, 12%).

Example 127

N-(5-chloro-3-hydroxypyridin-2-yl)-1-(5-cyanothiophen-3-yl)methanesulfonamide

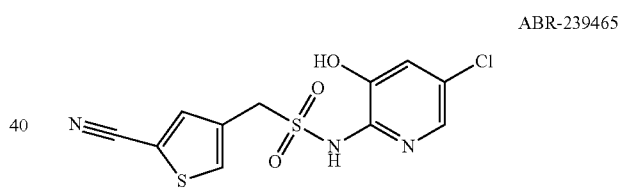

ABR-239465

The procedure to prepare N-(6-chloro-4-hydroxy-pyridazin-3-yl)-1-(2-chloro-5-cyano-phenyl)methanesulfonamide was used except that N-(5-chloro-3-methoxypyridin-2-yl)-1-(5-cyanothiophen-3-yl)methanesulfonamide was substituted for N-(6-chloro-4-methoxy-pyridazin-3-yl)-1-(2-chloro-5-cyanophenyl)methanesulfonamide (24%).

Example 128

5-bromo-6-chloro-N-[4-hydroxy-6-(trifluoromethyl)pyridin-3-yl]pyridine-3-sulfonamide

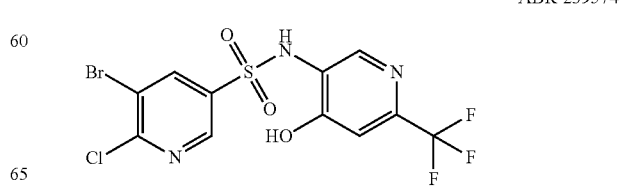

ABR-239574

To a stirred solution of 5-amino-2-(trifluoromethyl)pyridin-4-ol (130 mg, 0.73 mmol) and N,N-dimethylpyridin-4-amine (4.4 mg, 0.036 mmol) in pyridine (1.5 mL) at 0° C. was added 5-bromo-6-chloropyridine-3-sulfonyl chloride (220 mg, 0.759 mmol). The reaction mixture was stirred at room temperature for 1 hr. More 5-bromo-6-chloropyridine-3-sulfonyl chloride (26 mg, 0.091 mmol) was added and stirring continued for a further 1 hr. The pH was adjusted to 3 with 1M HCl, the mixture extracted with EtOAc (3×10 mL) and the organics combined, dried (MgSO₄), filtered and the filtrate concentrated to dryness. The crude material was purified by automated reverse phase HPLC (low pH method) to yield the title compound as an off white solid (36 mg, 12%).

Example 129

5-bromo-N-(5-chloro-4-hydroxypyridin-3-yl)-6-(piperidin-1-yl)pyridine-3-sulfonamide

ABR-239592

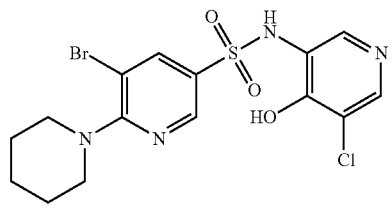

To a solution of 3-amino-5-chloropyridin-4-ol (200 mg, 50% purity, 0.692 mmol) in pyridine (2 mL) at 60° C. was added 5-bromo-6-chloropyridine-3-sulfonyl chloride (201 mg, 0.692 mmol) in portions over 1 min. The mixture was stirred for 1 hr at this temperature then the pyridine was evaporated and the purple oil treated with piperidine (2 mL) and the mixture refluxed 1 hr. The piperidine was evaporated and the oil subjected to automated reverse phase prep. HPLC (low pH method) to afford the title compound as an off white solid (38 mg, 12%).

Example 130

N-(5-chloro-6-cyano-3-hydroxypyridin-2-yl)-1-(3,5-dichlorophenyl)methane-sulfonamide

ABR-239641

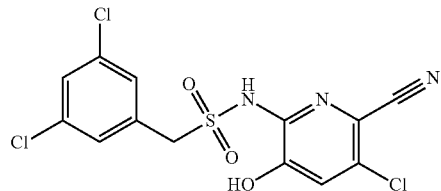

The procedure to prepare N-(6-chloro-4-hydroxypyridazin-3-yl)-1-(2-chloro-5-cyano-phenyl)methanesulfonamide was used except that N-(5-chloro-6-cyano-3-methoxy-pyridin-2-yl)-1-(3,5-dichlorophenyl) methanesulfonamide was substituted for N-(6-chloro-4-methoxypyridazin-3-yl)-1-(2-chloro-5-cyanophenyl) methanesulfonamide (8%).

Example 131

N-[5-(cyclopentanesulfonyl)-3-hydroxypyridin-2-yl]-1-(3,5-dichlorophenyl)methane-sulfonamide

ABR-239466

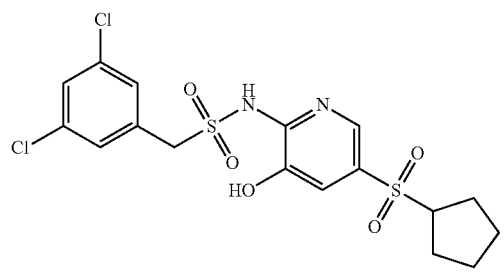

The procedure to prepare 1-(3,5-dichlorophenyl)-N-[6-(ethanesulfonyl)-4-hydroxy-pyridazin-3-yl]methanesulfonamide was used except that N-[5-(cyclopentanesulfonyl)-3-methoxypyridin-2-yl]-1-(3,5-dichlorophenyl) methanesulfonamide was substituted for 1-(3,5-dichlorophenyl)-N-(6-ethanesulfonyl-4-methoxypyridazin-3-yl)methanesulfonamide and chloroform was used in place of DCM. Purification was achieved using flash silica chromatography (eluent: 1.5% MeOH:DCM) and then by recrystallisation from CHCl₃/MeOH/pentane (7%).

Example 132

N-[4-hydroxy-6-(trifluoromethyl)pyridin-3-yl]-6-methylpyridine-3-sulfonamide

ABR-239589

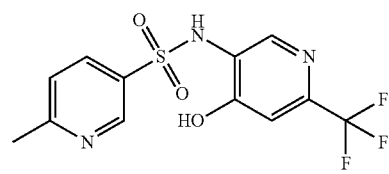

To a stirred solution of 5-amino-2-(trifluoromethyl)pyridin-4-ol (150 mg at 50% purity, 0.421 mmol) in pyridine at 80° C. was added 6-methylpyridine-3-sulfonyl chloride (prepared according to a method described in WO 2007/023186 A1), 55 mg, 0.29 mmol). The mixture was stirred for 1 hr at this temperature then the pyridine was evaporated. The residue was purified by low pH automated preparative HPLC to afford the title compound as a white solid (10 mg, 7%).

Example 133

1-(3,5-dichlorophenyl)-N-[4-hydroxy-6-(trifluoromethyl)pyridin-3-yl]methane-sulfonamide

ABR-239576

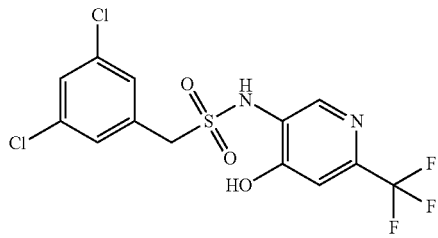

The procedure to prepare 5-bromo-6-chloro-N-[4-hydroxy-6-(trifluoromethyl)pyridin-3-yl]pyridine-3-sulfonamide was used except that 3,5-dichlorophenyl)methanesulfonyl chloride was substituted for 5-bromo-6-chloropyridine-3-sulfonyl chloride. HPLC purification used the high pH method; (15%).

Example 134

N-(5-chloro-3-hydroxy-6-methanesulfonylpyridin-2-yl)-1-(3,5-dichlorophenyl)-methanesulfonamide

ABR-239671

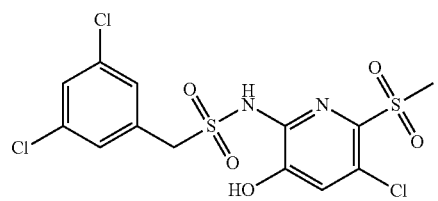

The procedure to prepare N-(6-chloro-4-hydroxypyridazin-3-yl)-1-(2-chloro-5-cyano-phenyl)methanesulfonamide was used except that N-(5-chloro-6-methanesulfonyl-3-methoxypyridin-2-yl)-1-(3,5-dichlorophenyl)methanesulfonamide was substituted for N-(6-chloro-4-methoxypyridazin-3-yl)-1-(2-chloro-5-cyanophenyl)methanesulfonamide. Further purification was achieved by trituration with DCM (17%).

Example 135

1-(3,4-dichlorophenyl)-N-[4-hydroxy-6-(trifluoromethyl)pyridin-3-yl]methane-sulfonamide

ABR-239573

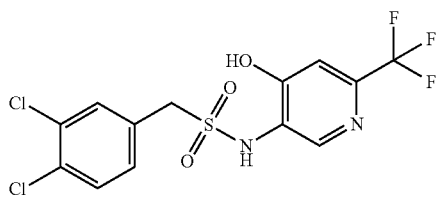

The procedure to prepare 5-bromo-6-chloro-N-[4-hydroxy-6-(trifluoromethyl)pyridin-3-yl]pyridine-3-sulfonamide was used except that (3,4-dichlorophenyl)methanesulfonyl chloride was substituted for 5-bromo-6-chloropyridine-3-sulfonyl chloride (12%).

Example 136

N-(5-chloro-3-hydroxypyridin-2-yl)-6-(dimethylamino)-5-methanesulfonylpyridine-3-sulfonamide

ABR-239481

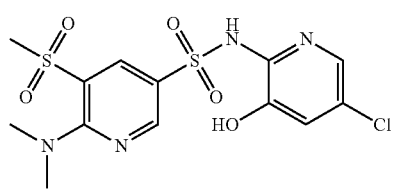

The procedure to prepare N-(6-chloro-4-hydroxypyridazin-3-yl)-1-(2-chloro-5-cyano-phenyl)methanesulfonamide was used except that N-(5-chloro-3-methoxypyridin-2-yl)-6-(dimethylamino)-5-methanesulfonylpyridine-3-sulfonamide was substituted for N-(6-chloro-4-methoxypyridazin-3-yl)-1-(2-chloro-5-cyanophenyl) methanesulfonamide. Purification was by silica chromatography (eluent EtOAc:hexane 1:1, 20%).

Example 137

5-bromo-N-[4-hydroxy-6-(trifluoromethyl)pyridin-3-yl]-6-methoxypyridine-3-sulfonamide

ABR-239575

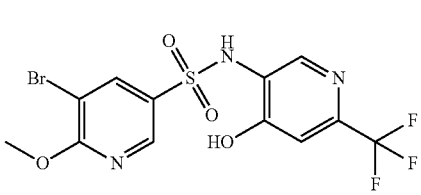

Sodium methoxide (5.4M, 0.1 mL, 0.54 mmol) was added to THF (3 mL) at room temperature then 5-bromo-6-chloro-N-[4-hydroxy-6-(trifluoromethyl)pyridin-3-yl]-pyridine-3-sulfonamide (30 mg, 0.069 mmol) was added and the reaction heated to 60° C. for 5 hrs. The mixture was diluted with EtOAc (30 mL) and washed subsequently with water (10 mL) and brine (10 mL). The organic phase was dried over MgSO$_4$, filtered and concentrated in vacuo to give the title compound as an off white solid (16 mg, 54%).

Example 138

N-(5-cyano-4-hydroxypyridin-3-yl)-1-(3,5-dichlorophenyl)methanesulfonamide

ABR-239566

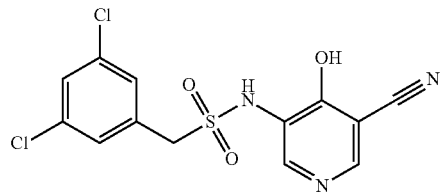

To a solution of N-(5-bromo-4-hydroxypyridin-3-yl)-1-(3,5-dichlorophenyl)methane-sulfonamide (390 mg, 0.94 mmol) in NMP (9 mL) was added copper(I) cyanide (422 mg, 4.71 mmol) and the mixture heated at 175° C. for 5 hrs. The cooled reaction mixture was diluted with EtOAc (100 mL) and washed with brine (30 mL×4). The organic phase was dried ($Na_2SO_4$), filtered and concentrated and the residue purified by automated reverse phase HPLC (high followed by low pH methods) to give the title compound as a pink solid (82 mg, 24%).

Example 139

1-(3,5-dichlorophenyl)-N-[4-hydroxy-6-(3-hydroxypropanesulfonyl)pyridazin-3-yl]methanesulfonamide

ABR-239531

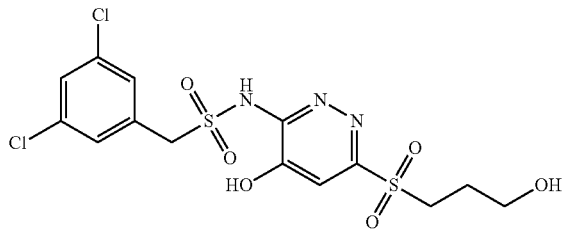

The procedure to prepare N-(6-chloro-4-hydroxypyridazin-3-yl)-1-(2-chloro-5-cyano-phenyl)methanesulfonamide was used except that 1-(3,5-dichlorophenyl)-N-[4-methoxy-6-(3-methoxypropanesulfonyl)pyridazin-3-yl]methanesulfonamide was substituted for N-(6-chloro-4-methoxypyridazin-3-yl)-1-(2-chloro-5-cyanophenyl)methanesulfonamide (6%).

Example 140

N-[6-(cyclopentanesulfonyl)-4-hydroxypyridazin-3-yl]-1-(3,5-dichlorophenyl)-methanesulfonamide

ABR-239499

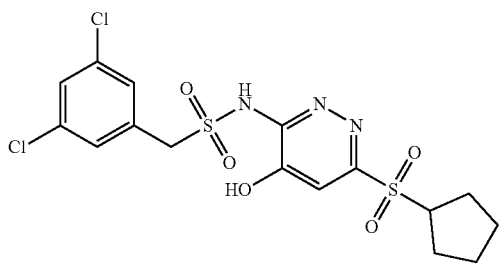

The procedure to prepare 1-(3,5-dichlorophenyl)-N-[6-(ethanesulfonyl)-4-hydroxy-pyridazin-3-yl]methanesulfonamide was used except that N-[6-(cyclopentane sulfonyl)-4-methoxypyridazin-3-yl]-1-3,5-dichlorophenyl) methanesulfonamide was substituted for 1-(3,5-dichlorophenyl)-N-[6-(ethanesulfonyl)-4-methoxypyridazin-3-yl] methane-sulfonamide (12%).

Example 141

(+/−)-N-(5-bromo-3-hydroxypyrazin-2-yl)-1-(3,5-dichlorophenyl)-2,2,2-trifluoroethane-1-sulfonamide

ABR-239717

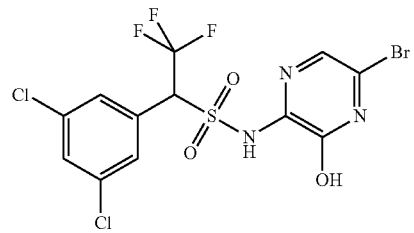

1M $BBr_3$ in DCM (284 µL, 0.284 mmol) was added to a solution of (+/−)-N-(5-bromo-3-methoxypyrazin-2-yl)-1-(3, 5-dichlorophenyl)-2,2,2-trifluoroethane-1-sulfonamide (20 mg, 0.03 mmol) in DCM (2 mL) under nitrogen. The reaction was allowed to stir at room temperature for 2 hrs, then to stand for 48 hrs. The reaction was diluted with DCM (10 mL), washed with 1 N HCl (2×3 mL), brine (3 mL), dried over anhydrous $Na_2SO_4$, filtered and the filtrate was concentrated in vacuo. The residue was purified by flash column chromatography over silica (Biotage 10 g SNAP cartridge, eluting with a gradient of heptane:EtOAc 1:1 to 0:1 then EtOAc:MeOH 1:0 to 9:1 to afford desired product as an off white solid. The product was suspended in DCM (10 mL) and extracted into the aqueous phase by extracting with 2M $K_2CO_3$ (3×3 mL). The combined extractions were washed with DCM (3×5 mL) then brought to pH 1 by the addition of 3 N HCl. The aqueous phase was then re-extracted with DCM (5×10 mL). The combined organic extractions were washed with brine (10 mL), dried over anhydrous $Na_2SO_4$, filtered and the filtrate was concentrated in vacuo to afford the title compound (11 mg, 70%) as an off white solid.

Example 142

3-[(5-bromo-3-hydroxypyrazin-2-yl)sulfamoyl]-N,N-diethylbenzamide

ABR-239694

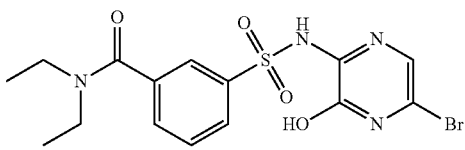

To a stirring solution of 3-[(5-bromo-3-hydroxypyrazin-2-yl)sulfamoyl]benzoic acid (110 mg, 0.29 mmol) in DMF (8 mL), HATU (168 mg, 0.44 mmol) and DIPEA (0.88 mL, 0.88 mmol) was added and the mixture left to stir for 30 mins at 60° C. in a sealed tube. Diethylamine (0.060 mL, 0.59 mmol) was added to the reaction mixture and the reaction was left stirring for 2 hrs at 60° C. The brown reaction mixture was concentrated in vacuo before being dissolved in 1:1 DMSO:MeOH and being purified directly via automated reverse phase HPLC to afford the title compound as an off-white solid (12 mg, 9%).

Example 143

N-(2-chloro-5-hydroxypyrimidin-4-yl)-1-(3,5-dichlorophenyl)methanesulfonamide

ABR-239721

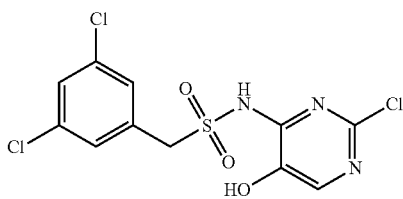

The procedure to prepare N-(6-chloro-4-hydroxy-pyridazin-3-yl)-1-(2-chloro-5-cyano-phenyl)methanesulfonamide was used except that N-(2-chloro-5-methoxy-pyrimidin-4-yl)-1-(3,5-dichlorophenyl)methanesulfonamide was substituted for N-(6-chloro-4-methoxypyridazin-3-yl)-1-(2-chloro-5-cyanophenyl)methanesulfonamide (24%).

Example 144

3,4-dichloro-N-(2-chloro-5-hydroxypyrimidin-4-yl)benzene-1-sulfonamide

ABR-239720

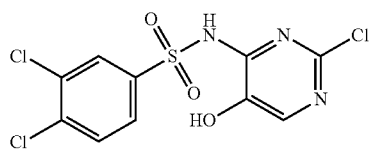

The procedure to prepare N-(6-chloro-4-hydroxy-pyridazin-3-yl)-1-(2-chloro-5-cyano-phenyl)methanesulfonamide was used except that 3,4-dichloro-N-(2-chloro-5-methoxy-pyrimidin-4-yl)benzene-1-sulfonamide was substituted for N-(6-chloro-4-methoxy-pyridazin-3-yl)-1-(2-chloro-5-cyanophenyl)methanesulfonamide (3%).

Example 145

3,5-dichloro-N-(2-chloro-5-hydroxypyrimidin-4-yl)benzene-1-sulfonamide

ABR-239735

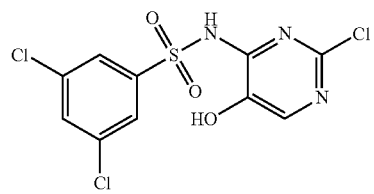

The procedure to prepare N-(6-chloro-4-hydroxy-pyridazin-3-yl)-1-(2-chloro-5-cyano-phenyl)methanesulfonamide was used except that 3,5-dichloro-N-(2-chloro-5-methoxy-pyrimidin-4-yl)benzene-1-sulfonamide was substituted for N-(6-chloro-4-methoxy-pyridazin-3-yl)-1-(2-chloro-5-cyanophenyl)methanesulfonamide (44%).

Example 146

3-[(6-chloro-4-hydroxypyridazin-3-yl)sulfamoyl]-N,N-diethylbenzamide

ABR-239737

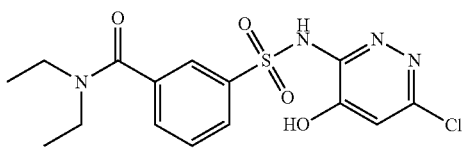

The procedure to prepare 3-[(5-bromo-3-hydroxypyrazin-2-yl)sulfamoyl]-N,N-diethyl-benzamide was used except that 3-[(6-chloro-4-hydroxypyridazin-3-yl)sulfamoyl]benzoic acid was substituted for 3-[(5-bromo-3-hydroxypyrazin-2-yl)sulfamoyl]benzoic acid and heating of the second stage of the reaction was at 80° C. rather than 60° C. (42%).

Example 147

N-(6-chloro-4-hydroxypyridazin-3-yl)-1-(4-cyanophenyl)methanesulfonamide

ABR-239722

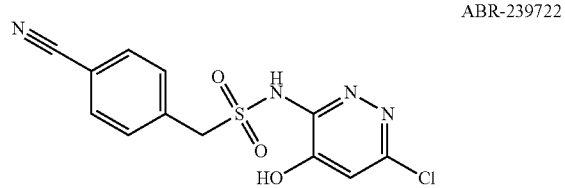 [SMILES: N#Cc1ccc(CS(=O)(=O)Nc2nnc(Cl)cc2O)cc1]

To a stirred solution of N-(6-chloro-4-methoxypyridazin-3-yl)-1-(4-cyanophenyl)-methanesulfonamide (274 mg, 0.81 mmol) in DCM (30 mL) was added 1M BBr$_3$ in DCM (3.24 mL, 3.24 mmol) and the mixture left stirring for 3.5 hrs. The reaction mixture was quenched with water (20 mL), the layers were separated, the aqueous layer was extracted with DCM (2×30 mL), all organic layers were combined and were concentrated in vacuo to a yellow solid which was mostly starting material. The aqueous layer was further extracted with EtOAc (3×30 mL), the organic layers were combined and concentrated in vacuo to afford 53 mg of a yellow solid which was also mostly starting material.

The aqueous layer was filtered to obtain a white solid which was dissolved in 1:1 DMSO:MeOH and purified via automated reverse phase HPLC (low pH method) to afford the title compound as a white solid (23 mg, 9%).

Example 148

N-(6-chloro-4-hydroxypyridazin-3-yl)-1-(5-cyano-2-fluorophenyl)methane-sulfonamide

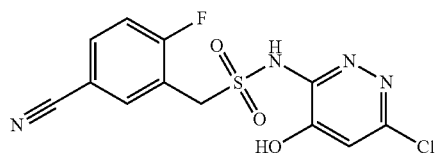

ABR-239742

The procedure to prepare N-(6-chloro-4-hydroxy-pyridazin-3-yl)-1-(2-chloro-5-cyano-phenyl)methanesulfonamide was used except that N-(6-chloro-4-methoxy-pyridazin-3-yl)-1-(5-cyano-2-fluorophenyl) methanesulfonamide was substituted for N-(6-chloro-4-methoxypyridazin-3-yl)-1-(2-chloro-5-cyanophenyl)methanesulfonamide (28%).

Example 149

N-(6-chloro-4-hydroxypyridazin-3-yl)-1-(3-cyano-5-fluorophenyl)methane-sulfonamide

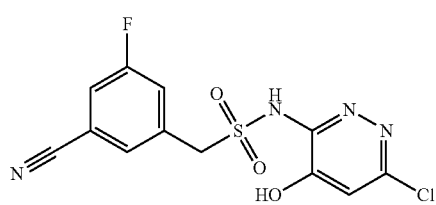

ABR-239743

The procedure to prepare N-(6-chloro-4-hydroxy-pyridazin-3-yl)-1-(2-chloro-5-cyano-phenyl)methanesulfonamide was used except that N-(6-chloro-4-methoxy-pyridazin-3-yl)-1-(3-cyano-5-fluorophenyl) methanesulfonamide was substituted for N-(6-chloro-4-methoxypyridazin-3-yl)-1-(2-chloro-5-cyanophenyl) methanesulfonamide (28%).

Example 150

1-(2-chloro-5-cyanophenyl)-N-(2-chloro-5-hydroxy-pyrimidin-4-yl)methane-sulfonamide

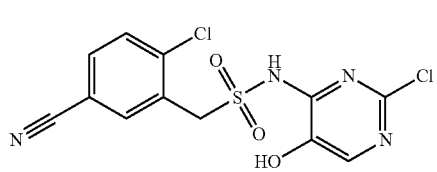

ABR-239744

The procedure to prepare N-(6-chloro-4-hydroxy-pyridazin-3-yl)-1-(2-chloro-5-cyano-phenyl)methanesulfonamide was use except that 1-(2-chloro-5-cyanophenyl)-N-(2-chloro-5-methoxypyrimidin-4-yl)methanesulfonamide was substituted for N-(6-chloro-4-methoxypyridazin-3-yl)-1-(2-chloro-5-cyanophenyl)methanesulfonamide (34%).

Example 151

2-chloro-N-(6-chloro-4-hydroxypyridazin-3-yl)-4-cyanobenzene-1-sulfonamide

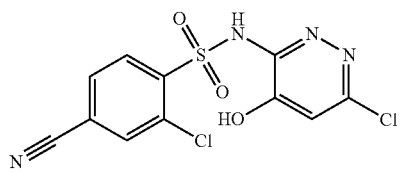

ABR-239745

The procedure to prepare N-(6-chloro-4-hydroxy-pyridazin-3-yl)-1-(2-chloro-5-cyano-phenyl)methanesulfonamide was used except that 2-chloro-N-(6-chloro-4-methoxy-pyridazin-3-yl)-4-cyanobenzene-1-sulfonamide was substituted for N-(6-chloro-4-methoxypyridazin-3-yl)-1-(2-chloro-5-cyanophenyl)methanesulfonamide (10%).

Example 152

3-chloro-N-(6-chloro-4-hydroxypyridazin-3-yl)-4-fluorobenzene-1-sulfonamide

ABR-239748

The procedure to prepare N-(6-chloro-4-hydroxy-pyridazin-3-yl)-1-(2-chloro-5-cyano-phenyl)methanesulfonamide was used except that 3-chloro-N-(6-chloro-4-methoxy-pyridazin-3-yl)-4-fluorobenzene-1-sulfonamide was substituted for N-(6-chloro-4-methoxypyridazin-3-yl)-1-(2-chloro-5-cyanophenyl)methanesulfonamide (30%).

Example 153

3,5-dichloro-N-(5-cyano-4-hydroxypyridin-3-yl)benzene-1-sulfonamide

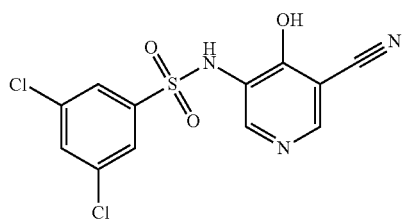

ABR-239750

To a solution of N-(5-bromo-4-hydroxypyridin-3-yl)-3,5-dichlorobenzene-1-sulfonamide (367 mg, 0.92 mmol) in NMP (9 mL) was added copper(I) cyanide (413 mg, 4.61 mmol) and the mixture heated at 175° C. for 6 hrs. The cooled reaction mixture was diluted with EtOAc (100 mL) and washed with brine (30 mL×4). The organic phase was dried ($Na_2SO_4$), filtered and concentrated to give a brown residue which was triturated with MeOH. Further purification was achieved by automated reverse phase HPLC (basic method) giving the title compound as a white solid (46 mg, 14%).

Example 154

3-chloro-N-(6-chloro-4-hydroxypyridazin-3-yl)-5-fluorobenzene-1-sulfonamide

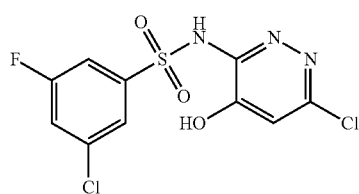

ABR-239754

The procedure to prepare N-(6-chloro-4-hydroxy-pyridazin-3-yl)-1-(2-chloro-5-cyano-phenyl)methanesulfonamide was used except that 3-chloro-N-(6-chloro-4-methoxy-pyridazin-3-yl)-5-fluorobenzene-1-sulfonamide was substituted for N-(6-chloro-4-methoxypyridazin-3-yl)-1-(2-chloro-5-cyanophenyl)methanesulfonamide (29%).

Example 155

3,5-dichloro-N-(4-hydroxy-6-methanesulfonylpyridin-3-yl)benzene-1-sulfonamide

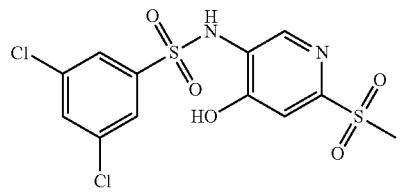

ABR-239755

The procedure to prepare N-(6-chloro-4-hydroxy-pyridazin-3-yl)-1-(2-chloro-5-cyano-phenyl)methanesulfonamide was used except that 3,5-dichloro-N-(6-methanesulfonyl-4-methoxypyridin-3-yl)benzene-1-sulfonamide was substituted for N-(6-chloro-4-methoxy-pyridazin-3-yl)-1-(2-chloro-5 cyanophenyl)methanesulfonamide (35%).

Example 156

3,5-dichloro-N-(6-chloro-4-hydroxypyridin-3-yl)benzene-1-sulfonamide

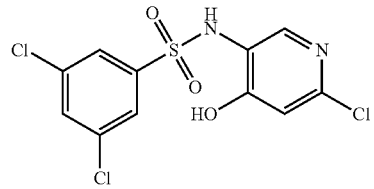

ABR-239756

The procedure to prepare N-(6-chloro-4-hydroxy-pyridazin-3-yl)-1-(2-chloro-5-cyano-phenyl)methanesulfonamide was used except that 3,5-dichloro-N-(6-chloro-4-methoxy-pyridin-3-yl)benzene-1-sulfonamide was substituted for N-(6-chloro-4-methoxy-pyridazin-3-yl)-1-(2-chloro-5cyanophenyl)methanesulfonamide and HPLC was done using a neutral method (ammonium bicarbonate buffer as mobile phase) (7%).

Example 157

1-(3,5-dichlorophenyl)-N-[5-hydroxy-2-(trifluoromethyl)pyrimidin-4-yl]methane-sulfonamide

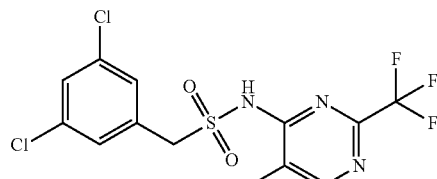

ABR-239760

To a stirring solution of 1-(3,5-dichlorophenyl)-N-[5-methoxy-2-(trifluoromethyl)-pyrimidin-4-yl]methanesulfonamide (130 mg, 0.31 mmol) in DCM (15 mL) was added 1M BBr$_3$ in DCM (1.25 mL) was added and the mixture stirred for 5 hrs. Water was added slowly to quench the reaction and extracted with DCM (3×30 mL). Most of the product was in the aqueous phase which was re-extracted using EtOAc. The EtOAc layer was dried (Na$_2$SO$_4$), filtered and concentrated in vacuo to yield the title compound as a white solid (80 mg, 64%).

Example 158

3-chloro-5-fluoro-N-[5-hydroxy-2-(trifluoromethyl)pyrimidin-4-yl]benzene-1-sulfonamide

ABR-239761

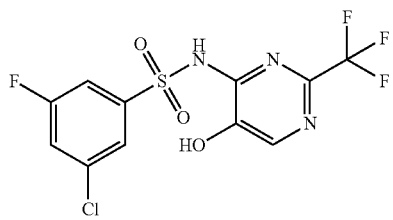

The procedure to prepare N-(6-chloro-4-hydroxypyridazin-3-yl)-1-(2-chloro-5-cyano-phenyl)methanesulfonamide was used except that 3-chloro-5-fluoro-N-[5-methoxy-2-(trifluoromethyl)pyrimidin-4-yl]benzene-1-sulfonamide was substituted for N-(6-chloro-4-methoxypyridazin-3-yl)-1-(2-chloro-5-cyanophenyl)methanesulfonamide (35%).

Example 159

3,5-dichloro-N-(3-hydroxy-5-methanesulfonylpyrazin-2-yl)benzene-1-sulfonamide

ABR-239762

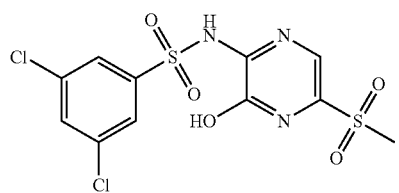

To a stirred solution of 3,5-dichloro-N-(5-methanesulfonyl-3-methoxypyrazin-2-yl)-benzene-1-sulfonamide (150 mg, 0.36 mmol) in DCM (25 mL) was added a solution of 1M BBr$_3$ in DCM (2.18 mL). On stirring a white precipitate formed. Additional DCM (25 ml) was added and the reaction was sonicated to get the solid back into solution and stirring continued for a further 30 mins. The reaction was quenched by the addition of sat NaHCO$_3$ (aq) until the reaction was pH 7. The reaction was re-acidified to pH 2 using 2M HCl and diluted with water (40 mL). A white precipitate that persisted throughout the adjustment of the pH was collected by filtration. This precipitate was dissolved in MeOH, acidified with 2M HCl(aq) and concentrated. The residue was dissolved in EtOAc (100 mL) and diluted with water (50 mL). The pH of the aqueous layer was adjusted to 2 using 2 M HCl (aq). The layers were separated and the organic layer was dried (Na$_2$SO$_4$), filtered and concentrated giving the title compound as a white solid (73 mg, 50%).

Example 160

3-chloro-4-[(6-chloro-4-hydroxypyridazin-3-yl)sulfamoyl]-N,N-diethylbenzamide

ABR-239763

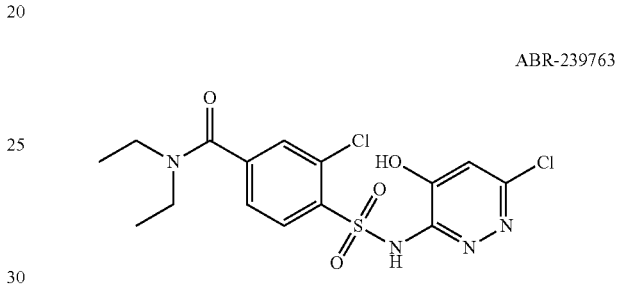

The procedure to prepare 3-[(5-chloro-4-hydroxypyridin-3-yl)sulfamoyl]-N,N-diethyl-benzamide was used except that 3-chloro-4-[(6-chloro-4-hydroxypyridazin-3-yl)-sulfamoyl]benzoic acid was substituted for 3-[(5-chloro-4-hydroxypyridin-3-yl)-sulfamoyl]benzoic acid and the reaction was heated at 60° C. for 2 hrs in a sealed tube (54%).

Example 161

3-chloro-5-{[(6-chloro-4-hydroxypyridazin-3-yl)sulfamoyl]methyl}-N,N-diethylbenzamide

ABR-239769

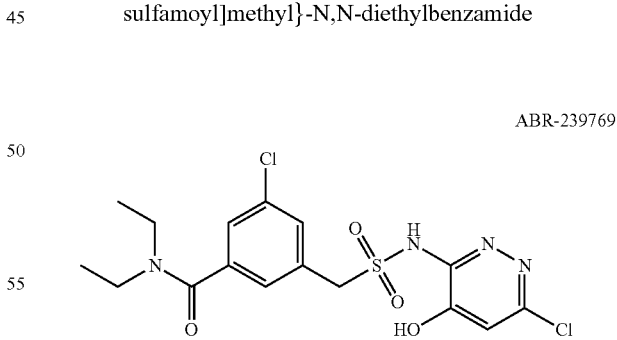

The procedure to prepare N-(6-chloro-4-hydroxypyridazin-3-yl)-1-(2-chloro-5-cyano-phenyl)methanesulfonamide was used except that 3-chloro-5-{[(6-chloro-4-methoxy-pyridazin-3-yl)sulfamoyl]methyl}-N,N-diethylbenzamide was substituted for N-(6-chloro-4-methoxypyridazin-3-yl)-1-(2-chloro-5-cyanophenyl)methanesulfonamide (8%).

Example 162

N-(6-chloro-4-hydroxypyridazin-3-yl)-3-cyano-5-fluorobenzene-1-sulfonamide

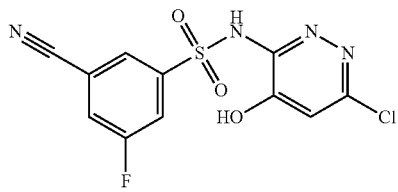

ABR-239771

The procedure to prepare N-(6-chloro-4-hydroxy-pyridazin-3-yl)-1-(2-chloro-5-cyano-phenyl)methanesulfonamide was used except that N-(6-chloro-4-methoxy-pyridazin-3-yl)-3-cyano-5-fluorobenzene-1-sulfonamide was substituted for N-(6-chloro-4-methoxy-pyridazin-3-yl)-1-(2-chloro-5-cyanophenyl)methanesulfonamide (4%).

Example 163

3-chloro-5-fluoro-N-[4-hydroxy-6-(trifluoromethyl)pyridazin-3-yl]benzene-1-sulfonamide

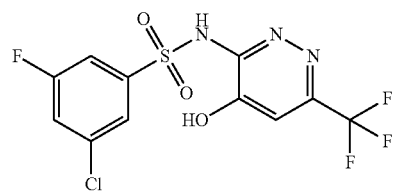

ABR-239772

4-methoxy-6-(trifluoromethyl)pyridazin-3-amine (115 mg, 0.595 mmol) was dissolved in THF (3 ml) under $N_2$ and sodium hydride added (60%, 26 mg, 0.655 mmol) and the mixture stirred for 20 mins until gas evolution ceased. 3-chloro-5-fluorobenzene-1-sulfonyl chloride (136 mg, 0.595 mmol) was added and the mixture stirred at room temperature overnight. The mixture was quenched with 2M HCl (5 mL), water was added (10 mL) and the products extracted into DCM. The combined organic phases were dried ($Na_2SO_4$), the mixture filtered and the filtrate concentrated to dryness. Silica chromatography (eluent: 0-100% ethyl acetate in heptane) gave the intermediate methyl ether which was demethylated with $BBr_3$ in DCM as in previous procedures. Aqueous work up and then purification by automated reverse phase HPLC (low pH method) gave the title compound (17 mg, 8%).

Example 164

1-(3,4-dichlorophenyl)-N-[5-hydroxy-2-(trifluoromethyl)pyrimidin-4-yl]methane-sulfonamide

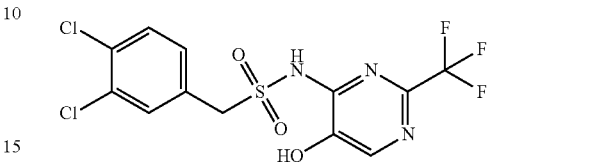

ABR-239773

The procedure to prepare N-(6-chloro-4-hydroxy-pyridazin-3-yl)-1-(2-chloro-5-cyano-phenyl)methanesulfonamide was used except that 1-(3,4-dichlorophenyl)-N-[5-methoxy-2-(trifluoromethyl)pyrimidin-4-yl]methanesulfonamide was substituted for N-(6-chloro-4-methoxypyridazin-3-yl)-1-(2-chloro-5-cyanophenyl)methanesulfonamide (37%).

Example 165

N-(6-chloro-4-hydroxypyridazin-3-yl)-1-(2,5-dichlorothiophen-3-yl)methane-sulfonamide

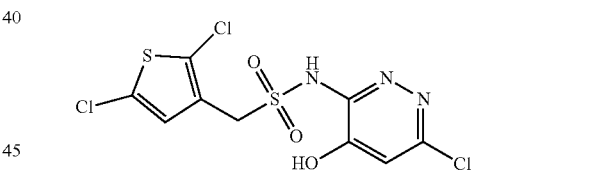

ABR-239775

To a stirring solution of N-(6-chloro-4-methoxypyridazin-3-yl)-1-(2,5-dichlorothiophen-3-yl)methanesulfonamide (170 mg, 0.39 mmol) in DCM (40 mL) at 0° C. was added 1M $BBr_3$ in DCM (1.18 mL, 1.18 mmol) and the reaction mixture was left to stir for 30 mins. A further 500 μL of 1M $BBr_3$ in DCM was added and the mixture was kept at 0° C. for a further 90 mins. The reaction mixture was then allowed to warm slightly (still kept below 10° C.) and a further 200 μL of 1M $BBr_3$ in DCM was added and the mixture was left to stir for a further 45 mins. Then it was re-cooled back to 0° C. and quenched with ice-cold water. The aqueous was then extracted with DCM (3×30 mL), the combined organics were dried over $MgSO_4$ then concentrated under reduced pressure to yield a brown solid which was purified by automated reverse phase HPLC (low pH method) to afford the title compound as a white solid (40 mg, 27%).

Example 166

3,5-dichloro-N-(4-hydroxy-6-methanesulfonylpyridazin-3-yl)benzene-1-sulfonamide

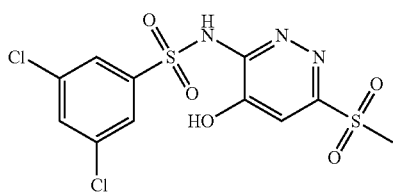

ABR-239776

The procedure to prepare N-(6-chloro-4-hydroxypyridazin-3-yl)-1-(2-chloro-5-cyano-phenyl)methanesulfonamide was used except that 3,5-dichloro-N-(6-methanesulfonyl-4-methoxypyridazin-3-yl)benzene-1-sulfonamide was substituted for N-(6-chloro-4-methoxypyridazin-3-yl)-1-(2-chloro-5-cyanophenyl)methanesulfonamide (37%).

Example 167

1-(3,5-dichlorophenyl)-N-(3-hydroxypyridin-4-yl) methanesulfonamide

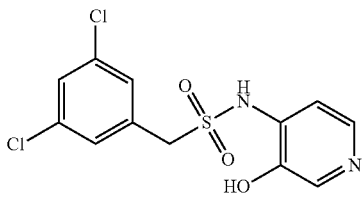

ABR-239434

To a solution of 4-amino-3-methoxypyridine (93 mg, 0.75 mmol) in pyridine (1 mL) was added (3,5-dichlorophenyl)methanesulfonyl chloride (195 mg, 0.75 mmol). The mixture was stirred at room temperature for 16 h. The intermediate product was collected by filtration, dried in vacuum, suspended in DCM (2 mL), then treated with 1M BBr₃ in DCM (0.52 mL, 0.52 mmol) at 0° C. and the solution stirred at room temperature for 16 h. The reaction was quenched with water and ice and the resulting solid precipitate was collected by filtration. The solid was warmed in EtOH (2 mL) and 1M HCl (1 mL) for 4 hour at 70° C. The mixture was diluted with water and the resulting solid precipitate was collected by filtration and dried to afford 1-(3,5-dichlorophenyl)-N-(3-hydroxypyridin-4-yl)methanesulfonamide as an off-white solid (10 mg, 4%).

Example 168

6-(2,5-dichlorothiophene-3-sulfonamido)-5-hydroxypyridine-3-carboxylic acid

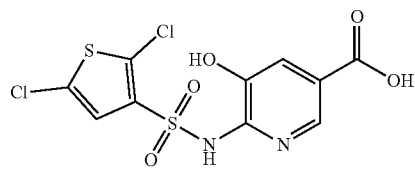

ABR-239564

To a solution of Methyl 6-(2,5-dichlorothiophene-3-sulfonamido)-5-hydroxypyridine-3-carboxylate (26 mg, 0.07 mmol) in methanol (1.1 mL) was added 1M NaOH (1.5 mL) and the mixture stirred at 60° C. for 5 hours. The mixture was filtered and the filtrate acidified with 5 M HCl until pH below 3. The resulting solid was filtered off, washed with water and dried to give 6-(2,5-dichlorothiophene-3-sulfonamido)-5-hydroxy-pyridine-3-carboxylic acid as an off-white solid (10 mg, 40%).

Example 169

N-(2-chloro-3-hydroxypyridin-4-yl)-1-(3,5-dichlorophenyl)methanesulfonamide

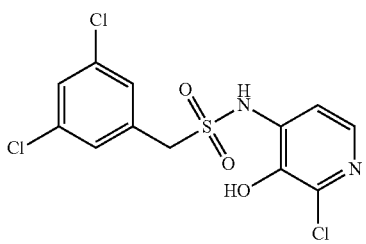

ABR-239757

To a solution of 4-amino-2-chloro-3-methoxypyridine (160 mg, 1.0 mmol) in pyridine (1.5 mL) was added (3,5-dichlorophenyl)methanesulfonyl chloride (260 mg, 1.0 mmol). The mixture was stirred at room temperature for 16 h. The solvent was evaporated and ethanol (5 mL) was added to the residue followed by addition of water (2 mL). The intermediate product was collected by filtration, dried in vacuum, suspended in CHCl₃ (6 mL), then treated with 1M BBr₃ in DCM (2.1 mL, 2.1 mmol) at 0° C. and the solution stirred at room temperature for 16 h. The mixture is cooled in an ice bath and 1,2-propane-diol (0.7 mL) was added followed by the addition of n-propanol (3 mL). The mixture was concentrated to remove CHCl₃, then diluted with n-propanol (3 mL) and 5 M HCl (0.4 mL) and heated to 80° C. After ½ hour the solution was cooled to room temperature and water added until first sign of precipitate. After stirring ½ hour, remaining product/boron complex was filtered off and additional water was added to the residual solution. The obtained second precipitate was filtered off to afford 1-(3,5-dichlorophenyl)-N-(2-chloro-3-hydroxypyridin-4-yl) methanesulfonamide as an off-white solid (175 mg, 48%).

Example 170

3,5-dichloro-N-(2-chloro-3-hydroxypyridin-4-yl) benzene-1-sulfonamide

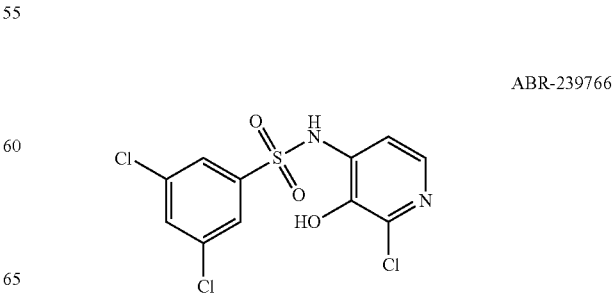

ABR-239766

The procedure for preparation of 1-(3,5-dichlorophenyl)-N-(2-chloro-3-hydroxypyridin-4-yl)methanesulfonamide was used except that 3,5-dichlorobenzenesulphonyl chloride was substituted for (3,5-dichlorophenyl)methanesulfonyl chloride.

Example 171

N-(3-hydroxypyridin-2-yl)-3-(trifluoromethyl)benzene-1-sulfonamide

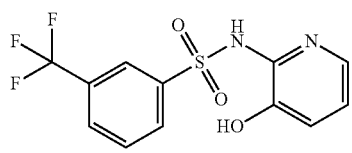

ABR-239447

3-(Trifluoromethyl)benzenesulfonyl chloride (773 mg) and 2-amino-3-benzyloxypyridine (407 mg) were allowed to react according to procedure A and then hydrogenated in water/sodium hydroxide using palladium on charcoal as catalyst. The catalyst was filtered off and the product was precipitated upon addition of hydrochloric acid (1 M). The precipitate was isolated by filtration, dried, and gave the title compound (153 mg, 24% yield).

Example 172

N-(5-chloro-2-hydroxypyridin-3-yl)-1-(3,4-dichlorophenyl)methanesulfonamide

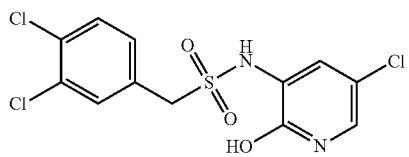

ABR-239560

Prepared from (3,4-dichlorophenyl)methanesulfonyl chloride and 3-amino-5-chloro-2-methoxypyridine (1.0 mmol) using procedures A and B in 12% overall yield.

Example 173

N-(5,6-dichloro-2-hydroxypyridin-3-yl)-1-(3,5-dichlorophenyl)methanesulfonamide

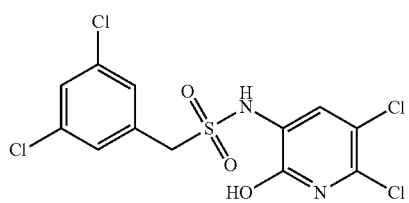

ABR-239562

Prepared from (3,5-dichlorophenyl)methanesulfonyl chloride and 3-amino-5,6-dichloro-2-methoxypyridine (1.23 mmol) using procedures A and B in 80% overall yield.

Example 174

N-(6-chloro-2-hydroxypyridin-3-yl)-1-(3,4-dichlorophenyl)methanesulfonamide

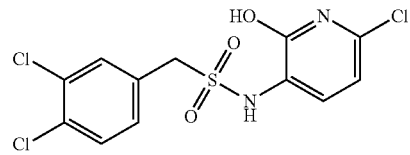

ABR-239580

Prepared from (3,4-dichlorophenyl)methanesulfonyl chloride and 3-amino-6-chloro-2-methoxypyridine (1.0 mmol) using procedures A and B in 43% overall yield.

Example 175

N-(6-chloro-2-hydroxypyridin-3-yl)-1-(3,5-dichlorophenyl)methanesulfonamide

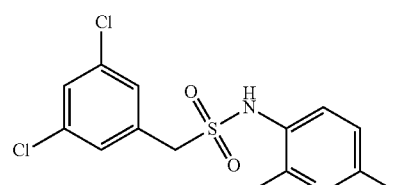

ABR-239581

Prepared from (3,5-dichlorophenyl)methanesulfonyl chloride and 3-amino-6-chloro-2-methoxypyridine (1.0 mmol) using procedures A and B in 88% overall yield.

Example 176

5-bromo-N-(6-chloro-2-hydroxypyridin-3-yl)-6-methoxypyridine-3-sulfonamide

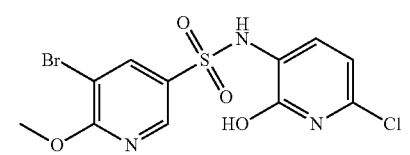

ABR-239583

Prepared from 5-bromo-6-chloropyridine-3-sulfonyl chloride and 3-amino-6-chloro-2-methoxypyridine (1.0 mmol) using procedures A and B, omitting heating in ethanol and NaOH during procedure A, and reacting the resulting compound after procedure B in 1 M NaOMe/MeOH at 80° C. for 3 h followed by precipitation with acetic acid in water which gave the title compound in 33% overall yield.

Example 177

N-(5,6-dibromo-3-hydroxypyrazin-2-yl)-1-(3,4-dichlorophenyl)methanesulfonamide

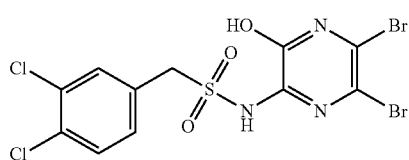

ABR-239653

Isolated in low yield (5%) as a byproduct during the preparation of ABR-239417 (Example 75). A possible explanation for its formation would be small amounts of bromine formed during the storage of 1 M boron tribromide solutions. The bromine has then reacted with ABR-239417 to give the title compound.

Example 178

N-(6-chloro-2-hydroxypyridin-3-yl)-1-[4-(trifluoromethyl)phenyl]methane-sulfonamide

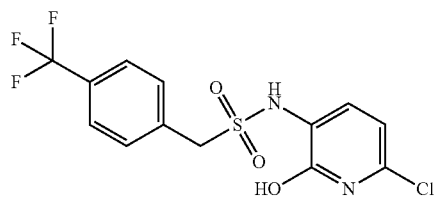

ABR-239672

Prepared from (4-trifluoromethylphenyl)methanesulfonyl chloride and 3-amino-6-chloro-2-methoxypyridine (1.0 mmol) using procedures A and B in 50% overall yield.

Example 179

N-(6-chloro-2-hydroxypyridin-3-yl)-4-propylbenzene-1-sulfonamide

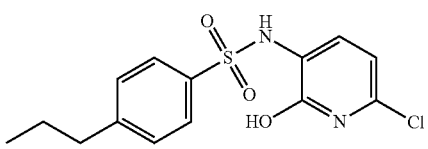

ABR-239673

Prepared from 4-n-butylbenzenesulfonyl chloride and 3-amino-6-chloro-2-methoxypyridine (1.0 mmol) using procedures A and B in 57% overall yield.

Example 180

3,4-dichloro-N-(6-chloro-2-hydroxypyridin-3-yl)benzene-1-sulfonamide

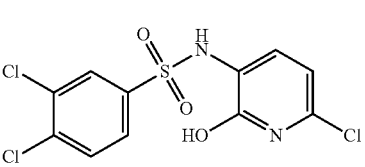

ABR-239674

Prepared from 3,4-dichlorobenzenesulfonyl chloride and 3-amino-6-chloro-2-methoxypyridine (1.0 mmol) using procedures A and B in 32% overall yield.

Example 181

N-(6-chloro-2-hydroxypyridin-3-yl)-1-(5,6-dichloropyridin-3-yl)methane-sulfonamide

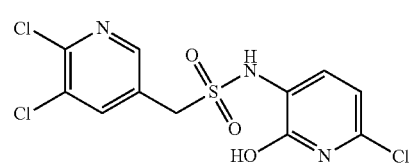

ABR-239718

Prepared from 1-(5,6-dichloropyridin-3-yl)methanesulfonylchloride and 3-amino-6-chloro-2-methoxypyridine (3.0 mmol) using procedures A and B, omitting heating in ethanol and NaOH during procedure A, in 27% overall yield.

Example 182

N-(6-chloro-2-hydroxypyridin-3-yl)-1-(5-chloro-6-methoxypyridin-3-yl)methane-sulfonamide

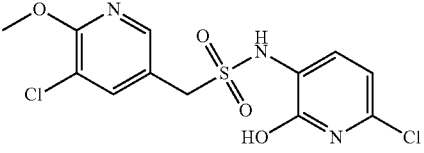

ABR-239724

Prepared from ABR-239718 (0.3 mmol) by heating in 1 M NaOMe/MeOH at 80° C. for 72 h and isolating the precipitated sodium salt. The salt was then stirred in a mixture of acetic acid in methanol/water and the title compound (55 mg, 50% yield) was isolated by filtration.

Example 183

N-(5-chloro-4-hydroxypyridin-3-yl)-1-(5,6-dichloro-pyridin-3-yl)methane-sulfonamide

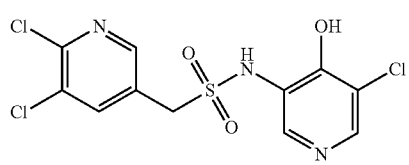

ABR-239726

Prepared from 1-(5,6-dichloropyridin-3-yl)methanesulfonylchloride (1.5 mmol) and 3-amino-5-chloropyridin-4-ol (1.0 mmol) by heating in pyridine at 90° C. for 3 and partitioning the mixture between ethyl acetate, water and acetic acid. The organic phase was concentrated and the residue was crystallised from methanol and gave the title compound (90 mg, 24% yield).

Example 184

N-(5-chloro-4-hydroxypyridin-3-yl)-1-(5-chloro-6-methoxypyridin-3-yl)methane-sulfonamide

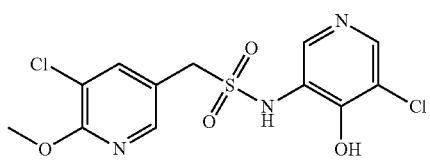

ABR-239740

Prepared from ABR-239726 (80 mg) by heating in 1 M NaOMe/MeOH at 80° C. for 18 h, then adding acetic acid and water and collecting the precipitate. Drying the precipitate gave the title compound (67 mg, 83% yield).

Example 185

N-(6-chloro-2-hydroxypyridin-3-yl)-1-[5-chloro-6-(pyrrolidin-1-yl)pyridin-3-yl]-methanesulfonamide

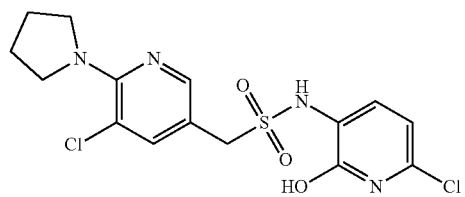

ABR-239741

Prepared from ABR-239718 (60 mg) by heating in pyrrolidine (2 mL) at 80° C. for 3 h, concentrating the mixture and dissolving the residue in abs. ethanol and precipitating the title compound by adding acetic acid and water. Yield after filtration and drying was 42 mg (64% yield).

Example 186

N-(6-chloro-2-hydroxypyridin-3-yl)-1-[3-chloro-5-(ethylsulfanyl)phenyl]methane-sulfonamide

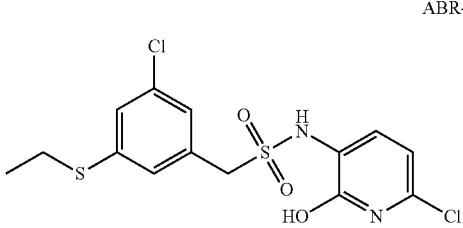

ABR-239758

(3,5-dichlorophenyl)methanesulfonyl chloride and 3-amino-6-chloro-2-methoxypyridine was reacted using procedure A. The formed intermediate 1-(3,5-dichlorophenyl)-N-(6-chloro-2-methoxy-pyridin-3-yl)methanesulfonamide (100 mg, 0.26 mmol) and sodium ethanethiolate (110 mg, 1.04 mmol) were heated in DMF (1.5 mL) at 100 degree C. for 18 h. The mixture was then diluted with water and acetic acid and the precipitate was isolated and dried to give the title compound (60 mg, 56% yield). H-nmr, 500 mHz, δ 1.27 (t, 3H), 3.00 (q, 2H), 4.61 (s, 2H), 6.79 (broad signal, 1H), 7.28 (d, 2H), 7.34 (s, 1H), 7.48 (d, 1H), 9.30 (bs, 1H), 12.50 (bs, 1H). (M+H)=393, (M−H)=391.

Example 187

3,5-dichloro-N-[6-(ethanesulfonyl)-2-hydroxypyridin-3-yl]benzene-1-sulfonamide

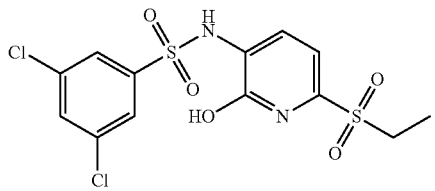

ABR-239768

Prepared from 3,5-dichlorobenzenesulfonylchloride and 3-amino-6-ethanesulfonyl-2-methoxypyridine (1.0 mmol) using procedures A and B in 74% overall yield.

Example 188

1-(3,5-dichlorophenyl)-N-[6-(ethanesulfonyl)-2-hydroxypyridin-3-yl]methane-sulfonamide

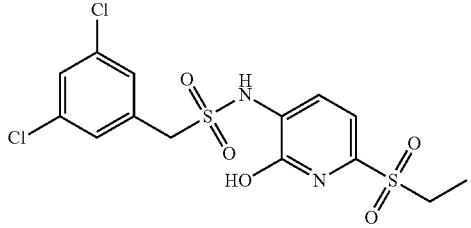

ABR-239774

Prepared from (3,5-dichlorophenyl)methanesulfonylchloride and 3-amino-6-ethane-sulfonyl-2-methoxypyridine (1.0 mmol) using procedures A and B in 81% overall yield.

Example 189

N-(5-cyano-3-hydroxypyridin-2-yl)-1-(3,5-dichlorophenyl)methanesulfonamide

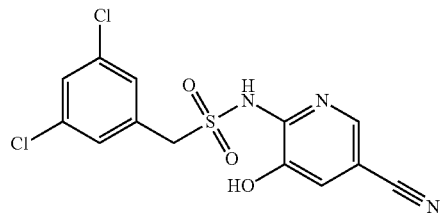

ABR-239401

To a solution of N-(5-cyano-3-methoxypyridin-2-yl)-1-(3,5-dichlorophenyl)-methanesulfonamide (180 mg, 0.48 mmol) in DCM (25 mL) was added 1M $BBr_3$ in DCM (1.90 mL, 1.90 mmol) in four portions over 5 hrs. The mixture was quenched by the addition of saturated $NaHCO_3$ (20 mL) and more DCM was added (50 mL). The phases were separated and the organic phase was washed with brine (20 mL), dried ($Na_2SO_4$), the mixture filtered and the filtrate evaporated to dryness to afford a brown oil which was purified by automated reverse phase HPLC (low pH method) to afford the title compound as an off-white solid (32 mg, 18%).

Example 190

5-chloro-N-(5-chloro-4-hydroxypyridin-3-yl)-6-methylpyridine-3-sulfonamide

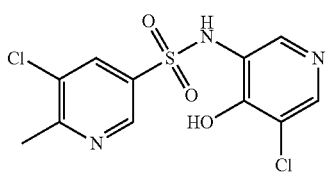

ABR-239630

To a solution of 3-amino-4-hydroxy-5-chloropyridine (200 mg, 1.38 mmol) in pyridine (3 mL) at 80° C. was added a solution of the 5-chloro-6-methylpyridine-3-sulfonyl chloride (219 mg, 0.97 mmol) in DCM (3 mL) dropwise. The mixture was stirred for 1 hr at this temperature and then the pyridine was evaporated. The residue was purified by automated reverse phase HPLC (low pH method). Further purification was achieved by slurrying with 1:1 MeOH/water followed by filtration to afford the title compound as a purple solid (28 mg, 6%).

Example 191

N-(5-chloro-4-hydroxypyridin-3-yl)-5-cyano-6-methoxypyridine-3-sulfonamide

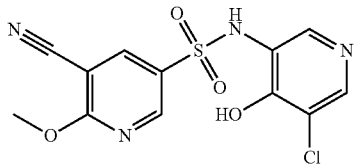

ABR-239631

A solution of 5-bromo-N-(5-chloro-4-hydroxypyridin-3-yl)-6-methoxypyridine-3-sulfonamide (90 mg, 0.23 mmol) in NMP (1 mL) was treated with solid copper(I) cyanide (102 mg, 1.14 mmol) and the mixture stirred at 165° C. for 3 hrs. The cooled reaction mixture was then partitioned between EtOAc (50 mL) and 2M $NH_3$. The phases were separated and the organic phase was washed with brine (5 mL), dried ($Na_2SO_4$), the mixture filtered and the filtrate evaporated to dryness to afford a brown oil which was purified by automated reverse phase HPLC (low pH method) to afford the title compound as an off-white solid (9 mg, 11%).

Example 192

N-(5-chloro-4-hydroxypyridin-3-yl)-6-methoxy-5-phenylpyridine-3-sulfonamide

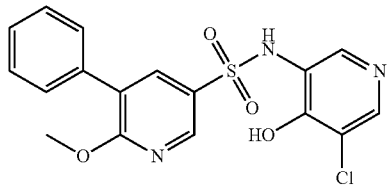

ABR-239629

A flask charged with 5-bromo-N-(5-chloro-4-hydroxypyridin-3-yl)-6-methoxypyridine-3-sulfonamide (150 mg, 0.38 mmol), phenylboronic acid (56 mg, 0.46 mmol), cesium carbonate (495 mg, 1.52 mmol), Pd(dppf)$Cl_2$.DCM (31 mg, 0.04 mmol), EtOH (5 mL) and water (1 mL) was degassed with $N_2$ and then refluxed for 2 hrs. The EtOH was evaporated and then water (5 mL) and EtOAc (60 ml) were added. The phases were separated and the organic phase was washed with brine (20 mL), dried ($Na_2SO_4$), the mixture was filtered and the filtrate evaporated to dryness to afford a black solid which was purified by automated reverse phase HPLC (low pH method). Further purification was achieved by slurrying in MeOH followed by filtration to afford the title compound as an off-white solid (22 mg, 13%).

Example 193

N-(5-chloro-3-hydroxypyridin-2-yl)-5-phenylpyridine-3-sulfonamide

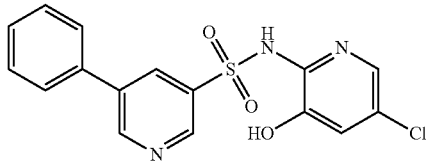

ABR-239347

To a stirred solution of N-(5-chloro-3-methoxypyridin-2-yl)-5-phenylpyridine-3-sulfonamide (150 mg, 0.40 mmol) in DCM (6 mL) at −10° C. was added BBr$_3$ (300 mg, 1.20 mmol). The reaction was allowed to warm to room temperature and was stirred for 16 hrs. The reaction mixture was neutralised with saturated NaHCO$_3$ and extracted with EtOAc. The organic layer was dried (Na$_2$SO$_4$), the mixture was filtered and the filtrate evaporated to dryness to give the crude product which was purified by preparative TLC (eluent 10% MeOH in DCM). Further purification, by automated reverse phase HPLC (low pH method), gave the title compound as an off-white solid (40 mg, 28%).

Example 194

N-(6-chloro-4-hydroxypyridazin-3-yl)-1-(3-chloro-5-cyanophenyl)methane-sulfonamide

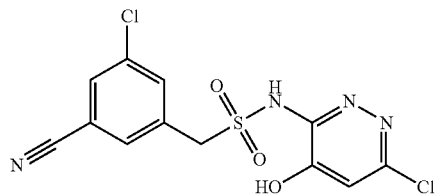

ABR-239509

The procedure to prepare N-(6-chloro-4-hydroxypyridazin-3-yl)-1-(3,4-difluorophenyl)-methanesulfonamide was used except that (3-chloro-5-cyanophenyl)methanesulfonyl chloride was substituted for (3,4-difluorophenyl)methanesulfonyl chloride and 6-chloro-4-methoxypyridazin-3-amine was substituted for 6-chloro-4-methoxypyridazin-3-amine (3%).

Example 195

5-bromo-6-chloro-N-(6-chloro-4-hydroxypyridazin-3-yl)pyridine-3-sulfonamide

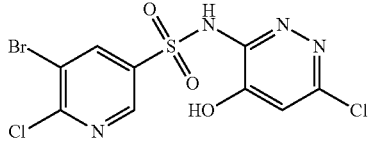 [SMILES: O=S(=O)(Nc1nnc(Cl)cc1O)c1cnc(Cl)c(Br)c1]

To a solution of 5-bromo-6-chloro-N-(6-chloro-4-methoxypyridazin-3-yl)pyridine-3-sulfonamide (1.03 g, 2.49 mmol) in DCM (150 mL) was added 1M BBr$_3$ in DCM (15 mL, 15 mmol) and the reaction stirred for 4 hrs. Neat BBr$_3$ (1 mL) was added and the mixture warmed to 45° C. and stirred overnight. The cooled mixture was diluted with more DCM (100 mL) and water, and then filtered. The solid was washed with water and dried in air to afford the title compound as a white solid.

Example 196

N-(5-bromo-4-hydroxypyridin-3-yl)-3,5-dichlorobenzene-1-sulfonamide

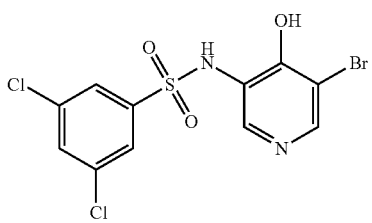 [SMILES: O=S(=O)(Nc1cncc(Br)c1O)c1cc(Cl)cc(Cl)c1]

To a stirred suspension of 3-amino-5-bromopyridin-4-ol (500 mg, 2.65 mmol) in pyridine (15 mL) was added 3,5-dichlorobenzene-1-sulfonyl chloride (585 mg, 2.38 mmol) in one portion. The reaction was stirred for 1 hr at room temperature, concentrated and the residue diluted with EtOAc (100 ml) and washed with water (30 ml) and brine (30 ml). The organic phase was dried (Na$_2$SO$_4$), filtered and concentrated. The crude product was triturated in the minimum volume of MeOH giving the desired product as a pink solid (733 mg, 77% yield).

NMR and mass spectral data for Examples of the invention are shown in Table 1.

TABLE 1

| ABR ref. | Ex. | Chemical name | M ± H$^+$ (m/z) | $^1$H NMR |
|---|---|---|---|---|
| 238823 | 1 | 5-bromo-6-chloro-N-(5-chloro-2-hydroxypyridin-3-yl)pyridine-3-sulfonamide | | (400 MHz, DMSO) δ 7.35 (dd, 2H) 8.54 (d, 1H), 8.73 (d, 1H), 11.48 (s, 1H), 11.74 (d, 1H). |
| 238066 | 2 | N-(4-hydroxypyridin-3-yl)-benzenesulfonamide | 250.9 | (500 MHz, MeOD) δ 6.31 (d, 1H), 7.44-7.52 (m, 1H), 7.54-7.63 (m, 1H), 7.80-7.86 (m, 2 H), 8.01 (d, 1H). |
| 238845 | 3 | N-(4-hydroxypyridin-3-yl)-4-(trifluoromethyl)-benzene-1-sulfonamide | 318.8 | (500 MHz, DMSO-d6) δ 6.09 (d,1 H), 7.58 (d,1H), 7.80 (s, 1H), 7.91 (d, 1H), 7.99 (d, 2H). |

TABLE 1-continued

| ABR ref. | Ex. | Chemical name | M ± H+ (m/z) | $^1$H NMR |
|---|---|---|---|---|
| 238846 | 4 | N-(4-hydroxypyridin-3-yl)-4-(trifluoromethoxy)benzene-1-sulfonamide | 334.8 | (500 MHz, DMSO-d6) δ ppm 6.10 (d, 1H), 7.51 (d, 2H), 7.58 (d, 1H), 7.79 (s, 1H), 7.92 (d, 2H). |
| 239202 | 5 | N-(5-chloro-3-hydroxy-pyridin-2-yl)-1-phenyl-methanesulfonamide | 298.9 | (500 MHz, MeOD) δ 4.59 (s, 2H), 7.17 (d, 1H), 7.35 (m, 5H), 7.84 (s, 1H) |
| 239224 | 6 | N-(5-chloro-3-hydroxy-pyridin-2-yl)-6-(pyrrolidin-1-yl)-pyridine-3-sulfonamide, formate salt | 355.1 | (250 MHz, MeOD) δ 2.07 (t, 4H), 3.53 (bs, 4H), 6.68 (d, 1H), 7.07 (d, 1H), 7.65 (d, 1H), 8.03-8.12 (m, 2H), 8.58 (d, 1H). |
| 239225 | 7 | N-(5-chloro-3-hydroxy-pyridin-2-yl)pyridine-3-sulfonamide | 286.0 | (500 MHz, MeOD) δ 7.10 (d 1H), 7.58-7.61 (m, 1H), 7.63 (d, 1H), 8.45 (dt, 1H), 8.74 (dd, 1H), 9.17 (d, 1H). |
| 239226 | 8 | 6-chloro-N-(5-chloro-3-hydroxypyridin-2-yl)-pyridine-3-sulfonamide | 320.0 | (500 MHz, MeOD) δ 7.11 (d 1H), 7.57-7.68 (m, 2H), 8.36-8.45 (m, 2H), 8.97 (d, 1H). |
| 239247 | 9 | N-(5-chloro-3-hydroxy-pyridin-2-yl)-1-(3,5-dichloro-phenyl)methanesulfonamide | 366.6 | (500 MHz, CDCl3) δ 4.28 (s, 2H), 7.07 (m, 2H),. 7.20-7.22 (m, 2H), 7.22-7.24 (m, 1H). |
| 239248 | 10 | N-(5-chloro-3-hydroxy-pyridin-2-yl)-6-[(propan-2-yl)amino]pyridine-3-sulfonamide | 343.0 | (500 MHz, MeOD) δ 1.22 (d, 6H), 3.99-4.16 (m, 1H), 6.46 (d, 1H), 7.06 (d, 1H), 7.65 (d, 1H), 7.85 (dd, 1H), 8.55 (d, 1H). |
| 239249 | 11 | 5-bromo-6-chloro-N-[3-hydroxy-5-(propan-2-yl)-pyridin-2-yl]pyridine-3-sulfonamide | 405.5 | (500 MHz, MeOD) δ 1.23 (d, 6H), 2.82 (h, 1H), 7.17 (s, 1H), 7.33 (s, 1H), 8.63 (d, 1H), 8.86 (d, 1H). |
| 239254 | 12 | N-(5-chloro-3-hydroxy-pyridin-2-yl)-1-(3-cyano-phenyl)methanesulfonamide | 324.0 | (500 MHz, MeOD) δ 4.93 (s, 2H), 7.19 (d, 1H), 7.54 (m, 1H), 7.69 (d, 1H), 7.72 (d, 1H), 7.75 (s, 1H), 7.85 (s, 1H). |
| 239269 | 13 | (+/−)-5-bromo-6-chloro-N-[3-hydroxy-5-(1-hydroxy-propan-2-yl)pyridin-2-yl]-pyridine-3-sulfonamide | 421.6 | (500 MHz, MeOD) δ 1.22 (d, 3H), 2.78 (h, 1H), 3.53-3.68 (m, 2H), 7.13 (d, 1H), 7.36 (s, 1H), 8.63 (d, 1H), 8.86 (d, 1H). |
| 239270 | 14 | 5-bromo-6-chloro-N-(3-hydroxypyridin-2-yl)-pyridine-3-sulfonamide | 363.9 | (500 MHz, MeOD) δ 6.83 (dd, 1H), 7.19 (dd, 1H), 7.47 (d, 1H), 8.66 (d, 1H), 8.88 (d, 1H). |
| 239271 | 15 | N-(5-chloro-3-hydroxy-pyridin-2-yl)-1-(2,4-dichloro-phenyl)methanesulfonamide | 366.8 | (500 MHz, MeOD) δ 5.05 (s, 2H), 7.18 (d,1H), 7.35 (dd 1H), 7.48-7.56 (m, 2H), 7.82 (s, 1H). |
| 239272 | 16 | N-(5-chloro-3-hydroxy-pyridin-2-yl)-1-(4-cyano-phenyl)methanesulfonamide | 323.8 | (500 MHz, MeOD) δ 4.96 (s, 2H), 7.17 (d, 1H), 7.57 (d, 2H), 7.72 (d, 2H), 7.80-7.88 (m, 1H). |
| 239290 | 17 | N-(5-chloro-3-hydroxy-pyridin-2-yl)-1-pyridin-3-ylmethanesulfonamide | 300.0 | (500 MHz, MeOD) δ 4.92 (s, 2H), 7.14 (d, 1H), 7.44 (dd, 1H), 7.81 (s, 1H), 7.89 (d, 1H), 8.51 (m, 2H). |
| 239291 | 18 | 5-bromo-N-(5-chloro-3-hydroxypyridin-2-yl)-6-(pyrrolidin-1-yl)pyridine-3-sulfonamide | 432.8 | (500 MHz, MeOD) δ 1.89-2.04 (m, 4H), 3.72-3.89 (m, 4H), 7.09 (d, 1H), 7.67 (d, 1H), 8.26 (d, 1H), 8.57 (d, 1H). |
| 239314 | 19 | N-(5-chloro-3-hydroxy-pyridin-2-yl)-1-(3,5-difluoro-phenyl)methanesulfonamide | 334.8 | (500 MHz, CDCl3) δ 4.95 (s, 2H), 6.90-7.12 (m, 3H), 7.20 (s, 1H), 7.86 (s, 1H). |
| 239315 | 20 | N-(5-chloro-3-hydroxy-pyridin-2-yl)-1-(2,5-dichloro-thiophen-3-yl)methane-sulfonamide | | (500 MHz, MeOD) δ 4.84 (s, 2H), 7.00 (s, 1H), 7.17 (d, 1H), 7.81 (s, 1H). |
| 239316 | 21 | N-(5-chloro-3-hydroxy-pyridin-2-yl)-1-(3,4-dichloro-phenyl)methanesulfonamide | 366.8 | (500 MHz, MeOD) δ 7.18 (d, 1H), 7.30 (dd, 1H), 7.50 (d, 1H), 7.54 (d, 1H), 7.86 (s, 1H). |
| 239317 | 22 | N-(5-chloro-3-hydroxy-pyridin-2-yl)-1-(3-chloro-5-fluorophenyl)methanesulfon-amide | 350.8 | (500 MHz, MeOD) δ 4.86 (s, 2H), 7.12 (1H), 7.17-7.35 (m, 3H), 7.85 (d, 1H). |

TABLE 1-continued

| ABR ref. | Ex. | Chemical name | M ± H⁺ (m/z) | ¹H NMR |
|---|---|---|---|---|
| 239318 | 23 | 1-(2,4-dichlorophenyl)-N-(4-hydroxypyridin-3-yl)-methanesulfonamide | 332.7 | (500 MHz, CDCl₃) δ 4.64 (s, 2H), 6.47 (d,1H), 7.30 (dd, 1H), 7.45 (d, 1H), 7.54 (d, 1H), 7.67 (dd, 1H), 7.83 (d, 1H). |
| 239321 | 24 | 1-(3,5-dichlorophenyl)-N-(4-hydroxypyridin-3-yl)-methanesulfonamide | 332.7 | (500 MHz, MeOD) δ 4.52 (s, 2H), 6.48 (d,1H), 7.37 (m, 1H), 7.40 (d, 2H), 7.65 (dd, 1H), 7.83 (d, 1H). |
| 239331 | 25 | 3,5-dichloro-N-(5-chloro-3-hydroxypyridin-2-yl)-benzene-1-sulfonamide | 352.8 | (500 MHz, MeOD) δ 7.13 (d, 1H), 7.65-7.67 (m, 1H), 7.69-7.73 (m, 1H), 7.95-8.01 (m, 2H). |
| 239332 | 26 | 3,4-dichloro-N-(5-chloro-3-hydroxypyridin-2-yl)-benzene-1-sulfonamide | 352.8 | (500 MHz, MeOD) δ 7.12 (d, 1H), 7.66 (d, 1H), 7.71 (d, 1H), 7.94 (dd, 1H), 8.20 (d, 1H). |
| 239333 | 27 | N-(5-chloro-3-hydroxy-pyridin-2-yl)-1-(3-chlorophenyl)methanesulfonamide | 332.8 | (500 MHz, MeOD) δ 7.18 (d, 1H), 7.28-7.38 (m, 3H), 7.40 (s, 1H), 7.85 (s, 1H). |
| 239334 | 28 | N-(5-chloro-3-hydroxy-pyridin-2-yl)-1-(4-chlorophenyl)methanesulfonamide | 332.8 | (500 MHz, MeOD) δ 7.17 (d, 1H), 7.35 (s, 4H), 7.84 (s, 1H). |
| 239335 | 29 | N-(5-chloro-3-hydroxy-pyridin-2-yl)-1-(2-chlorophenyl)methanesulfonamide | 332.8 | (500 MHz, MeOD) δ 5.07 (s, 2H), 7.18 (d, 1H), 7.31 (m, 1H), 7.35 (m, 1H), 7.44 (dd, 1H), 7.52 (dd, 1H), 7.82 (s, 1H). |
| 239336 | 30 | N-(5-chloro-3-hydroxy-pyridin-2-yl)-1-(2,5-dichlorophenyl)methanesulfonamide | 366.8 | (500 MHz, MeOD) δ 5.04 (s, 2H), 7.19 (d, 1H), 7.37 (dd, 1H), 7.44 (d, 1H), 7.55 (d, 1H), 7.81 (d,1H), |
| 239337 | 31 | N-(5-chloro-3-hydroxy-pyridin-2-yl)-1-(3,4-difluorophenyl)methanesulfonamide | 334.9 | (500 MHz, MeOD) δ 7.18 (dd, 2H), 7.20-7.27 (m, 1H), 7.31 (ddd, 1H), 7.86 (s, 1H). |
| 239338 | 32 | 1-(3,5-dichlorophenyl)-N-(3-hydroxy-5-methanesulfonyl-pyridin-2-yl)methane-sulfonamide | 410.8 | (500 MHz, MeOD) δ 3.17 (s, 3H), 7.35 (d, 2H), 7.44 (m, 1H), 7.50 (d, 1H), 8.30 (s, 1H). |
| 239514 | 33 | N-(5-chloro-3-hydroxy-pyridin-2-yl)-1-(3-chloro-5-cyanophenyl)methane-sulfonamide | 357.5 | (500 MHz, MeOD) δ 4.92 (s, 2H), 7.20 (d, 1H), 7.70 (s, 1H), 7.72 (s, 1H), 7.81 (d, 1H), 7.85 (s, 1H). |
| 239520 | 34 | 3-chloro-5-{[(5-chloro-3-hydroxypyridin-2-yl)-sulfamoyl]methyl}benzamide | 276.0 | (500 MHz, MeOD) δ 4.91 (s, 2H), 7.16 (d, 1H), 7.58 (s, 1H), 7.81 (s, 2H), 7.87 (d, 1H). |
| 239359 | 35 | 1-(5-chloro-2-fluorophenyl)-N-(5-chloro-3-hydroxy-pyridin-2-yl)methane-sulfonamide | 351.3 | (400 MHz, DMSO) δ 4.89 (s, 2H), 7.20 (d, 1H), 7.28 (m, 1H), 7.43-7.50 (m, 2H), 7.87 (s, 1H), 10.35 (s, 2H). |
| 239372 | 36 | N-(6-hydroxy-pyridazin-3-yl)-1-(3,5-dichlorophenyl)methane-sulfonamide | 367.7 | (500 MHz, MeOD) δ 4.78 (s, 2H), 6.57 (s, 1H), 7.38 (d, 2H), 7.47 (m, 1H). |
| 239373 | 37 | N-(5-chloro-3-hydroxy-pyridin-2-yl)-1-(2,3-dichlorophenyl)methanesulfonamide | 366.8 | (500 MHz, MeOD) δ 5.13 (s, 2H), 7.18 (d, 1H), 7.30 (m, 1H), 7.47 (dd, 1H), 7.55 (dd, 1H), 7.81 (s, 1H). |
| 239374 | 38 | N-(5-chloro-3-hydroxy-pyridin-2-yl)-1-(2,6-dichlorophenyl)methanesulfonamide | 366.8 | (250 MHz, MeOD) δ 5.27 (s, 2H), 7.15 (d, 1H), 7.27-7.47 (m, 3H), 7.77 (d, 1H). |
| 239405 | 39a | N-(5-chloro-3-hydroxy-pyridin-2-yl)-1-(3,5-dichlorophenyl)ethane-1-sulfonamide, enantiomer 1 | 380.8 | (500 MHz, Methanol-d4) δ 1.78 (d, 3H),), 5.16 (s, 1H), 7.16 (d 1H), 7.36-7.50 (m, 3H), 7.80 (s, 1H). |
| 239406 | 39b | N-(5-chloro-3-hydroxy-pyridin-2-yl)-1-(3,5-dichlorophenyl)ethane-1-sulfonamide, enantiomer 2 | 380.8 | (500 MHz, MeOD) δ 1.78 (d, 3H), 5.17 (s, 1H), 7.16 (d, 1H), 7.34-7.45 (m, 3H), 7.80 (s, 1H). |
| 239183 | 40 | 5-bromo-N-(5-chloro-3-hydroxypyridin-2-yl)-pyridine-3-sulfonamide | 364.3 | (400 MHz, DMSO) δ 7.16 (s, 1H), 7.68 (s, 1H), 8.49 (d, 1H), 8.95 (s, 1H), 9.03 (d, 1H), 10.78 (s, 1H). |
| 239239 | 41 | N-(5-chloro-3-hydroxy-pyridin-2-yl)-6-(trifluoromethyl)pyridine-3-sulfonamide | 354.1 | (400 MHz, DMSO) δ 7.19 (d, 1H), 7.70 (d, 1H), 8.17 (d, 1H), 8.60 (dd, 1H), 9.26 (d, 1H), 10.91 (s, 2H). |

TABLE 1-continued

| ABR ref. | Ex. | Chemical name | M ± H+ (m/z) | 1H NMR |
|---|---|---|---|---|
| 239262 | 42 | N-(5-chloro-3-hydroxy-pyridin-2-yl)-3-(trifluoro-methoxy)benzene-1-sulfonamide | 369.1 | (400 MHz, CDCl3) δ 7.16 (s, 1H), 7.32 (s, 1H), 7.41 (d, 1H), 7.54 (m, 1H), 7.77 (s, 1H), 7.85 (d, 1H) |
| 239049 | 43 | N-(5-bromo-3-hydroxy-pyridin-2-yl)benzene-sulfonamide | 329.1 | (400 MHz, CDCl3) δ 7.25 (s, 1H), 7.48 (t, 3H), 7.56 (t, 1H), 7.86-7.93 (m, 2H) |
| 239050 | 44 | N-(5-bromo-3-hydroxy-pyridin-2-yl)-2,5-dichloro-thiophene-3-sulfonamide | 403.2 | (400 MHz, DMSO) 6 7.29 (t, 1H), 7.35 (s, 1H), 7.75 (s, 1H), 10.76 (s, 2H) |
| 239275 | 45 | N-(5-bromo-3-hydroxy-pyridin-2-yl)-3-(trifluoro-methoxy)benzene-1-sulfonamide | 413.0 | (400 MHz, DMSO) δ 7.24 (d, 1H), 7.61-7.66 (m, 1H), 7.67 (d, 1H), 7.71 (m, 1H), 7.93 (s, 1H), 7.95-8.00 (m, 1H), 10.61 (s, 2H) |
| 239304 | 46 | 5-bromo-N-(5-bromo-3-hydroxypyridin-2-yl)-6-chloropyridine-3-sulfonamide | 441.9 | (400 MHz, DMSO) δ 7.30 (d, 1H), 7.78 (s, 1H), 8.64 (d, 1H), 8.90 (d, 1H), 10.85 (s, 2H) |
| 239327 | 47 | N-(5-bromo-3-hydroxy-pyridin-2-yl)-6-(trifluoro-methyl)pyridine-3-sulfon-amide | 398.1 | (400 MHz, DMSO) δ 7.26 (d, 1H), 7.73 (s, 1H), 8.14 (d, 1H), 8.58 (d, 1H), 9.24 (s, 1H), 10.84 (s, 2H). |
| 239345 | 48 | 5-bromo-N-(5-bromo-3-hydroxypyridin-2-yl)-6-methoxypyridine-3-sulfon-amide | 438.0 | (400 MHz, DMSO) δ 3.99 (d, 3H), 7.20 (d, 1H), 7.71 (d, 1H), 8.43 (d, 1H), δ 8.65 (d, 1H). |
| 239238 | 49 | N-(3-hydroxypyridin-2-yl)-6-(trifluoromethyl)pyridine-3-sulfonamide | 320.1 | (400 MHz, DMSO) δ 6.86 (bs, 1H), 7.19 (d, 1H), 7.52 (bs, 1H), 8.16 (dd, 1H), 8.57 (d, 1H), 9.26 (s, 1H), 12.69 (s, 1H) |
| 239215 | 50 | methyl 6-(2,5-dichloro-thiophene-3-sulfonamido)-5-hydroxypyridine-3-carboxylate | 383.1 | (400 MHz, CDCl3) δ 3.92 (s, 3H), 7.22 (s, 1H), 7.64 (d, 1H), 7.92 (s, 1H), 12.22 (s, 1H) |
| 239216 | 51 | methyl 6-benzenesulfon-amido-5-hydroxypyridine-3-carboxylate | 309.2 | (400 MHz, CDCl3) δ 3.90 (d, 3H), 6.84 (s, 1H), 7.47-7.60 (m, 4H), 7.89 (s, 1H), 7.93-7.96 (m, 2H), 12.042-12.52 (m, 1H) |
| 238979 | 52 | 4-bromo-3-fluoro-N-(4-hydroxypyridin-3-yl)-benzene-1-sulfonamide | 347.2 | (400 MHz, DMSO) 6 6.10 (d, 1H), 7.52 (d, 1H), 7.58 (d, 1H), 7.78 (s, 1H), 7.80 (d, 1H), 7.87 (t, 1H), 11.42 (s, 1H). |
| 239323 | 53 | N-(5-chloro-2-hydroxy-pyridin-3-yl)-3-(trifluoro-methoxy)benzene-1-sulfon-amide | 369.3 | (400 MHz, DMSO) 6 7.32 (d, J = 2.7 Hz, 1H), 7.39 (d, J = 2.5 Hz, 1H), 7.77-7.66 (m, 2H), 7.84 (s, 1H), 7.92-7.87 (m, 1H), 10.16 (s, 1H), 12.21 (s, 1H) |
| 239324 | 54 | N-(5-chloro-2-hydroxy-pyridin-3-yl)-6-(trifluoro-methyl)pyridine-3-sulfon-amide | 354.1 | (400 MHz, DMSO) δ 7.05 (m, 2H), 8.03 (m, 1H), 8.38 (d, 1H), 9.07 (s, 1H), 11.33 (s, 1H) |
| 239326 | 55 | 5-bromo-N-(5-chloro-2-hydroxypyridin-3-yl)-6-methoxypyridine-3-sulfon-amide | 394.2 | (400 MHz, DMSO) δ 3.99 (s, 3H), 7.38 (2xs, 2H), 8.47 (d, 1H), 8.57 (d, 1H), 10.04 (bs, 1H), 12.23 (bs, 1H). |
| 238857 | 56 | 2,5-dichloro-N-(5-chloro-3-hydroxypyridin-2-yl)-thiophene-3-sulfonamide | | (500 MHz, DMSO) δ 7.29 (d, 1H), 7.37 (s, 1H), 7.72 (s, 1H), 10.8 (bs, 1H), 10.9 (bs, 1H). |
| 238733 | 57 | N-(5-chloro-4-hydroxypyridin-3-yl)-6-(trifluoromethyl)pyridine-3-sulfonamide | | (500 MHz, MeOD) δ 7.93 (d, 1H), 7.98 (d, 1H), 8.06 (d, 1H), 8.42 (dd, 1H), 9.04 (d, 1H). |
| 238734 | 58 | 5-bromo-6-chloro-N-(5-chloro-4-hydroxypyridin-3-yl)pyridine-3-sulfonamide | | (500 MHz, DMSO) δ 7.90 (d, 1H), 8.10 (d, 1H), 8.56 (d, 1H), 8.69 (d, 1H), 10.2 (bs, 1H), 12.1 (bs, 1H). |
| 238901 | 59 | 5-bromo-N-(5-chloro-4-hydroxypyridin-3-yl)-6-methoxypyridine-3-sulfonamide | | (500 MHz, DMSO) δ 3.99 (s, 3H), 7.87 (d, 1H), 8.07 (d, 1H), 8.39 (d, 1H), 8.46 (d, 1H), 9.8 (bs, 1H), 12.1 (bs, 1H). |

TABLE 1-continued

| ABR ref. | Ex. | Chemical name | M ± H⁺ (m/z) | ¹H NMR |
|---|---|---|---|---|
| 239044 | 60 | 5-bromo-N-(5-chloro-4-hydroxypyridin-3-yl)-pyridine-3-sulfonamide | | (500 MHz, DMSO) δ 7.90 (d, 1H), 8.09 (d, 1H), 8.41 (t, 1H), 8.84 (d, 1H), 8.96 (d, 1H), 12.1 (bs, 1H). |
| 238580 | 61 | 5-bromo-6-chloro-N-(4-hydroxypyridin-3-yl)-pyridine-3-sulfonamide | | (500 MHz, DMSO) δ 6.16 (d, 1H), 7.62 (d, 1H), 7.86 (s, 1H), 8.56 (d, 1H), 8.68 (d, 1H). |
| 238868 | 62 | 5-bromo-N-(4-hydroxypyridin-3-yl)-6-methoxypyridine-3-sulfonamide | | (500 MHz, DMSO) δ 3.98 (s, 3H), 6.12 (d, 1H), 7.60 (d, 1H), 7.83 (d, 1H), 8.40 (d, 1H), 8.45 (d, 1H), 11.5 (bs, 1H). |
| 238581 | 63 | 2,5-dichloro-N-(4-hydroxypyridin-3-yl)-thiophene-3-sulfonamide | | (500 MHz, DMSO) δ 6.20 (d, 1H), 7.41 (s, 1H), 7.64 (d, 1H), 7.79 (d, 1H), 11.6 (bs, 1H). |
| 238582 | 64 | N-(4-hydroxypyridin-3-yl)-6-(trifluoromethyl)pyridine-3-sulfonamide | | (500 MHz, DMSO) δ 6.34 (d, 1H), 7.68 (dd, 1H), 7.95 (d, 1H), 8.08 (d, 1H), 8.44 (dd, 1H), 9.07 (bs, 1H). |
| 238615 | 65 | 3,4-difluoro-N-(4-hydroxy-pyridin-3-yl)benzene-1-sulfonamide | | (500 MHz, DMSO) δ 6.13 (d, 1H), 7.57-7.68 (m, 3H), 7.80 (d, 1H), 7.89-7.96 (m, 1H). |
| 239168 | 66 | 3,4-dichloro-N-(4-hydroxy-pyridin-3-yl)benzene-1-sulfonamide | | (500 MHz, DMSO) δ 6.13 (d, 1H), 7.60 (d, 1H), 7.70 (dd, 1H), 7.77-7.82 (m, 2H), 8.04 (d, 1H). |
| 238612 | 67 | N-(2-hydroxypyridin-3-yl)-6-(trifluoromethyl)pyridine-3-sulfonamide | | (500 MHz, DMSO) δ 6.17 (t, 1H), 7.18 (s, 1H), 7.42 (s, 1H), 8.11 (d, 1H), 8.45 (d, 1H), 9.11 (s, 1H), 10.2 (bs, 1H), 11.8 (bs, 1H). |
| 238610 | 68 | 5-bromo-6-chloro-N-(2-hydroxypyridin-3-yl)-pyridine-3-sulfonamide | | (500 MHz, DMSO) δ 6.21 (t, 1H), 7.25 (bs, 1H), 7.48 (dd, 1H), 8.61 (d, 1H), 8.73 (d, 1H), 10.1 (bs, 1H), 12.0 (bs, 1H). |
| 238611 | 69 | 2,5-dichloro-N-(2-hydroxy-pyridin-3-yl)thiophene-3-sulfonamide | | (500 MHz, DMSO) δ 6.20 (t, 1H), 7.25 (dd, 1H), 7.37-7.42 (m, 2H), 9.8 (bs, 1H), 12.0 (bs, 1H). |
| 239286 | 70 | N-(6-chloro-4-hydroxy-pyridin-3-yl)-1-(3,4-dichloro-phenyl)methanesulfonamide | | (500 MHz, DMSO) δ 4.55 (s, 2H), 6.87 (bs, 1H), 7.42 (dd, 1H), 7.63 (d, 1H), 7.70 (d, 1H), 8.02 (bs, 1H), 9.30 (bs, 1H), 11.90 (bs, 1H). |
| 238942 | 71 | 5-bromo-N-(5-chloro-3-hydroxypyridin-2-yl)-6-methoxypyridine-3-sulfonamide | | (500 MHz, MeOD) δ 4.07 (s, 3H), 7.11 (d, 1H), 7.68 (d, 1H), 8.50 (d, 1H), 8.74 (d, 1H). |
| 239281 | 72 | 3,4-dichloro-N-(3-hydroxypyridin-4-yl)benzene-1-sulfonamide | | (500 MHz, DMSO) δ 7.23 (d, 1H), 7.75-7.85 (m, 4H), 8.01 (s, 1H), 13.0 (bs, 1H). |
| 239167 | 73 | 2,5-dichloro-N-(6-chloro-4-hydroxypyridin-3-yl)thiophene-3-sulfonamide | | (500 MHz, DMSO) δ 6.80 (s, 1H), 7.25 (s, 1H), 8.00 (s, 1H), 10.24 (bs, 1H), 11.80 (bs, 1H). |
| 239129 | 74 | 2,5-dichloro-N-(5-chloro-2-hydroxypyridin-3-yl)thiophene-3-sulfonamide | | (500 MHz, DMSO) δ 7.37 (d, 1H), 7.43 (s, 1H), 7.49 (d, 1H), 10.25 (bs, 1H), 12.30 (bs, 1H). |
| 239417 | 75 | N-(5-bromo-3-hydroxy-pyrazine-2-yl)-3,4-dichloro-phenylmethanesulfonamide | | (500 MHz, DMSO) δ 4.85 (s, 2H), 7.27 (d, 1H), 7.59 (s, 1H), 7.65 (d, 1H), 7.70-7.90 (bs, 1H), 10.60 (bs, 1H), 13.30 (bs, 1H). |
| 239462 | 76 | N-(5-bromo-3-hydroxypyrazin-2-yl)-1-(3,4-dichlorophenyl)methane-sulfonamide | 335.8 | (500 MHz, MeOD) δ 4.77 (s, 2H), 6.55 (s, 1H), 7.19 (s, 1H), 7.23-7.31 (m, 1H), 7.32-7.39 (m, 1H). |
| 239468 | 77 | 1-(3,5-dichlorophenyl)-N-[3-hydroxy-5-(propane-2-sulfonyl)pyridin-2-yl]methanesulfonamide | 439.2 | (500 MHz, MeOD), δ 1.30 (d, 6H), 3.34 (m, 1H), 7.33 (s, 2H), 7.43 (s, 2H), 8.26 (s, 1H), |

TABLE 1-continued

| ABR ref. | Ex. | Chemical name | M ± H⁺ (m/z) | ¹H NMR |
|---|---|---|---|---|
| 239604 | 78 | N-(5-chloro-3-hydroxy-pyrazin-2-yl)-1-(3,5-dichlorophenyl)methane-sulfonamide | 367.8 | (500 MHz, DMSO) δ 4.87 (s, 2H), 7.37 (s, 2H), 7.64 (s, 1H), 7.78 (s, 1H). |
| 239614 | 79 | 5-bromo-N-(5-chloro-4-hydroxypyridin-3-yl)-6-phenoxypyridine-3-sulfonamide | 456.0 | (500 MHz, MeOD) δ 7.13 (d, 2H), 7.26 (t, 1H), 7.42 (t, 2H), 7.98 (s, 1H), 8.01 (s, 1H), 8.29 (d, 1H), 8.41 (d, 1H). |
| 239618 | 80 | N-(5-bromo-3-hydroxy-pyrazin-2-yl)-1-(3,5-dichlorophenyl)methane-sulfonamide | 411.8 | (250 MHz, DMSO) δ 4.83 (s, 2H), 7.39 (d, 2H), 7.54 (m, 1H), 7.63 (s, 1H). |
| 239494 | 81 | N-(6-chloro-4-hydroxy-pyridazin-3-yl)-1-(2,4-dichlorophenyl)methane-sulfonamide | 367.8 | (500 MHz, MeOD) δ 4.96 (s, 2H), 6.51 (s, 1H), 7.37 (d, 1H), 7.52-7.60 (m, 2H). |
| 239498 | 82 | 1-(3,5-dichlorophenyl)-N-(4-hydroxy-6-iodopyridazin-3-yl)methanesulfonamide | −458.1 | (400 MHz, MeOD) δ 4.78 (s, 2H), 6.72 (s, 1H), 7.35 (d, 2H), 7.61 (t, 1H). |
| 239497 | 83 | N-(6-bromo-4-hydroxy-pyridazin-3-yl)-1-(3,5-dichlorophenyl)methane-sulfonamide | 412.1 | (400 MHz, MeOD) δ 4.63 (s, 2H), 6.50 (s, 1H), 7.24 (d, 2H), 7.33 (t, 1H). |
| 239570 | 84 | 3-bromo-N-(5-bromo-4-hydroxypyridin-3-yl)-4-methoxybenzene-1-sulfonamide | 436.8 | (500 MHz, DMSO) δ 3.91 (s, 3H), 7.22 (d, 1H), 7.75 (dd, 1H), 7.82 (s, 1H), 7.99 (d, 1H), 8.10 (s, 1H). |
| 239571 | 85 | N-(6-chloro-4-hydroxy-pyridazin-3-yl)-1-(2-chloro-5-cyanophenyl)methane-sulfonamide | 358.9 | (500 MHz, DMSO) δ 4.96 (s, 2H), 6.48 (s, 1H), 7.73 (d, 1H), 7.87 (dd, 1H), 7.95 (d, 1H). |
| 239593 | 86 | N-(5-chloro-4-hydroxy-pyridin-3-yl)-6-phenoxy-pyridine-3-sulfonamide | 377.9 | (500 MHz, DMSO) δ 7.17 (m, 3H), 7.27 (m, 1H), 7.45 (m, 2H), 7.85 (s, 1H), 8.03 (s, 1H), 8.19 (dd, 1H), 8.45 (d, 1H). |
| 239522 | 87 | N-(6-chloro-4-hydroxy-pyridin-3-yl)-1-(3,5-dichlorophenyl)methane-sulfonamide | 366.9 365.9 | (500 MHz, MeOD) δ 4.50 (s, 2H), 6.78 (s, 1H), 7.40 (s, 3H), 8.02 (s, 1H). |
| 239676 | 88 | 1-(3-chlorophenyl)-N-[5-(ethanesulfonyl)-3-hydroxy-pyrazin-2-yl]methane-sulfonamide | 391.8 | (500 MHz, MeOD) δ 1.26 (t, 3H), 3.26-3.30 (m, 2H), 4.79 (s, 2H), 7.26-7.38 (m, 3H), 7.42 (s, 1H), 7.80 (s, 1H). |
| 239610 | 89 | 3,5-dichloro-N-(5-chloro-4-hydroxypyridin-3-yl)-benzene-1-sulfonamide | 352.9 351.9 | (500 MHz, DMSO-d6) δ 7.69-7.83 (m, 2H), 7.84 (s, 1H), 7.92 (s, 1H), 8.05 (s, 1H). |
| 239486 | 90 | N-(6-chloro-4-hydroxy-pyridazin-3-yl)-1-(2-chloro-phenyl)methane-sulfonamide | 333.8 | (500 MHz, MeOD) δ 4.99 (s, 2H), 6.54 (s, 1H), 7.31-7.41 (m, 2H), 7.45 (d, 1H), 7.56 (dd, 1H). |
| 239567 | 91 | 5-bromo-N-(5-bromo-4-hydroxypyridin-3-yl)-6-methoxypyridine-3-sulfonamide | 437.8 | (500 MHz, MeOD) δ 4.04 (s, 3H), 8.05 (s, 1H), 8.08 (s, 1H), 8.27 (d, 1H), 8.46 (d, 1H). |
| 239637 | 92 | N-(6-bromo-5-chloro-3-hydroxypyridin-2-yl)-1-(3,5-dichlorophenyl)methane-sulfonamide | 444.7 | (500 MHz, MeOD) δ 7.29 (s, 1H), 7.37 (s, 2H), 7.46 (s, 1H). |
| 239654 | 93 | 1-(2-chlorophenyl)-N-(4-hydroxy-6-methanesulfonyl-pyridazin-3-yl)methane-sulfonamide | 377.8 | (500 MHz, MeOD) δ 3.28 (s, 3H), 5.00 (s, 2H), 6.98 (s, 1H), 7.25-7.39 (m, 2H), 7.44 (d, 1H), 7.57 (d, 1H). |
| 239532 | 94 | N-(6-chloro-4-hydroxy-pyridazin-3-yl)-1-(3-chloro-5-fluorophenyl)methane-sulfonamide | 351.8 | (250 MHz, MeOD) δ 4.78 (s, 2H), 6.54 (s, 1H), 7.13 (d, 1H), 7.18-7.31 (m, 2H). |
| 239477 | 95 | 3,5-dichloro-N-(6-chloro-4-hydroxypyridazin-3-yl)-benzene-1-sulfonamide | 353.6 | (500 MHz, MeOD) _ 6.48 (s, 1H), 7.77 (s, 1H), 8.03 (s, 2H). |
| 239485 | 96 | N-(6-chloro-4-hydroxy-pyridazin-3-yl)-1-(3-chloro-phenyl)methanesulfonamide | 333.8 | (500 MHz, MeOD) δ 4.78 (s, 2H), 6.54 (s, 1H), 7.29-7.41 (m, 3H), 7.43 (s, 1H). |
| 239565 | 97 | N-(5-bromo-4-hydroxy-pyridin-3-yl)-1-(3,5-dichloro-phenyl)methanesulfonamide | | (500 MHz, DMSO) δ 4.61 (s, 2H), 7.52 (s, 2H), 7.57 (s, 1H), 7.69 (s, 1H), 8.18 (s, 1H), 11.99 (s, 1H). |

TABLE 1-continued

| ABR ref. | Ex. | Chemical name | M ± H⁺ (m/z) | ¹H NMR |
|---|---|---|---|---|
| 239605 | 98 | 3-[(5-chloro-4-hydroxy-pyridin-3-yl)sulfamoyl]-N,N-diethylbenzamide | 384.1 | (500 MHz, DMSO) δ 0.96 (s, 3H), 1.15 (s, 3H), 3.07 (s, 4H), 7.59 (m, 2H), 7.68 (s, 1H), 7.81-7.87 (m, 2H), 8.03 (s, 1H), 11.96 (s, 1H). |
| 239635 | 99 | 1-(3,4-difluorophenyl)-N-(4-hydroxy-6-methanesulfonyl-pyridazin-3-yl)methane-sulfonamide | 379.9 | (500 MHz, DMSO) δ 3.23 (s, 3H), 4.78 (d, 2H), 6.57 (s, 1H), 7.16 (s, 1H), 7.32-7.51 (m, 2H). |
| 239591 | 100 | 3-chloro-N-(5-chloro-4-hydroxypyridin-3-yl)-4-methylbenzene-1-sulfonamide | 332.9 | (500 MHz, DMSO) δ 2.38 (s, 3H), 7.51 (d, 1H), 7.63 (dd, 1H), 7.83 (d, 1H), 7.85 (d, 1H), 8.04 (d, 1H). |
| 239612 | 101 | 5-bromo-N-(5-chloro-4-hydroxypyridin-3-yl)-6-(propan-2-yloxy)pyridine-3-sulfonamide | 422.0 | (500 MHz, MeOD) δ 1.36 (d, 6H), 5.38 (hept, 1H), 7.98 (s, 1H), 8.03 (s, 1H), 8.25 (d, 1H), 8.40 (d, 1H). |
| 239607 | 102 | 3-chloro-N-(5-chloro-4-hydroxypyridin-3-yl)-4-(trifluoromethoxy)benzene-1-sulfonamide | 402.8 | (500 MHz, DMSO) δ 7.74 (s, 1H), 7.85 (s, 2H), 8.06 (s, 1H), 8.12 (s, 1H). |
| 239613 | 103 | N-(5-cyano-3-hydroxy-pyrazin-2-yl)-1-(3,5-dichloro-phenyl)methane-sulfonamide | 358.8 | (250 MHz, DMSO, 368K) δ 4.77 (s, 2H), 7.42 (s, 2H), 7.53 (s, 1H), 7.70 (s, 1H). |
| 239512 | 104 | 1-(3,5-dichlorophenyl)-N-[4-hydroxy-6-(propane-1-sulfonyl)pyridazin-3-yl]methanesulfonamide | −438.4 | (400 MHz, MeOD) δ 1.04 (t, 3H), 1.74 (m, 2H), 3.33 (m, 2H), 4.71 (s, 2H), 6.88 (s, 1H), 7.36 (s, 1H), 7.43 (s, 2H). |
| 239413 | 105 | N-(5-chloro-3-hydroxy-pyridin-2-yl)-1-(3,5-dimethoxy-phenyl)methane-sulfonamide | −357.3 | (400 MHz, MeOD) δ 3.61 (s, 6H), 4.67 (s, 2H), 6.34 (d, 1H), 6.38 (d, 2H), 7.05 (s, 1H), 7.50 (dd, 1H), 7.75 (s, 1H). |
| 239428 | 106 | 5-chloro-N-(5-chloro-3-hydroxypyridin-2-yl)-6-(dimethylamino)pyridine-3-sulfonamide | 363.1 | (400 MHz, DMSO) δ 3.11 (s, 6H), 7.15 (d, 1H), 7.74 (d, 1H), 8.09 (d, 1H), 8.57 (d, 1H), 10.22 (s, 1H), 10.88 (s, 1H). |
| 239553 | 107 | N-(2-chloro-4-hydroxy-pyrimidin-5-yl)-1-(3,5-dichlorophenyl)methane-sulfonamide | 367.8 | (500 MHz, DMSO) δ 4.08 (s, 1H), 4.62 (s, 2H), 7.47 (m, 2H), 7.60 (m, 1H), 7.78 (s, 1H), 9.45 (s, 1H). |
| 239467 | 108 | 1-(3,5-dichlorophenyl)-N-[5-(ethanesulfonyl)-3-hydroxy-pyridin-2-yl]methane-sulfonamide | −423.3 | (400 MHz, MeOD) δ 8.22 (s, 1H), 1.17 (t, 3H), 3.14 (q, 2H), 7.23 (s, 2H), 7.33 (s, 1H), 7.36 (s, 1H). |
| 239478 | 109 | 3,4-dichloro-N-(6-chloro-4-hydroxypyridazin-3-yl)benzene-1-sulfonamide | 353.7 | (500 MHz, MeOD) δ 6.46 (s, 1H), 7.76 (d, 1H), 7.97 (dd, 1H), 8.23 (d, 1H). |
| 239568 | 110 | N-(5-chloro-4-hydroxy-pyridin-3-yl)-1-(3,5-dichloro-phenyl)methanesulfonamide | 367.0 | (500 MHz, DMSO-d6) δ 4.61 (s, 3H), 7.52 (d, 2H), 7.57 (t, 1H), 7.69 (d, 1H), 8.10 (d, 1H), 8.97 (s, 1H), 12.02 (s, 1H). |
| 239524 | 111 | 1-(3,5-dichlorophenyl)-N-[6-(ethanesulfonyl)-4-hydroxy-pyridazin-3-yl]methane-sulfonamide | 426.2 | (400 MHz, DMSO) δ 1.16 (t, 3H), 3.37 (q, 2H), 4.80 (s, 2H), 6.59 (s, 1H), 7.11 (s, 3H), 7.37 (d, 2H), 7.57 (m, 1H). |
| 239619 | 112 | 1-(3,5-dichlorophenyl)-N-(3-hydroxy-5-methanesulfonyl-pyrazin-2-yl)methane-sulfonamide | 412.0 | (250 MHz, DMSO, 368K) δ 3.22 (s, 3H), 4.82 (s, 2H), 7.44 (s, 2H), 7.54 (s, 1H), 7.85 (s, 1H). |
| 239491 | 113 | 2,5-dichloro-N-(6-chloro-4-hydroxypyridazin-3-yl)thiophene-3-sulfonamide | 360.1 | (400 MHz, DMSO) δ 7.33 (s, 1H), 6.50 (s, 1H). |
| 239502 | 114 | 5-bromo-N-(6-chloro-4-hydroxypyridazin-3-yl)-6-methoxypyridine-3-sulfonamide | 395.3 | (500 MHz, DMSO) δ 4.03 (s, 3H), 6.54 (s, 1H), 8.47 (d, 1H), 8.70 (d, 1H). |
| 239461 | 115 | N-(6-chloro-4-hydroxy-pyridazin-3-yl)-1-(2,3-dichlorophenyl)methane-sulfonamide | 367.7 | (500 MHz, MeOD) δ 5.05 (s, 2H), 6.54 (s, 1H), 7.29-7.36 (m, 1H), 7.52 (d, 1H), 7.57 (d, 1H). |
| 239501 | 116 | N-(6-chloro-4-hydroxy-pyridazin-3-yl)-3-(trifluoro-methoxy)benzene-1-sulfonamide | −368.3 | (400 MHz, DMSO) δ 6.52 (d, 1H), 7.73 (dd, Hz, 2H), 7.90 (s, 1H), 7.97 (d, 1H). |

TABLE 1-continued

| ABR ref. | Ex. | Chemical name | M ± H⁺ (m/z) | ¹H NMR |
|---|---|---|---|---|
| 239600 | 117 | 6-(azetidin-1-yl)-5-bromo-N-(5-chloro-4-hydroxypyridin-3-yl)pyridine-3-sulfonamide | 418.9 | (500 MHz, DMSO) δ 2.20-2.34 (m, 2H), 4.31 (t, 4H), 7.84 (s, 1H), 8.00-8.15 (m, 2H), 8.31 (s, 1H). |
| 239525 | 118 | 1-(3,5-dichlorophenyl)-N-[4-hydroxy-6-(propane-2-sulfonyl)pyridazin-3-yl]methanesulfonamide | 440.4 | (400 MHz, MeOD) δ 1.31 (d, 6H), 3.55-3.60 (m, 1H), 4.73 (s, 2H), 6.90 (s, 1H), 7.34 (s, 1H), 7.47 (s, 2H). |
| 239611 | 119 | 5-bromo-N-(5-chloro-4-hydroxypyridin-3-yl)-6-ethoxypyridine-3-sulfonamide | 407.9 | (500 MHz, MeOD) δ 1.39 (t, 3H), 4.46 (q, 2H), 7.95 (s, 1H),), 8.02 (s, 1H), 8.24 (d, 1H), 8.41 (d, 1H). |
| 239411 | 120 | 5-bromo-N-(5-chloro-3-hydroxypyridin-2-yl)-6-(dimethylamino)pyridine-3-sulfonamide | 407.1 | (400 MHz, CDCl₃) δ 3.16 (d, 6H), 7.16 (s, 1H), 7.41 (s, 1H), 8.12 (s, 1H), 8.55 (s, 1H). |
| 239628 | 121 | N-(6-chloro-4-hydroxy-pyridazin-3-yl)-3-cyano-benzene-1-sulfonamide | 310.8 | (500 MHz, DMSO-d6) δ 6.53 (m, 1H), 7.82 (m, 1H), 8.14 (d, 1H), 8.24 (d, 1H), 8.36 (s, 1H). |
| 239554 | 122 | 3-chloro-N-(5-chloro-4-hydroxypyridin-3-yl)-4-methoxy-benzene-1-sulfonamide | 349.0 | (500 MHz, DMSO-d6) δ 3.91 (s, 3H),), 7.25 (d, 1H), 7.70 (dd, 1H), 7.79-7.84 (m, 1H), 7.86 (d, 1H), 8.03 (m, 1H). |
| 239555 | 123 | 3-bromo-N-(5-chloro-4-hydroxypyridin-3-yl)-4-methoxybenzene-1-sulfonamide | 392.9 | (500 MHz, DMSO) δ 3.91 (s, 3H), 7.21 (d, 1H), 7.75 (dd, 1H), 7.82 (s, 1H), 8.00 (d, 1H), 8.04 (s, 1H). |
| 239457 | 124 | 1-(3,5-dichlorophenyl)-N-[3-hydroxy-5-(propane-1-sulfonyl)pyridin-2-yl]methanesulfonamide | 439.1 | (400 MHz, DMSO) δ 0.90 (t, 3H), 1.55 (m, 2H), 3.22-3.27 (m, 2H), 4.88 (s, 2H), 7.29 (d, 2H), 7.41 (d, 1H), 7.54 (m, 1H), 8.17 (s,1H). |
| 239449 | 125 | N-(6-chloro-4-hydroxy-pyridazin-3-yl)-1-(3,4-dichlorophenyl)methane-sulfonamide | 367.7 | (500 MHz, MeOD) δ 4.78 (s, 2H), 6.55 (s, 1H), 7.32 (d, 1H), 7.53 (d, 1H), 7.57 (s, 1H). |
| 239450 | 126 | 1-(3,5-dichlorophenyl)-N-(4-hydroxy-6-methanesulfonylpyridazin-3-yl)methanesulfonamide | 412.2 | (400 MHz, MeOD) δ 3.20 (s, 3H), 4.72 (s, 2H), 6.92 (s, 1H), 7.35 (s, 1H), 7.48 (s, 2H), |
| 239465 | 127 | N-(5-chloro-3-hydroxy-pyridin-2-yl)-1-(5-cyano-thiophen-3-yl)methane-sulfonamide | 330.2 | (400 MHz, MeOD) δ 4.91 (s, 2H), 7.16 (d, 1H),), 7.73 (d, 1H), 7.76-7.84 (m, 2H). |
| 239574 | 128 | 5-bromo-6-chloro-N-[4-hydroxy-6-(trifluoromethyl)-pyridin-3-yl]pyridine-3-sulfonamide | 431.9 | (500 MHz, MeOD) δ , 6.91 (s, 1H)., 8.33 (s, 2H), 8.54 (d, 1H) |
| 239592 | 129 | 5-bromo-N-(5-chloro-4-hydroxypyridin-3-yl)-6-(piperidin-1-yl)pyridine-3-sulfonamide | | (500 MHz, DMSO) δ 1.61 (s, 6H), 7.85 (s, 1H), 8.04 (s, 1H), 8.19 (d, 1H), 8.43 (d, 1H). |
| 239641 | 130 | N-(5-chloro-6-cyano-3-hydroxypyridin-2-yl)-1-(3,5-dichlorophenyl)methane-sulfonamide | 392.0 | (500 MHz, MeOD) δ 4.87 (s, 2H), 7.24 (s, 1H), 7.35 (d, 2H), 7.47 (t, 1H). |
| 239466 | 131 | N-[5-(cyclopentanesulfonyl)-3-hydroxypyridin-2-yl]-1-(3,5-dichlorophenyl)-methanesulfonamide | 465.3 | (400 MHz, DMSO) δ 1.59 (m, 4H), 1.84 (d, 4H), 3.79 (m, 1H), 4.99 (s, 2H), 7.31 (s, 2H), 7.43 (s, 1H), 7.61 (s, 1H), 8.27 (s, 1H). |
| 239589 | 132 | N-[4-hydroxy-6-(trifluoro-methyl)pyridin-3-yl]-6-methylpyridine-3-sulfonamide | 333.9 | (500 MHz, MeOD) δ 2.60 (s, 3H), 7.05 (s, 1H), 7.44 (d, 1H), 8.06 (dd, 1H), 8.50 (s, 1H), 8.78 (d, 1H). |
| 239576 | 133 | 1-(3,5-dichlorophenyl)-N-[4-hydroxy-6-(trifluoromethyl)-pyridin-3-yl]methane-sulfonamide | 400.9 | (500 MHz, MeOD) δ 4.55 (s, 2H), 7.12 (s, 1H), 7.34 (m,1H), 7.39 (d, 2H), 8.36 (s, 1H). |
| 239671 | 134 | N-(5-chloro-3-hydroxy-6-methanesulfonylpyridin-2-yl)-1-(3,5-dichlorophenyl)-methane sulfonamide | 444.8 | (500 MHz, MeOD) δ 3.31 (bs, 3H), 4.93 (s, 2H), 6.98 (s, 1H), 7.38 (d, 2H), 7.40 (s, 1H). |
| 239573 | 135 | 1-(3,4-dichlorophenyl)-N-[4-hydroxy-6-(trifluoromethyl)-pyridin-3-yl]methane-sulfonamide | 400.8 | (500 MHz, MeOD) δ 4.54 (s, 2H), 7.08 (s, 1H), 7.34 (dd, 1H), 7.43 (d, 1H), 7.56 (d, 1H), 8.32 (s, 1H). |

TABLE 1-continued

| ABR ref. | Ex. | Chemical name | M ± H⁺ (m/z) | ¹H NMR |
|---|---|---|---|---|
| 239481 | 136 | N-(5-chloro-3-hydroxy-pyridin-2-yl)-6-(dimethyl-amino)-5-methanesulfonyl-pyridine-3-sulfonamide | 407.2 | (400 MHz, DMSO) δ 3.22 (s, 6H), 3.44 (s, 3H), 7.18 (d, 1H), 7.76 (d, 1H), 8.71 (d, 1H), 8.79 (d, 1H). |
| 239575 | 137 | 5-bromo-N-[4-hydroxy-6-(trifluoromethyl)pyridin-3-yl]-6-methoxypyridine-3-sulfonamide | 427.9 | (500 MHz, MeOD) δ 3.93 (s, 3H), 6.95 (s, 1H), 8.17 (d, 1H), 8.31 (s, 1H), 8.38 (s, 1H) |
| 239566 | 138 | N-(5-cyano-4-hydroxy-pyridin-3-yl)-1-(3,5-dichloro-phenyl)methanesulfonamide | 358.0 | (500 MHz, DMSO-d6) δ 4.64 (s, 2H), 7.48 (d, 2H), 7.57 (m, 1H), 7.70 (d, 1H), 8.39 (d, 1H), 9.10 (s, 1H). |
| 239531 | 139 | 1-(3,5-dichlorophenyl)-N-[4-hydroxy-6-(3-hydroxy-propanesulfonyl)pyridazin-3-yl]methanesulfonamide | 456.3 | (400 MHz, MeOD) δ 1.85-1.951 (m, 2H), 3.40 (t, 2H), 3.63 (t, 2H), 4.68 (s, 2H), 6.78 (s, 1H), 7.38 (d, 1H), 7.39 (s, 2H). |
| 239499 | 140 | N-[6-(cyclopentanesulfonyl)-4-hydroxypyridazin-3-yl]-1-(3,5-dichlorophenyl)-methanesulfonamide | 466.2 | 400 MHz, MeOD) δ 1.70 (m, 4H), 2.00 (m, 4H), 3.91 (m, 1H), 4.71 (s, 2H), 6.94 (s, 1H), 7.34 (s, 1H), 7.49 (s, 2H). |
| 239717 | 141 | (+/−)-N-(5-bromo-3-hydroxy-pyrazin-2-yl)-1-(3,5-dichlorophenyl)-2,2,2-trifluoroethane-1-sulfonamide | 479.8 | (500 MHz, MeOD) δ 5.93-6.06 (m, 1H), 7.50-7.65 (m, 4H). |
| 239694 | 142 | 3-[(5-bromo-3-hydroxy-pyrazin-2-yl)sulfamoyl]-N,N-diethylbenzamide | 428.9 | (500 MHz, MeOD) δ 2.65 (t, 3H), 2.83 (t, 3H), 4.81 (d, 2H), 5.13 (d, 2H), 8.81 (s, 1H), 9.17-9.25 (m, 2H), 9.59-9.63 (m, 1H), 9.70 (m, 1H). |
| 239721 | 143 | N-(2-chloro-5-hydroxy-pyrimidin-4-yl)-1-(3,5-dichlorophenyl)methane-sulfonamide | | (500 MHz, DMSO) δ 4.90 (s, 2H), 7.31-7.38 (m, 2H), 7.64 (s, 1H), 7.97 (s, 1H). |
| 239720 | 144 | 3,4-dichloro-N-(2-chloro-5-hydroxypyrimidin-4-yl)benzene-1-sulfonamide | 353.7 | (500 MHz, DMSO) δ 7.99-7.82 (m, 3H), 8.23 (d, 1H). |
| 239735 | 145 | 3,5-dichloro-N-(2-chloro-5-hydroxypyrimidin-4-yl)benzene-1-sulfonamide | 353.6 | (500 MHz, DMSO) δ 7.91 (s, 1H), 7.97 (s, 3H). |
| 239737 | 146 | 3-[(6-chloro-4-hydroxy-pyridazin-3-yl)sulfamoyl]-N,N-diethylbenzamide | 384.9 | (500 MHz, DMSO) δ 0.99 (s, 3H), 1.16 (s, 3H), 6.53 (s, 1H), 7.61-7.71 (m, 2H), 7.91 (s, 1H), 8.01 (m, 1H). |
| 239722 | 147 | N-(6-chloro-4-hydroxy-pyridazin-3-yl)-1-(4-cyano-phenyl)methanesulfonamide | 325.0 | (500 MHz, DMSO) δ 4.88 (s, 2H), 6.42 (s, 1H), 7.52 (d, 2H), 7.83 (d, 2H). |
| 239742 | 148 | N-(6-chloro-4-hydroxy-pyridazin-3-yl)-1-(5-cyano-2-fluorophenyl)methane-sulfonamide | 342.9 | (500 MHz, DMSO) δ 4.88 (s, 2H), 6.62 (s, 1H), 7.49 (t, 1H), 7.90-8.02 (m, 2H). |
| 239743 | 149 | N-(6-chloro-4-hydroxy-pyridazin-3-yl)-1-(3-cyano-5-fluorophenyl)methane-sulfonamide | 342.9 | (500 MHz, DMSO) δ 4.87 (s, 2H), 6.64 (s, 1H), 7.57 (d, 1H), 7.66 (s, 1H), 7.82-7.96 (m, 1H). |
| 239744 | 150 | 1-(2-chloro-5-cyanophenyl)-N-(2-chloro-5-hydroxy-pyrimidin-4-yl)methane-sulfonamide | 358.9 | (250 MHz, DMSO) δ 5.09 (s, 2H), 7.73 (d, 1H), 7.88 (dd, 1H), 7.94-8.00 (m, 2H). |
| 239745 | 151 | 2-chloro-N-(6-chloro-4-hydroxypyridazin-3-yl)-4-cyanobenzene-1-sulfonamide | 344.9 | (250 MHz, DMSO) δ 6.62 (s, 1H), 8.03 (d, 1H), 8.19 (d, 1H), 8.24 (s, 1H). |
| 239748 | 152 | 3-chloro-N-(6-chloro-4-hydroxypyridazin-3-yl)-4-fluorobenzene-1-sulfonamide | 337.8 | (250 MHz, DMSO) δ 6.52 (s, 1H), 7.66 (t, 1H), 7.92-8.01 (m, 1H), 8.15 (dd, 1H). |
| 239750 | 153 | 3,5-dichloro-N-(5-cyano-4-hydroxypyridin-3-yl)-benzene-1-sulfonamide | 343.8 | (500 MHz, DMSO-d6) δ 7.82 (d, 2H), 7.90 (d, 1H), 7.95 (t, 1H), 8.37 (s, 1H). |
| 239754 | 154 | 3-chloro-N-(6-chloro-4-hydroxypyridazin-3-yl)-5-fluorobenzene-1-sulfonamide | 337.9 | (500 MHz, DMSO) δ 6.58 (s, 1H), 7.73-7.79 (m, 1H), 7.83 (d, 1H), 7.85 (s, 1H). |
| 239755 | 155 | 3,5-dichloro-N-(4-hydroxy-6-methanesulfonylpyridin-3-yl)benzene-1-sulfonamide | 396.9 | (500 MHz, MeOD-d4) δ 3.17 (s, 3H), 7.37 (s, 1H), 7.72 (d, 1H), 7.75 (d, 2H), 8.53 (s, 1H). |

TABLE 1-continued

| ABR ref. | Ex. | Chemical name | M ± H⁺ (m/z) | ¹H NMR |
|---|---|---|---|---|
| 239756 | 156 | 3,5-dichloro-N-(6-chloro-4-hydroxypyridin-3-yl)-benzene-1-sulfonamide | 352.8 | (500 MHz, MeOD-d4) δ 6.70 (s, 1H), 7.69(d, 2H), 7.70 (d, 1H), 8.12 (s, 1H). |
| 239760 | 157 | 1-(3,5-dichlorophenyl)-N-[5-hydroxy-2-(trifluoromethyl)-pyrimidin-4-yl]methane-sulfonamide | 402.0 | (250 MHz, DMSO) δ 4.97 (s, 2H), 7.32 (s, 2H), 7.65 (t, 1H), 8.24 (s, 1H). |
| 239761 | 158 | 3-chloro-5-fluoro-N-[5-hydroxy-2-(trifluoromethyl)-pyrimidin-4-yl]benzene-1-sulfonamide | 372.0 | (250 MHz, DMSO) δ 7.72-7.85 (m, 2H), 7.89 (s, 1H), 8.11 (s, 1H). |
| 239762 | 159 | 3,5-dichloro-N-(3-hydroxy-5-methanesulfonylpyrazin-2-yl)benzene-1-sulfonamide | 397.8 | (500 MHz, MeOD-d4) δ 3.14 (s, 3H), 7.69-7.87 (m, 2H), 8.04 (d, 2H). |
| 239763 | 160 | 3-chloro-4-[(6-chloro-4-hydroxypyridazin-3-yl)-sulfamoyl]-N,N-diethyl-benzamide | 418.9 | (500 MHz, MeOD) δ 1.15 (t, 3H), 1.27 (t, 3H), 3.27 (q, 2H), 3.57 (q, 2H), 6.50 (s, 1H), 7.53 (dd, 1H), 7.62 (d, 1H), 8.32 (d, 1H). |
| 239769 | 161 | 3-chloro-5-{[(6-chloro-4-hydroxypyridazin-3-yl)-sulfamoyl]methyl}-N,N-diethylbenzamide | 433.3 | (500 MHz, MeOD) δ 1.09 (t, 3H),1.23 (t, 3H), 3.24 (d, 2H), 3.53 (d, 2H), 4.82 (s, 2H), 6.55 (s, 1H), 7.29 (t, 1H), 7.38-7.46 (m, 1H), 7.51 (t, 1H). |
| 239771 | 162 | N-(6-chloro-4-hydroxy-pyridazin-3-yl)-3-cyano-5-fluorobenzene-1-sulfonamide | 328.8 | (500 MHz, DMSO) δ 6.59 (s, 1H), 8.10 (dd, 1H), 8.22 (bs, 2H). |
| 239772 | 163 | 3-chloro-5-fluoro-N-[4-hydroxy-6-(trifluoromethyl)-pyridazin-3-yl]benzene-1-sulfonamide | 371.9 | (500 MHz, DMSO) δ 6.95 (s, 1H), 7.78 (d, 2H), 7.87 (s, 1H). |
| 239773 | 164 | 1-(3,4-dichlorophenyl)-N-[5-hydroxy-2-(trifluoromethyl)-pyrimidin-4-yl]methane-sulfonamide | 401.8 | (250 MHz, DMSO) δ 4.95 (s, 2H), 7.22 (dd, 1H), 7.54 (d, 1H), 7.64 (d, 1H), 8.21 (s, 1H). |
| 239775 | 165 | N-(6-chloro-4-hydroxy-pyridazin-3-yl)-1-(2,5-dichlorothiophen-3-yl)-methanesulfonamide | 373.6 | (500 MHz, DMSO) δ 4.75 (s, 2H), 6.60 (s, 1H), 7.08 (s, 1H). |
| 239776 | 166 | 3,5-dichloro-N-(4-hydroxy-6-methanesulfonylpyridazin-3-yl)benzene-1-sulfonamide | 398.0 | (500 MHz, DMSO) δ 3.17 (s, 3H), 5.74 (s, 1H), 7.71 (m, 1H), 7.82 (d, 2H). |
| 239434 | 167 | 1-(3,5-dichlorophenyl)-N-(3-hydroxypyridin-4-yl)-methanesulfonamide | | (500 MHz, DMSO-d6) δ 4.31 (2, 2H), 7.19 (d, 1H), 7.45 (d, 2H), 7.52 (d, 1H), 7.73 (bd, 1H), 7.77 (bs, 1H), 12.7 (bs, 1H). |
| 239564 | 168 | 6-(2,5-dichlorothiophene-3-sulfonamido)-5-hydroxy-pyridine-3-carboxylic acid | | (500 MHz, DMSO-d6 + TFA) δ 7.44 (s,1 H), 7.50 (d,1H), 8.07 (s, 1H). |
| 239757 | 169 | N-(2-chloro-3-hydroxy-pyridin-4-yl)-1-(3,5-dichloro-phenyl)methanesulfonamide | | (500 MHz, DMSO-d6) δ 4.73 (s, 2H), 7.20 (d, 1H), 7.40 (s, 2H), 7.59 (s, 1H), 7.72 (d, 1H), 9.8 (bs, 1H), 10.1 (bs, 1H). |
| 239766 | 170 | 3,5-dichloro-N-(2-chloro-3-hydroxypyridin-4-yl)-benzene-1-sulfonamide | | (500 MHz, DMSO-d6) δ 7.26 (d, 1H), 7.79 (d, 1H), 7.93 (d, 2H), 8.00 (t, 1H), 10.3 (bs, 2H). |
| 239447 | 171 | N-(3-hydroxypyridin-2-yl)-3-(trifluoromethyl)benzene-1-sulfonamide | −317 | (500 MHz, DMSO) δ 6.82 (bs, 1H), 7.15 (d, 1H), 7.52 (bs, 1H), 7.81 (t, 1H), 8.00 (d, 1H), 8.25 (d, 1H), 8.33 (s, 1H) |
| 239560 | 172 | N-(5-chloro-2-hydroxy-pyridin-3-yl)-1-(3,4-dichloro-phenyl)methanesulfonamide | −365 | (500 MHz, DMSO) δ 4.75 (s, 2H), 7.01 (d, 1H), 7.33 (d, 1H), 7.38 (dd, 1H), 7.61 (d, 1H), 7.63 (d, 1H), 9.10 (bs, 1H), 12.25 (bs, 1H) |
| 239562 | 173 | N-(5,6-dichloro-2-hydroxy-pyridin-3-yl)-1-(3,5-dichloro-phenyl)methanesulfonamide | −399 | (500 MHz, DMSO) δ 4.62 (s, 2H), 7.41 (d, 2H), 7.56 (m, 2H), 9.66 (bs, 1H), 12.70 (bs, 1H) |
| 239580 | 174 | N-(6-chloro-2-hydroxy-pyridin-3-yl)-1-(3,4-dichloro-phenyl)methanesulfonamide | −365 | (500 MHz, DMSO) δ 4.60 (s,2H), 6.80 (bs, 1H), 7.38 (dd, 1H), 7.47(d, 1H), 7.62 (d, 1H), 7.65 (d, 1H), 9.30 (bs, 1H), 12.50 (bs, 1H) |

TABLE 1-continued

| ABR ref. | Ex. | Chemical name | M ± H+ (m/z) | 1H NMR |
|---|---|---|---|---|
| 239581 | 175 | N-(6-chloro-2-hydroxy-pyridin-3-yl)-1-(3,5-dichloro-phenyl)methanesulfonamide | | (500 MHz, DMSO) δ 4.60 (s, 2H), 6.78 (bs, 1H), 7.46 (d, 2H), 7.48 (d, 1H), 7.59 (t, 1H), 9.30 (s, 1H), 12.50 (bs, 1H) |
| 239583 | 176 | 5-bromo-N-(6-chloro-2-hydroxypyridin-3-yl)-6-methoxypyridine-3-sulfonamide | −392 | (500 MHz, DMSO) δ 4.00 (s, 3H), 6.86 (bs, 1H), 7.57 (d, 1H), 8.27 (s, 1H), 8.44 (s, 1H), 10.02 (bs, 1H), 12.13 (bs, 1H) |
| 239653 | 177 | N-(5,6-dibromo-3-hydroxy-pyrazin-2-yl)-1-(3,4-dichlorophenyl)methane-sulfonamide | −488 | (500 MHz, DMSO) δ 4.84 (s, 2H), 7.29 (dd, 1H), 7.61 (d, 1H), 7.64 (d, 1H) |
| 239672 | 178 | N-(6-chloro-2-hydroxy-pyridin-3-yl)-1-[4-(trifluoro-methyl)phenyl]methane-sulfonamide | | (500 MHz, DMSO) δ 4.68 (s, 2H), 6.74 (bs, 1H), 7.43 (d, 1H), 7.62 (d, 2H), 7.71 (d, 2H), 9.30 (bs, 1H), 12.50 (bs, 1H) |
| 239673 | 179 | N-(6-chloro-2-hydroxy-pyridin-3-yl)-4-propyl-benzene-1-sulfonamide | | (500 MHz, DMSO) δ 0.90 (t, 3H), 1.61 (m, 2H), 2.65 (t, 2H), 6.82 (bs, 1H), 7.43 (d, 2H), 7.55 (d, 1H), 7.72 (d, 2H), 9.69 (bs, 1H), 12.11 (bs, 1H) |
| 239674 | 180 | 3,4-dichloro-N-(6-chloro-2-hydroxypyridin-3-yl)-benzene-1-sulfonamide | | (500 MHz, DMSO) δ 6.85 (bs, 1H), 7.56 (d, 1H), 7.66 (dd, 1H), 7.84 (d, 1H), 7.96 (d, 1H), 10.15 (bs, 1H), 12.20 (bs, 1H) |
| 239718 | 181 | N-(6-chloro-2-hydroxy-pyridin-3-yl)-1-(5,6-dichloro-pyridin-3-yl)methane-sulfonamide | | (500 MHz, DMSO) δ 4.68 (s, 2H), 6.82 (d, 1H), 7.59 (d, 1H), 8.18 (s, 1H), 8.42 (s, 1H), 9.48 (bs, 1H), 12.24 (bs, 1H) |
| 239724 | 182 | N-(6-chloro-2-hydroxy-pyridin-3-yl)-1-(5-chloro-6-methoxypyridin-3-yl)-methanesulfonamide | 364 | (500 MHz, DMSO) δ 3.98 (s, 3H), 4.59 (s, 2H), 6.83 (bs, 1H), 7.54 (d, 1H), 7.92 (s, 1H), 8.15 (s, 1H), 9.35 (bs, 1H), 12.57 (bs, 1H) |
| 239726 | 183 | N-(5-chloro-4-hydroxy-pyridin-3-yl)-1-(5,6-dichloropyridin-3-yl)-methanesulfonamide | | (500 MHz, DMSO) δ 4.67 (s, 2H), 7.79 (d, 1H), 8.17 (d, 1H), 8.35 (d, 1H), 8.49 (d, 1H), 9.20 (bs, 1H), 12.10 (bs, 1H) |
| 239740 | 184 | N-(5-chloro-4-hydroxypyridin-3-yl)-1-(5-chloro-6-methoxypyridin-3-yl)methanesulfonamide | | (500 MHz, DMSO) δ 3.97 (s, 3H), 4.57 (s, 2H), 7.74 (d, 1H), 8.02 (d, 1H), 8.15 (d, 1H), 8.18 (d, 1H) |
| 239741 | 185 | N-(6-chloro-2-hydroxy-pyridin-3-yl)-1-[5-chloro-6-(pyrrolidin-1-yl)pyridin-3-yl]methanesulfonamide | | (500 MHz, DMSO) δ 1.90 (m, 4H), 3.60 (t, 4H), 4.45 (s, 2H), 6.82 (bs, 1H), 7.49 (bs, 1H), 7.62 (d, 1H), 8.00 (d, 1H), 9.21 (bs, 1H), 12.46 (bs, 1H) |
| 239758 | 186 | N-(6-chloro-2-hydroxy-pyridin-3-yl)-1-[3-chloro-5-(ethylsulfanyl)phenyl]-methanesulfonamide | 393 | (500 MHz, DMSO) δ 1.27 (t, 3H), 3.00 (q, 2H), 4.61 (s, 2H), 6.79 (broad signal, 1H), 7.28 (d, 2H), 7.34 (s, 1H), 7.48 (d, 1H), 9.30 (bs, 1H), 12.50 (bs, 1H). |
| 239768 | 187 | 3,5-dichloro-N-[6-(ethane-sulfonyl)-2-hydroxypyridin-3-yl]benzene-1-sulfonamide | 411 | (500 MHz, DMSO) δ 1.13 (t, 3H), 3.35 (m, 2H), 7.53 (bs, 1H), 7.83 (bs, 1H), 7.92 (bs, 2H), 8.04 (t, 1H), 10.54 (bs, 1H), 12.83 (bs, 1H) |
| 239774 | 188 | 1-(3,5-dichlorophenyl)-N-[6-(ethanesulfonyl)-2-hydroxy-pyridin-3-yl]methane-sulfonamide | 425 | (500 MHz, DMSO) δ 1.16 (t, 3H), 3.35 (m, 2H), 4.75 (s, 2H), 7.44 (bs, 1H), 7.48 (s, 2H), 7.65 (s, 1H), 7.76 (bs, 1H), 9.76 (bs, 1H), 12.88 (bs, 1H) |
| 239401 | 189 | N-(5-cyano-3-hydroxy-pyridin-2-yl)-1-(3,5-dichloro-phenyl)methanesulfonamide | 357.8 | (500 MHz, MeOD) δ 4.89 (s, 2H). 7.27-7.38 (m, 3H), 7.45 (t, 1H), 8.18 (s, 1H). |
| 239630 | 190 | 5-chloro-N-(5-chloro-4-hydroxypyridin-3-yl)-6-methylpyridine-3-sulfonamide | 333.9 | (500 MHz, DMSO) δ 2.61 (s, 3H), 7.88 (s, 1H), 8.07 (s, 1H), 8.23 (s, 1H), 8.69 (s, 1H). |

TABLE 1-continued

| ABR ref. | Ex. | Chemical name | M ± H⁺ (m/z) | ¹H NMR |
|---|---|---|---|---|
| 239631 | 191 | N-(5-chloro-4-hydroxy-pyridin-3-yl)-5-cyano-6-methoxypyridine-3-sulfonamide | 340.9 | (500 MHz, MeOD) δ 4.13 (s, 3H), 8.00 (s, 1H), 8.05 (s, 1H), 8.47 (d, 1H), 8.70 (d, 1H). |
| 239629 | 192 | N-(5-chloro-4-hydroxy-pyridin-3-yl)-6-methoxy-5-phenylpyridine-3-sulfonamide | 391.9 | (500 MHz, DMSO) δ 3.94 (s, 3H), 7.41-7.51 (m, 3H), 7.56 (d, 2H), 7.89 (s, 1H), 8.03-8.11 (m, 2H), 8.50 (s, 1H). |
| 239347 | 193 | N-(5-chloro-3-hydroxy-pyridin-2-yl)-5-phenyl-pyridine-3-sulfonamide | 362.1 | (400 MHz, DMSO) δ 7.14 (d, 1H), 7.45-7.52 (m, 1H), 7.52-7.60 (m, 2H), 7.70 (d, 1H), 7.77 (dd, 2H), 8.55 (t, 1H), 9.05 (d, 1H), 9.11 (d, 1H), 10.66 (s, 2H). |
| 239509 | 194 | N-(6-chloro-4-hydroxy-pyridazin-3-yl)-1-(3-chloro-5-cyanophenyl)methane-sulfonamide | 358.9 | (500 MHz, MeOD) δ 4.84 (s, 2H), 6.55 (s, 1H), 7.73 (s, 1H), 7.76 (s, 1H), 7.83 (s, 1H) |
|  | 195 | 5-bromo-6-chloro-N-(6-chloro-4-hydroxypyridazin-3-yl)pyridine-3-sulfonamide | 398.7 |  |
|  | 196 | N-(5-bromo-4-hydroxypyridin-3-yl)-3,5-dichlorobenzene-1-sulfonamide |  | 250 MHz, DMSO-d6) δ 7.78 (s, 2H), 7.81-7.88 (m, 1H), 7.93 (s, 1H), 8.06-8.22 (m, 1H) |

Biological Assays

Biological Reagents Prepared and Purified for S100A9 Related Assays

Recombinant Human S100A9 Wild Type

Cultivation:

Expression of rhS100A9 wt was performed by shake flask cultivations of the working cell bank BL21(DE3)/pET1120 (pLR757) with 0.5 mM IPTG induction. Cell pellets were frozen.

Purification of Inclusion Bodies:

The *E. coli* pellets were thawed at RT with 150 mL Lysis buffer (50 mM Tris/HCl, 1 mM EDTA, 25% Saccarose, pH 8.0) and sonicated 3×15 s under ice in a beaker. Thereafter 10 µL of 1 M $MgCl_2$ (10 mM end conc.)/mL pellet solution, 1 µL 1 M $MnCl_2$ (1 mM end conc.)/mL pellet solution and 1 µL 10 mg/mL DNase I (10 µg/mL end conc.)/mL pellet solution were added. After 30 min of incubation in RT a detergent buffer (20 mM Tris/HCl, pH 7.5, 2 mM EDTA, 1% Nonidet P-40) with protease inhibitor (Complete Mini Protease Inhibitors, Roche), 1-2 tablets/25 mL was added in a 1:1 volume ratio. The solution was centrifuged at 14,000×g, 5° C., for 20 min. The pellet was resuspended with 90 mL 0.5% Triton X-100, 1 mM EDTA for sonication 3×15 s and was spinned down again. This wash and sonication procedure was repeated for additionally 5 times.

Resuspension and Folding:

Milli-Q water was used in all solutions and dialysis steps. The final pellet was resuspended in 100 mL of 8 M urea, 40 mM DTT in 500 mM $NaH_2PO_4$ buffer, pH 1.8. When the solution was clear it was centrifuged at 20,000×g, 5° C. for 25 min. The supernatant containing the resuspended inclusion bodies was set to pH 2 with the 500 mM phosphate buffer, pH 1.8.

First dialysis of the supernatant was against 5 L 50 mM $NaH_2PO_4$ buffer, 1.5 mM DTT, pH 2 for 6 h. Second dialysis against 5 L 10 mM Na-acetate buffer, 150 mM NaCl, 1.5 mM DTT, pH 4 for 15 h. Third dialysis against 5 L 10 mM Na-acetate buffer, 150 mM NaCl, 1.5 mM DTT, pH 4 for 8 h. Fourth dialysis against 5 L 20 mM Tris/HCl, 150 mM NaCl, 1.5 mM DTT, pH 7.2 for 16 h. Fifth dialysis against 5 L 20 mM Tris/HCl, 1 mM EDTA, 1 mM EGTA, 1.5 mM DTT, pH 8.5 for 6 h. Centrifugation was done at 22,000×g, 5° C. for 30 min.

Purification by Chromatography:

All chromatography columns and resins were purchased from GE HealtCare, Sweden. DTT was added to a final concentration of 1.5 mM. An anion-exchange chromatography on a HiPrep Q FF 16/10 column was run at a flow-rate of 1.5 mL/min using a 0-1 M NaCl gradient in 20 mM Tris, 1 mM EDTA, 1 mM EGTA, 1.5 mM DTT, pH 8.5 for elution of proteins. The same buffer, without NaCl, was used for equilibration and washing before elution. The pooled fractions containing rhS100A9 wt were concentrated to 1.5 mL using Centriprep YM-3 (Amicon, USA). The size-exclusion chromatography on a Superdex 75 16/790 column was run at a flow-rate of 0.5 mL/min using a HBS-N buffer (10 mM Hepes, 150 mM NaCl, pH 7.4) supplemented with 10 mM DTT. A PD-10 was run for buffer exchange to 10 mM Hepes, 150 mM NaCl, pH 7.5.

Biacore Binding Assays

The $Ca^{2+}$ and $Zn^{2+}$ dependent interaction of S100A9 with its target receptors—e.g. RAGE, TLR4/MD2 and EMMPRIN—was studied using surface plasmon resonance (SPR) technology (Björk et al. 2009). Briefly, S100A9 was injected over RAGE, TLR4/MD2 or EMMPRIN, immobilized via primary amines on a Biacore sensor chip, in the presence of physiological concentrations of $Ca^{2+}$ and $Zn^{2+}$ allowing label-free and real-time analysis of these interactions. Recombinant human RAGE and EMMPRIN, both fused with human IgG1Fc, and TLR4/MD2 were all purchased from R&D Systems. Obviously, the assay can be reversed in the way that S100A9 is immobilized and RAGE, TLR4/MD2 or EMMPRIN is injected. The person of ordinary skill in the art will be able to perform essentially the same assay directed to the interaction of S100A9 and TLR4/MD2 or EMMPRIN.

Figure 2A:
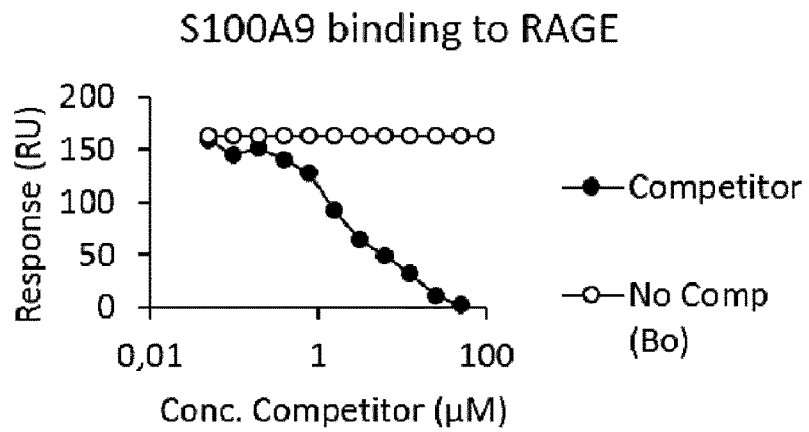
FIGS. 2A, 2B and 2C are graphs showing the competitive binding of the compound of Example 59 (ABR-238901) to S100A9 in the presence of (FIG. 2A) RAGE, (FIG. 2B) TLR4/MD2 and (FIG. 2C) EMMPRIN. In the assay, S100A9 was injected (2 min; 30 μL/min) at ~1.3 μg/mL over amine coupled human RAGE/Fc (density~3.0 kRU), TLR4/MD2 (density~3.9 kRU) or EMMPRIN/Fc (density~2.9 kRU)±0.049-100 μM ABR-238901. Binding of S100A9 to (A) RAGE, (B) TLR4/MD2 or (C) EMMPRIN in the absence or presence of competitor is expressed as responses in resonance units (RU) on the Y-axis and were plotted versus competitor concentration and fit to a sigmoidal dose-response model for calculation of concentration yielding 50% inhibition ($IC_{50}$). Assay buffer—10 mM HEPES, 0.15 M NaCl, pH 7.4 (HBS buffer), containing 0.005% v/v Surfactant P20, 1 mM $Ca^{2+}$ and 20 μM $Zn^{2+}$. After each cycle, regeneration was made by a 30 μL pulse of 3 mM EDTA in HBS buffer.
Figure 2B:
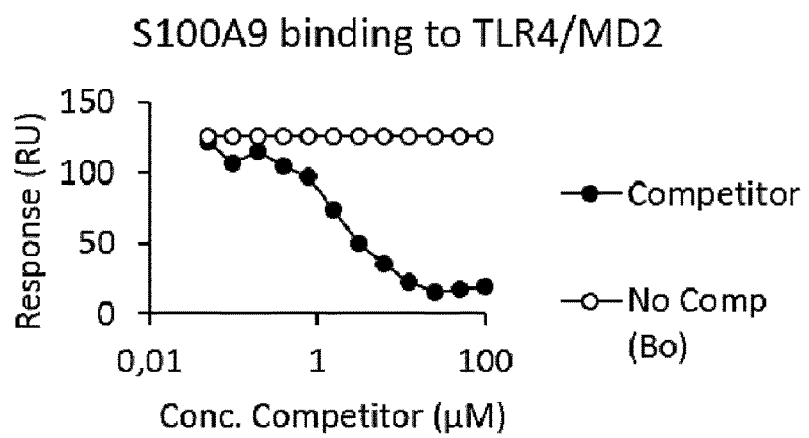
Figure 2C:
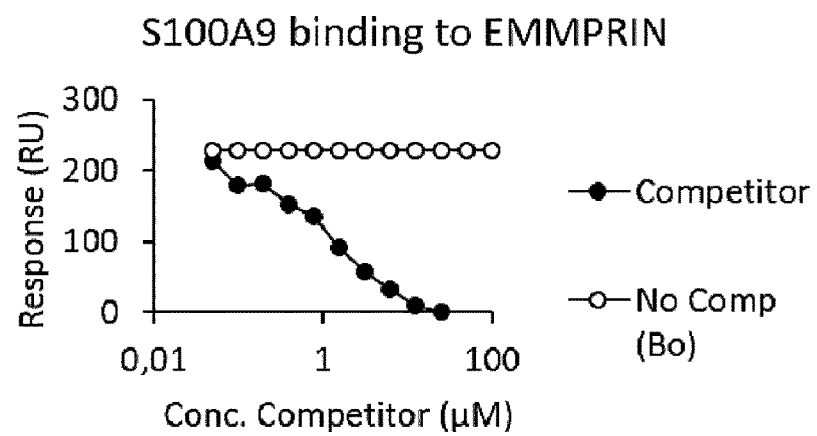

The assay showed the inhibitory effect of studied inventive compounds on protein-protein interactions between S100A9 and RAGE, TLR4/MD2 or EMMPRIN, respectively, cf. FIG. 2.

Inhibition Assay, Biot-hS100A9:hRAGE-Fc
Principle.

The AlphaScreen (Amplified Luminescent Proximity Homogeneous Assay) contains two types of beads, Alpha Donor beads and Acceptor beads (PerkinElmer). Upon laser excitation at 680 nm a photosensitizer in the Donor bead converts ambient oxygen to a more excited singlet state. The singlet oxygen molecule diffuses (maximum 200 nm) to react with a thioxene derivative in the Acceptor bead and generates a chemiluminescence reaction. Fluorophores in the Acceptor bead subsequently emit light at 520-620 nm which can be detected in the EnVision® Multilabel plate Reader (PerkinElmer). The beads are light sensitive and all work with the beads is performed under subdued light conditions or using green filters on light sources (Roscolux Chroma Green #389, Rosco).

In the AlphaScreen Inhibition Assay described here, protein A (*Staphylococcus aureus*) conjugated Acceptor beads are used together with streptavidin coated Donor beads (Perkin Elmer 6760617M). The Acceptor beads are pre-incubated with Fc-tagged recombinant human RAGE (rhRAGE-Fc) allowing binding of the rhRAGE-Fc to protein A on the beads. Biotinylated human S100A9 (biot-hS100A9) is pre-incubated with the low molecular test compounds. The pre-mixes are then added to the wells of a micro-plate and incubated allowing interaction between biot-hS100A9 and rhRAGE-Fc. Subsequent addition of streptavidin coated Donor beads causes binding of the streptavidin to the biotinylated hS100A9. After an additional incubation the signal is measured.

Without inhibitory compounds, the interaction of biot-hS100A9 to rhRAGE-Fc will bring the Acceptor and Donor beads in close proximity thus generating a high signal. With an inhibitor present the complex will not form resulting in a decreased signal.

Chemicals and reagents.
AlphaScreen® General IgG (Protein A) Detection Kit, (PerkinElmer 6760617M)
HBS-P buffer (GE Healthcare, BR-1003-68)
HBS-N buffer (GE Healthcare, BR-1003-69)
$CaCl_2$ in HBS-P
$ZnCl_2$ in Milli-Q water
DMSO
Biotinylated hS100A9, (biotinylated via cystein by EZ-link Iodoacetyl-PEG2-Biotin reagent (Pierce no. 21334), in HBS-N
rhRAGE-Fc (R&D Systems, 1145-RG-50), in HBS-P Procedure.

The AlphaScreen assay method is used for screening of the inhibitory effect of different compound samples at fixed concentrations or for IC50 determination by varying the compound concentrations. Samples of test compounds and references are prepared from solutions in DMSO. Relevant reference inhibitors and DMSO are used as controls for defined inhibition and non-inhibition, respectively in the assay. The percent inhibition in assay for test compounds and references are calculated by comparing their obtained assay signals with the signal values for the control with only DMSO (no compound).

Assay concentration of biotinylated hS100A9 and rhRAGE-Fc are batch dependent, and are determined and defined by separate cross-titration experiments using this AlphaScreen inhibition method to verify the optimal setup regarding signal strength and achievement of a defined inhibition with relevant reference compounds. The Final assay concentrations of Acceptor and Donor beads are 20 µg/mL.

Experimental Set Up for Screening, Preparation of Solutions and Beads.

Assay buffer is prepared by adding $CaCl_2$ and $ZnCl_2$ to HBS-P and is used freshly prepared in the experiment.

Biotin-hS100A9 solution for the experiment is prepared by dilution of appropriate amount of stock solution biot-hS100A9 in assay buffer (with $CaCl_2$ and $ZnCl_2$) and incubation in room temperature for 30 minutes.

rhRAGE-Fc solution for the experiment is prepared by dilution appropriate amount of rhRAGE-Fc stock in assay buffer.

Protein A Acceptor beads are diluted in assay buffer and are added to an equal volume of the prepared diluted rhRAGE-Fc solution. The beads are light sensitive. The vial is covered with aluminum foil and incubated at room temperature in the dark until biot-hS100A9+ compound incubation is finished (see below).

Streptavidin-coated Donor beads are diluted in assay buffer. The beads are very light sensitive. The vial is covered with aluminum foil and incubated at room temperature in the dark until use (see below).

Dilution of Samples and Incubation with Biot-hS100A9

Samples of test compounds, appropriate references and DMSO control are diluted in assay buffer.

The diluted test compounds, references and DMSO control are added to wells on a Greiner micro titer 96 well plate (PP, u-bottom (no. 650201)) and appropriate amount of diluted biot-hS100A9 solution are added to each well with samples (final DMSO conc. <1.25% (v/v)). The plate is covered with a plate seal and is incubated in the dark on an orbital plate shaker for 1 h at room temperature.

Incubation of Biot-hS100A9+Compound Samples and rhRAGE-Fc-Acceptor Beads in Optiplate When the biot-hS100A9+ compound incubation is finished the solutions are transferred to Optiplate (Optiplate 384 white, Perkin Elmer no. 6007299) and rhRAGE-Fc-Acceptor bead solution is added to each well (use green filtered light). The plate is covered with a plate seal and incubated in the dark in a plate incubator at 25° C. nominally for 40 minutes.

Incubation of Biot-hS100A9+Compound Samples and rhRAGE-Fc-Acceptor and Donor Beads in Optiplate After incubation Donor bead solution is added to each well (use green filtered light). The plate is covered with a plate seal and incubated in the dark in a plate incubator at 25° C. nominally. After 50 minutes, the plate is incubated (in the dark) on the bench next to the EnVision® instrument for 10 minutes, for temperature equilibrium.

Reading of Optiplate in EnVision® Multilabel Plate Reader

The plate seal is removed and the plate is placed in the EnVision® for 5 minutes before reading.

Calculations

Percent (%) inhibition for each sample (test compound or reference) is calculated using the formula: 1−(Signal sample/Signal DMSO)×100%.

The IC50 values for a number of compounds of the invention in the S100A9-RAGE inhibition assay are listed in Table 2.

TABLE 2

| Ex. No. | ABR ref | IC50 µM |
|---|---|---|
| 9 | 239247 | 0.12 |
| 11 | 239249 | >1 |
| 13 | 239269 | 3.1 |

TABLE 2-continued

| Ex. No. | ABR ref | IC50 μM |
|---|---|---|
| 20 | 239315 | <1 |
| 32 | 239338 | 0.14 |
| 36 | 239372 | 0.1 |
| 40 | 239183 | 3.0 |
| 41 | 239239 | >1 |
| 59 | 238901 | 2.80 |
| 62 | 238868 | 4.4 |
| 63 | 238581 | 4.6 |
| 70 | 239286 | 0.80 |
| 73 | 239167 | 1.2 |
| 74 | 239129 | 2.6 |
| 75 | 239417 | 0.25 |
| 76 | 239462 | <1 |
| 85 | 239571 | 0.98 |
| 88 | 239676 | >1 |
| 89 | 239610 | 2.10 |
| 94 | 239532 | 0.30 |
| 95 | 239477 | 0.7 |
| 96 | 239485 | 0.41 |
| 97 | 239565 | 3.8 |
| 102 | 239607 | 2.2 |
| 103 | 239613 | <1 |
| 107 | 239553 | 4.00 |
| 111 | 239524 | 0.1 |
| 112 | 239619 | 0.42 |
| 113 | 239491 | 2.0 |
| 114 | 239502 | 1.0 |
| 122 | 239554 | >1 |
| 127 | 239465 | 1.11 |
| 130 | 239641 | 0.39 |
| 131 | 239466 | 0.12 |
| 134 | 239671 | 0.53 |
| 136 | 239481 | >1 |
| 137 | 239575 | 1.8 |
| 138 | 239566 | 3.9 |
| 139 | 239531 | <1 |
| 141 | 239717 | <1 |
| 143 | 239721 | 0.18 |
| 144 | 239720 | <1 |
| 155 | 239755 | >1 |
| 157 | 239760 | <1 |
| 159 | 239762 | 1.8 |
| 161 | 239769 | 5.1 |
| 163 | 239772 | >1 |
| 167 | 239434 | <1 |
| 170 | 239766 | <1 |
| 172 | 239560 | 3.1 |
| 173 | 239562 | <1 |
| 178 | 239672 | >1 |
| 179 | 239673 | <1 |
| 182 | 239724 | <1 |
| 185 | 239741 | <1 |
| 186 | 239758 | <1 |
| 188 | 239774 | <1 |
| 189 | 239401 | 0.12 |

In Vivo Model MC38/Mouse.

Figure 3A:
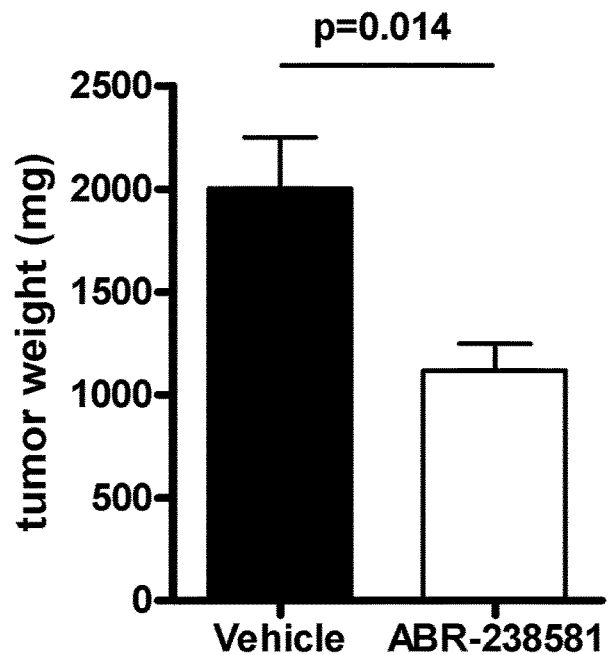
FIGS. 3A and 3B are bar charts showing the effect of compound treatment on MC38-C215 tumor growth. Mice were inoculated with tumor cells s.c. and treatment with (A) Example 63 (ABR-238581) as shown in FIG. 3A or (B) Example 59 (ABR-238901) as shown in FIG. 3B was started the following day. Treatment (30 mg/kg) was given daily per orally. At end-point (day 15 and 16, respectively), mice were sacrificed and tumors excised and weighed. Error bars indicate SEM. The difference in tumor weight between treatment groups was statistically evaluated by non-parametric Mann-Whitney U test.
Figure 3B:
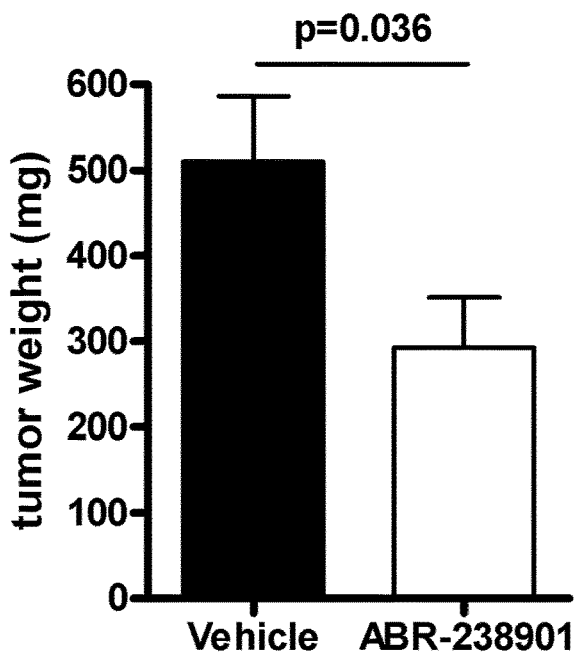

Female C57Bl/6 mice about seven weeks old were purchased. Before the onset of the studies the mice were acclimatized at the laboratory for at least one week. The mice were routinely used at the aged of 8 to 12 weeks. In all experiments a control group of mice was randomly selected. The control group was handled exactly as the treated group but not administrated with any drug compound. Provoking the tumor disease was made by subcutaneous injections with 100 000 or 500 000 MC38-C215 cells in 100 μl matrigel (day 0). This cell line was C215-transfected murine MC38 colon adenocarcinoma cells which were cultured in $R_{10}$ medium (RPMI-1640 with Ultraglutamine supplemented with 10% fetal bovine serum, 50 μM β-mercaptoethanol and 0.5 mg/ml G418 Sulfate). From day 7 the tumor growth was measured three times a week with a caliper and tumor volume was calculated. The tumor volume was calculated as $V=L \times W^2 \times 0.4$, where V is the volume ($mm^2$), L is the length (mm) and W is the width (mm) and L> or =W (Attia 1966). When tumors in the control group had reached a suitable size the experiment was completed and all the mice were sacrificed (usually on day 12-16) and the tumors were dissected out and the tumor mass was determined. Results are shown in FIG. 3.

Prodrug Assay

ABR-239313, 239470 and 239749 were administered to seven C57 Bl/6 mice as a cassette formulation either intravenously (4 animals, nominal 1 mg/kg) or per oral (3 animals, nominal 5 mg/kg).

Blood samples were collected at time points ranging from 5 minutes to 7 hours after administration. After sample withdrawal, plasma was directly separated and frozen until analysis.

The plasma as well as the formulation samples were analyzed with respect to the concentration of ABR-239313, 239470, 239749 and the corresponding demethylated compounds, i.e. Examples 9, 75 and 73 (ABR-239247, 239417 and 239167) by means of LC-MS.

The samples were precipitated with acidified acetonitrile and centrifuged prior to injection on LC-MS system (consisting of a triple quadrupole instrument operated in negative MRM ionization mode, and a fast-gradient reversed-phase LC on a Symmetry Shield RP18, 2×30 mm, 3.5 um column).

In Table 3 the concentrations of each analyte are presented.

TABLE 3

| | | | Prodrug | Parent | Prodrug | Parent | Prodrug | Parent |
|---|---|---|---|---|---|---|---|---|
| | | | | | Formulation | | | |
| Route | | Time (h) | 239313 Conc. (μM) | 239247 Conc. (μM) | 239470 Conc. (μM) | 239417 Conc. (μM) | 239749 Conc. (μM) | 239167 Conc. (μM) |
| — | Predose | 0 | <LLOQ | <LLOQ | <LLOQ | <LLOQ | <LLOQ | <LLOQ |
| i.v. | Solution | 0.083 | 6.3 | 0.044 | 25.2 | 0.12 | 32.2 | 0.089 |
| i.v. | Solution | 0.5 | 0.55 | 0.005 | 16.8 | 0.32 | 19.3 | 0.20 |
| i.v. | Solution | 1 | 0.084 | 0.003 | 17.5 | 0.32 | 23.7 | 0.19 |
| i.v. | Solution | 2 | 0.38 | 0.006 | 14.9 | 0.32 | 17.5 | 0.21 |
| i.v. | Solution | 4 | 0.17 | 0.004 | 9.2 | 0.21 | 7.8 | 0.18 |
| i.v. | Solution | 7 | 0.15 | 0.004 | 6.2 | 0.20 | 2.5 | 0.13 |
| p.o. | Solution | 0.5 | 3.6 | 0.045 | 51.7 | 0.57 | 86.8 | 0.46 |
| p.o. | Solution | 1 | 1.6 | 0.026 | 69.4 | 0.86 | 91.6 | 0.49 |
| p.o. | Solution | 2 | 1.3 | 0.021 | 78.9 | 0.80 | 109.2 | 0.69 |

TABLE 3-continued

| Route | | Time (h) | Prodrug 239313 Conc. (µM) | Parent 239247 Conc. (µM) | Prodrug Formulation 239470 Conc. (µM) | Parent 239417 Conc. (µM) | Prodrug 239749 Conc. (µM) | Parent 239167 Conc. (µM) |
|---|---|---|---|---|---|---|---|---|
| p.o. | Solution | 4 | 0.85 | 0.012 | 59.4 | 0.63 | 47.1 | 0.61 |
| p.o. | Solution | 7 | 0.70 | 0.019 | 73.5 | 1.10 | 50.3 | 0.78 |
| Formulation solution 0.1 mg/ml | | | 41% | <0.1% | 99% | <0.8% | 108% | <0.7% |
| Formulation solution 1 mg/ml | | | 82% | <0.1% | 113% | <0.8% | 118% | <0.7% |

LLOQ = 0.05, 0.002, 0.02, 0.01, 0.02 and 0.01 µM for 239313, 239247, 239470, 239417, 239749 and 239167, respectively.

Abbreviations Used

AcOH acetic acid
CHRM cryopreserved hepatocyte recovery medium
DCM dichloromethane
DMF N,N-dimethyl formamide
DMSO dimethyl sulfoxide
DTT dithiothreitol
EDTA ethylenediaminetetraacetic acid
EGTA ethylene glycol tetraacetic acid
EtOAc ethyl acetate
EtOH ethanol
FAC S fluorescence-activated cell sorting
HPLC high performance liquid chromatography
hrs hours
IPTG isopropyl 3-D-1-thiogalactopyranoside
KHB Krebs-Henseleit bicarbonate buffer
min minutes
NMR nuclear magnetic resonance
PBS phosphate buffered saline
PBST phosphate buffered saline Tween-20
RT room temperature
SFC supercritical fluid chromatography
THF tetrahydrofuran
TLC thin layer chromatography

REFERENCES

Acharyya S et al., A CXCL1 paracrine network links cancer chemoresistance and metastasis. Cell 2012, 150(1), 165-7
Andersen K et al, J Org Chem, 53(20), 4667, 1988
Andersen K et al, J Org Chem, 47(10), 1884, 1982
Arai K et al., S100A8 and S100A9 overexpression is associated with poor pathological parameters in invasive ductal carcinoma of the breast. Curr Cancer Drug Targets 2008, 8(4): 243-52
Attia M, et al. (1966). Cancer Res., 26: 1787-1800
Bhardwaj R S et al., The calcium-binding proteins MRP8 and MRP14 form a membrane-associated heterodimer in a subset of monocytes/macrophages present in acute but absent in chronic inflammatory lesions. Eur J Immunol 1992, 22:1891-97
Björk P et al., Identification of human S100A9 as a novel target for treatment of autoimmune disease via binding to quinoline-3-carboxamides. PLoS Biol. 2009, 7(4):e97
Cesaro A et al., An inflammation loop orchestrated by S100A9 and calprotectin is critical for development of arthritis. PLoS One 2012, 7:e45478.
Chang K A et al., The role of S100a9 in the pathogenesis in Alzheimer's disease: the therapeutic effects of S100a9 knockdown or knockout. Neurodegener Dis 2012, 10(1-4):27-9
Cheng P et al., Inhibition of dendritic cell differentiation and accumulation of myeloid-derived suppressor cells in cancer is regulated by S100A9 protein. J Exp Med 2008, 205(10), 2235-49
Deane R et al., A multimodal RAGE-specific inhibitor reduces amyloid b-mediated brain disorder in a mouse model of Alzheimer disease. J Clin Invest 2013. 122(4): 1377-92
Foell D et al., S100 proteins in phagocytes: a novel group of damage-associated moleculat pattern molecules. J Leukoc Biol 2007, 81:28-37
Foell D et al., Proinflammatory S100 proteins in arthritis and autoimmune disease. Arthritis Rheum 2004, 50, 3762-3771
Ghavami S et al., S100A8/S100A9 at low concentration promotes tumor cell growth via RAGE ligation and MAP kinase-dependent pathway. J Leukoc Biol 2008, 83(6), 1484-92
Ha T et al., S100a9 knockdown decreases the memory impairment and the neuropathology in Tg2576 mice, AD animal model. PLoS one 2010, 5(1):e8840
Hibino T et al., S100A9 is a novel ligand of EMMPRIN that promotes melanoma metastasis. Cancer Res 2012 Nov. 7 Epub ahead of print
Hiratsuka S et al., Tumour-mediated upregulation of chemoattractants and recruitment of myeloid cells predetermines lung metastasis. Nat Cell Biol. 8(12), 1369-75 (2006)
Hsieh J-H et al, J Comp-Aid Mol Des, 22(9), 593, 2008
Int. Appl. No. PCT/JP2007/070581; Publ. No. WO 2008050732
Int. Appl. No. PCT/EP2010/052589; Publ. No. WO 2010100127
Int. Appl. No. PCT/CA2010/000779; Publ. No. WO 2010132999
Int. Appl. No. PCT/EP2010/062300; Publ. No. WO 2011023677
Int. Appl. No. PCT/US2011/020414; Publ. No. WO 2011085126
Koshiro A, Chem Pharm Bull, 7, 725, 1959
Marenholz I et al., S100 proteins in mouse and man: from evolution to function and pathology (including an update of the nomenclature). BBRC2004, 322:1111-22
Nakagone T et al, Chem Pharm Bull, 14(10), 1074, 1966
Riva M et al., Induction of nuclear factor-kappaB responses by the S100A9 protein is Toll-like receptor-4-dependent. Immunology 2012, 137:172-182
Ryckman C et al., Proinflammatory activities of S100: proteins S100A8, S100A9, and S100A8/A9 induce neutrophil chemotaxis and adhesion J. Immunol. 170, 3233-42 (2003)

Shepherd C E et al., inflammatory S100A9 and S100A12 proteins in Alzheimers disease. Neurobiol Aging 2006, 27:1554-1563

Sinha P et al., Proinflammatory S100 proteins regulate the ackumulation of myeloid-derived suppressor cells. J Immunol 2008, 181:4666-4675

Srikrishna G et al., S100A8 and S100A9: New insights into their roles in malignancy. J Innate Immun 2012, 4:31-40 van Lent P et al., Active Involvement of Alarmins S100A8 and S100A9 in the Regulation of Synovial Activation and Joint Destruction During Mouse and Human Osteoarthritis. Arthritis & Rheumatism 2012, 64(5), 1466-76

Wang L et al., Increased myeloid-derived suppressor cells in gastric cancer correlate with cancer stage and plasma S100A8/A9 proinflammatory proteins. J Immunol 2013, 190:794-804

The invention claimed is:

1. A method of treatment of colon cancer, by administering, to a mammal in need of such treatment, a compound of formula (I)

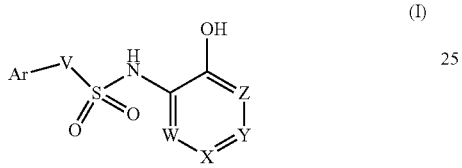

or a pharmaceutically acceptable salt thereof;
wherein
W is N or CH;
X is N or $CR_1$;
Y is N or $CR_2$;
Z is N or $CR_3$;
at least one and at most two of W, X, Y and Z are N;
$R_1$ is H, halogen, $S(O)_2C1-C3$ alkyl, cyano, or C1-C3 alkyl optionally substituted with one or more halogen(s);
$R_2$ is H, halogen, cyano, C(O)OH, C(O)OC1-C3 alkyl, C1-C3 alkyl optionally substituted with one or more F; hydroxy-C1-C3 alkyl, $S(O)_2C1-C3$ alkyl, $S(O)_2C3-C6$ cycloalkyl or $S(O)_2C1-C3$ hydroxyalkyl;
$R_3$ is H, halogen or cyano;
V is $(CHR_4)_m$;
m is 0 or 1;
$R_4$ is H or C1-C3 alkyl optionally substituted with one or more halogen(s);
Ar is

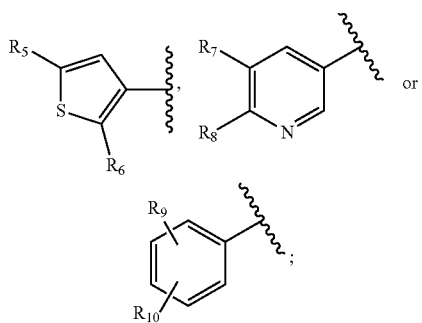

$R_5$ is H, halogen or cyano;
$R_6$ is H or halogen;
$R_7$ is H, halogen, C1-C3 alkyl, cyano, $S(O)_2C1-C3$ alkyl, or phenyl;
$R_8$ is H, halogen, C1-C3 alkyl optionally substituted with one or more F; C1-C3 alkoxy optionally substituted with one or more F; phenoxy, $NHR_{11}$, or $NR_{11}R_{12}$;
$R_9$ is H, halogen, cyano, C1-C3 alkyl optionally substituted with one or more F; C1-C3 alkylthio optionally substituted with one or more F; C1-C3 alkoxy optionally substituted with one or more F; or C(O)$NR_{13}R_{14}$;
$R_{10}$ is H, halogen, cyano, C1-C3 alkyl optionally substituted with one or more F; C1-C3 alkylthio optionally substituted with one or more F; C1-C3 alkoxy optionally substituted with one or more F; or C(O)$NR_{13}R_{14}$;
$R_{11}$ is C1-C3 alkyl;
$R_{12}$ is C1-C3 alkyl; or
$R_{11}$ and $R_{12}$, together with the nitrogen atom to which they are both attached, form a ring of formula

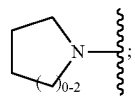

$R_{13}$ is H or C1-C3 alkyl; and
$R_{14}$ is H or C1-C3 alkyl;
provided that the compound is not selected from
3,4-difluoro-N-(2-hydroxypyridin-3-yl)benzene-1-sulfonamide,
N-[5-bromo-3-hydroxypyridin-2-yl]-4-methylbenzenesulfonamide,
N-(1,2-dihydro-2-oxo-3-pyridinyl)-2-(trifluoromethyl)-benzenesulfonamide,
4-chloro-N-(1,2-dihydro-2-oxo-3-pyridinyl)-3-(trifluoromethyl)-benzenesulfonamide,
4-chloro-N-(3-hydroxy-2-pyridinyl)-benzenesulfonamide,
3-trifluoromethyl-N-(3-hydroxy-2-pyridinyl)-benzenesulfonamide,
4-methyl-N-(3-hydroxy-2-pyridinyl)-benzenesulfonamide,
4-methyl-N-(2-hydroxy-3-pyridinyl)-benzenesulfonamide, and
4-methyl-N-(2,3-dihydro-3-oxo-4-pyridazinyl)-benzenesulfonamide or its tautomer
4-methyl-N-(3-hydroxy-4-pyridazinyl)-benzenesulfonamide.

2. The method of claim 1, wherein Ar is

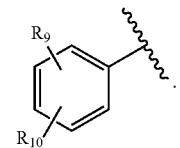

3. The method of claim 1, wherein Ar is

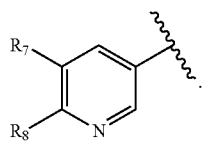

4. The method of claim 1, wherein Ar is

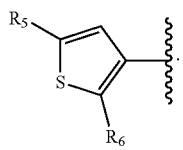

5. The method of claim 1, wherein one of $R_9$ and $R_{10}$ is halogen and the other one is selected from H, halogen, cyano, C1-C3 alkyl optionally substituted with one or more F; C1-C3 alkylthio optionally substituted with one or more F; C1-C3 alkoxy optionally substituted with one or more F; and $C(O)NR_{13}R_{14}$.

6. The method of claim 1, wherein $R_9$ is H or halogen and $R_{10}$ is halogen or cyano.

7. The method of claim 1, wherein $R_7$ is H or halogen, and $R_8$ is H, C1-C3 alkyl optionally substituted with one or more F; or C1-C3 alkoxy optionally substituted with one or more F.

8. The method of claim 1, wherein $R_5$ and $R_6$ are halogens.

9. The method of claim 1, wherein Y is $CR_2$.

10. The method of claim 1, wherein W is N.

11. The method of claim 1, wherein X is N.

12. The method of claim 1, wherein Y is CH, Z is $CR_3$, and $R_3$ is halogen.

13. The method of claim 1, wherein Y is $CR_2$, Z is CH, and $R_2$ is halogen or $S(O)_2$C1-C3 alkyl.

14. The method of claim 1, wherein m is 1 and $R_4$ is H.

15. The method of claim 1, wherein m is 0.

16. The method of claim 1, wherein the compound is selected from 5-bromo-6-chloro-N-(5-chloro-2-hydroxypyridin-3-yl)pyridine-3-sulfonamide;
N-(4-hydroxypyridin-3-yl)benzenesulfonamide;
N-(4-hydroxypyridin-3-yl)-4-(trifluoromethyl)benzene-1-sulfonamide;
N-(4-hydroxypyridin-3-yl)-4-(trifluoromethoxy)benzene-1-sulfonamide;
N-(5-chloro-3-hydroxypyridin-2-yl)-1-phenylmethanesulfonamide;
N-(5-chloro-3-hydroxypyridin-2-yl)-6-(pyrrolidin-1-yl)pyridine-3-sulfonamide;
N-(5-chloro-3-hydroxypyridin-2-yl)pyridine-3-sulfonamide;
6-chloro-N-(5-chloro-3-hydroxypyridin-2-yl)pyridine-3-sulfonamide;
N-(5-chloro-3-hydroxypyridin-2-yl)-1-(3,5-dichlorophenyl)methanesulfonamide;
N-(5-chloro-3-hydroxypyridin-2-yl)-6-[(propan-2-yl)amino]pyridine-3-sulfonamide;
5-bromo-6-chloro-N-[3-hydroxy-5-(propan-2-yl)pyridin-2-yl]pyridine-3-sulfonamide;
N-(5-chloro-3-hydroxypyridin-2-yl)-1-(3-cyanophenyl)methanesulfonamide;
(+)-5-bromo-6-chloro-N-[3-hydroxy-5-(1-hydroxypropan-2-yl)pyridin-2-yl]pyridine-3-sulfonamide;
(−)-5-bromo-6-chloro-N-[3-hydroxy-5-(1-hydroxypropan-2-yl)pyridin-2-yl]pyridine-3-sulfonamide;
5-bromo-6-chloro-N-(3-hydroxypyridin-2-yl)pyridine-3-sulfonamide;
N-(5-chloro-3-hydroxypyridin-2-yl)-1-(2,4-dichlorophenyl)methanesulfonamide;
N-(5-chloro-3-hydroxypyridin-2-yl)-1-(4-cyanophenyl)methanesulfonamide;
N-(5-chloro-3-hydroxypyridin-2-yl)-1-pyridin-3-ylmethanesulfonamide;
5-bromo-N-(5-chloro-3-hydroxypyridin-2-yl)-6-(pyrrolidin-1-yl)pyridine-3-sulfonamide;
N-(5-chloro-3-hydroxypyridin-2-yl)-1-(3,5-difluorophenyl)methanesulfonamide;
N-(5-chloro-3-hydroxypyridin-2-yl)-1-(2,5-dichlorothiophen-3-yl)methanesulfonamide;
N-(5-chloro-3-hydroxypyridin-2-yl)-1-(3,4-dichlorophenyl)methanesulfonamide;
N-(5-chloro-3-hydroxypyridin-2-yl)-1-(3-chloro-5-fluorophenyl)methanesulfonamide;
1-(2,4-dichlorophenyl)-N-(4-hydroxypyridin-3-yl)methanesulfonamide;
1-(3,5-dichlorophenyl)-N-(4-hydroxypyridin-3-yl)methanesulfonamide;
3,5-dichloro-N-(5-chloro-3-hydroxypyridin-2-yl)benzene-1-sulfonamide;
3,4-dichloro-N-(5-chloro-3-hydroxypyridin-2-yl)benzene-1-sulfonamide;
N-(5-chloro-3-hydroxypyridin-2-yl)-1-(3-chlorophenyl)methanesulfonamide;
N-(5-chloro-3-hydroxypyridin-2-yl)-1-(4-chlorophenyl)methanesulfonamide;
N-(5-chloro-3-hydroxypyridin-2-yl)-1-(2-chlorophenyl)methanesulfonamide;
N-(5-chloro-3-hydroxypyridin-2-yl)-1-(2,5-dichlorophenyl)methanesulfonamide;
N-(5-chloro-3-hydroxypyridin-2-yl)-1-(3,4-difluorophenyl)methanesulfonamide;
1-(3,5-dichlorophenyl)-N-(3-hydroxy-5-methanesulfonylpyridin-2-yl)methane-sulfonamide;
N-(5-chloro-3-hydroxypyridin-2-yl)-1-(3-chloro-5-cyanophenyl)methanesulfonamide;
3-chloro-5-{[(5-chloro-3-hydroxypyridin-2-yl)sulfamoyl]methyl}benzamide;
1-(5-chloro-2-fluorophenyl)-N-(5-chloro-3-hydroxypyridin-2-yl)methanesulfonamide;
N-(6-chloro-4-hydroxypyridazin-3-yl)-1-(3,5-dichlorophenyl)methanesulfonamide;
N-(5-chloro-3-hydroxypyridin-2-yl)-1-(2,3-dichlorophenyl)methanesulfonamide;
N-(5-chloro-3-hydroxypyridin-2-yl)-1-(2,6-dichlorophenyl)methanesulfonamide;
(1R)—N-(5-chloro-3-hydroxypyridin-2-yl)-1-(3,5-dichlorophenyl)ethane-1-sulfonamide;
(1S)—N-(5-chloro-3-hydroxypyridin-2-yl)-1-(3,5-dichlorophenyl)ethane-1-sulfonamide;
5-bromo-N-(5-chloro-3-hydroxypyridin-2-yl)pyridine-3-sulfonamide;
N-(5-chloro-3-hydroxypyridin-2-yl)-6-(trifluoromethyl)pyridine-3-sulfonamide;
N-(5-chloro-3-hydroxypyridin-2-yl)-3-(trifluoromethoxy)benzene-1-sulfonamide;
N-(5-bromo-3-hydroxypyridin-2-yl)benzene sulfonamide;

N-(5-bromo-3-hydroxypyridin-2-yl)-2,5-dichlorothiophene-3-sulfonamide;
N-(5-bromo-3-hydroxypyridin-2-yl)-3-(trifluoromethoxy)benzene-1-sulfonamide;
5-bromo-N-(5-bromo-3-hydroxypyridin-2-yl)-6-chloropyridine-3-sulfonamide;
N-(5-bromo-3-hydroxypyridin-2-yl)-6-(trifluoromethyl)pyridine-3-sulfonamide;
5-bromo-N-(5-bromo-3-hydroxypyridin-2-yl)-6-methoxypyridine-3-sulfonamide;
N-(3-hydroxypyridin-2-yl)-6-(trifluoromethyl)pyridine-3-sulfonamide
methyl 6-(2,5-dichlorothiophene-3-sulfonamido)-5-hydroxypyridine-3-carboxylate;
methyl 6-benzenesulfonamido-5-hydroxypyridine-3-carboxylate;
4-bromo-3-fluoro-N-(4-hydroxypyridin-3-yl)benzene-1-sulfonamide;
N-(5-chloro-2-hydroxypyridin-3-yl)-6-(trifluoromethyl)pyridine-3-sulfonamide;
5-bromo-N-(5-chloro-2-hydroxypyridin-3-yl)-6-methoxypyridine-3-sulfonamide;
2,5-dichloro-N-(5-chloro-3-hydroxypyridin-2-yl)thiophene-3-sulfonamide;
N-(5-chloro-4-hydroxypyridin-3-yl)-6-(trifluoromethyl)pyridine-3-sulfonamide;
5-bromo-6-chloro-N-(5-chloro-4-hydroxypyridin-3-yl)pyridine-3-sulfonamide;
5-bromo-N-(5-chloro-4-hydroxypyridin-3-yl)-6-methoxypyridine-3-sulfonamide;
5-bromo-N-(5-chloro-4-hydroxypyridin-3-yl)pyridine-3-sulfonamide;
5-bromo-6-chloro-N-(4-hydroxypyridin-3-yl)pyridine-3-sulfonamide;
5-bromo-N-(4-hydroxypyridin-3-yl)-6-methoxypyridine-3-sulfonamide;
2,5-dichloro-N-(4-hydroxypyridin-3-yl)thiophene-3-sulfonamide;
N-(4-hydroxypyridin-3-yl)-6-(trifluoromethyl)pyridine-3-sulfonamide;
3,4-difluoro-N-(4-hydroxypyridin-3-yl)benzene-1-sulfonamide;
3,4-dichloro-N-(4-hydroxypyridin-3-yl)benzene-1-sulfonamide;
N-(2-hydroxypyridin-3-yl)-6-(trifluoromethyl)pyridine-3-sulfonamide;
5-bromo-6-chloro-N-(2-hydroxypyridin-3-yl)pyridine-3-sulfonamide;
2,5-dichloro-N-(2-hydroxypyridin-3-yl)thiophene-3-sulfonamide;
N-(6-chloro-4-hydroxypyridin-3-yl)-1-(3,4-dichlorophenyl)methanesulfonamide;
5-bromo-N-(5-chloro-3-hydroxypyridin-2-yl)-6-methoxypyridine-3-sulfonamide;
3,4-dichloro-N-(3-hydroxypyridin-4-yl)benzene-1-sulfonamide;
2,5-dichloro-N-(6-chloro-4-hydroxypyridin-3-yl)thiophene-3-sulfonamide;
2,5-dichloro-N-(5-chloro-2-hydroxypyridin-3-yl)thiophene-3-sulfonamide;
N-(5-bromo-3-hydroxypyrazin-2-yl)-1-(3,4-dichlorophenyl)methanesulfonamide;
N-(6-chloro-4-hydroxypyridazin-3-yl)-1-(3,4-difluorophenyl)methanesulfonamide;
1-(3,5-dichlorophenyl)-N-[3-hydroxy-5-(propane-2-sulfonyl)pyridin-2-yl]methane-sulfonamide;
N-(5-chloro-3-hydroxypyrazin-2-yl)-1-(3,5-dichlorophenyl)methanesulfonamide;
5-bromo-N-(5-chloro-4-hydroxypyridin-3-yl)-6-phenoxypyridine-3-sulfonamide;
N-(5-bromo-3-hydroxypyrazin-2-yl)-1-(3,5-dichlorophenyl)methanesulfonamide;
N-(6-chloro-4-hydroxypyridazin-3-yl)-1-(2,4-dichlorophenyl)methanesulfonamide;
1-(3,5-dichlorophenyl)-N-(4-hydroxy-6-iodopyridazin-3-yl)methanesulfonamide;
N-(6-bromo-4-hydroxypyridazin-3-yl)-1-(3,5-dichlorophenyl)methanesulfonamide;
3-bromo-N-(5-bromo-4-hydroxypyridin-3-yl)-4-methoxybenzene-1-sulfonamide;
N-(6-chloro-4-hydroxypyridazin-3-yl)-1-(2-chloro-5-cyanophenyl)methane-sulfonamide;
N-(5-chloro-4-hydroxypyridin-3-yl)-6-phenoxypyridine-3-sulfonamide;
N-(6-chloro-4-hydroxypyridazin-3-yl)-1-(3,5-dichlorophenyl)methanesulfonamide;
1-(3-chlorophenyl)-N-[5-(ethanesulfonyl)-3-hydroxypyrazin-2-yl]methane-sulfonamide;
3,5-dichloro-N-(5-chloro-4-hydroxypyridin-3-yl)benzene-1-sulfonamide;
N-(6-chloro-4-hydroxypyridazin-3-yl)-1-(2-chlorophenyl)methanesulfonamide;
5-bromo-N-(5-bromo-4-hydroxypyridin-3-yl)-6-methoxypyridine-3-sulfonamide;
N-(6-bromo-5-chloro-3-hydroxypyridin-2-yl)-1-(3,5-dichlorophenyl)methane-sulfonamide;
1-(2-chlorophenyl)-N-(4-hydroxy-6-methanesulfonylpyridazin-3-yl)methane-sulfonamide;
N-(6-chloro-4-hydroxypyridazin-3-yl)-1-(3-chloro-5-fluorophenyl)methane-sulfonamide;
3,5-dichloro-N-(6-chloro-4-hydroxypyridazin-3-yl)benzene-1-sulfonamide;
N-(6-chloro-4-hydroxypyridazin-3-yl)-1-(3-chlorophenyl)methanesulfonamide;
N-(5-bromo-4-hydroxypyridin-3-yl)-1-(3,5-dichlorophenyl)methanesulfonamide;
3-[(5-chloro-4-hydroxypyridin-3-yl)sulfamoyl]-N,N-diethylbenzamide;
1-(3,4-difluorophenyl)-N-(4-hydroxy-6-methanesulfonylpyridazin-3-yl)methane-sulfonamide;
3-chloro-N-(5-chloro-4-hydroxypyridin-3-yl)-4-methylbenzene-1-sulfonamide;
5-bromo-N-(5-chloro-4-hydroxypyridin-3-yl)-6-(propan-2-yloxy)pyridine-3-sulfonamide;
3-chloro-N-(5-chloro-4-hydroxypyridin-3-yl)-4-(trifluoromethoxy)benzene-1-sulfonamide;
N-(5-cyano-3-hydroxypyrazin-2-yl)-1-(3,5-dichlorophenyl)methanesulfonamide;
1-(3,5-dichlorophenyl)-N-[4-hydroxy-6-(propane-1-sulfonyl)pyridazin-3-yl]methane-sulfonamide;
N-(5-chloro-3-hydroxypyridin-2-yl)-1-(3,5-dimethoxyphenyl)methanesulfonamide;
5-chloro-N-(5-chloro-3-hydroxypyridin-2-yl)-6-(dimethylamino)pyridine-3-sulfonamide;
N-(2-chloro-4-hydroxypyrimidin-5-yl)-1-(3,5-dichlorophenyl)methanesulfonamide;
1-(3,5-dichlorophenyl)-N-[5-(ethanesulfonyl)-3-hydroxypyridin-2-yl]methane-sulfonamide;
3,4-dichloro-N-(6-chloro-4-hydroxypyridazin-3-yl)benzene-1-sulfonamide;
N-(5-chloro-4-hydroxypyridin-3-yl)-1-(3,5-dichlorophenyl)methanesulfonamide;

1-(3,5-dichlorophenyl)-N-[6-(ethanesulfonyl)-4-hydroxypyridazin-3-yl]methane-sulfonamide;
1-(3,5-dichlorophenyl)-N-(3-hydroxy-5-methanesulfonylpyrazin-2-yl)methane-sulfonamide;
2,5-dichloro-N-(6-chloro-4-hydroxypyridazin-3-yl)thiophene-3-sulfonamide;
5-bromo-N-(6-chloro-4-hydroxypyridazin-3-yl)-6-methoxypyridine-3-sulfonamide;
N-(6-chloro-4-hydroxypyridazin-3-yl)-1-(2,3-dichlorophenyl)methanesulfonamide;
N-(6-chloro-4-hydroxypyridazin-3-yl)-3-(trifluoromethoxy)benzene-1-sulfonamide;
6-(azetidin-1-yl)-5-bromo-N-(5-chloro-4-hydroxypyridin-3-yl)pyridine-3-sulfonamide;
1-(3,5-dichlorophenyl)-N-[4-hydroxy-6-(propane-2-sulfonyl)pyridazin-3-yl]methane-sulfonamide;
5-bromo-N-(5-chloro-4-hydroxypyridin-3-yl)-6-ethoxypyridine-3-sulfonamide;
5-bromo-N-(5-chloro-3-hydroxypyridin-2-yl)-6-(dimethylamino)pyridine-3-sulfonamide;
N-(6-chloro-4-hydroxypyridazin-3-yl)-3-cyanobenzene-1-sulfonamide;
3-chloro-N-(5-chloro-4-hydroxypyridin-3-yl)-4-methoxybenzene-1-sulfonamide;
3-bromo-N-(5-chloro-4-hydroxypyridin-3-yl)-4-methoxybenzene-1-sulfonamide;
1-(3,5-dichlorophenyl)-N-[3-hydroxy-5-(propane-1-sulfonyl)pyridin-2-yl]methane-sulfonamide;
N-(6-chloro-4-hydroxypyridazin-3-yl)-1-(3,4-dichlorophenyl)methanesulfonamide;
1-(3,5-dichlorophenyl)-N-(4-hydroxy-6-methanesulfonylpyridazin-3-yl)methane-sulfonamide;
N-(5-chloro-3-hydroxypyridin-2-yl)-1-(5-cyanothiophen-3-yl)methanesulfonamide;
5-bromo-6-chloro-N-[4-hydroxy-6-(trifluoromethyl)pyridin-3-yl]pyridine-3-sulfonamide;
5-bromo-N-(5-chloro-4-hydroxypyridin-3-yl)-6-(piperidin-1-yl)pyridine-3-sulfonamide;
N-(5-chloro-6-cyano-3-hydroxypyridin-2-yl)-1-(3,5-dichlorophenyl)methane-sulfonamide;
N-[5-(cyclopentanesulfonyl)-3-hydroxypyridin-2-yl]-1-(3,5-dichlorophenyl)methane-sulfonamide;
N-[4-hydroxy-6-(trifluoromethyl)pyridin-3-yl]-6-methylpyridine-3-sulfonamide;
1-(3,5-dichlorophenyl)-N-[4-hydroxy-6-(trifluoromethyl)pyridin-3-yl]methane-sulfonamide;
N-(5-chloro-3-hydroxy-6-methanesulfonylpyridin-2-yl)-1-(3,5-dichlorophenyl)-methanesulfonamide;
1-(3,4-dichlorophenyl)-N-[4-hydroxy-6-(trifluoromethyl)pyridin-3-yl]methane-sulfonamide;
N-(5-chloro-3-hydroxypyridin-2-yl)-6-(dimethylamino)-5-methanesulfonylpyridine-3-sulfonamide;
5-bromo-N-[4-hydroxy-6-(trifluoromethyl)pyridin-3-yl]-6-methoxypyridine-3-sulfonamide;
N-(5-cyano-4-hydroxypyridin-3-yl)-1-(3,5-dichlorophenyl)methanesulfonamide;
1-(3,5-dichlorophenyl)-N-[4-hydroxy-6-(3-hydroxypropanesulfonyl)pyridazin-3-yl]methanesulfonamide;
N-[6-(cyclopentanesulfonyl)-4-hydroxypyridazin-3-yl]-1-(3,5-dichlorophenyl)methane-sulfonamide;
(+/−)-N-(5-bromo-3-hydroxypyrazin-2-yl)-1-(3,5-dichlorophenyl)-2,2,2-trifluoro-ethane-1-sulfonamide;
3-[(5-bromo-3-hydroxypyrazin-2-yl)sulfamoyl]-N,N-diethylbenzamide;
N-(2-chloro-5-hydroxypyrimidin-4-yl)-1-(3,5-dichlorophenyl)methanesulfonamide;
3,4-dichloro-N-(2-chloro-5-hydroxypyrimidin-4-yl)benzene-1-sulfonamide;
3,5-dichloro-N-(2-chloro-5-hydroxypyrimidin-4-yl)benzene-1-sulfonamide;
3-[(6-chloro-4-hydroxypyridazin-3-yl)sulfamoyl]-N,N-diethylbenzamide;
N-(6-chloro-4-hydroxypyridazin-3-yl)-1-(4-cyanophenyl)methanesulfonamide;
N-(6-chloro-4-hydroxypyridazin-3-yl)-1-(5-cyano-2-fluorophenyl)methane-sulfonamide;
N-(6-chloro-4-hydroxypyridazin-3-yl)-1-(3-cyano-5-fluorophenyl)methane-sulfonamide;
1-(2-chloro-5-cyanophenyl)-N-(2-chloro-5-hydroxypyrimidin-4-yl)methane-sulfonamide;
2-chloro-N-(6-chloro-4-hydroxypyridazin-3-yl)-4-cyanobenzene-1-sulfonamide;
3-chloro-N-(6-chloro-4-hydroxypyridazin-3-yl)-4-fluorobenzene-1-sulfonamide;
3,5-dichloro-N-(5-cyano-4-hydroxypyridin-3-yl)benzene-1-sulfonamide;
3-chloro-N-(6-chloro-4-hydroxypyridazin-3-yl)-5-fluorobenzene-1-sulfonamide;
3,5-dichloro-N-(4-hydroxy-6-methanesulfonylpyridin-3-yl)benzene-1-sulfonamide;
3,5-dichloro-N-(6-chloro-4-hydroxypyridin-3-yl)benzene-1-sulfonamide;
1-(3,5-dichlorophenyl)-N-[5-hydroxy-2-(trifluoromethyl)pyrimidin-4-yl]methane-sulfonamide;
3-chloro-5-fluoro-N-[5-hydroxy-2-(trifluoromethyl)pyrimidin-4-yl]benzene-1-sulfonamide;
3,5-dichloro-N-(3-hydroxy-5-methanesulfonylpyrazin-2-yl)benzene-1-sulfonamide;
3-chloro-4-[(6-chloro-4-hydroxypyridazin-3-yl)sulfamoyl]-N,N-diethylbenzamide;
3-chloro-5-{[(6-chloro-4-hydroxypyridazin-3-yl)sulfamoyl]methyl}-N,N-diethyl-benzamide;
N-(6-chloro-4-hydroxypyridazin-3-yl)-3-cyano-5-fluorobenzene-1-sulfonamide;
3-chloro-5-fluoro-N-[4-hydroxy-6-(trifluoromethyl)pyridazin-3-yl]benzene-1-sulfonamide;
1-(3,4-dichlorophenyl)-N-[5-hydroxy-2-(trifluoromethyl)pyrimidin-4-yl]methane-sulfonamide;
N-(6-chloro-4-hydroxypyridazin-3-yl)-1-(2,5-dichlorothiophen-3-yl)methane-sulfonamide;
3,5-dichloro-N-(4-hydroxy-6-methanesulfonylpyridazin-3-yl)benzene-1-sulfonamide;
1-(3,5-dichlorophenyl)-N-(3-hydroxypyridin-4-yl)methanesulfonamide;
6-(2,5-dichlorothiophene-3-sulfonamido)-5-hydroxypyridine-3-carboxylic acid;
N-(2-chloro-3-hydroxypyridin-4-yl)-1-(3,5-dichlorophenyl)methanesulfonamide;
3,5-dichloro-N-(2-chloro-3-hydroxypyridin-4-yl)benzene-1-sulfonamide;
N-(3-hydroxypyridin-2-yl)-3-(trifluoromethyl)benzene-1-sulfonamide;
N-(5-chloro-2-hydroxypyridin-3-yl)-1-(3,4-dichlorophenyl)methanesulfonamide;
N-(5,6-dichloro-2-hydroxypyridin-3-yl)-1-(3,5-dichlorophenyl)methanesulfonamide;
N-(6-chloro-2-hydroxypyridin-3-yl)-1-(3,4-dichlorophenyl)methanesulfonamide;
N-(6-chloro-2-hydroxypyridin-3-yl)-1-(3,5-dichlorophenyl)methanesulfonamide;
5-bromo-N-(6-chloro-2-hydroxypyridin-3-yl)-6-methoxypyridine-3-sulfonamide;

N-(5,6-dibromo-3-hydroxypyrazin-2-yl)-1-(3,4-dichlorophenyl)methanesulfonamide;
N-(6-chloro-2-hydroxypyridin-3-yl)-1-[4-(trifluoromethyl)phenyl]methane-sulfonamide;
N-(6-chloro-2-hydroxypyridin-3-yl)-4-propylbenzene-1-sulfonamide;
3,4-dichloro-N-(6-chloro-2-hydroxypyridin-3-yl)benzene-1-sulfonamide;
N-(6-chloro-2-hydroxypyridin-3-yl)-1-(5,6-dichloropyridin-3-yl)methane-sulfonamide;
N-(6-chloro-2-hydroxypyridin-3-yl)-1-(5-chloro-6-methoxypyridin-3-yl)methane-sulfonamide;
N-(5-chloro-4-hydroxypyridin-3-yl)-1-(5,6-dichloropyridin-3-yl)methane-sulfonamide;
N-(5-chloro-4-hydroxypyridin-3-yl)-1-(5-chloro-6-methoxypyridin-3-yl)methane-sulfonamide;
N-(6-chloro-2-hydroxypyridin-3-yl)-1-[5-chloro-6-(pyrrolidin-1-yl)pyridin-3-yl]-methanesulfonamide;
N-(6-chloro-2-hydroxypyridin-3-yl)-1-[3-chloro-5-(ethylsulfanyl)phenyl]methane-sulfonamide;
3,5-dichloro-N-[6-(ethanesulfonyl)-2-hydroxypyridin-3-yl]benzene-1-sulfonamide;
1-(3,5-dichlorophenyl)-N-[6-(ethanesulfonyl)-2-hydroxypyridin-3-yl]methane-sulfonamide;
N-(5-cyano-3-hydroxypyridin-2-yl)-1-(3,5-dichlorophenyl)methanesulfonamide;
5-chloro-N-(5-chloro-4-hydroxypyridin-3-yl)-6-methylpyridine-3-sulfonamide;
N-(5-chloro-4-hydroxypyridin-3-yl)-5-cyano-6-methoxypyridine-3-sulfonamide;
N-(5-chloro-4-hydroxypyridin-3-yl)-6-methoxy-5-phenylpyridine-3-sulfonamide;
N-(5-chloro-3-hydroxypyridin-2-yl)-5-phenylpyridine-3-sulfonamide;
N-(6-chloro-4-hydroxypyridazin-3-yl)-1-(3-chloro-5-cyanophenyl)methane-sulfonamide;
5-bromo-6-chloro-N-(6-chloro-4-hydroxypyridazin-3-yl)pyridine-3-sulfonamide; and
N-(5-bromo-4-hydroxypyridin-3-yl)-3,5-dichlorobenzene-1-sulfonamide;
or a pharmaceutically acceptable salt thereof.

17. A method of inhibiting interaction between S100A9 and its interaction partners in a mammal, by administering to said mammal a compound of formula (I)

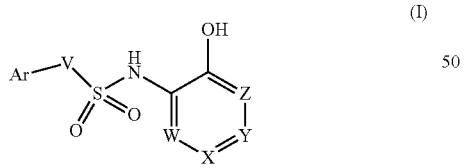

(I)

or a pharmaceutically acceptable salt thereof;
wherein
W is N or CH;
X is N or $CR_1$;
Y is N or $CR_2$;
Z is N or $CR_3$;
at least one and at most two of W, X, Y and Z are N;
$R_1$ is H, halogen, $S(O)_2$C1-C3 alkyl, cyano, or C1-C3 alkyl optionally substituted with one or more halogen(s);
$R_2$ is H, halogen, cyano, C(O)OH, C(O)OC1-C3 alkyl, C1-C3 alkyl optionally substituted with one or more F; hydroxy-C1-C3 alkyl, $S(O)_2$C1-C3 alkyl, $S(O)_2$C3-C6 cycloalkyl or $S(O)_2$C1-C3 hydroxyalkyl;
$R_3$ is H, halogen or cyano;
V is $(CHR_4)_m$;
m is 0 or 1;
$R_4$ is H or C1-C3 alkyl optionally substituted with one or more halogen(s);
Ar is

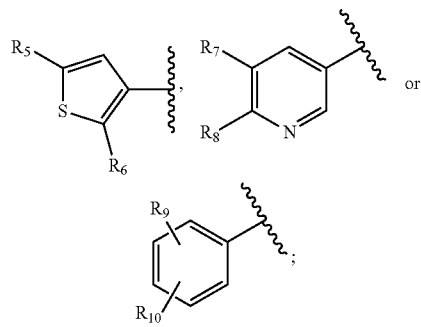

$R_5$ is H, halogen or cyano;
$R_6$ is H or halogen;
$R_7$ is H, halogen, C1-C3 alkyl, cyano, $S(O)_2$C1-C3 alkyl, or phenyl;
$R_8$ is H, halogen, C1-C3 alkyl optionally substituted with one or more F; C1-C3 alkoxy optionally substituted with one or more F; phenoxy, $NHR_{11}$, or $NR_{11}R_{12}$;
$R_9$ is H, halogen, cyano, C1-C3 alkyl optionally substituted with one or more F; C1-C3 alkylthio optionally substituted with one or more F; C1-C3 alkoxy optionally substituted with one or more F; or C(O)$NR_{13}R_{14}$;
$R_{10}$ is H, halogen, cyano, C1-C3 alkyl optionally substituted with one or more F; C1-C3 alkylthio optionally substituted with one or more F; C1-C3 alkoxy optionally substituted with one or more F; or C(O)$NR_{13}R_{14}$;
$R_{11}$ is C1-C3 alkyl;
$R_{12}$ is C1-C3 alkyl; or
$R_{11}$ and $R_{12}$, together with the nitrogen atom to which they are both attached, form a ring of formula

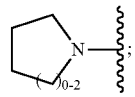

$R_{13}$ is H or C1-C3 alkyl; and
$R_{14}$ is H or C1-C3 alkyl;
provided that the compound is not selected from
3,4-difluoro-N-(2-hydroxypyridin-3-yl)benzene-1-sulfonamide,
N-[5-bromo-3-hydroxypyridin-2-yl]-4-methylbenzenesulfonamide,
N-(1,2-dihydro-2-oxo-3-pyridinyl)-2-(trifluoromethyl)-benzenesulfonamide,
4-chloro-N-(1,2-dihydro-2-oxo-3-pyridinyl)-3-(trifluoromethyl)-benzenesulfonamide,
4-chloro-N-(3-hydroxy-2-pyridinyl)-benzenesulfonamide, 3-trifluoromethyl-N-(3-hydroxy-2-pyridinyl)-benzene-sulfonamide,
4-methyl-N-(3-hydroxy-2-pyridinyl)-benzenesulfonamide,
4-methyl-N-(2-hydroxy-3-pyridinyl)-benzenesulfonamide, and
4-methyl-N-(2,3-dihydro-3-oxo-4-pyridazinyl)-benzenesulfonamide or its tautomer
4-methyl-N-(3-hydroxy-4-pyridazinyl)-benzenesulfonamide.

18. The method of claim 17, wherein the interaction partners are selected from the group consisting of RAGE, TLR4 and EMMPRIN.

19. The method of claim 17, wherein the inhibition of said interaction is used to treat a disorder or condition selected from the group consisting of cancer, an inflammatory disorder, an autoimmunity disorder and a neurodegenerative disorder.

20. The method of claim 19, wherein the disorder is cancer.

21. The method of claim 17, wherein Ar is

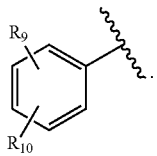

22. The method of claim 17, wherein Ar is

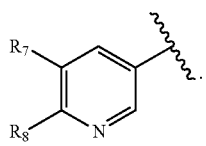

23. The method of claim 17, wherein Ar is

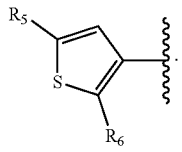

24. The method of claim 17, wherein one of $R_9$ and $R_{10}$ is halogen and the other one is selected from H, halogen, cyano, C1-C3 alkyl optionally substituted with one or more F; C1-C3 alkylthio optionally substituted with one or more F; C1-C3 alkoxy optionally substituted with one or more F; and $C(O)NR_{13}R_{14}$.

25. The method of claim 17, wherein $R_9$ is H or halogen and $R_{10}$ is halogen or cyano.

26. The method of claim 17, wherein $R_7$ is H or halogen, and $R_8$ is H, C1-C3 alkyl optionally substituted with one or more F; or C1-C3 alkoxy optionally substituted with one or more F.

27. The method of claim 17, wherein $R_5$ and $R_6$ are halogens.

28. The method of claim 17, wherein Y is $CR_2$.

29. The method of claim 17, wherein W is N.

30. The method of claim 17, wherein X is N.

31. The method of claim 17, wherein Y is CH, Z is $CR_3$, and $R_3$ is halogen.

32. The method of claim 17, wherein Y is $CR_2$, Z is CH, and $R_2$ is halogen or $S(O)_2$C1-C3 alkyl.

33. The method of claim 17, wherein m is 1 and $R_4$ is H.

34. The method of claim 17, wherein m is 0.

35. The method of claim 17, wherein the compound is selected from
5-bromo-6-chloro-N-(5-chloro-2-hydroxypyridin-3-yl)pyridine-3-sulfonamide;
N-(4-hydroxypyridin-3-yl)benzenesulfonamide;
N-(4-hydroxypyridin-3-yl)-4-(trifluoromethyl)benzene-1-sulfonamide;
N-(4-hydroxypyridin-3-yl)-4-(trifluoromethoxy)benzene-1-sulfonamide;
N-(5-chloro-3-hydroxypyridin-2-yl)-1-phenylmethanesulfonamide;
N-(5-chloro-3-hydroxypyridin-2-yl)-6-(pyrrolidin-1-yl)pyridine-3-sulfonamide;
N-(5-chloro-3-hydroxypyridin-2-yl)pyridine-3-sulfonamide;
6-chloro-N-(5-chloro-3-hydroxypyridin-2-yl)pyridine-3-sulfonamide;
N-(5-chloro-3-hydroxypyridin-2-yl)-1-(3,5-dichlorophenyl)methanesulfonamide;
N-(5-chloro-3-hydroxypyridin-2-yl)-6-[(propan-2-yl)amino]pyridine-3-sulfonamide;
5-bromo-6-chloro-N-[3-hydroxy-5-(propan-2-yl)pyridin-2-yl]pyridine-3-sulfonamide;
N-(5-chloro-3-hydroxypyridin-2-yl)-1-(3-cyanophenyl)methanesulfonamide;
(+)-5-bromo-6-chloro-N-[3-hydroxy-5-(1-hydroxypropan-2-yl)pyridin-2-yl]pyridine-3-sulfonamide;
(−)-5-bromo-6-chloro-N-[3-hydroxy-5-(1-hydroxypropan-2-yl)pyridin-2-yl]pyridine-3-sulfonamide;
5-bromo-6-chloro-N-(3-hydroxypyridin-2-yl)pyridine-3-sulfonamide;
N-(5-chloro-3-hydroxypyridin-2-yl)-1-(2,4-dichlorophenyl)methanesulfonamide;
N-(5-chloro-3-hydroxypyridin-2-yl)-1-(4-cyanophenyl)methanesulfonamide;
N-(5-chloro-3-hydroxypyridin-2-yl)-1-pyridin-3-ylmethanesulfonamide;
5-bromo-N-(5-chloro-3-hydroxypyridin-2-yl)-6-(pyrrolidin-1-yl)pyridine-3-sulfonamide;
N-(5-chloro-3-hydroxypyridin-2-yl)-1-(3,5-difluorophenyl)methanesulfonamide;
N-(5-chloro-3-hydroxypyridin-2-yl)-1-(2,5-dichlorothiophen-3-yl)methanesulfonamide;
N-(5-chloro-3-hydroxypyridin-2-yl)-1-(3,4-dichlorophenyl)methanesulfonamide;
N-(5-chloro-3-hydroxypyridin-2-yl)-1-(3-chloro-5-fluorophenyl)methanesulfonamide;
1-(2,4-dichlorophenyl)-N-(4-hydroxypyridin-3-yl)methanesulfonamide;
1-(3,5-dichlorophenyl)-N-(4-hydroxypyridin-3-yl)methanesulfonamide;
3,5-dichloro-N-(5-chloro-3-hydroxypyridin-2-yl)benzene-1-sulfonamide;
3,4-dichloro-N-(5-chloro-3-hydroxypyridin-2-yl)benzene-1-sulfonamide;
N-(5-chloro-3-hydroxypyridin-2-yl)-1-(3-chlorophenyl)methanesulfonamide;
N-(5-chloro-3-hydroxypyridin-2-yl)-1-(4-chlorophenyl)methanesulfonamide;
N-(5-chloro-3-hydroxypyridin-2-yl)-1-(2-chlorophenyl)methanesulfonamide;

N-(5-chloro-3-hydroxypyridin-2-yl)-1-(2,5-dichlorophenyl)methanesulfonamide;
N-(5-chloro-3-hydroxypyridin-2-yl)-1-(3,4-difluorophenyl)methanesulfonamide;
1-(3,5-dichlorophenyl)-N-(3-hydroxy-5-methanesulfonylpyridin-2-yl)methane-sulfonamide;
N-(5-chloro-3-hydroxypyridin-2-yl)-1-(3-chloro-5-cyanophenyl)methanesulfonamide;
3-chloro-5-{[(5-chloro-3-hydroxypyridin-2-yl)sulfamoyl]methyl}benzamide;
1-(5-chloro-2-fluorophenyl)-N-(5-chloro-3-hydroxypyridin-2-yl)methanesulfonamide;
N-(6-chloro-4-hydroxypyridazin-3-yl)-1-(3,5-dichlorophenyl)methanesulfonamide;
N-(5-chloro-3-hydroxypyridin-2-yl)-1-(2,3-dichlorophenyl)methanesulfonamide;
N-(5-chloro-3-hydroxypyridin-2-yl)-1-(2,6-dichlorophenyl)methanesulfonamide;
(1R)—N-(5-chloro-3-hydroxypyridin-2-yl)-1-(3,5-dichlorophenyl)ethane-1-sulfonamide;
(1S)—N-(5-chloro-3-hydroxypyridin-2-yl)-1-(3,5-dichlorophenyl)ethane-1-sulfonamide;
5-bromo-N-(5-chloro-3-hydroxypyridin-2-yl)pyridine-3-sulfonamide;
N-(5-chloro-3-hydroxypyridin-2-yl)-6-(trifluoromethyl)pyridine-3-sulfonamide;
N-(5-chloro-3-hydroxypyridin-2-yl)-3-(trifluoromethoxy)benzene-1-sulfonamide;
N-(5-bromo-3-hydroxypyridin-2-yl)benzene sulfonamide;
N-(5-bromo-3-hydroxypyridin-2-yl)-2,5-dichlorothiophene-3-sulfonamide;
N-(5-bromo-3-hydroxypyridin-2-yl)-3-(trifluoromethoxy)benzene-1-sulfonamide;
5-bromo-N-(5-bromo-3-hydroxypyridin-2-yl)-6-chloropyridine-3-sulfonamide;
N-(5-bromo-3-hydroxypyridin-2-yl)-6-(trifluoromethyl)pyridine-3-sulfonamide;
5-bromo-N-(5-bromo-3-hydroxypyridin-2-yl)-6-methoxypyridine-3-sulfonamide;
N-(3-hydroxypyridin-2-yl)-6-(trifluoromethyl)pyridine-3-sulfonamide
methyl 6-(2,5-dichlorothiophene-3-sulfonamido)-5-hydroxypyridine-3-carboxylate;
methyl 6-benzenesulfonamido-5-hydroxypyridine-3-carboxylate;
4-bromo-3-fluoro-N-(4-hydroxypyridin-3-yl)benzene-1-sulfonamide;
N-(5-chloro-2-hydroxypyridin-3-yl)-6-(trifluoromethyl)pyridine-3-sulfonamide;
5-bromo-N-(5-chloro-2-hydroxypyridin-3-yl)-6-methoxypyridine-3-sulfonamide;
2,5-dichloro-N-(5-chloro-3-hydroxypyridin-2-yl)thiophene-3-sulfonamide;
N-(5-chloro-4-hydroxypyridin-3-yl)-6-(trifluoromethyl)pyridine-3-sulfonamide;
5-bromo-6-chloro-N-(5-chloro-4-hydroxypyridin-3-yl)pyridine-3-sulfonamide;
5-bromo-N-(5-chloro-4-hydroxypyridin-3-yl)-6-methoxypyridine-3-sulfonamide;
5-bromo-N-(5-chloro-4-hydroxypyridin-3-yl)pyridine-3-sulfonamide;
5-bromo-N-(6-chloro-4-hydroxypyridin-3-yl)pyridine-3-sulfonamide;
5-bromo-N-(4-hydroxypyridin-3-yl)-6-methoxypyridine-3-sulfonamide;
2,5-dichloro-N-(4-hydroxypyridin-3-yl)thiophene-3-sulfonamide;
N-(4-hydroxypyridin-3-yl)-6-(trifluoromethyl)pyridine-3-sulfonamide;
3,4-difluoro-N-(4-hydroxypyridin-3-yl)benzene-1-sulfonamide;
3,4-dichloro-N-(4-hydroxypyridin-3-yl)benzene-1-sulfonamide;
N-(2-hydroxypyridin-3-yl)-6-(trifluoromethyl)pyridine-3-sulfonamide;
5-bromo-6-chloro-N-(2-hydroxypyridin-3-yl)pyridine-3-sulfonamide;
2,5-dichloro-N-(2-hydroxypyridin-3-yl)thiophene-3-sulfonamide;
N-(6-chloro-4-hydroxypyridin-3-yl)-1-(3,4-dichlorophenyl)methanesulfonamide;
5-bromo-N-(5-chloro-3-hydroxypyridin-2-yl)-6-methoxypyridine-3-sulfonamide;
3,4-dichloro-N-(3-hydroxypyridin-4-yl)benzene-1-sulfonamide;
2,5-dichloro-N-(6-chloro-4-hydroxypyridin-3-yl)thiophene-3-sulfonamide;
2,5-dichloro-N-(5-chloro-2-hydroxypyridin-3-yl)thiophene-3-sulfonamide;
N-(5-bromo-3-hydroxypyrazin-2-yl)-1-(3,4-dichlorophenyl)methanesulfonamide;
N-(6-chloro-4-hydroxypyridazin-3-yl)-1-(3,4-difluorophenyl)methanesulfonamide;
1-(3,5-dichlorophenyl)-N-[3-hydroxy-5-(propane-2-sulfonyl)pyridin-2-yl]methane-sulfonamide;
N-(5-chloro-3-hydroxypyrazin-2-yl)-1-(3,5-dichlorophenyl)methanesulfonamide;
5-bromo-N-(5-chloro-4-hydroxypyridin-3-yl)-6-phenoxypyridine-3-sulfonamide;
N-(5-bromo-3-hydroxypyrazin-2-yl)-1-(3,5-dichlorophenyl)methanesulfonamide;
N-(6-chloro-4-hydroxypyridazin-3-yl)-1-(2,4-dichlorophenyl)methanesulfonamide;
1-(3,5-dichlorophenyl)-N-(4-hydroxy-6-iodopyridazin-3-yl)methanesulfonamide;
N-(6-bromo-4-hydroxypyridazin-3-yl)-1-(3,5-dichlorophenyl)methanesulfonamide;
3-bromo-N-(5-bromo-4-hydroxypyridin-3-yl)-4-methoxybenzene-1-sulfonamide;
N-(6-chloro-4-hydroxypyridazin-3-yl)-1-(2-chloro-5-cyanophenyl)methane-sulfonamide;
N-(5-chloro-4-hydroxypyridin-3-yl)-6-phenoxypyridine-3-sulfonamide;
N-(6-chloro-4-hydroxypyridin-3-yl)-1-(3,5-dichlorophenyl)methanesulfonamide;
1-(3-chlorophenyl)-N-[5-(ethanesulfonyl)-3-hydroxypyrazin-2-yl]methane-sulfonamide;
3,5-dichloro-N-(5-chloro-4-hydroxypyridin-3-yl)benzene-1-sulfonamide;
N-(6-chloro-4-hydroxypyridazin-3-yl)-1-(2-chlorophenyl)methanesulfonamide;
5-bromo-N-(5-bromo-4-hydroxypyridin-3-yl)-6-methoxypyridine-3-sulfonamide;
N-(6-bromo-5-chloro-3-hydroxypyridin-2-yl)-1-(3,5-dichlorophenyl)methane-sulfonamide;
1-(2-chlorophenyl)-N-(4-hydroxy-6-methanesulfonylpyridazin-3-yl)methane-sulfonamide;
N-(6-chloro-4-hydroxypyridazin-3-yl)-1-(3-chloro-5-fluorophenyl)methane-sulfonamide;
3,5-dichloro-N-(6-chloro-4-hydroxypyridazin-3-yl)benzene-1-sulfonamide;

N-(6-chloro-4-hydroxypyridazin-3-yl)-1-(3-chlorophenyl)methanesulfonamide;
N-(5-bromo-4-hydroxypyridin-3-yl)-1-(3,5-dichlorophenyl)methanesulfonamide;
3-[(5-chloro-4-hydroxypyridin-3-yl)sulfamoyl]-N,N-diethylbenzamide;
1-(3,4-difluorophenyl)-N-(4-hydroxy-6-methanesulfonylpyridazin-3-yl)methane-sulfonamide;
3-chloro-N-(5-chloro-4-hydroxypyridin-3-yl)-4-methylbenzene-1-sulfonamide;
5-bromo-N-(5-chloro-4-hydroxypyridin-3-yl)-6-(propan-2-yloxy)pyridine-3-sulfonamide;
3-chloro-N-(5-chloro-4-hydroxypyridin-3-yl)-4-(trifluoromethoxy)benzene-1-sulfonamide;
N-(5-cyano-3-hydroxypyrazin-2-yl)-1-(3,5-dichlorophenyl)methanesulfonamide;
1-(3,5-dichlorophenyl)-N-[4-hydroxy-6-(propane-1-sulfonyl)pyridazin-3-yl]methane-sulfonamide;
N-(5-chloro-3-hydroxypyridin-2-yl)-1-(3,5-dimethoxyphenyl)methanesulfonamide;
5-chloro-N-(5-chloro-3-hydroxypyridin-2-yl)-6-(dimethylamino)pyridine-3-sulfonamide;
N-(2-chloro-4-hydroxypyrimidin-5-yl)-1-(3,5-dichlorophenyl)methanesulfonamide;
1-(3,5-dichlorophenyl)-N-[5-(ethanesulfonyl)-3-hydroxypyridin-2-yl]methane-sulfonamide;
3,4-dichloro-N-(6-chloro-4-hydroxypyridazin-3-yl)benzene-1-sulfonamide;
N-(5-chloro-4-hydroxypyridin-3-yl)-1-(3,5-dichlorophenyl)methanesulfonamide;
1-(3,5-dichlorophenyl)-N-[6-(ethanesulfonyl)-4-hydroxypyridazin-3-yl]methane-sulfonamide;
1-(3,5-dichlorophenyl)-N-(3-hydroxy-5-methanesulfonylpyrazin-2-yl)methane-sulfonamide;
2,5-dichloro-N-(6-chloro-4-hydroxypyridazin-3-yl)thiophene-3-sulfonamide;
5-bromo-N-(6-chloro-4-hydroxypyridazin-3-yl)-6-methoxypyridine-3-sulfonamide;
N-(6-chloro-4-hydroxypyridazin-3-yl)-1-(2,3-dichlorophenyl)methanesulfonamide;
N-(6-chloro-4-hydroxypyridazin-3-yl)-3-(trifluoromethoxy)benzene-1-sulfonamide;
6-(azetidin-1-yl)-5-bromo-N-(5-chloro-4-hydroxypyridin-3-yl)pyridine-3-sulfonamide;
1-(3,5-dichlorophenyl)-N-[4-hydroxy-6-(propane-2-sulfonyl)pyridazin-3-yl]methane-sulfonamide;
5-bromo-N-(5-chloro-4-hydroxypyridin-3-yl)-6-ethoxypyridine-3-sulfonamide;
5-bromo-N-(5-chloro-3-hydroxypyridin-2-yl)-6-(dimethylamino)pyridine-3-sulfonamide;
N-(6-chloro-4-hydroxypyridazin-3-yl)-3-cyanobenzene-1-sulfonamide;
3-chloro-N-(5-chloro-4-hydroxypyridin-3-yl)-4-methoxybenzene-1-sulfonamide;
3-bromo-N-(5-chloro-4-hydroxypyridin-3-yl)-4-methoxybenzene-1-sulfonamide;
1-(3,5-dichlorophenyl)-N-[3-hydroxy-5-(propane-1-sulfonyl)pyridin-2-yl]methane-sulfonamide;
N-(6-chloro-4-hydroxypyridazin-3-yl)-1-(3,4-dichlorophenyl)methanesulfonamide;
1-(3,5-dichlorophenyl)-N-(4-hydroxy-6-methanesulfonylpyridazin-3-yl)methane-sulfonamide;
N-(5-chloro-3-hydroxypyridin-2-yl)-1-(5-cyanothiophen-3-yl)methanesulfonamide;
5-bromo-6-chloro-N-[4-hydroxy-6-(trifluoromethyl)pyridin-3-yl]pyridine-3-sulfonamide;
5-bromo-N-(5-chloro-4-hydroxypyridin-3-yl)-6-(piperidin-1-yl)pyridine-3-sulfonamide;
N-(5-chloro-6-cyano-3-hydroxypyridin-2-yl)-1-(3,5-dichlorophenyl)methane-sulfonamide;
N-[5-(cyclopentanesulfonyl)-3-hydroxypyridin-2-yl]-1-(3,5-dichlorophenyl)methane-sulfonamide;
N-[4-hydroxy-6-(trifluoromethyl)pyridin-3-yl]-6-methylpyridine-3-sulfonamide;
1-(3,5-dichlorophenyl)-N-[4-hydroxy-6-(trifluoromethyl)pyridin-3-yl]methane-sulfonamide;
N-(5-chloro-3-hydroxy-6-methanesulfonylpyridin-2-yl)-1-(3,5-dichlorophenyl)-methanesulfonamide;
1-(3,4-dichlorophenyl)-N-[4-hydroxy-6-(trifluoromethyl)pyridin-3-yl]methane-sulfonamide;
N-(5-chloro-3-hydroxypyridin-2-yl)-6-(dimethylamino)-5-methanesulfonylpyridine-3-sulfonamide;
5-bromo-N-[4-hydroxy-6-(trifluoromethyl)pyridin-3-yl]-6-methoxypyridine-3-sulfonamide;
N-(5-cyano-4-hydroxypyridin-3-yl)-1-(3,5-dichlorophenyl)methanesulfonamide;
1-(3,5-dichlorophenyl)-N-[4-hydroxy-6-(3-hydroxypropanesulfonyl)pyridazin-3-yl]methanesulfonamide;
N-[6-(cyclopentanesulfonyl)-4-hydroxypyridazin-3-yl]-1-(3,5-dichlorophenyl)methane-sulfonamide;
(+/−)-N-(5-bromo-3-hydroxypyrazin-2-yl)-1-(3,5-dichlorophenyl)-2,2,2-trifluoro-ethane-1-sulfonamide;
3-[(5-bromo-3-hydroxypyrazin-2-yl)sulfamoyl]-N,N-diethylbenzamide;
N-(2-chloro-5-hydroxypyrimidin-4-yl)-1-(3,5-dichlorophenyl)methanesulfonamide;
3,4-dichloro-N-(2-chloro-5-hydroxypyrimidin-4-yl)benzene-1-sulfonamide;
3,5-dichloro-N-(2-chloro-5-hydroxypyrimidin-4-yl)benzene-1-sulfonamide;
3-[(6-chloro-4-hydroxypyridazin-3-yl)sulfamoyl]-N,N-diethylbenzamide;
N-(6-chloro-4-hydroxypyridazin-3-yl)-1-(4-cyanophenyl)methanesulfonamide;
N-(6-chloro-4-hydroxypyridazin-3-yl)-1-(5-cyano-2-fluorophenyl)methane-sulfonamide;
N-(6-chloro-4-hydroxypyridazin-3-yl)-1-(3-cyano-5-fluorophenyl)methane-sulfonamide;
1-(2-chloro-5-cyanophenyl)-N-(2-chloro-5-hydroxypyrimidin-4-yl)methane-sulfonamide;
2-chloro-N-(6-chloro-4-hydroxypyridazin-3-yl)-4-cyanobenzene-1-sulfonamide;
3-chloro-N-(6-chloro-4-hydroxypyridazin-3-yl)-4-fluorobenzene-1-sulfonamide;
3,5-dichloro-N-(5-cyano-4-hydroxypyridin-3-yl)benzene-1-sulfonamide;
3-chloro-N-(6-chloro-4-hydroxypyridazin-3-yl)-5-fluorobenzene-1-sulfonamide;
3,5-dichloro-N-(4-hydroxy-6-methanesulfonylpyridin-3-yl)benzene-1-sulfonamide;
3,5-dichloro-N-(6-chloro-4-hydroxypyridin-3-yl)benzene-1-sulfonamide;
1-(3,5-dichlorophenyl)-N-[5-hydroxy-2-(trifluoromethyl)pyrimidin-4-yl]methane-sulfonamide;
3-chloro-5-fluoro-N-[5-hydroxy-2-(trifluoromethyl)pyrimidin-4-yl]benzene-1-sulfonamide;
3,5-dichloro-N-(3-hydroxy-5-methanesulfonylpyrazin-2-yl)benzene-1-sulfonamide;
3-chloro-4-[(6-chloro-4-hydroxypyridazin-3-yl)sulfamoyl]-N,N-di ethylbenzamide;
3-chloro-5-{[(6-chloro-4-hydroxypyridazin-3-yl)sulfamoyl]methyl}-N,N-diethyl-benzamide;

N-(6-chloro-4-hydroxypyridazin-3-yl)-3-cyano-5-fluorobenzene-1-sulfonamide;

3-chloro-5-fluoro-N-[4-hydroxy-6-(trifluoromethyl)pyridazin-3-yl]benzene-1-sulfonamide;

1-(3,4-dichlorophenyl)-N-[5-hydroxy-2-(trifluoromethyl)pyrimidin-4-yl]methane-sulfonamide;

N-(6-chloro-4-hydroxypyridazin-3-yl)-1-(2,5-dichlorothiophen-3-yl)methane-sulfonamide;

3,5-dichloro-N-(4-hydroxy-6-methanesulfonylpyridazin-3-yl)benzene-1-sulfonamide;

1-(3,5-dichlorophenyl)-N-(3-hydroxypyridin-4-yl)methanesulfonamide;

6-(2,5-dichlorothiophene-3-sulfonamido)-5-hydroxypyridine-3-carboxylic acid;

N-(2-chloro-3-hydroxypyridin-4-yl)-1-(3,5-dichlorophenyl)methanesulfonamide;

3,5-dichloro-N-(2-chloro-3-hydroxypyridin-4-yl)benzene-1-sulfonamide;

N-(3-hydroxypyridin-2-yl)-3-(trifluoromethyl)benzene-1-sulfonamide;

N-(5-chloro-2-hydroxypyridin-3-yl)-1-(3,4-dichlorophenyl)methanesulfonamide;

N-(5,6-dichloro-2-hydroxypyridin-3-yl)-1-(3,5-dichlorophenyl)methanesulfonamide;

N-(6-chloro-2-hydroxypyridin-3-yl)-1-(3,4-dichlorophenyl)methanesulfonamide;

N-(6-chloro-2-hydroxypyridin-3-yl)-1-(3,5-dichlorophenyl)methanesulfonamide;

5-bromo-N-(6-chloro-2-hydroxypyridin-3-yl)-6-methoxypyridine-3-sulfonamide;

N-(5,6-dibromo-3-hydroxypyrazin-2-yl)-1-(3,4-dichlorophenyl)methanesulfonamide;

N-(6-chloro-2-hydroxypyridin-3-yl)-1-[4-(trifluoromethyl)phenyl]methane-sulfonamide;

N-(6-chloro-2-hydroxypyridin-3-yl)-4-propylbenzene-1-sulfonamide;

3,4-dichloro-N-(6-chloro-2-hydroxypyridin-3-yl)benzene-1-sulfonamide;

N-(6-chloro-2-hydroxypyridin-3-yl)-1-(5,6-dichloropyridin-3-yl)methane-sulfonamide;

N-(6-chloro-2-hydroxypyridin-3-yl)-1-(5-chloro-6-methoxypyridin-3-yl)methane-sulfonamide;

N-(5-chloro-4-hydroxypyridin-3-yl)-1-(5,6-dichloropyridin-3-yl)methane-sulfonamide;

N-(5-chloro-4-hydroxypyridin-3-yl)-1-(5-chloro-6-methoxypyridin-3-yl)methane-sulfonamide;

N-(6-chloro-2-hydroxypyridin-3-yl)-1-[5-chloro-6-(pyrrolidin-1-yl)pyridin-3-yl]-methanesulfonamide;

N-(6-chloro-2-hydroxypyridin-3-yl)-1-[3-chloro-5-(ethylsulfanyl)phenyl]methane-sulfonamide;

3,5-dichloro-N-[6-(ethanesulfonyl)-2-hydroxypyridin-3-yl]benzene-1-sulfonamide;

1-(3,5-dichlorophenyl)-N-[6-(ethanesulfonyl)-2-hydroxypyridin-3-yl]methane-sulfonamide;

N-(5-cyano-3-hydroxypyridin-2-yl)-1-(3,5-dichlorophenyl)methanesulfonamide;

5-chloro-N-(5-chloro-4-hydroxypyridin-3-yl)-6-methylpyridine-3-sulfonamide;

N-(5-chloro-4-hydroxypyridin-3-yl)-5-cyano-6-methoxypyridine-3-sulfonamide;

N-(5-chloro-4-hydroxypyridin-3-yl)-6-methoxy-5-phenylpyridine-3-sulfonamide;

N-(5-chloro-3-hydroxypyridin-2-yl)-5-phenylpyridine-3-sulfonamide;

N-(6-chloro-4-hydroxypyridazin-3-yl)-1-(3-chloro-5-cyanophenyl)methane-sulfonamide;

5-bromo-6-chloro-N-(6-chloro-4-hydroxypyridazin-3-yl)pyridine-3-sulfonamide; and N-(5-bromo-4-hydroxypyridin-3-yl)-3,5-dichlorobenzene-1-sulfonamide;

or a pharmaceutically acceptable salt thereof.

36. The method of claim 20, wherein the cancer is colon cancer.

37. The method of claim 19, wherein the disorder is an inflammatory disorder.

38. The method of claim 19, wherein the disorder is an autoimmunity disorder.

39. The method of claim 19, wherein the disorder is a neurodegenerative disorder.

* * * * *